US006610523B1

(12) United States Patent
Davis et al.

(10) Patent No.: US 6,610,523 B1
(45) Date of Patent: Aug. 26, 2003

(54) CYTOKINE-, STRESS-, AND ONCOPROTEIN-ACTIVATED HUMAN PROTEIN KINASE KINASES

(75) Inventors: Roger J. Davis, Princeton, MA (US); Alan Whitmarsh, Shrewsbury, MA (US); Cathy Tournier, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/593,653

(22) Filed: Jun. 13, 2000

Related U.S. Application Data

(60) Division of application No. 08/888,429, filed on Jul. 7, 1997, now Pat. No. 6,136,596, which is a continuation-in-part of application No. 08/530,950, filed on Sep. 19, 1995, now Pat. No. 5,736,381, which is a continuation-in-part of application No. 08/446,083, filed on May 19, 1995, now Pat. No. 5,804,427.

(51) Int. Cl.$^7$ ............................ C12N 9/12; C12N 15/54
(52) U.S. Cl. ...................................... 435/194; 536/232
(58) Field of Search ............................. 435/194; 536/23.2

(56) References Cited

U.S. PATENT DOCUMENTS 5,753,446 A    5/1998  Johnson ....................... 435/7.1

FOREIGN PATENT DOCUMENTS

| WO | WO 94/24159 | 10/1994 |
| WO | WO 95/28421 | 10/1995 |

OTHER PUBLICATIONS

Cuenda, A. et al. "Differential activation of stress–activated protein kinase kinases SKK4/MKK7 and SKK1/MKK4 by the mixed–lineage kinase–2 and mitogen–activated protein kinase kinase(MKK) kinase–1," *Biochemical Journal* 333(1):11–15, (Jul. 1, 1998).

Davis "MAPKs: New JNK Expands Group" *Elsevier Science Ltd*. TIBS 19:470–473, (1994).

Dent, P. et al. "Activation of Mitogen–Activated Protein Kinase Kinase by v-Raf in NIH 3T3 Cells and in Vitro," *Science* 257:1404–1407, (Sep. 4, 1992).

Dérijard et al. "Independent Human MAP Kinase Signal Transduction Pathways Defined By MEK and MKK Isoforms" *Science* 267:682–685, (1995).

Dérijard et al. "JNK1: A Protein Kinase Stimulated By UV Light and Ha–Ras That Binds and Phosphorylates . . . " *Cell* 76:1025–1037, (1994).

English, et al. "Isolation of MEK5 and Differential Expression of Alternatively Spliced Forms" *J. Biol. Chem.* 270:28897–28902, (1995).

Freshney et al. "Interleukin–1 Activates a Novel Protein Kinase Cascade That Results In the Phosphorylation of Hsp27" *Cell* 78:1039–1049, (1994).

Galcheva–Gargova et al. "An Osmosensing Signal Transduction Pathway In Mammalian Cells" *Science* 265:806–808, (1994).

Gupta et al. "Transcription Factor ATF2 Regulation By the JNK Signal Transduction Pathway" *Science* 267:389–393, (1995).

Han et al. "Characterization of the Structure and Function of a Novel MAP Kinase Kinase (MKK6)" *J. Biol. Chem.* 271:2886–2891, (Feb. 1996).

Hibi et al. "Identification of an Oncoprotein–and UV–Responsive Protein That Binds and Potentiates . . . " *Genes & Dev.* 7:2135–2148, (1993).

Irie, K. et al., "MKK1 and MKK2, Which Encode *Saccharomyces cervisiae* Mitogen–Activated Protein Kinase–Kinase Homologs, Function in the Pathway Mediated by Protein Kinase C," *Molecular and Cellular Biology* 13(5):3076–3083, (May 1993).

Lin et al. "Identification of a Dual Specificity Kinase That Activate the Jun Kinases and p38–Mpk2" *Science* 268:286–290, (1995).

Meirer et al. "Cellular Stresses and Cytokines activate Multiple Mitogen–Activated–Protein Kinase . . . " *Europ. J. of Biochem.* 236:796–805, (1996).

Minden et al. "Differential Activation of ERK and JNK Mitogen–Activated Protein Kinases by Raf–1 and MEKK" *Science* 266:1719–1723, (1994).

Moodie, S.A. et al., "Complexes of Ras–GTP with Raf–1 and Mitogen–Activated Protein Kinase Kinase," *Science* 260:1658–1661, (Jun. 11, 1993).

Moriguchi et al. "Evidence for Multiple Activators for Stress–Activated protein Kinases/c–Jun Amino . . . " *J. Biol. Chem.* 270:12969–12972, (1995).

Moriguchi et al. "Purification and Identification of a Major Activator for p38 from Osmotically Shocked Cells" *J. Biol. Chem.* 271:26891–26988, (1996).

Nishina et al. "Stress–Signalling Kinase Sek1 Protects Thymocytes from Apoptosis . . . " *Nature* 385:350–353, (1997).

Raingeaud et al "Pro–Inflammatory Cytokines and Environmental Stress Cause p38 Mitogen–Activated . . . " *J. Biol. Chem.* 270:7420–7426, (1995).

Rouse et al. "A Novel Kinase Cascade Triggered By Stress and Heat Shock that Stimulates MAPKAP Kinase . . . " *Cell* 78:1027–1037, (1994).

(List continued on next page.)

*Primary Examiner*—Rebecca E. Prouty
(74) *Attorney, Agent, or Firm*—Fish & Richardson P.C.

(57) ABSTRACT

Disclosed are human mitogen-activated (MAP) kinase kinase isoforms (MKKs). MKKs mediate unique signal transduction pathways that activate human MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

4 Claims, 54 Drawing Sheets

OTHER PUBLICATIONS

Sanchez et al. "Role of SAPK/ERK Kinase–1 in the Stress–Activated Pathway Regulating Transcription . . . " *Nature* 372:794–798, (1994).

Seger et al. "Human T–Cell Mitogen–Activated Protein Kinases Are Related to Yeast Signal Transduction Kinases" *J. Biol. Chem.* 267:25628–25631, (1992).

Sluss et al. "Signal Transduction By Tumor Necrosis Factor Mediated By JNK Protein Kinases" *Mol. and Cell. Biol.* 14:8376–8384, (1994).

Tournier, C. et al., "Mitogen–activated Protein Kinase Kinase 7 Is An Activator of the c–Jun NH(sub)2–Terminal Kinase," *Proceedings of the National Academy of Sciences* 94:7337–7342, (Jul. 1997).

Traverse, S. et al., "Sustained Activation of the Mitogen–activated Protein (MAP) Kinase Cascade May be Required for Differentiation of PC12 Cells," *Biochem. J.* 288:351–355, (1992).

Whitmarsh et al. "Integration of MAP Kinase Signal Transduction Pathways At the Serum Response Element" *Science* 269:403–407, (1995).

Wu et al. "Identification and Characterization of a New Mammalian Mitogen–Activated Protein Kinase Kinases, MKK2" *Molecular and Cellular Biology* 13:4539–4548, (1993).

Xia et al. "Opposing Effects of ERK and JNK–p38 MAP Kinases On Apoptosis" *Science* 270:1326–1331, (1995).

Yan et al. "Activation of Stress–Activated Protein Kinase by MEKK1 Phosphorylation of Its Activator SEK1" *Nature* 372:798–800, (1994).

Yang et al. "Targeted Disruption of the MKK4 Gene Causes Embryonic Death, Inhibition of c–Jun . . . " *Proc. Nat'l. Acad. Sci. USA* 94:3004–3009, (1997).

Yashar et al. "Novel Members of the Mitogen–Activated Protein Kinase Activator Family in Xenopus Laevis" *Mol. and Cell. Biol.* 13:5738–5748, (1993).

FIG. 1

```
          5        10        15        20        25        30        35        40        45        50        55        60
          *                  *                  *                  *                  *                  *
TGGCTGGCAA TGGCCTTGCT GACCTCGAGC CGGGCCCACG TGGGGACCTT TGGAGCACAG
ACCGACCGTT ACCGGAACGA CTGGAGCTCG GCCCGGGTGC ACCCCTGGAA ACCTCGTGTC 65        70        75        80        85        90        95       100       105       110       115       120
          *                  *                  *                  *                  *                  *
CCTACGATCC TGGTGCAAGG CCGGTGGATG CAGAGGCCAG TCCATATACC ACCCAGGCCT
GGATGCTAGG ACCACGTTCC GGCCACCTAC GTCTCCGGTC AGGTATATGG TGGGTCCGGA 125       130       135       140       145       150       155       160       165       170       175       180
          *                  *                  *                  *                  *                  *
GCGAGGAGCG TGGTCCCCAC CCATCCAGCC CATATGTGCA AGTGCCCTTG ACAGAGAGGC
CGCTCCTCGC ACCAGGGGTG GGTAGGTCGG GTATACACGT TCACGGGAAC TGTCTCTCCG 185       190       195       200       205       210       215       220       225       230       235       240
          *                  *                  *                  *                  *                  *
TGGTCATATC CATGGTGACC ATTTATGGGC CACAACAGGT CCCCATCTGC GCAGTGAACC
ACCAGTATAG GTACCACTGG TAAATACCCG GTGTTGTCCA GGGGTAGACG CGTCACTTGG 245       250       255       260       265       270       275       280       285       290       295       300
          *                  *                  *                  *                  *                  *
CTGTGCTGAG CACCTTGCAG ACGTGATCTT GCTTCGTCCT GCAGCACTGT GCGGGGCAGG
GACACGACTC GTGGAACGTC TGCACTAGAA CGAAGCAGGA CGTCGTGACA CGCCCCGTCC 305       310       315       320       325       330       335       340       345       350       355
          *                  *                  *                  *                  *
AAAATCCAAG AGGAAGAAGG ATCTACGGAT ATCCTGC ATG TCC AAG CCA CCC GCA
TTTTAGGTTC TCCTTCTTCC TAGATGCCTA TAGGACG TAC AGG TTC GGT GGG CGT
                                         Met Ser Lys Pro Pro Ala>

360       365       370       375       380       385       390       395       400
          *                  *                  *                  *                  *
CCC AAC CCC ACA CCC CCC CGG AAC CTG GAC TCC CGG ACC TTC ATC ACC
GGG TTG GGG TGT GGG GGG GCC TTG GAC CTG AGG GCC TGG AAG TAG TGG
Pro Asn Pro Thr Pro Pro Arg Asn Leu Asp Ser Arg Thr Phe Ile Thr>

405       410       415       420       425       430       435       440       445       450
          *                  *                  *                  *                  *
ATT GGA GAC AGA AAC TTT GAG GTG GAG GCT GAT GAC TTG GTG ACC ATC
TAA CCT CTG TCT TTG AAA CTC CAC CTC CGA CTA CTG AAC CAC TGG TAG
Ile Gly Asp Arg Asn Phe Glu Val Glu Ala Asp Asp Leu Val Thr Ile>

455       460       465       470       475       480       485       490       495
          *                  *                  *                  *                  *
TCA GAA CTG GGC CGT GGA GCC TAT GGG GTG GTA GAG AAG GTG CGG CAC
AGT CTT GAC CCG GCA CCT CGG ATA CCC CAC CAT CTC TTC CAC GCC GTG
Ser Glu Leu Gly Arg Gly Ala Tyr Gly Val Val Glu Lys Val Arg His>

500       505       510       515       520       525       530       535       540       545
      *                  *                  *                  *                  *
GCC CAG AGC GGC ACC ATC ATG GCC GTG AAG CGG ATC CGG GCC ACC GTG
CGG GTC TCG CCG TGG TAG TAC CGG CAC TTC GCC TAG GCC CGG TGG CAC
Ala Gln Ser Gly Thr Ile Met Ala Val Lys Arg Ile Arg Ala Thr Val>

550       555       560       565       570       575       580       585       590       595
      *                  *                  *                  *                  *
AAC TCA CAG GAG CAG AAG CGG CTC CTC ATG GAC CTG GAC ATC AAC ATG
TTG AGT GTC CTC GTC TTC GCC GAG GAG TAC CTG GAC CTG TAG TTG TAC
Asn Ser Gln Glu Gln Lys Arg Leu Leu Met Asp Leu Asp Ile Asn Met>
```

FIG. 4A

```
     600       605       610       615       620       625       630       635       640
      *                   *                   *                   *                   *
     CGC       ACG       GTC       GAC       TGT       TTC       TAC       ACT       GTC       ACC       TTC       TAC       GGG       GCA       CTA       TTC
     GCG       TGC       CAG       CTG       ACA       AAG       ATG       TGA       CAG       TGG       AAG       ATG       CCC       CGT       GAT       AAG
     Arg       Thr       Val       Asp       Cys       Phe       Tyr       Thr       Val       Thr       Phe       Tyr       Gly       Ala       Leu       Phe>

645       650       655       660       665       670       675       680       685       690
                *                   *                   *                   *                   *
     AGA       GAG       GGA       GAC       GTG       TGG       ATC       TGC       ATG       GAG       CTC       ATG       GAC       ACA       TCC       TTG
     TCT       CTC       CCT       CTG       CAC       ACC       TAG       ACG       TAC       CTC       GAG       TAC       CTG       TGT       AGG       AAC
     Arg       Glu       Gly       Asp       Val       Trp       Ile       Cys       Met       Glu       Leu       Met       Asp       Thr       Ser       Leu>

695       700       705       710       715       720       725       730       735
      *                   *                   *                   *
     GAC       AAG       TTC       TAC       CGG       AAG       GTG       CTG       GAT       AAA       AAC       ATG       ACA       ATT       CCA       GAG
     CTG       TTC       AAG       ATG       GCC       TTC       CAC       GAC       CTA       TTT       TTG       TAC       TGT       TAA       GGT       CTC
     Asp       Lys       Phe       Tyr       Arg       Lys       Val       Leu       Asp       Lys       Asn       Met       Thr       Ile       Pro       Glu>

740       745       750       755       760       765       770       775       780       785
      *                   *                   *                   *                   *
     GAC       ATC       CTT       GGG       GAG       ATT       GCT       GTG       TCT       ATC       GTG       CGG       GCC       CTG       GAG       CAT
     CTG       TAG       GAA       CCC       CTC       TAA       CGA       CAC       AGA       TAG       CAC       GCC       CGG       GAC       CTC       GTA
     Asp       Ile       Leu       Gly       Glu       Ile       Ala       Val       Ser       Ile       Val       Arg       Ala       Leu       Glu       His>

790       795       800       805       810       815       820       825       830       835
      *                   *                   *                   *                   *
     CTG       CAC       AGC       AAG       CTG       TCG       GTG       ATC       CAC       AGA       GAT       GTG       AAG       CCC       TCC       AAT
     GAC       GTG       TCG       TTC       GAC       AGC       CAC       TAG       GTG       TCT       CTA       CAC       TTC       GGG       AGG       TTA
     Leu       His       Ser       Lys       Leu       Ser       Val       Ile       His       Arg       Asp       Val       Lys       Pro       Ser       Asn>

840       845       850       855       860       865       870       875       880
                *                   *                   *                   *                   *
     GTC       CTT       ATC       AAC       AAG       GAG       GGC       CAT       GTG       AAG       ATG       TGT       GAC       TTT       GGC       ATC
     CAG       GAA       TAG       TTG       TTC       CTC       CCG       GTA       CAC       TTC       TAC       ACA       CTG       AAA       CCG       TAG
     Val       Leu       Ile       Asn       Lys       Glu       Gly       His       Val       Lys       Met       Cys       Asp       Phe       Gly       Ile>

885       890       895       900       905       910       915       920       925       930
                *                   *                   *                   *                   *
     AGT       GGC       TAC       TTG       GTG       GAC       TCT       GTG       GCC       AAG       ACG       ATG       GAT       GCC       GGC       TGC
     TCA       CCG       ATG       AAC       CAC       CTG       AGA       CAC       CGG       TTC       TGC       TAC       CTA       CGG       CCG       ACG
     Ser       Gly       Tyr       Leu       Val       Asp       Ser       Val       Ala       Lys       Thr       Met       Asp       Ala       Gly       Cys>

935       940       945       950       955       960       965       970       975
                          *                   *                   *                   *
     AAG       CCC       TAC       ATG       GCC       CCT       GAG       AGG       ATC       AAC       CCA       GAG       CTG       AAC       CAG       AAG
     TTC       GGG       ATG       TAC       CGG       GGA       CTC       TCC       TAG       TTG       GGT       CTC       GAC       TTG       GTC       TTC
     Lys       Pro       Tyr       Met       Ala       Pro       Glu       Arg       Ile       Asn       Pro       Glu       Leu       Asn       Gln       Lys>

980       985       990       995      1000      1005      1010      1015      1020      1025
      *                   *                   *                   *                   *
     GGC       TAC       AAT       GTC       AAG       TCC       GAC       GTC       TGG       AGC       CTG       GGC       ATC       ACC       ATG       ATT
     CCG       ATG       TTA       CAG       TTC       AGG       CTG       CAG       ACC       TCG       GAC       CCG       TAG       TGG       TAC       TAA
     Gly       Tyr       Asn       Val       Lys       Ser       Asp       Val       Trp       Ser       Leu       Gly       Ile       Thr       Met       Ile>

1030      1035      1040      1045      1050      1055      1060      1065      1070      1075
                          *                   *                   *                   *
     GAG       ATG       GCC       ATC       CTG       CGG       TTC       CCT       TAC       GAG       TCC       TGG       GGG       ACC       CCG       TTC
     CTC       TAC       CGG       TAG       GAC       GCC       AAG       GGA       ATG       CTC       AGG       ACC       CCC       TGG       GGC       AAG
     Glu       Met       Ala       Ile       Leu       Arg       Phe       Pro       Tyr       Glu       Ser       Trp       Gly       Thr       Pro       Phe>

```
          *              *              *              *              *
     CAG CAG CTG AAG CAG GTG GTG GAG GAG CCG TCC CCC CAG CTC CCA GCC
     GTC GTC GAC TTC GTC CAC CAC CTC CTC GGC AGG GGG GTC GAG GGT CGG
     Gln Gln Leu Lys Gln Val Val Glu Glu Pro Ser Pro Gln Leu Pro Ala>

1125   1130   1135   1140   1145   1150   1155   1160   1165   1170
       *             *             *              *             *
     GAC CGT TTC TCC CCC GAG TTT GTG GAC TTC ACT GCT CAG TGC CTG AGG
     CTG GCA AAG AGG GGG CTC AAA CAC CTG AAG TGA CGA GTC ACG GAC TCC
     Asp Arg Phe Ser Pro Glu Phe Val Asp Phe Thr Ala Gln Cys Leu Arg>

1175   1180   1185   1190   1195   1200   1205   1210   1215
       *             *             *      *              *
     AAG AAC CCC GCA GAG CGT ATG AGC TAC CTG GAG CTG ATG GAG CAC CCC
     TTC TTG GGG CGT CTC GCA TAC TCG ATG GAC CTC GAC TAC CTC GTG GGG
     Lys Asn Pro Ala Glu Arg Met Ser Tyr Leu Glu Leu Met Glu His Pro>

1220  1225  1230   1235  1240   1245  1250  1255   1260  1265
  *             *             *             *             *
     TTC TTC ACC TTG CAC AAA ACC AAG AAG ACG GAC ATT GCT GCC TTC GTG
     AAG AAG TGG AAC GTG TTT TGG TTC TTC TGC CTG TAA CGA CGG AAG CAC
     Phe Phe Thr Leu His Lys Thr Lys Lys Thr Asp Ile Ala Ala Phe Val>

1270   1275   1280   1285   1290  1295 1300   1305 1310   1315 1320
       *             *             *             *             *
     AAG AAG ATC CTG GGA GAA GAC TCA TAGGGCTG GGCCTCGGAC CCCACTCCGG
     TTC TTC TAG GAC CCT CTT CTG AGT ATCCCCGAC CCGGAGCCTG GGGTGAGGCC
     Lys Lys Ile Leu Gly Glu Asp Ser>  (SEQ ID NO:2)

1325 1330   1335 1340   1345 1350   1355 1360   1365 1370   1375 1380
             *             *             *             *             *
     CCCTCCAGAG CCCCACAGCC CCATCTGCGG GGGCAGTGCT CACCCACACC ATAAGCTACT
     GGGAGGTCTC GGGGTGTCGG GGTAGACGCC CCCGTCACGA GTGGGTGTGG TATTCGATGA 1385 1390   1395 1400   1405 1410   1415 1420   1425 1430   1435 1440
             *             *             *             *             *
     GCCATCCTGG CCCAGGGCAT CTGGGAGGAA CCGAGGGGGC TGCTCCCACC TGGCTCTGTG
     CGGTAGGACC GGGTCCCGTA GACCCTCCTT GGCTCCCCCG ACGAGGGTGG ACCGAGACAC 1445 1450   1455 1460   1465 1470   1475 1480   1485 1490   1495 1500
             *             *             *             *             *
     GCGAGCCATT TGTCCCAAGT GCCAAAGAAG CAGACCATTG GGCTCCCAG CCAGGCCCTT
     CGCTCGGTAA ACAGGGTTCA CGGTTTCTTC GTCTGGTAAC CCCGAGGGTC GGTCCGGGAA 1505 1510   1515 1520   1525 1530   1535 1540   1545 1550   1555 1560
             *             *             *             *             *
     GTCGGCCCCA CCAGTGCCTC TCCCTGCTGC TCCTAGGACC CGTCTCCAGC TGCTGAGATC
     CAGCCGGGGT GGTCACGGAG AGGGACGACG AGGATCCTGG GCAGAGGTCG ACGACTCTAG 1565 1570   1575 1580   1585 1590   1595 1600   1605 1610   1615 1620
             *             *             *             *             *
     CTGGACTGAG GGGGCCTGGA TGCCCCCTGT GGATGCTGCT GCCCCTGCAC AGCAGGCTGC
     GACCTGACTC CCCCGGACCT ACGGGGGACA CCTACGACGA CGGGGACGTG TCGTCCGACG 1625 1630   1635 1640   1645 1650   1655 1660   1665 1670   1675 1680
             *             *             *             *             *
     CAGTGCCTGG GTGGATGGGC CACCGCCTTG CCCAGCCTGG ATGCCATCCA AGTTGTATAT
     GTCACGGACC CACCTACCCG GTGGCGGAAC GGGTCGGACC TACGGTAGGT TCAACATATA 1685 1690   1695 1700   1705 1710   1715 1720   1725 1730   1735 1740
             *             *             *             *             *
     TTTTTTAATC TCTCGACTGA ATGGACTTTG CACACTTTGG CCCAGGGTGG CCACACCTCT
```
FIG. 4C

```
AAAAAATTAG AGAGCTGACT TACCTGAAAC GTGTGAAACC GGGTCCCACC GGTGTGGAGA 1745 1750  1755 1760  1765 1770  1775 1780  1785 1790  1795 1800
     *          *          *          *          *          *
ATCCCGGCTT TGGTGCGGGG TACACAAGAG GGGATGAGTT GTGTGAATAC CCCAAGACTC
TAGGGCCGAA ACCACGCCCC ATGTGTTCTC CCCTACTCAA CACACTTATG GGGTTCTGAG 1805 1810  1815 1820  1825 1830  1835 1840  1845 1850  1855 1860
     *          *          *          *          *          *
CCATGAGGGA GATGCCATGA GCCGCCCAAG GCCTTCCCCT GGCACTGGCA AACAGGGCCT
GGTACTCCCT CTACGGTACT CGGCGGGTTC CGGAAGGGGA CCGTGACCGT TTGTCCCGGA 1865 1870  1875 1880  1885 1890  1895 1900  1905 1910  1915 1920
     *          *          *          *          *          *
CTGCGGAGCA CACTGGCTCA CCCAGTCCTG CCCGCCACCG TTATCGGTGT CATTCACCTT
GACGCCTCGT GTGACCGAGT GGGTCAGGAC GGGCGGTGGC AATAGCCACA GTAAGTGGAA 1925 1930  1935 1940  1945 1950  1955 1960  1965 1970  1975 1980
     *          *          *          *          *          *
TCGTGTTTTT TTTAATTTAT CCTCTGTTGA TTTTTTCTTT TGCTTTATGG GTTTGGCTTG
AGCACAAAAA AAATTAAATA GGAGACAACT AAAAAAGAAA ACGAAATACC CAAACCGAAC 1985 1990  1995 2000  2005 2010  2015 2020  2025 2030
     *          *          *          *          *
TTTTTCTTGC ATGGTTTGGA GCTGATCGCT TCTCCCCCAC CCCCTAGGGG   (SEQ ID NO: 1)
AAAAAGAACG TACCAAACCT CGACTAGCGA AGAGGGGGTG GGGGATCCCC
```

FIG. 4D

```
         5         10        15        20        25        30        35        40        45        50        55        60
         *                   *                   *                   *                   *                   *
TAGCTGCAGC ACAGCCTTCC CTAACGTTGC AACTGGGGGA AAAATCACTT TCCAGTCTGT
ATCGACGTCG TGTCGGAAGG GATTGCAACG TTGACCCCCT TTTTAGTGAA AGGTCAGACA 65        70        75        80        85        90        95       100       105       110       115       120
         *                   *                   *                   *                   *                   *
TTTGCAAGGT GTGCATTTCC ATCTTGATTC CCTGAAAGTC CATCTGCTGC ATCGGTCAAG
AAACGTTCCA CACGTAAAGG TAGAACTAAG GGACTTTCAG GTAGACGACG TAGCCAGTTC 125       130       135       140       145       150       155       160       165       170       175       180
         *                   *                   *                   *                   *                   *
AGAAACTCCA CTTGCATGAA GATTGCACGC CTGCAGCTTG CATCTTTGTT GCAAAACTAG
TCTTTGAGGT GAACGTACTT CTAACGTGCG GACGTCGAAC GTAGAAACAA CGTTTTGATC 185       190       195       200       205       210       215       220       225       230       235       240
         *                   *                   *                   *                   *                   *
CTACAGAAGA GAAGCAAGGC AAAGTCTTTT GTGCTCCCCT CCCCCATCAA AGGAAAGGGG
GATGTCTTCT CTTCGTTCCG TTTCAGAAAA CACGAGGGGA GGGGGTAGTT TCCTTTCCCC 245       250       255       260       265       270       275       280       285
         *                   *                   *                   *
AAA ATG TCT CAG TCG AAA GGC AAG AAG CGA AAC CCT GGC CTT AAA ATT
TTT TAC AGA GTC AGC TTT CCG TTC TTC GCT TTG GGA CCG GAA TTT TAA
    Met Ser Gln Ser Lys Gly Lys Lys Arg Asn Pro Gly Leu Lys Ile>

290       295       300       305       310       315       320       325       330       335
  *                   *                   *                   *                   *
CCA AAA GAA GCA TTT GAA CAA CCT CAG ACC AGT TCC ACA CCA CCT AGA
GGT TTT CTT CGT AAA CTT GTT GGA GTC TGG TCA AGG TGT GGT GGA TCT
Pro Lys Glu Ala Phe Glu Gln Pro Gln Thr Ser Ser Thr Pro Pro Arg>

340       345       350       355       360       365       370       375       380
  *                   *                   *                   *
GAT TTA GAC TCC AAG GCT TGC ATT TCT ATT GGA AAT CAG AAC TTT GAG
CTA AAT CTG AGG TTC CGA ACG TAA AGA TAA CCT TTA GTC TTG AAA CTC
Asp Leu Asp Ser Lys Ala Cys Ile Ser Ile Gly Asn Gln Asn Phe Glu>

385       390       395       400       405       410       415       420       425       430
  *                   *                   *                   *                   *
GTG AAG GCA GAT GAC CTG GAG CCT ATA ATG GAA CTG GGA CGA GGT GCG
CAC TTC CGT CTA CTG GAC CTC GGA TAT TAC CTT GAC CCT GCT CCA CGC
Val Lys Ala Asp Asp Leu Glu Pro Ile Met Glu Leu Gly Arg Gly Ala>

435       440       445       450       455       460       465       470       475       480
  *                   *                   *                   *                   *
TAC GGG GTG GTG GAG AAG ATG CGG CAC GTG CCC AGC GGG CAG ATC ATG
ATG CCC CAC CAC CTC TTC TAC GCC GTG CAC GGG TCG CCC GTC TAG TAC
Tyr Gly Val Val Glu Lys Met Arg His Val Pro Ser Gly Gln Ile Met>

485       490       495       500       505       510       515       520       525
  *                   *                   *                   *
GCA GTG AAG CGG ATC CGA GCC ACA GTA AAT AGC CAG GAA CAG AAA CGG
CGT CAC TTC GCC TAG GCT CGG TGT CAT TTA TCG GTC CTT GTC TTT GCC
Ala Val Lys Arg Ile Arg Ala Thr Val Asn Ser Gln Glu Gln Lys Arg>

530       535       540       545       550       555       560       565       570       575
  *                   *                   *                   *                   *
CTA CTG ATG GAT TTG GAT ATT TCC ATG AGG ACG GTG GAC TGT CCA TTC
GAT GAC TAC CTA AAC CTA TAA AGG TAC TCC TGC CAC CTG ACA GGT AAG
```

FIG. 5A

```
    Leu Leu Met Asp Leu Asp Ile Ser Met Arg Thr Val Asp Cys Pro Phe>
    580     585     590     595     600     605     610     615     620
     *               *               *               *               *
    ACT GTC ACC TTT TAT GGC GCA CTG TTT CGG GAG GGT GAT GTG TGG ATC
    TGA CAG TGG AAA ATA CCG CGT GAC AAA GCC CTC CCA CTA CAC ACC TAG
    Thr Val Thr Phe Tyr Gly Ala Leu Phe Arg Glu Gly Asp Val Trp Ile>
625     630     635     640     645     650     655     660     665     670
 *               *               *               *               *
TGC ATG GAG CTC ATG GAT ACA TCA CTA GAT AAA TTC TAC AAA CAA GTT
ACG TAC CTC GAG TAC CTA TGT AGT GAT CTA TTT AAG ATG TTT GTT CAA
Cys Met Glu Leu Met Asp Thr Ser Leu Asp Lys Phe Tyr Lys Gln Val>
    675     680     685     690     695     700     705     710     715     720
     *               *               *               *               *
    ATT GAT AAA GGC CAG ACA ATT CCA GAG GAC ATC TTA GGG AAA ATA GCA
    TAA CTA TTT CCG GTC TGT TAA GGT CTC CTG TAG AAT CCC TTT TAT CGT
    Ile Asp Lys Gly Gln Thr Ile Pro Glu Asp Ile Leu Gly Lys Ile Ala>
        725     730     735     740     745     750     755     760     765
         *               *               *               *
        GTT TCT ATT GTA AAA GCA TTA GAA CAT TTA CAT AGT AAG CTG TCT GTC
        CAA AGA TAA CAT TTT CGT AAT CTT GTA AAT GTA TCA TTC GAC AGA CAG
        Val Ser Ile Val Lys Ala Leu Glu His Leu His Ser Lys Leu Ser Val>
770     775     780     785     790     795     800     805     810     815
 *               *               *               *               *
ATT CAC AGA GAC GTC AAG CCT TCT AAT GTA CTC ATC AAT GCT CTC GGT
TAA GTG TCT CTG CAG TTC GGA AGA TTA CAT GAG TAG TTA CGA GAG CCA
Ile His Arg Asp Val Lys Pro Ser Asn Val Leu Ile Asn Ala Leu Gly>
    820     825     830     835     840     845     850     855     860
     *               *               *               *               *
    CAA GTG AAG ATG TGC GAT TTT GGA ATC AGT GGC TAC TTG GTG GAC TCT
    GTT CAC TTC TAC ACG CTA AAA CCT TAG TCA CCG ATG AAC CAC CTG AGA
    Gln Val Lys Met Cys Asp Phe Gly Ile Ser Gly Tyr Leu Val Asp Ser>
865     870     875     880     885     890     895     900     905     910
 *               *               *               *               *
GTT GCT AAA ACA ATT GAT GCA GGT TGC AAA CCA TAC ATG GCC CCT GAA
CAA CGA TTT TGT TAA CTA CGT CCA ACG TTT GGT ATG TAC CGG GGA CTT
Val Ala Lys Thr Ile Asp Ala Gly Cys Lys Pro Tyr Met Ala Pro Glu>
    915     920     925     930     935     940     945     950     955     960
     *               *               *               *               *
    AGA ATA AAC CCA GAG CTC AAC CAG AAG GGA TAC AGT GTG AAG TCT GAC
    TCT TAT TTG GGT CTC GAG TTG GTC TTC CCT ATG TCA CAC TTC AGA CTG
    Arg Ile Asn Pro Glu Leu Asn Gln Lys Gly Tyr Ser Val Lys Ser Asp>
        965     970     975     980     985     990     995    1000    1005
         *               *               *               *
        ATT TGG AGT CTG GGC ATC ACG ATG ATT GAG TTG GCC ATC CTT CGA TTT
        TAA ACC TCA GAC CCG TAG TGC TAC TAA CTC AAC CGG TAG GAA GCT AAA
        Ile Trp Ser Leu Gly Ile Thr Met Ile Glu Leu Ala Ile Leu Arg Phe>
1010    1015    1020    1025    1030    1035    1040    1045    1050    1055
 *               *               *               *               *
CCC TAT GAT TCA TGG GGA ACT CCA TTT CAG CAG CTC AAA CAG GTG GTA
GGG ATA CTA AGT ACC CCT TGA GGT AAA GTC GTC GAG TTT GTC CAC CAT
Pro Tyr Asp Ser Trp Gly Thr Pro Phe Gln Gln Leu Lys Gln Val Val>
```

FIG. 5B

```
       1060      1065      1070      1075      1080      1085      1090      1095      1100
         *                   *                   *                   *                   *
       GAG GAG CCA TCG CCA CAA CTC CCA GCA GAC AAG TTC TCT GCA GAG TTT
       CTC CTC GGT AGC GGT GTT GAG GGT CGT CTG TTC AAG AGA CGT CTC AAA
       Glu Glu Pro Ser Pro Gln Leu Pro Ala Asp Lys Phe Ser Ala Glu Phe>

1105      1110      1115      1120      1125      1130      1135      1140      1145      1150
    *                   *                   *                   *                   *
  GTT GAC TTT ACC TCA CAG TGC TTA AAG AAG AAT TCC AAA GAA CGG CCT
  CAA CTG AAA TGG AGT GTC ACG AAT TTC TTC TTA AGG TTT CTT GCC GGA
  Val Asp Phe Thr Ser Gln Cys Leu Lys Lys Asn Ser Lys Glu Arg Pro>

1155      1160      1165      1170      1175      1180      1185      1190      1195      1200
         *                   *                   *                   *                   *
       ACA TAC CCA GAG CTA ATG CAA CAT CCA TTT TTC ACC CTA CAT GAA TCC
       TGT ATG GGT CTC GAT TAC GTT GTA GGT AAA AAG TGG GAT GTA CTT AGG
       Thr Tyr Pro Glu Leu Met Gln His Pro Phe Phe Thr Leu His Glu Ser>

1205      1210      1215      1220      1225      1230      1235      1240      1245      1250
              *                   *                   *                   *                   *
            AAA GGA ACA GAT GTG GCA TCT TTT GTA AAA CTG ATT CTT GGA GAC TAAAA
            TTT CCT TGT CTA CAC CGT AGA AAA CAT TTT GAC TAA GAA CCT CTG ATTTT
            Lys Gly Thr Asp Val Ala Ser Phe Val Lys Leu Ile Leu Gly Asp> (SEQ ID NO:4)

1255 1260    1265 1270    1275 1280    1285 1290    1295 1300    1305 1310
              *              *              *              *              *
       AGCAGTGGAC  TTAATCGGTT  GACCCTACTG  TGGATTGGTG  GGTTTCGGGG  TGAAGCAAGT
       TCGTCACCTG  AATTAGCCAA  CTGGGATGAC  ACCTAACCAC  CCAAAGCCCC  ACTTCGTTCA 1315 1320    1325 1330    1335 1340    1345 1350    1355 1360    1365 1370
              *              *              *              *              *
       TCACTACAGC  ATCAATAGAA  AGTCATCTTT  GAGATAATTT  AACCCTGCCT  CTCAGAGGGT
       AGTGATGTCG  TAGTTATCTT  TCAGTAGAAA  CTCTATTAAA  TTGGGACGGA  GAGTCTCCCA 1375 1380    1385 1390    1395 1400    1405 1410    1415 1420    1425 1430
              *              *              *              *              *
       TTTCTCTCCC  AATTTTCTTT  TTACTCCCCC  TCTTAAGGGG  GCCTTGGAAT  CTATAGTATA
       AAAGAGAGGG  TTAAAAGAAA  AATGAGGGGG  AGAATTCCCC  CGGAACCTTA  GATATCATAT 1435 1440    1445 1450    1455 1460    1465 1470    1475 1480    1485 1490
              *              *              *              *              *
       GAATGAACTG  TCTAGATGGA  TGAATTATGA  TAAAGGCTTA  GGACTTCAAA  AGGTGATTAA
       CTTACTTGAC  AGATCTACCT  ACTTAATACT  ATTTCCGAAT  CCTGAAGTTT  TCCACTAATT 1495 1500    1505 1510    1515 1520    1525 1530    1535 1540    1545 1550
              *              *              *              *              *
       ATATTTAATG  ATGTGTCATA  TGAGTCCTCA  AAAAAAAAAA  AAAAAAAAAA  AAAAAAAAAA
       TATAAATTAC  TACACAGTAT  ACTCAGGAGT  TTTTTTTTTT  TTTTTTTTTT  TTTTTTTTTT 1555 1560    1565 1570    1575 1580    1585 1590    1595 1600
              *              *              *              *
       AAAAAAAAAA  AAAAAAAAAA  AAAAAAAAAA  AAAAAAAAAA  AAAAAAAAAA  AA  (SEQ ID NO:3)
       TTTTTTTTTT  TTTTTTTTTT  TTTTTTTTTT  TTTTTTTTTT  TTTTTTTTTT  TT
```

FIG. 5C

```
      5         10        15        20        25        30        35        40        45        50        55
      *                             *                             *                             *
CTAGGGTCCC CGGCGCCAGG CCACCCGGCC GTCAGCAGC ATG CAG GGT AAA CGC AAA
GATCCCAGGG GCCGCGGTCC GGTGGGCCGG CAGTCGTCG TAC GTC CCA TTT GCG TTT
                                           Met Gln Gly Lys Arg Lys>

60        65        70        75        80        85        90        95       100       105
      *                             *                             *                             *
GCA CTG AAG TTG AAT TTT GCA AAT CCA CCT TTC AAA TCT ACA GCA AGG
CGT GAC TTC AAC TTA AAA CGT TTA GGT GGA AAG TTT AGA TGT CGT TCC
Ala Leu Lys Leu Asn Phe Ala Asn Pro Pro Phe Lys Ser Thr Ala Arg>

110       115       120       125       130       135       140       145       150
      *                   *                   *                   *                   *
TTT ACT CTG AAT CCC AAT CCT ACA GGA GTT CAA AAC CCA CAC ATA GAG
AAA TGA GAC TTA GGG TTA GGA TGT CCT CAA GTT TTG GGT GTG TAT CTC
Phe Thr Leu Asn Pro Asn Pro Thr Gly Val Gln Asn Pro His Ile Glu>

155       160       165       170       175       180       185       190       195       200
      *                   *                   *                   *                             *
AGA CTG AGA ACA CAC AGC ATT GAG TCA TCA GGA AAA CTG AAG ATC TCC
TCT GAC TCT TGT GTG TCG TAA CTC AGT AGT CCT TTT GAC TTC TAG AGG
Arg Leu Arg Thr His Ser Ile Glu Ser Ser Gly Lys Leu Lys Ile Ser>

205       210       215       220       225       230       235       240       245
      *                   *                   *                   *
CCT GAA CAA CAC TGG GAT TTC ACT GCA GAG GAC TTG AAA GAC CTT GGA
GGA CTT GTT GTG ACC CTA AAG TGA CGT CTC CTG AAC TTT CTG GAA CCT
Pro Glu Gln His Trp Asp Phe Thr Ala Glu Asp Leu Lys Asp Leu Gly>

250       255       260       265       270       275       280       285       290       295
 *                   *                   *                   *                   *
GAA ATT GGA CGA GGA GCT TAT GGT TCT GTC AAC AAA ATG GTC CAC AAA
CTT TAA CCT GCT CCT CGA ATA CCA AGA CAG TTG TTT TAC CAG GTG TTT
Glu Ile Gly Arg Gly Ala Tyr Gly Ser Val Asn Lys Met Val His Lys>

300       305       310       315       320       325       330       335       340       345
      *                   *                   *                   *                   *
CCA AGT GGG CAA ATA ATG GCA GTT AAA AGA ATT CGG TCA ACA GTG GAT
GGT TCA CCC GTT TAT TAC CGT CAA TTT TCT TAA GCC AGT TGT CAC CTA
Pro Ser Gly Gln Ile Met Ala Val Lys Arg Ile Arg Ser Thr Val Asp>

350       355       360       365       370       375       380       385       390
      *                   *                   *                   *                   *
GAA AAA GAA CAA AAA CAA CTT CTT ATG GAT TTG GAT GTA GTA ATG CGG
CTT TTT CTT GTT TTT GTT GAA GAA TAC CTA AAC CTA CAT CAT TAC GCC
Glu Lys Glu Gln Lys Gln Leu Leu Met Asp Leu Asp Val Val Met Arg>

395       400       405       410       415       420       425       430       435       440
 *                   *                   *                   *                   *
AGT AGT GAT TGC CCA TAC ATT GTT CAG TTT TAT GGT GCA CTC TTC AGA
TCA TCA CTA ACG GGT ATG TAA CAA GTC AAA ATA CCA CGT GAG AAG TCT
Ser Ser Asp Cys Pro Tyr Ile Val Gln Phe Tyr Gly Ala Leu Phe Arg>

445       450       455       460       465       470       475       480       485
      *                   *                   *                   *
GAG GGT GAC TGT TGG ATC TGT ATG GAA CTC ATG TCT ACC TCG TTT GAT
CTC CCA CTG ACA ACC TAG ACA TAC CTT GAG TAC AGA TGG AGC AAA CTA
Glu Gly Asp Cys Trp Ile Cys Met Glu Leu Met Ser Thr Ser Phe Asp>
```

FIG. 6A

```
      490       495       500       505       510       515       520       525       530       535
       *                   *                   *                   *                   *
     AAG TTT TAC AAA TAT GTA TAT AGT GTA TTA GAT GAT GTT ATT CCA GAA
     TTC AAA ATG TTT ATA CAT ATA TCA CAT AAT CTA CTA CAA TAA GGT CTT
     Lys Phe Tyr Lys Tyr Val Tyr Ser Val Leu Asp Asp Val Ile Pro Glu>

540       545       550       555       560       565       570       575       580       585
       *                   *                   *                   *                   *
     GAA ATT TTA GGC AAA ATC ACT TTA GCA ACT GTG AAA GCA CTA AAC CAC
     CTT TAA AAT CCG TTT TAG TGA AAT CGT TGA CAC TTT CGT GAT TTG GTG
     Glu Ile Leu Gly Lys Ile Thr Leu Ala Thr Val Lys Ala Leu Asn His>

590       595       600       605       610       615       620       625       630
            *                   *                   *                   *                   *
     TTA AAA GAA AAC TTG AAA ATT ATT CAC AGA GAT ATC AAA CCT TCC AAT
     AAT TTT CTT TTG AAC TTT TAA TAA GTG TCT CTA TAG TTT GGA AGG TTA
     Leu Lys Glu Asn Leu Lys Ile Ile His Arg Asp Ile Lys Pro Ser Asn>

635       640       645       650       655       660       665       670       675       680
                 *                   *                   *                   *                   *
     ATT CTT CTG GAC AGA AGT GGA AAT ATT AAG CTC TGT GAC TTC GGC ATC
     TAA GAA GAC CTG TCT TCA CCT TTA TAA TTC GAG ACA CTG AAG CCG TAG
     Ile Leu Leu Asp Arg Ser Gly Asn Ile Lys Leu Cys Asp Phe Gly Ile>

685       690       695       700       705       710       715       720       725
       *                   *                   *                   *                   *
     AGT GGA CAG CTT GTG GAC TCT ATT GCC AAG ACA AGA GAT GCT GGC TGT
     TCA CCT GTC GAA CAC CTG AGA TAA CGG TTC TGT TCT CTA CGA CCG ACA
     Ser Gly Gln Leu Val Asp Ser Ile Ala Lys Thr Arg Asp Ala Gly Cys>

730       735       740       745       750       755       760       765       770       775
       *                   *                   *                   *                   *
     AGG CCA TAC ATG GCA CCT GAA AGA ATA GAC CCA AGC GCA TCA CGA CAA
     TCC GGT ATG TAC CGT GGA CTT TCT TAT CTG GGT TCG CGT AGT GCT GTT
     Arg Pro Tyr Met Ala Pro Glu Arg Ile Asp Pro Ser Ala Ser Arg Gln>

780       785       790       795       800       805       810       815       820       825
       *                   *                   *                   *                   *
     GGA TAT GAT GTC CGC TCT GAT GTC TGG AGT TTG GGG ATC ACA TTG TAT
     CCT ATA CTA CAG GCG AGA CTA CAG ACC TCA AAC CCC TAG TGT AAC ATA
     Gly Tyr Asp Val Arg Ser Asp Val Trp Ser Leu Gly Ile Thr Leu Tyr>

830       835       840       845       850       855       860       865       870
            *                   *                   *                   *                   *
     GAG TTG GCC ACA GGC CGA TTT CCT TAT CCA AAG TGG AAT AGT GTA TTT
     CTC AAC CGG TGT CCG GCT AAA GGA ATA GGT TTC ACC TTA TCA CAT AAA
     Glu Leu Ala Thr Gly Arg Phe Pro Tyr Pro Lys Trp Asn Ser Val Phe>

875       880       885       890       895       900       905       910       915       920
                 *                   *                   *                   *                   *
     GAT CAA CTA ACA CAA GTC GTG AAA GGA GAT CCT CCG CAG CTG AGT AAT
     CTA GTT GAT TGT GTT CAG CAC TTT CCT CTA GGA GGC GTC GAC TCA TTA
     Asp Gln Leu Thr Gln Val Val Lys Gly Asp Pro Pro Gln Leu Ser Asn>

925       930       935       940       945       950       955       960       965
       *                   *                   *                   *                   *
     TCT GAG GAA AGG GAA TTC TCC CCG AGT TTC ATC AAC TTT GTC AAC TTG
     AGA CTC CTT TCC CTT AAG AGG GGC TCA AAG TAG TTG AAA CAG TTG AAC
     Ser Glu Glu Arg Glu Phe Ser Pro Ser Phe Ile Asn Phe Val Asn Leu>

```
TGC CTT ACG AAG GAT GAA TCC AAA AGG CCA AAG TAT AAA GAG CTT CTG
ACG GAA TGC TTC CTA CTT AGG TTT TCC GGT TTC ATA TTT CTC GAA GAC
Cys Leu Thr Lys Asp Glu Ser Lys Arg Pro Lys Tyr Lys Glu Leu Leu>

1020   1025   1030   1035   1040   1045 1050   1055   1060   1065
  *             *             *              *             *
AAA CAT CCC TTT ATT TTG ATG TAT GAA GAA CGT GCC GTT GAG GTC GCA
TTT GTA GGG AAA TAA AAC TAC ATA CTT CTT GCA CGG CAA CTC CAG CGT
Lys His Pro Phe Ile Leu Met Tyr Glu Glu Arg Ala Val Glu Val Ala>

1070   1075 1080   1085   1090 1095   1100   1105   1110
    *             *             *              *             *
TGC TAT GTT TGT AAA ATC CTG GAT CAA ATG CCA GCT ACT CCC AGC TCT
ACG ATA CAA ACA TTT TAG GAC CTA GTT TAC GGT CGA TGA GGG TCG AGA
Cys Tyr Val Cys Lys Ile Leu Asp Gln Met Pro Ala Thr Pro Ser Ser>

1115   1120  1125   1130   1135 1140   1145 1150   1155 1160   1165 1170
  *             *             *              *             *              *
CCC ATG TAT GTC GAT TG ATATCGYTGC TACATCAGAC TCTAGAAAAA AGGGCTGAGA
GGG TAC ATA CAG CTA AC TATAGCRACG ATGTAGTCTG AGATCTTTTT TCCCGACTCT
Pro Met Tyr Val Asp>  (SEQ ID NO:6)

1175 1180   1185 1190   1195 1200   1205 1210   1215 1220   1225 1230
    *             *              *             *             *              *
GGAAGCAAGA CGTAAAGAAT TTTCATCCCG TATCACAGTG TTTTTATTGC TCGCCCAGAC
CCTTCGTTCT GCATTTCTTA AAAGTAGGGC ATAGTGTCAC AAAAATAACG AGCGGGTCTG 1235 1240   1245 1250   1255 1260   1265 1270   1275 1280   1285 1290
    *             *             *              *             *              *
ACCATGTGCA ATAAGATTGG TGTTCGTTTC CATCATGTCT GTATACTCCT GTCACCTAGA
TGGTACACGT TATTCTAACC ACAAGCAAAG GTAGTACAGA CATATGAGGA CAGTGGATCT 1295 1300   1305 1310   1315 1320   1325 1330   1335 1340   1345 1350
    *             *             *              *             *              *
ACGTGCATCC TTGTAATACC TGATTGATCA CACAGTGTTA GTGCTGGTCA GAGAGACCTC
TGCACGTAGG AACATTATGG ACTAACTAGT GTGTCACAAT CACGACCAGT CTCTCTGGAG 1355 1360   1365 1370   1375 1380   1385 1390   1395 1400   1405 1410
    *             *             *              *             *              *
ATCCTGCTCT TTTGTGATGA ACATATTCAT GAAATGTGGA AGTCAGTACG ATCAAGTTGT
TAGGACGAGA AAACACTACT TGTATAAGTA CTTTACACCT TCAGTCATGC TAGTTCAACA 1415 1420   1425 1430   1435 1440   1445 1450   1455 1460   1465 1470
    *             *             *              *             *              *
TGACTGTGAT TAGATCACAT CTTAAATTCA TTTCTAGACT CAAAACCTGG AGATGCAGCT
ACTGACACTA ATCTAGTGTA GAATTTAAGT AAAGATCTGA GTTTTGGACC TCTACGTCGA 1475 1480   1485 1490   1495 1500   1505 1510   1515 1520   1525 1530
    *             *             *              *             *              *
ACTGGAATGG TGTTTTGTCA GACTTCCAAA TCCTGGAAGG ACACAGTGAT GAATGTACTA
TGACCTTACC ACAAAACAGT CTGAAGGTTT AGGACCTTCC TGTGTCACTA CTTACATGAT 1535 1540   1545 1550   1555 1560   1565 1570   1575 1580   1585 1590
    *             *             *              *             *              *
TATCTGAACA TAGAAACTCG GGCTTGAGTG AGAAGAGCTT GCACAGCCAA CGAGACACAT
ATAGACTTGT ATCTTTGAGC CCGAACTCAC TCTTCTCGAA CGTGTCGGTT GCTCTGTGTA 1595 1600   1605 1610   1615 1620   1625 1630   1635 1640   1645 1650
    *             *             *              *             *              *
TGCCTTCTGG AGCTGGGAGA CAAAGGAGGA ATTTACTTTC TTCACCAAGT GCAATAGATT
ACGGAAGACC TCGACCCTCT GTTTCCTCCT TAAATGAAAG AAGTGGTTCA CGTTATCTAA
```

FIG. 6C

```
1655 1660  1665 1670  1675 1680  1685 1690  1695 1700  1705 1710
    *          *          *          *          *          *
ACTGATGTGA TATTCTGTTG CTTTACAGTT ACAGTTGATG TTTGGGGATC GATGTGCTCA
TGACTACACT ATAAGACAAC GAAATGTCAA TGTCAACTAC AAACCCCTAG CTACACGAGT 1715 1720  1725 1730  1735 1740  1745 1750  1755 1760  1765 1770
    *          *          *          *          *          *
GCCAAATTTC CTGTTTGAAA TATCATGTTA AATTAGAATG AATTTATCTT TACCAAAAAC
CGGTTTAAAG GACAAACTTT ATAGTACAAT TTAATCTTAC TTAAATAGAA ATGGTTTTTG 1775 1780  1785 1790  1795 1800  1805 1810  1815 1820  1825 1830
    *          *          *          *          *          *
CATGTTGCGT TCAAAGAGGT GAACATTAAA ATATAGAGAC AGGACAGAAT GTGTTCTTTT
GTACAACGCA AGTTTCTCCA CTTGTAATTT TATATCTCTG TCCTGTCTTA CACAAGAAAA 1835 1840  1845 1850  1855 1860  1865 1870  1875 1880  1885 1890
    *          *          *          *          *          *
CTCCTCTACC AGTCCTATTT TTCAATGGGA AGACTCAGGA GTCTGCCACT TGTCAAAGAA
GAGGAGATGG TCAGGATAAA AAGTTACCCT TCTGAGTCCT CAGACGGTGA ACAGTTTCTT 1895 1900  1905 1910  1915 1920  1925 1930  1935 1940  1945 1950
    *          *          *          *          *          *
GGTGCTGATC CTAAGAATTT TTCATTCTCA GAATTCGGTG TGCTGCCAAC TTGATGTTCC
CCACGACTAG GATTCTTAAA AAGTAAGAGT CTTAAGCCAC ACGACGGTTG AACTACAAGG 1955 1960  1965 1970  1975 1980  1985 1990  1995 2000  2005 2010
    *          *          *          *          *          *
ACCTGCCACA AACCACCAGG ACTGAAAGAA GAAAACAGTA CAGAAGGCAA AGTTTACAGA
TGGACGGTGT TTGGTGGTCC TGACTTTCTT CTTTTGTCAT GTCTTCCGTT TCAAATGTCT 2015 2020  2025 2030  2035 2040  2045 2050  2055 2060  2065 2070
    *          *          *          *          *          *
TGTTTTTAAT TCTAGTATTT TATCTGGAAC AACTTGTAGC AGCTATATAT TTCCCCTTGG
ACAAAAATTA AGATCATAAA ATAGACCTTG TTGAACATCG TCGATATATA AAGGGGAACC 2075 2080  2085 2090  2095 2100  2105 2110  2115 2120  2125 2130
    *          *          *          *          *          *
TCCCAAGCCT GATACTTTAG CCATCATAAC TCACTAACAG GGAGAAGTAG CTAGTAGCAA
AGGGTTCGGA CTATGAAATC GGTAGTATTG AGTGATTGTC CCTCTTCATC GATCATCGTT 2135 2140  2145 2150  2155 2160  2165 2170  2175 2180  2185 2190
    *          *          *          *          *          *
TGTGCCTTGA TTGATTAGAT AAAGATTTCT AGTAGGCAGC AAAAGACCAA ATCTCAGTTG
ACACGGAACT AACTAATCTA TTTCTAAAGA TCATCCGTCG TTTTCTGGTT TAGAGTCAAC 2195 2200  2205 2210  2215 2220  2225 2230  2235 2240  2245 2250
    *          *          *          *          *          *
TTTGCTTCTT GCCATCACTG GTCCAGGTCT TCAGTTTCCG AATCTCTTTC CCTTCCCCTG
AAACGAAGAA CGGTAGTGAC CAGGTCCAGA AGTCAAAGGC TTAGAGAAAG GGAAGGGGAC 2255 2260  2265 2270  2275 2280  2285 2290  2295 2300  2305 2310
    *          *          *          *          *          *
TGGTCTATTG TCGCTATGTG ACTTGCGCTT AATCCAATAT TTTGCCTTTT TTCTATATCA
ACCAGATAAC AGCGATACAC TGAACGCGAA TTAGGTTATA AAACGGAAAA AAGATATAGT 2315 2320  2325 2330  2335 2340  2345 2350  2355 2360  2365 2370
    *          *          *          *          *          *
AAAAACCTTT ACAGTTAGCA GGGATGTTCC TTACCGAGGA TTTTTAACCC CCAATCTCTC
TTTTTGGAAA TGTCAATCGT CCCTACAAGG AATGGCTCCT AAAAATTGGG GGTTAGAGAG 2375 2380  2385 2390  2395 2400  2405 2410  2415 2420  2425 2430
    *          *          *          *          *          *
```

FIG. 6D

```
ATAATCGCTA GTGTTTAAAA GGCTAAGAAT AGTGGGGCCC AACCGATGTG GTAGGTGATA
TATTAGCGAT CACAAATTTT CCGATTCTTA TCACCCCGGG TTGGCTACAC CATCCACTAT 2435 2440  2445 2450  2455 2460  2465 2470  2475 2480  2485 2490
            *          *          *          *          *          *
AAGAGGCATC TTTTCTAGAG ACACATTGGA CCAGATGAGG ATCCGAAACG GCAGCCTTTA
TTCTCCGTAG AAAAGATCTC TGTGTAACCT GGTCTACTCC TAGGCTTTGC CGTCGGAAAT 2495 2500  2505 2510  2515 2520  2525 2530  2535 2540  2545 2550
            *          *          *          *          *          *
CGTTCATCAC CTGCTAGAAC CTCTCGTAGT CCATCACCAT TTCTTGGCAT TGGAATTCTA
GCAAGTAGTG GACGATCTTG GAGAGCATCA GGTAGTGGTA AAGAACCGTA ACCTTAAGAT 2555 2560  2565 2570  2575 2580  2585 2590  2595 2600  2605 2610
            *          *          *          *          *          *
CTGGAAAAAA ATACAAAAAG CAAAACAAAA CCCTCAGCAC TGTTACAAGA GGCCATTTAA
GACCTTTTTT TATGTTTTTC GTTTTGTTTT GGGAGTCGTG ACAATGTTCT CCGGTAAATT 2615 2620  2625 2630  2635 2640  2645 2650  2655 2660  2665 2670
            *          *          *          *          *          *
GTATCTTGTG CTTCTTCACT TACCCATTAG CCAGGTTCTC ATTAGGTTTT GCTTGGGCCT
CATAGAACAC GAAGAAGTGA ATGGGTAATC GGTCCAAGAG TAATCCAAAA CGAACCCGGA 2675 2680  2685 2690  2695 2700  2705 2710  2715 2720  2725 2730
            *          *          *          *          *          *
CCCTGGCACT GAACCTTAGG CTTTGTATGA CAGTGAAGCA GCACTGTGAG TGGTTCAAGC
GGGACCGTGA CTTGGAATCC GAAACATACT GTCACTTCGT CGTGACACTC ACCAAGTTCG 2735 2740  2745 2750  2755 2760  2765 2770  2775 2780  2785 2790
            *          *          *          *          *          *
ACACTGGAAT ATAAAACAGT CATGGCCTGA GATGCAGGTG ATGCCATTAC AGAACCAAAT
TGTGACCTTA TATTTTGTCA GTACCGGACT CTACGTCCAC TACGGTAATG TCTTGGTTTA 2795 2800  2805 2810  2815 2820  2825 2830  2835 2840  2845 2850
            *          *          *          *          *          *
CGTGGCACGT ATTGCTGTGT CTCCTCTCAG AGTGACAGTC ATAAATACTG TCAAACAATA
GCACCGTGCA TAACGACACA GAGGAGAGTC TCACTGTCAG TATTTATGAC AGTTTGTTAT 2855 2860  2865 2870  2875 2880  2885 2890  2895 2900  2905 2910
            *          *          *          *          *          *
AAGGGAGAAT GGTGCTGTTT AAAGTCACAT CCCTGTAAAT TGCAGAATTC AAAAGTGATT
TTCCCTCTTA CCACGACAAA TTTCAGTGTA GGGACATTTA ACGTCTTAAG TTTTCACTAA 2915 2920  2925 2930  2935 2940  2945 2950  2955 2960  2965 2970
            *          *          *          *          *          *
ATCTCTTTGA TCTACTTGCC TCATTTCCCT ATCTTCTCCC CCACGGTATC CTAAACTTTA
TAGAGAAACT AGATGAACGG AGTAAAGGGA TAGAAGAGGG GGTGCCATAG GATTTGAAAT 2975 2980  2985 2990  2995 3000  3005 3010  3015 3020  3025 3030
            *          *          *          *          *          *
GACTTCCCAC TGTTCTGAAA GGAGACATTG CTCTATGTCT GCCTTCGACC ACAGCAAGCC
CTGAAGGGTG ACAAGACTTT CCTCTGTAAC GAGATACAGA CGGAAGCTGG TGTCGTTCGG 3035 3040  3045 3050  3055 3060  3065 3070  3075 3080  3085 3090
            *          *          *          *          *          *
ATCATCCTCC ATTGCTCCCG GGGACTCAAG AGGAATCTGT TTCTCTGCTG TCAACTTCCC
TAGTAGGAGG TAACGAGGGC CCCTGAGTTC TCCTTAGACA AAGAGACGAC AGTTGAAGGG 3095 3100  3105 3110  3115 3120  3125 3130  3135 3140  3145 3150
            *          *          *          *          *          *
ATCTGGCTCA GCATAGGGTC ACTTTGCCAT TATGCAAATG GAGATAAAAG CAATTCTGGC
TAGACCGAGT CGTATCCCAG TGAAACGGTA ATACGTTTAC CTCTATTTTC GTTAAGACCG
```

FIG. 6E

```
      3155 3160   3165 3170   3175 3180   3185 3190   3195 3200   3205 3210
           *           *           *           *           *           *
      TGTCCAGGAG  CTAATCTGAC  CGTTCTATTG  TGTGGATGAC  CACATAAGAA  GGCAATTTTA
      ACAGGTCCTC  GATTAGACTG  GCAAGATAAC  ACACCTACTG  GTGTATTCTT  CCGTTAAAAT 3215 3220   3225 3230   3235 3240   3245 3250   3255 3260   3265 3270
           *           *           *           *           *           *
      GTGTATTAAT  CATAGATTAT  TATAAACTAT  AAACTTAAGG  GCAAGGAGTT  TATTACAATG
      CACATAATTA  GTATCTAATA  ATATTTGATA  TTTGAATTCC  CGTTCCTCAA  ATAATGTTAC 3275 3280   3285 3290   3295 3300   3305 3310   3315 3320   3325 3330
           *           *           *           *           *           *
      TATCTTTATT  AAAACAAAAG  GGTGTATAGT  GTTCACAAAC  TGTGAAAATA  GTGTAAGAAC
      ATAGAAATAA  TTTTGTTTTC  CCACATATCA  CAAGTGTTTG  ACACTTTTAT  CACATTCTTG 3335 3340   3345 3350   3355 3360   3365 3370   3375 3380   3385 3390
           *           *           *           *           *           *
      TGTACATTGT  GAGCTCTGGT  TATTTTTCTC  TTGTACCATA  GAAAAATGTA  TAAAAATTAT
      ACATGTAACA  CTCGAGACCA  ATAAAAGAG   AACATGGTAT  CTTTTTACAT  ATTTTTAATA 3395 3400   3405 3410   3415 3420   3425 3430   3435 3440   3445 3450
           *           *           *           *           *           *
      CAAAAAGCTA  ATGTGCAGGG  ATATTGCCTT  ATTTGTCTGT  AAAAAATGGA  GCTCAGTAAC
      GTTTTTCGAT  TACACGTCCC  TATAACGGAA  TAAACAGACA  TTTTTTACCT  CGAGTCATTG 3455 3460   3465 3470   3475 3480   3485 3490   3495
           *           *           *           *
      ATAACTGCTT  CTTGGAGCTT  TGGAATATTT  TATCCTGTAT  TCTTGTTT    (SEQ ID NO:5)
      TATTGACGAA  GAACCTCGAA  ACCTTATAAA  ATAGGACATA  AGAACAAA
```

FIG. 6F

```
              5         10        15        20        25        30        35        40        45        50
                        *                   *                   *                   *                   *
          CAACA ATG GCG GCT CCG AGC CCG AGC GGT GGC GGC GGC AGC GGC ACC CCC
          GTTGT TAC CGC CGA GGC TCG GGC TCG CCA CCG CCG CCG TCG CCG TGG GGG
                Met Ala Ala Pro Ser Pro Ser Gly Gly Gly Gly Ser Gly Thr Pro>

55        60        65        70        75        80        85        90        95
                        *                   *                   *                   *
          GGC CCC GTA GGG TCC CCG GCG CCA GGC CAC CCG GCC GTC AGC AGC ATG
          CCG GGG CAT CCC AGG GGC CGC GGT CCG GTG GGC CGG CAG TCG TCG TAC
          Gly Pro Val Gly Ser Pro Ala Pro Gly His Pro Ala Val Ser Ser Met>

100       105       110       115       120       125       130       135       140       145
                    *                   *                   *                   *                   *
          CAG GGT AAA CGC AAA GCA CTG AAG TTG AAT TTT GCA AAT CCA CCT TTC
          GTC CCA TTT GCG TTT CGT GAC TTC AAC TTA AAA CGT TTA GGT GGA AAG
          Gln Gly Lys Arg Lys Ala Leu Lys Leu Asn Phe Ala Asn Pro Pro Phe>

150       155       160       165       170       175       180       185       190
                         *                   *                   *                   *                   *
          AAA TCT ACA GCA AGG TTT ACT CTG AAT CCC AAT CCT ACA GGA GTT CAA
          TTT AGA TGT CGT TCC AAA TGA GAC TTA GGG TTA GGA TGT CCT CAA GTT
          Lys Ser Thr Ala Arg Phe Thr Leu Asn Pro Asn Pro Thr Gly Val Gln>

195       200       205       210       215       220       225       230       235       240
                    *                   *                   *                   *                   *
          AAC CCA CAC ATA GAG AGA CTG AGA ACA CAC AGC ATT GAG TCA TCA GGA
          TTG GGT GTG TAT CTC TCT GAC TCT TGT GTG TCG TAA CTC AGT AGT CCT
          Asn Pro His Ile Glu Arg Leu Arg Thr His Ser Ile Glu Ser Ser Gly>

245       250       255       260       265       270       275       280       285       290
                         *                   *                   *                   *                   *
          AAA CTG AAG ATC TCC CCT GAA CAA CAC TGG GAT TTC ACT GCA GAG GAC
          TTT GAC TTC TAG AGG GGA CTT GTT GTG ACC CTA AAG TGA CGT CTC CTG
          Lys Leu Lys Ile Ser Pro Glu Gln His Trp Asp Phe Thr Ala Glu Asp>

295       300       305       310       315       320       325       330       335
                              *                   *                   *                   *
          TTG AAA GAC CTT GGA GAA ATT GGA CGA GGA GCT TAT GGT TCT GTC AAC
          AAC TTT CTG GAA CCT CTT TAA CCT GCT CCT CGA ATA CCA AGA CAG TTG
          Leu Lys Asp Leu Gly Glu Ile Gly Arg Gly Ala Tyr Gly Ser Val Asn>

340       345       350       355       360       365       370       375       380       385
                    *                   *                   *                   *                   *
          AAA ATG GTC CAC AAA CCA AGT GGG CAA ATA ATG GCA GTT AAA AGA ATT
          TTT TAC CAG GTG TTT GGT TCA CCC GTT TAT TAC CGT CAA TTT TCT TAA
          Lys Met Val His Lys Pro Ser Gly Gln Ile Met Ala Val Lys Arg Ile>

390       395       400       405       410       415       420       425       430
                         *                   *                   *                   *                   *
          CGG TCA ACA GTG GAT GAA AAA GAA CAA AAA CAA CTT CTT ATG GAT TTG
          GCC AGT TGT CAC CTA CTT TTT CTT GTT TTT GTT GAA GAA TAC CTA AAC
          Arg Ser Thr Val Asp Glu Lys Glu Gln Lys Gln Leu Leu Met Asp Leu>

435       440       445       450       455       460       465       470       475       480
                    *                   *                   *                   *                   *
          GAT GTA GTA ATG CGG AGT AGT GAT TGC CCA TAC ATT GTT CAG TTT TAT
          CTA CAT CAT TAC GCC TCA TCA CTA ACG GGT ATG TAA CAA GTC AAA ATA
          Asp Val Val Met Arg Ser Ser Asp Cys Pro Tyr Ile Val Gln Phe Tyr>
```

FIG. 7A

```
     485       490       495       500       505       510       515       520       525       530
      *                   *                   *                   *                   *
     GGT GCA CTC TTC AGA GAG GGT GAC TGT TGG ATC TGT ATG GAA CTC ATG
     CCA CGT GAG AAG TCT CTC CCA CTG ACA ACC TAG ACA TAC CTT GAG TAC
     Gly Ala Leu Phe Arg Glu Gly Asp Cys Trp Ile Cys Met Glu Leu Met>

535       540       545       550       555       560       565       570       575
          *                   *                   *                   *
         TCT ACC TCG TTT GAT AAG TTT TAC AAA TAT GTA TAT AGT GTA TTA GAT
         AGA TGG AGC AAA CTA TTC AAA ATG TTT ATA CAT ATA TCA CAT AAT CTA
         Ser Thr Ser Phe Asp Lys Phe Tyr Lys Tyr Val Tyr Ser Val Leu Asp>

580       585       590       595       600       605       610       615       620       625
      *                   *                   *                   *                   *
     GAT GTT ATT CCA GAA GAA ATT TTA GGC AAA ATC ACT TTA GCA ACT GTG
     CTA CAA TAA GGT CTT CTT TAA AAT CCG TTT TAG TGA AAT CGT TGA CAC
     Asp Val Ile Pro Glu Glu Ile Leu Gly Lys Ile Thr Leu Ala Thr Val>

630       635       640       645       650       655       660       665       670
          *                   *                   *                   *                   *
         AAA GCA CTA AAC CAC TTA AAA GAA AAC TTG AAA ATT ATT CAC AGA GAT
         TTT CGT GAT TTG GTG AAT TTT CTT TTG AAC TTT TAA TAA GTG TCT CTA
         Lys Ala Leu Asn His Leu Lys Glu Asn Leu Lys Ile Ile His Arg Asp>

675       680       685       690       695       700       705       710       715       720
      *                   *                   *                   *                   *
     ATC AAA CCT TCC AAT ATT CTT CTG GAC AGA AGT GGA AAT ATT AAG CTC
     TAG TTT GGA AGG TTA TAA GAA GAC CTG TCT TCA CCT TTA TAA TTC GAG
     Ile Lys Pro Ser Asn Ile Leu Leu Asp Arg Ser Gly Asn Ile Lys Leu>

725       730       735       740       745       750       755       760       765       770
          *                   *                   *                   *                   *
         TGT GAC TTC GGC ATC AGT GGA CAG CTT GTG GAC TCT ATT GCC AAG ACA
         ACA CTG AAG CCG TAG TCA CCT GTC GAA CAC CTG AGA TAA CGG TTC TGT
         Cys Asp Phe Gly Ile Ser Gly Gln Leu Val Asp Ser Ile Ala Lys Thr>

775       780       785       790       795       800       805       810       815
              *                   *                   *                   *
             AGA GAT GCT GGC TGT AGG CCA TAC ATG GCA CCT GAA AGA ATA GAC CCA
             TCT CTA CGA CCG ACA TCC GGT ATG TAC CGT GGA CTT TCT TAT CTG GGT
             Arg Asp Ala Gly Cys Arg Pro Tyr Met Ala Pro Glu Arg Ile Asp Pro>

820       825       830       835       840       845       850       855       860       865
      *                   *                   *                   *                   *
     AGC GCA TCA CGA CAA GGA TAT GAT GTC CGC TCT GAT GTC TGG AGT TTG
     TCG CGT AGT GCT GTT CCT ATA CTA CAG GCG AGA CTA CAG ACC TCA AAC
     Ser Ala Ser Arg Gln Gly Tyr Asp Val Arg Ser Asp Val Trp Ser Leu>

870       875       880       885       890       895       900       905       910
          *                   *                   *                   *
         GGG ATC ACA TTG TAT GAG TTG GCC ACA GGC CGA TTT CCT TAT CCA AAG
         CCC TAG TGT AAC ATA CTC AAC CGG TGT CCG GCT AAA GGA ATA GGT TTC
         Gly Ile Thr Leu Tyr Glu Leu Ala Thr Gly Arg Phe Pro Tyr Pro Lys>

915       920       925       930       935       940       945       950       955       960
      *                   *                   *                   *                   *
     TGG AAT AGT GTA TTT GAT CAA CTA ACA CAA GTC GTG AAA GGA GAT CCT
     ACC TTA TCA CAT AAA CTA GTT GAT TGT GTT CAG CAC TTT CCT CTA GGA
     Trp Asn Ser Val Phe Asp Gln Leu Thr Gln Val Val Lys Gly Asp Pro>

```
CCG CAG CTG AGT AAT TCT GAG GAA AGG GAA TTC TCC CCG AGT TTC ATC
GGC GTC GAC TCA TTA AGA CTC CTT TCC CTT AAG AGG GGC TCA AAG TAG
Pro Gln Leu Ser Asn Ser Glu Glu Arg Glu Phe Ser Pro Ser Phe Ile>

1015    1020  1025    1030   1035    1040  1045    1050   1055
                    *              *              *              *
AAC TTT GTC AAC TTG TGC CTT ACG AAG GAT GAA TCC AAA AGG CCA AAG
TTG AAA CAG TTG AAC ACG GAA TGC TTC CTA CTT AGG TTT TCC GGT TTC
Asn Phe Val Asn Leu Cys Leu Thr Lys Asp Glu Ser Lys Arg Pro Lys>

1060    1065  1070    1075   1080    1085  1090    1095   1100    1105
  *              *              *              *              *
TAT AAA GAG CTT CTG AAA CAT CCC TTT ATT TTG ATG TAT GAA GAA CGT
ATA TTT CTC GAA GAC TTT GTA GGG AAA TAA AAC TAC ATA CTT CTT GCA
Tyr Lys Glu Leu Leu Lys His Pro Phe Ile Leu Met Tyr Glu Glu Arg>

1110   1115    1120   1125    1130   1135    1140   1145    1150
    *              *              *              *              *
GCC GTT GAG GTC GCA TGC TAT GTT TGT AAA ATC CTG GAT CAA ATG CCA
CGG CAA CTC CAG CGT ACG ATA CAA ACA TTT TAG GAC CTA GTT TAC GGT
Ala Val Glu Val Ala Cys Tyr Val Cys Lys Ile Leu Asp Gln Met Pro>

1155   1160    1165   1170    1175   1180    1185 1190   1195 1200
  *              *              *              *              *
GCT ACT CCC AGC TCT CCC ATG TAT GTC GAT TGATAT CGYTGCTACA
CGA TGA GGG TCG AGA GGG TAC ATA CAG CTA ACTATA GCRACGATGT
Ala Thr Pro Ser Ser Pro Met Tyr Val Asp> (SEQ ID NO:8)

1205 1210   1215 1220   1225 1230   1235 1240   1245 1250   1255 1260
        *           *            *            *            *            *
TCAGACTCTA GAAAAAAGGG CTGAGAGGAA GCAAGACGTA AAGAATTTTC ATCCCGTATC
AGTCTGAGAT CTTTTTTCCC GACTCTCCTT CGTTCTGCAT TTCTTAAAAG TAGGGCATAG 1265 1270   1275 1280   1285 1290   1295 1300   1305 1310   1315 1320
        *           *            *            *            *            *
ACAGTGTTTT TATTGCTCGC CCAGACACCA TGTGCAATAA GATTGGTGTT CGTTTCCATC
TGTCACAAAA ATAACGAGCG GGTCTGTGGT ACACGTTATT CTAACCACAA GCAAAGGTAG 1325 1330   1335 1340   1345 1350   1355 1360   1365 1370   1375 1380
        *           *            *            *            *            *
ATGTCTGTAT ACTCCTGTCA CCTAGAACGT GCATCCTTGT AATACCTGAT TGATCACACA
TACAGACATA TGAGGACAGT GGATCTTGCA CGTAGGAACA TTATGGACTA ACTAGTGTGT 1385 1390   1395 1400   1405 1410   1415 1420   1425 1430   1435 1440
        *           *            *            *            *            *
GTGTTAGTGC TGGTCAGAGA GACCTCATCC TGCTCTTTTG TGATGAACAT ATTCATGAAA
CACAATCACG ACCAGTCTCT CTGGAGTAGG ACGAGAAAAC ACTACTTGTA TAAGTACTTT 1445 1450   1455 1460   1465 1470   1475 1480   1485 1490   1495 1500
        *           *            *            *            *            *
TGTGGAAGTC AGTACGATCA AGTTGTTGAC TGTGATTAGA TCACATCTTA AATTCATTTC
ACACCTTCAG TCATGCTAGT TCAACAACTG ACACTAATCT AGTGTAGAAT TTAAGTAAAG 1505 1510   1515 1520   1525 1530   1535 1540   1545 1550   1555 1560
        *           *            *            *            *            *
TAGACTCAAA ACCTGGAGAT GCAGCTACTG GAATGGTGTT TTGTCAGACT TCCAAATCCT
ATCTGAGTTT TGGACCTCTA CGTCGATGAC CTTACCACAA AACAGTCTGA AGGTTTAGGA 1565 1570   1575 1580   1585 1590   1595 1600   1605 1610   1615 1620
        *           *            *            *            *            *
GGAAGGACAC AGTGATGAAT GTACTATATC TGAACATAGA AACTCGGGCT TGAGTGAGAA
CCTTCCTGTG TCACTACTTA CATGATATAG ACTTGTATCT TTGAGCCCGA ACTCACTCTT
```

FIG. 7C

```
     1625 1630   1635 1640   1645 1650   1655 1660   1665 1670   1675 1680
              *           *           *           *           *           *
     GAGCTTGCAC  AGCCAACGAG  ACACATTGCC  TTCTGGAGCT  GGGAGACAAA  GGAGGAATTT
     CTCGAACGTG  TCGGTTGCTC  TGTGTAACGG  AAGACCTCGA  CCCTCTGTTT  CCTCCTTAAA 1685 1690   1695 1700   1705 1710   1715 1720   1725 1730   1735 1740
              *           *           *           *           *           *
     ACTTTCTTCA  CCAAGTGCAA  TAGATTACTG  ATGTGATATT  CTGTTGCTTT  ACAGTTACAG
     TGAAAGAAGT  GGTTCACGTT  ATCTAATGAC  TACACTATAA  GACAACGAAA  TGTCAATGTC 1745 1750   1755 1760   1765 1770   1775 1780   1785 1790   1795 1800
              *           *           *           *           *           *
     TTGATGTTTG  GGGATCGATG  TGCTCAGCCA  AATTTCCTGT  TTGAAATATC  ATGTTAAATT
     AACTACAAAC  CCCTAGCTAC  ACGAGTCGGT  TTAAAGGACA  AACTTTATAG  TACAATTTAA 1805 1810   1815 1820   1825 1830   1835 1840   1845 1850   1855 1860
              *           *           *           *           *           *
     AGAATGAATT  TATCTTTACC  AAAAACCATG  TTGCGTTCAA  AGAGGTGAAC  ATTAAAATAT
     TCTTACTTAA  ATAGAAATGG  TTTTTGGTAC  AACGCAAGTT  TCTCCACTTG  TAATTTTATA 1865 1870   1875 1880   1885 1890   1895 1900   1905 1910   1915 1920
              *           *           *           *           *           *
     AGAGACAGGA  CAGAATGTGT  TCTTTTCTCC  TCTACCAGTC  CTATTTTTCA  ATGGGAAGAC
     TCTCTGTCCT  GTCTTACACA  AGAAAAGAGG  AGATGGTCAG  GATAAAAAGT  TACCCTTCTG 1925 1930   1935 1940   1945 1950   1955 1960   1965 1970   1975 1980
              *           *           *           *           *           *
     TCAGGAGTCT  GCCACTTGTC  AAAGAAGGTG  CTGATCCTAA  GAATTTTTCA  TTCTCAGAAT
     AGTCCTCAGA  CGGTGAACAG  TTTCTTCCAC  GACTAGGATT  CTTAAAAAGT  AAGAGTCTTA 1985 1990   1995 2000   2005 2010   2015 2020   2025 2030   2035 2040
              *           *           *           *           *           *
     TCGGTGTGCT  GCCAACTTGA  TGTTCCACCT  GCCACAAACC  ACCAGGACTG  AAAGAAGAAA
     AGCCACACGA  CGGTTGAACT  ACAAGGTGGA  CGGTGTTTGG  TGGTCCTGAC  TTTCTTCTTT 2045 2050   2055 2060   2065 2070   2075 2080   2085 2090   2095 2100
              *           *           *           *           *           *
     ACAGTACAGA  AGGCAAAGTT  TACAGATGTT  TTTAATTCTA  GTATTTTATC  TGGAACAACT
     TGTCATGTCT  TCCGTTTCAA  ATGTCTACAA  AAATTAAGAT  CATAAAATAG  ACCTTGTTGA 2105 2110   2115 2120   2125 2130   2135 2140   2145 2150   2155 2160
              *           *           *           *           *           *
     TGTAGCAGCT  ATATATTTCC  CCTTGGTCCC  AAGCCTGATA  CTTTAGCCAT  CATAACTCAC
     ACATCGTCGA  TATATAAAGG  GGAACCAGGG  TTCGGACTAT  GAAATCGGTA  GTATTGAGTG 2165 2170   2175 2180   2185 2190   2195 2200   2205 2210   2215 2220
              *           *           *           *           *           *
     TAACAGGGAG  AAGTAGCTAG  TAGCAATGTG  CCTTGATTGA  TTAGATAAAG  ATTTCTAGTA
     ATTGTCCCTC  TTCATCGATC  ATCGTTACAC  GGAACTAACT  AATCTATTTC  TAAAGATCAT 2225 2230   2235 2240   2245 2250   2255 2260   2265 2270   2275 2280
              *           *           *           *           *           *
     GGCAGCAAAA  GACCAAATCT  CAGTTGTTTG  CTTCTTGCCA  TCACTGGTCC  AGGTCTTCAG
     CCGTCGTTTT  CTGGTTTAGA  GTCAACAAAC  GAAGAACGGT  AGTGACCAGG  TCCAGAAGTC 2285 2290   2295 2300   2305 2310   2315 2320   2325 2330   2335 2340
              *           *           *           *           *           *
     TTTCCGAATC  TCTTTCCCTT  CCCCTGTGGT  CTATTGTCGC  TATGTGACTT  GCGCTTAATC
     AAAGGCTTAG  AGAAAGGGAA  GGGGACACCA  GATAACAGCG  ATACACTGAA  CGCGAATTAG 2345 2350   2355 2360   2365 2370   2375 2380   2385 2390   2395 2400
```

FIG. 7D

```
       *          *          *          *          *          *
CAATATTTTG CCTTTTTTCT ATATCAAAAA ACCTTTACAG TTAGCAGGGA TGTTCCTTAC
GTTATAAAAC GGAAAAAAGA TATAGTTTTT TGGAAATGTC AATCGTCCCT ACAAGGAATG 2405 2410 2415 2420  2425 2430 2435 2440  2445 2450 2455 2460
       *          *          *          *          *          *
CGAGGATTTT TAACCCCCAA TCTCTCATAA TCGCTAGTGT TTAAAAGGCT AAGAATAGTG
GCTCCTAAAA ATTGGGGGTT AGAGAGTATT AGCGATCACA AATTTTCCGA TTCTTATCAC 2465 2470 2475 2480  2485 2490 2495 2500  2505 2510 2515 2520
       *          *          *          *          *          *
GGGCCCAACC GATGTGGTAG GTGATAAAGA GGCATCTTTT CTAGAGACAC ATTGGACCAG
CCCGGGTTGG CTACACCATC CACTATTTCT CCGTAGAAAA GATCTCTGTG TAACCTGGTC 2525 2530 2535 2540  2545 2550 2555 2560  2565 2570 2575 2580
       *          *          *          *          *          *
ATGAGGATCC GAAACGGCAG CCTTTACGTT CATCACCTGC TAGAACCTCT CGTAGTCCAT
TACTCCTAGG CTTTGCCGTC GGAAATGCAA GTAGTGGACG ATCTTGGAGA GCATCAGGTA 2585 2590 2595 2600  2605 2610 2615 2620  2625 2630 2635 2640
       *          *          *          *          *          *
CACCATTTCT TGGCATTGGA ATTCTACTGG AAAAAAATAC AAAAAGCAAA ACAAAACCCT
GTGGTAAAGA ACCGTAACCT TAAGATGACC TTTTTTTATG TTTTTCGTTT TGTTTTGGGA 2645 2650 2655 2660  2665 2670 2675 2680  2685 2690 2695 2700
       *          *          *          *          *          *
CAGCACTGTT ACAAGAGGCC ATTTAAGTAT CTTGTGCTTC TTCACTTACC CATTAGCCAG
GTCGTGACAA TGTTCTCCGG TAAATTCATA GAACACGAAG AAGTGAATGG GTAATCGGTC 2705 2710 2715 2720  2725 2730 2735 2740  2745 2750 2755 2760
       *          *          *          *          *          *
GTTCTCATTA GGTTTTGCTT GGGCCTCCCT GGCACTGAAC CTTAGGCTTT GTATGACAGT
CAAGAGTAAT CCAAAACGAA CCCGGAGGGA CCGTGACTTG GAATCCGAAA CATACTGTCA 2765 2770 2775 2780  2785 2790 2795 2800  2805 2810 2815 2820
       *          *          *          *          *          *
GAAGCAGCAC TGTGAGTGGT TCAAGCACAC TGGAATATAA AACAGTCATG GCCTGAGATG
CTTCGTCGTG ACACTCACCA AGTTCGTGTG ACCTTATATT TTGTCAGTAC CGGACTCTAC 2825 2830 2835 2840  2845 2850 2855 2860  2865 2870 2875 2880
       *          *          *          *          *          *
CAGGTGATGC CATTACAGAA CCAAATCGTG GCACGTATTG CTGTGTCTCC TCTCAGAGTG
GTCCACTACG GTAATGTCTT GGTTTAGCAC CGTGCATAAC GACACAGAGG AGAGTCTCAC 2885 2890 2895 2900  2905 2910 2915 2920  2925 2930 2935 2940
       *          *          *          *          *          *
ACAGTCATAA ATACTGTCAA ACAATAAAGG GAGAATGGTG CTGTTTAAAG TCACATCCCT
TGTCAGTATT TATGACAGTT TGTTATTTCC CTCTTACCAC GACAAATTTC AGTGTAGGGA 2945 2950 2955 2960  2965 2970 2975 2980  2985 2990 2995 3000
       *          *          *          *          *          *
GTAAATTGCA GAATTCAAAA GTGATTATCT CTTTGATCTA CTTGCCTCAT TTCCCTATCT
CATTTAACGT CTTAAGTTTT CACTAATAGA GAAACTAGAT GAACGGAGTA AAGGGATAGA 3005 3010 3015 3020  3025 3030 3035 3040  3045 3050 3055 3060
       *          *          *          *          *          *
TCTCCCCCAC GGTATCCTAA ACTTTAGACT TCCCACTGTT CTGAAAGGAG ACATTGCTCT
AGAGGGGGTG CCATAGGATT TGAAATCTGA AGGGTGACAA GACTTTCCTC TGTAACGAGA 3065 3070 3075 3080  3085 3090 3095 3100  3105 3110 3115 3120
       *          *          *          *          *          *
ATGTCTGCCT TCGACCACAG CAAGCCATCA TCCTCCATTG CTCCCGGGGA CTCAAGAGGA
```

FIG. 7E

```
             TACAGACGGA AGCTGGTGTC GTTCGGTAGT AGGAGGTAAC GAGGGCCCCT GAGTTCTCCT 3125 3130  3135 3140  3145 3150  3155 3160  3165 3170  3175 3180
                     *          *          *          *          *          *
             ATCTGTTTCT CTGCTGTCAA CTTCCCATCT GGCTCAGCAT AGGGTCACTT TGCCATTATG
             TAGACAAAGA GACGACAGTT GAAGGGTAGA CCGAGTCGTA TCCCAGTGAA ACGGTAATAC 3185 3190  3195 3200  3205 3210  3215 3220  3225 3230  3235 3240
                     *          *          *          *          *          *
             CAAATGGAGA TAAAAGCAAT TCTGGCTGTC CAGGAGCTAA TCTGACCGTT CTATTGTGTG
             GTTTACCTCT ATTTTCGTTA AGACCGACAG GTCCTCGATT AGACTGGCAA GATAACACAC 3245 3250  3255 3260  3265 3270  3275 3280  3285 3290  3295 3300
                     *          *          *          *          *          *
             GATGACCACA TAAGAAGGCA ATTTTAGTGT ATTAATCATA GATTATTATA AACTATAAAC
             CTACTGGTGT ATTCTTCCGT TAAAATCACA TAATTAGTAT CTAATAATAT TTGATATTTG 3305 3310  3315 3320  3325 3330  3335 3340  3345 3350  3355 3360
                     *          *          *          *          *          *
             TTAAGGGCAA GGAGTTTATT ACAATGTATC TTTATTAAAA CAAAAGGGTG TATAGTGTTC
             AATTCCCGTT CCTCAAATAA TGTTACATAG AAATAATTTT GTTTTCCCAC ATATCACAAG 3365 3370  3375 3380  3385 3390  3395 3400  3405 3410  3415 3420
                     *          *          *          *          *          *
             ACAAACTGTG AAAATAGTGT AAGAACTGTA CATTGTGAGC TCTGGTTATT TTTCTCTTGT
             TGTTTGACAC TTTTATCACA TTCTTGACAT GTAACACTCG AGACCAATAA AAAGAGAACA 3425 3430  3435 3440  3445 3450  3455 3460  3465 3470  3475 3480
                     *          *          *          *          *          *
             ACCATAGAAA AATGTATAAA AATTATCAAA AAGCTAATGT GCAGGGATAT TGCCTTATTT
             TGGTATCTTT TTACATATTT TTAATAGTTT TTCGATTACA CGTCCCTATA ACGGAATAAA 3485 3490  3495 3500  3505 3510  3515 3520  3525 3530  3535 3540
                     *          *          *          *          *          *
             GTCTGTAAAA AATGGAGCTC AGTAACATAA CTGCTTCTTG GAGCTTTGGA ATATTTTATC
             CAGACATTTT TTACCTCGAG TCATTGTATT GACGAAGAAC CTCGAAACCT TATAAAATAG 3545 3550
                     *
             CTGTATTCTT GTTT   (SEQ ID NO:7)
             GACATAAGAA CAAA
```

FIG. 7F

```
          5        10        15        20        25        30        35        40        45        50
                   *                   *                   *                   *                   *
      CTCCCAACA ATG GCG GCT CCG AGC CCG AGC GGC GGC GGC GGC TCC GGG GGC
      GAGGGTTGT TAC CGC CGA GGC TCG GGC TCG CCG CCG CCG CCG AGG CCC CCG
                Met Ala Ala Pro Ser Pro Ser Gly Gly Gly Gly Ser Gly Gly>

55        60        65        70        75        80        85        90        95
                   *                   *                   *                   *
      GGC AGC GGC AGC GGC ACC CCC GGC CCC GTA GGG TCC CCG GCG CCA GGC
      CCG TCG CCG TCG CCG TGG GGG CCG GGG CAT CCC AGG GGC CGC GGT CCG
      Gly Ser Gly Ser Gly Thr Pro Gly Pro Val Gly Ser Pro Ala Pro Gly>

100       105       110       115       120       125       130       135       140       145
         *                   *                   *                   *                   *
      CAC CCG GCC GTC AGC AGC ATG CAG GGT AAA CGC AAA GCA CTG AAG TTG
      GTG GGC CGG CAG TCG TCG TAC GTC CCA TTT GCG TTT CGT GAC TTC AAC
      His Pro Ala Val Ser Ser Met Gln Gly Lys Arg Lys Ala Leu Lys Leu>

150       155       160       165       170       175       180       185       190       195
         *                   *                   *                   *                   *
      AAT TTT GCA AAT CCA CCT TTC AAA TCT ACA GCA AGG TTT ACT CTG AAT
      TTA AAA CGT TTA GGT GGA AAG TTT AGA TGT CGT TCC AAA TGA GAC TTA
      Asn Phe Ala Asn Pro Pro Phe Lys Ser Thr Ala Arg Phe Thr Leu Asn>

200       205       210       215       220       225       230       235       240
         *                   *                   *                   *                   *
      CCC AAT CCT ACA GGA GTT CAA AAC CCA CAC ATA GAG AGA CTG AGA ACA
      GGG TTA GGA TGT CCT CAA GTT TTG GGT GTG TAT CTC TCT GAC TCT TGT
      Pro Asn Pro Thr Gly Val Gln Asn Pro His Ile Glu Arg Leu Arg Thr>

245       250       255       260       265       270       275       280       285       290
                   *                   *                   *                   *                   *
      CAC AGC ATT GAG TCA TCA GGA AAA CTG AAG ATC TCC CCT GAA CAA CAC
      GTG TCG TAA CTC AGT AGT CCT TTT GAC TTC TAG AGG GGA CTT GTT GTG
      His Ser Ile Glu Ser Ser Gly Lys Leu Lys Ile Ser Pro Glu Gln His>

295       300       305       310       315       320       325       330       335
                   *                   *                   *                   *
      TGG GAT TTC ACT GCA GAG GAC TTG AAA GAC CTT GGA GAA ATT GGA CGA
      ACC CTA AAG TGA CGT CTC CTG AAC TTT CTG GAA CCT CTT TAA CCT GCT
      Trp Asp Phe Thr Ala Glu Asp Leu Lys Asp Leu Gly Glu Ile Gly Arg>

340       345       350       355       360       365       370       375       380       385
                   *                   *                   *                   *                   *
      GGA GCT TAT GGT TCT GTC AAC AAA ATG GTC CAC AAA CCA AGT GGG CAA
      CCT CGA ATA CCA AGA CAG TTG TTT TAC CAG GTG TTT GGT TCA CCC GTT
      Gly Ala Tyr Gly Ser Val Asn Lys Met Val His Lys Pro Ser Gly Gln>

390       395       400       405       410       415       420       425       430       435
                   *                   *                   *                   *                   *
      ATA ATG GCA GTT AAA AGA ATT CGG TCA ACA GTG GAT GAA AAA GAA CAA
      TAT TAC CGT CAA TTT TCT TAA GCC AGT TGT CAC CTA CTT TTT CTT GTT
      Ile Met Ala Val Lys Arg Ile Arg Ser Thr Val Asp Glu Lys Glu Gln>

440       445       450       455       460       465       470       475       480
                   *                   *                   *                   *                   *
      AAA CAA CTT CTT ATG GAT TTG GAT GTA GTA ATG CGG AGT AGT GAT TGC
      TTT GTT GAA GAA TAC CTA AAC CTA CAT CAT TAC GCC TCA TCA CTA ACG
      Lys Gln Leu Leu Met Asp Leu Asp Val Val Met Arg Ser Ser Asp Cys>
```

FIG. 8A

```
     485       490       495       500       505       510       515       520       525       530
       *                   *                   *                   *                   *
     CCA  TAC  ATT  GTT  CAG  TTT  TAT  GGT  GCA  CTC  TTC  AGA  GAG  GGT  GAC  TGT
     GGT  ATG  TAA  CAA  GTC  AAA  ATA  CCA  CGT  GAG  AAG  TCT  CTC  CCA  CTG  ACA
     Pro  Tyr  Ile  Val  Gln  Phe  Tyr  Gly  Ala  Leu  Phe  Arg  Glu  Gly  Asp  Cys>

535       540       545       550       555       560       565       570       575
            *                   *                   *                   *
          TGG  ATC  TGT  ATG  GAA  CTC  ATG  TCT  ACC  TCG  TTT  GAT  AAG  TTT  TAC  AAA
          ACC  TAG  ACA  TAC  CTT  GAG  TAC  AGA  TGG  AGC  AAA  CTA  TTC  AAA  ATG  TTT
          Trp  Ile  Cys  Met  Glu  Leu  Met  Ser  Thr  Ser  Phe  Asp  Lys  Phe  Tyr  Lys>

580       585       590       595       600       605       610       615       620       625
       *                   *                   *                   *                   *
     TAT  GTA  TAT  AGT  GTA  TTA  GAT  GAT  GTT  ATT  CCA  GAA  GAA  ATT  TTA  GGC
     ATA  CAT  ATA  TCA  CAT  AAT  CTA  CTA  CAA  TAA  GGT  CTT  CTT  TAA  AAT  CCG
     Tyr  Val  Tyr  Ser  Val  Leu  Asp  Asp  Val  Ile  Pro  Glu  Glu  Ile  Leu  Gly>

630       635       640       645       650       655       660       665       670       675
       *                   *                   *                   *                   *
     AAA  ATC  ACT  TTA  GCA  ACT  GTG  AAA  GCA  CTA  AAC  CAC  TTA  AAA  GAA  AAC
     TTT  TAG  TGA  AAT  CGT  TGA  CAC  TTT  CGT  GAT  TTG  GTG  AAT  TTT  CTT  TTG
     Lys  Ile  Thr  Leu  Ala  Thr  Val  Lys  Ala  Leu  Asn  His  Leu  Lys  Glu  Asn>

680       685       690       695       700       705       710       715       720
            *                   *                   *                   *
          TTG  AAA  ATT  ATT  CAC  AGA  GAT  ATC  AAA  CCT  TCC  AAT  ATT  CTT  CTG  GAC
          AAC  TTT  TAA  TAA  GTG  TCT  CTA  TAG  TTT  GGA  AGG  TTA  TAA  GAA  GAC  CTG
          Leu  Lys  Ile  Ile  His  Arg  Asp  Ile  Lys  Pro  Ser  Asn  Ile  Leu  Leu  Asp>

725       730       735       740       745       750       755       760       765       770
       *                   *                   *                   *                   *
     AGA  AGT  GGA  AAT  ATT  AAG  CTC  TGT  GAC  TTC  GGC  ATC  AGT  GGA  CAG  CTT
     TCT  TCA  CCT  TTA  TAA  TTC  GAG  ACA  CTG  AAG  CCG  TAG  TCA  CCT  GTC  GAA
     Arg  Ser  Gly  Asn  Ile  Lys  Leu  Cys  Asp  Phe  Gly  Ile  Ser  Gly  Gln  Leu>

775       780       785       790       795       800       805       810       815
            *                   *                   *                   *
          GTG  GAC  TCT  ATT  GCC  AAG  ACA  AGA  GAT  GCT  GGC  TGT  AGG  CCA  TAC  ATG
          CAC  CTG  AGA  TAA  CGG  TTC  TGT  TCT  CTA  CGA  CCG  ACA  TCC  GGT  ATG  TAC
          Val  Asp  Ser  Ile  Ala  Lys  Thr  Arg  Asp  Ala  Gly  Cys  Arg  Pro  Tyr  Met>

820       825       830       835       840       845       850       855       860       865
       *                   *                   *                   *                   *
     GCA  CCT  GAA  AGA  ATA  GAC  CCA  AGC  GCA  TCA  CGA  CAA  GGA  TAT  GAT  GTC
     CGT  GGA  CTT  TCT  TAT  CTG  GGT  TCG  CGT  AGT  GCT  GTT  CCT  ATA  CTA  CAG
     Ala  Pro  Glu  Arg  Ile  Asp  Pro  Ser  Ala  Ser  Arg  Gln  Gly  Tyr  Asp  Val>

870       875       880       885       890       895       900       905       910       915
            *                   *                   *                   *                   *
          CGC  TCT  GAT  GTC  TGG  AGT  TTG  GGG  ATC  ACA  TTG  TAT  GAG  TTG  GCC  ACA
          GCG  AGA  CTA  CAG  ACC  TCA  AAC  CCC  TAG  TGT  AAC  ATA  CTC  AAC  CGG  TGT
          Arg  Ser  Asp  Val  Trp  Ser  Leu  Gly  Ile  Thr  Leu  Tyr  Glu  Leu  Ala  Thr>

920       925       930       935       940       945       950       955       960
       *                   *                   *                   *
     GGC  CGA  TTT  CCT  TAT  CCA  AAG  TGG  AAT  AGT  GTA  TTT  GAT  CAA  CTA  ACA
     CCG  GCT  AAA  GGA  ATA  GGT  TTC  ACC  TTA  TCA  CAT  AAA  CTA  GTT  GAT  TGT
     Gly  Arg  Phe  Pro  Tyr  Pro  Lys  Trp  Asn  Ser  Val  Phe  Asp  Gln  Leu  Thr>

```
CAA GTC GTG AAA GGA GAT CCT CCG CAG CTG AGT AAT TCT GAG GAA AGG
GTT CAG CAC TTT CCT CTA GGA GGC GTC GAC TCA TTA AGA CTC CTT TCC
Gln Val Val Lys Gly Asp Pro Pro Gln Leu Ser Asn Ser Glu Glu Arg>

1015 1020  1025      1030 1035      1040 1045      1050 1055
                  *                *                *            *
GAA TTC TCC CCG AGT TTC ATC AAC TTT GTC AAC TTG TGC CTT ACG AAG
CTT AAG AGG GGC TCA AAG TAG TTG AAA CAG TTG AAC ACG GAA TGC TTC
Glu Phe Ser Pro Ser Phe Ile Asn Phe Val Asn Leu Cys Leu Thr Lys>

1060 1065  1070      1075 1080      1085 1090  1095      1100 1105
        *                *                *                *
GAT GAA TCC AAA AGG CCA AAG TAT AAA GAG CTT CTG AAA CAT CCC TTT
CTA CTT AGG TTT TCC GGT TTC ATA TTT CTC GAA GAC TTT GTA GGG AAA
Asp Glu Ser Lys Arg Pro Lys Tyr Lys Glu Leu Leu Lys His Pro Phe>

1110      1115      1120 1125      1130 1135      1140 1145      1150 1155
        *                *                *                *                *
ATT TTG ATG TAT GAA GAA CGT GCC GTT GAG GTC GCA TGC TAT GTT TGT
TAA AAC TAC ATA CTT CTT GCA CGG CAA CTC CAG CGT ACG ATA CAA ACA
Ile Leu Met Tyr Glu Glu Arg Ala Val Glu Val Ala Cys Tyr Val Cys>

1160      1165      1170 1175      1180 1185      1190      1195      1200
              *                *                *                *
AAA ATC CTG GAT CAA ATG CCA GCT ACT CCC AGC TCT CCC ATG TAT GTC
TTT TAG GAC CTA GTT TAC GGT CGA TGA GGG TCG AGA GGG TAC ATA CAG
Lys Ile Leu Asp Gln Met Pro Ala Thr Pro Ser Ser Pro Met Tyr Val>

1205      1210      1215 1220      1225 1230      1235 1240      1245 1250      1255 1260
        *                *                *                *                *           *
GAT TGAT ATCGCTGCTA CATCAGACTC TAGAAAAAAG GGCTGAGAGG AAGCAAGACG
CTA ACTA TAGCGACGAT GTAGTCTGAG ATCTTTTTTC CCGACTCTCC TTCGTTCTGC
Asp>   (SEQ ID NO:10)

1265 1270      1275 1280      1285 1290      1295 1300      1305 1310      1315 1320
        *                *                *                *                *           *
TAAAGAATTT TCATCCCGTA TCACAGTGTT TTTATTGCTC GCCCAGACAC CATGTGCAAT
ATTTCTTAAA AGTAGGGCAT AGTGTCACAA AAATAACGAG CGGGTCTGTG GTACACGTTA 1325 1330      1335 1340      1345 1350      1355 1360      1365 1370      1375 1380
        *                *                *                *                *           *
AAGATTGGTG TTCGTTTCCA TCATGTCTGT ATACTCCTGT CACCTAGAAC GTGCATCCTT
TTCTAACCAC AAGCAAAGGT AGTACAGACA TATGAGGACA GTGGATCTTG CACGTAGGAA 1385 1390      1395 1400      1405 1410      1415 1420      1425 1430      1435 1440
        *                *                *                *                *           *
GTAATACCTG ATTGATCACA CAGTGTTAGT GCTGGTCAGA GAGACCTCAT CCTGCTCTTT
CATTATGGAC TAACTAGTGT GTCACAATCA CGACCAGTCT CTCTGGAGTA GGACGAGAAA 1445 1450      1455 1460      1465 1470      1475 1480      1485 1490      1495 1500
        *                *                *                *                *           *
TGTGATGAAC ATATTCATGA AATGTGGAAG TCAGTACGAT CAAGTTGTTG ACTGTGATTA
ACACTACTTG TATAAGTACT TTACACCTTC AGTCATGCTA GTTCAACAAC TGACACTAAT 1505 1510      1515 1520      1525 1530      1535 1540      1545 1550      1555 1560
        *                *                *                *                *           *
GATCACATCT TAAATTCATT TCTAGACTCA AAACCTGGAG ATGCAGCTAC TGGAATGGTG
CTAGTGTAGA ATTTAAGTAA AGATCTGAGT TTTGGACCTC TACGTCGATG ACCTTACCAC 1565 1570      1575 1580      1585 1590      1595 1600      1605 1610      1615 1620
        *                *                *                *                *           *
TTTTGTCAGA CTTCCAAATC CTGGAAGGAC ACAGTGATGA ATGTACTATA TCTGAACATA
```

FIG. 8C

```
AAAACAGTCT GAAGGTTTAG GACCTTCCTG TGTCACTACT TACATGATAT AGACTTGTAT
1625 1630  1635 1640  1645 1650  1655 1660  1665 1670  1675 1680
          *           *           *           *           *
GAAACTCGGG CTTGAGTGAG AAGAGCTTGC ACAGCCAACG AGACACATTG CCTTCTGGAG
CTTTGAGCCC GAACTCACTC TTCTCGAACG TGTCGGTTGC TCTGTGTAAC GGAAGACCTC 1685 1690  1695 1700  1705 1710  1715 1720  1725 1730  1735 1740
          *           *           *           *           *
CTGGGAGACA AAGGAGGAAT TTACTTTCTT CACCAAGTGC AATAGATTAC TGATGTGATA
GACCCTCTGT TTCCTCCTTA AATGAAAGAA GTGGTTCACG TTATCTAATG ACTACACTAT 1745 1750  1755 1760  1765 1770  1775 1780  1785 1790  1795 1800
          *           *           *           *           *
TTCTGTTGCT TTACAGTTAC AGTTGATGTT TGGGGATCGA TGTGCTCAGC CAAATTTCCT
AAGACAACGA AATGTCAATG TCAACTACAA ACCCCTAGCT ACACGAGTCG GTTTAAAGGA 1805 1810  1815 1820  1825 1830  1835 1840  1845 1850  1855 1860
          *           *           *           *           *
GTTTGAAATA TCATGTTAAA TTAGAATGAA TTTATCTTTA CCAAAAACCA TGTTGCGTTC
CAAACTTTAT AGTACAATTT AATCTTACTT AAATAGAAAT GGTTTTTGGT ACAACGCAAG 1865 1870  1875 1880  1885 1890  1895 1900  1905 1910  1915 1920
          *           *           *           *           *
AAAGAGGTGA ACATTAAAAT ATAGAGACAG GACAGAATGT GTTCTTTTCT CCTCTACCAG
TTTCTCCACT TGTAATTTTA TATCTCTGTC CTGTCTTACA CAAGAAAAGA GGAGATGGTC 1925 1930  1935 1940  1945 1950  1955 1960  1965 1970  1975 1980
          *           *           *           *           *
TCCTATTTTT CAATGGGAAG ACTCAGGAGT CTGCCACTTG TCAAAGAAGG TGCTGATCCT
AGGATAAAAA GTTACCCTTC TGAGTCCTCA GACGGTGAAC AGTTTCTTCC ACGACTAGGA 1985 1990  1995 2000  2005 2010  2015 2020  2025 2030  2035 2040
          *           *           *           *           *
AAGAATTTTT CATTCTCAGA ATTCGGTGTG CTGCCAACTT GATGTTCCAC CTGCCACAAA
TTCTTAAAAA GTAAGAGTCT TAAGCCACAC GACGGTTGAA CTACAAGGTG GACGGTGTTT 2045 2050  2055 2060  2065 2070  2075 2080  2085 2090  2095 2100
          *           *           *           *           *
CCACCAGGAC TGAAAGAAGA AAACAGTACA GAAGGCAAAG TTTACAGATG TTTTTAATTC
GGTGGTCCTG ACTTTCTTCT TTTGTCATGT CTTCCGTTTC AAATGTCTAC AAAAATTAAG 2105 2110  2115 2120  2125 2130  2135 2140  2145 2150  2155 2160
          *           *           *           *           *
TAGTATTTTA TCTGGAACAA CTTGTAGCAG CTATATATTT CCCCTTGGTC CCAAGCCTGA
ATCATAAAAT AGACCTTGTT GAACATCGTC GATATATAAA GGGGAACCAG GGTTCGGACT 2165 2170  2175 2180  2185 2190  2195 2200  2205 2210  2215 2220
          *           *           *           *           *
TACTTTAGCC ATCATAACTC ACTAACAGGG AGAAGTAGCT AGTAGCAATG TGCCTTGATT
ATGAAATCGG TAGTATTGAG TGATTGTCCC TCTTCATCGA TCATCGTTAC ACGGAACTAA 2225 2230  2235 2240  2245 2250  2255 2260  2265 2270  2275 2280
          *           *           *           *           *
GATTAGATAA AGATTTCTAG TAGGCAGCAA AAGACCAAAT CTCAGTTGTT TGCTTCTTGC
CTAATCTATT TCTAAAGATC ATCCGTCGTT TTCTGGTTTA GAGTCAACAA ACGAAGAACG 2285 2290  2295 2300  2305 2310  2315 2320  2325 2330  2335 2340
          *           *           *           *           *
CATCACTGGT CCAGGTCTTC AGTTTCCGAA TCTCTTTCCC TTCCCCTGTG GTCTATTGTC
GTAGTGACCA GGTCCAGAAG TCAAAGGCTT AGAGAAAGGG AAGGGGACAC CAGATAACAG
```

FIG. 8D

```
       2345 2350  2355 2360  2365 2370  2375 2380  2385 2390  2395 2400
                *          *          *          *          *          *
       GCTATGTGAC TTGCGCTTAA TCCAATATTT TGCCTTTTTT CTATATCAAA AAACCTTTAC
       CGATACACTG AACGCGAATT AGGTTATAAA ACGGAAAAAA GATATAGTTT TTTGGAAATG 2405 2410  2415 2420  2425 2430  2435 2440  2445 2450  2455 2460
                *          *          *          *          *          *
       AGTTAGCAGG GATGTTCCTT ACCGAGGATT TTTAACCCCC AATCTCTCAT AATCGCTAGT
       TCAATCGTCC CTACAAGGAA TGGCTCCTAA AAATTGGGGG TTAGAGAGTA TTAGCGATCA 2465 2470  2475 2480  2485 2490  2495 2500  2505 2510  2515 2520
                *          *          *          *          *          *
       GTTTAAAAGG CTAAGAATAG TGGGGCCCAA CCGATGTGGT AGGTGATAAA GAGGCATCTT
       CAAATTTTCC GATTCTTATC ACCCCGGGTT GGCTACACCA TCCACTATTT CTCCGTAGAA 2525 2530  2535 2540  2545 2550  2555 2560  2565 2570  2575 2580
                *          *          *          *          *          *
       TTCTAGAGAC ACATTGGACC AGATGAGGAT CCGAAACGGC AGCCTTTACG TTCATCACCT
       AAGATCTCTG TGTAACCTGG TCTACTCCTA GGCTTTGCCG TCGGAAATGC AAGTAGTGGA 2585 2590  2595 2600  2605 2610  2615 2620  2625 2630  2635 2640
                *          *          *          *          *          *
       GCTAGAACCT CTCGTAGTCC ATCACCATTT CTTGGCATTG GAATTCTACT GGAAAAAAAT
       CGATCTTGGA GAGCATCAGG TAGTGGTAAA GAACCGTAAC CTTAAGATGA CCTTTTTTTA 2645 2650  2655 2660  2665 2670  2675 2680  2685 2690  2695 2700
                *          *          *          *          *          *
       ACAAAAAGCA AAACAAAACC CTCAGCACTG TTACAAGAGG CCATTTAAGT ATCTTGTGCT
       TGTTTTTCGT TTTGTTTTGG GAGTCGTGAC AATGTTCTCC GGTAAATTCA TAGAACACGA 2705 2710  2715 2720  2725 2730  2735 2740  2745 2750  2755 2760
                *          *          *          *          *          *
       TCTTCACTTA CCCATTAGCC AGGTTCTCAT TAGGTTTTGC TTGGGCCTCC CTGGCACTGA
       AGAAGTGAAT GGGTAATCGG TCCAAGAGTA ATCCAAAACG AACCCGGAGG GACCGTGACT 2765 2770  2775 2780  2785 2790  2795 2800  2805 2810  2815 2820
                *          *          *          *          *          *
       ACCTTAGGCT TTGTATGACA GTGAAGCAGC ACTGTGAGTG GTTCAAGCAC ACTGGAATAT
       TGGAATCCGA AACATACTGT CACTTCGTCG TGACACTCAC CAAGTTCGTG TGACCTTATA 2825 2830  2835 2840  2845 2850  2855 2860  2865 2870  2875 2880
                *          *          *          *          *          *
       AAAACAGTCA TGGCCTGAGA TGCAGGTGAT GCCATTACAG AACCAAATCG TGGCACGTAT
       TTTTGTCAGT ACCGGACTCT ACGTCCACTA CGGTAATGTC TTGGTTTAGC ACCGTGCATA 2885 2890  2895 2900  2905 2910  2915 2920  2925 2930  2935 2940
                *          *          *          *          *          *
       TGCTGTGTCT CCTCTCAGAG TGACAGTCAT AAATACTGTC AAACAATAAA GGGAGAATGG
       ACGACACAGA GGAGAGTCTC ACTGTCAGTA TTTATGACAG TTTGTTATTT CCCTCTTACC 2945 2950  2955 2960  2965 2970  2975 2980  2985 2990  2995 3000
                *          *          *          *          *          *
       TGCTGTTTAA AGTCACATCC CTGTAAATTG CAGAATTCAA AAGTGATTAT CTCTTTGATC
       ACGACAAATT TCAGTGTAGG GACATTTAAC GTCTTAAGTT TTCACTAATA GAGAAACTAG 3005 3010  3015 3020  3025 3030  3035 3040  3045 3050  3055 3060
                *          *          *          *          *          *
       TACTTGCCTC ATTTCCCTAT CTTCTCCCCC ACGGTATCCT AAACTTTAGA CTTCCCACTG
       ATGAACGGAG TAAAGGGATA GAAGAGGGGG TGCCATAGGA TTTGAAATCT GAAGGGTGAC 3065 3070  3075 3080  3085 3090  3095 3100  3105 3110  3115 3120
                *          *          *          *          *          *
```

FIG. 8E

```
TTCTGAAAGG AGACATTGCT CTATGTCTGC CTTCGACCAC AGCAAGCCAT CATCCTCCAT
AAGACTTTCC TCTGTAACGA GATACAGACG GAAGCTGGTG TCGTTCGGTA GTAGGAGGTA 3125 3130  3135 3140  3145 3150  3155 3160  3165 3170  3175 3180
            *          *          *          *          *          *
TGCTCCCGGG GACTCAAGAG GAATCTGTTT CTCTGCTGTC AACTTCCCAT CTGGCTCAGC
ACGAGGGCCC CTGAGTTCTC CTTAGACAAA GAGACGACAG TTGAAGGGTA GACCGAGTCG 3185 3190  3195 3200  3205 3210  3215 3220  3225 3230  3235 3240
            *          *          *          *          *          *
ATAGGGTCAC TTTGCCATTA TGCAAATGGA GATAAAAGCA ATTCTGGCTG TCCAGGAGCT
TATCCCAGTG AAACGGTAAT ACGTTTACCT CTATTTTCGT TAAGACCGAC AGGTCCTCGA 3245 3250  3255 3260  3265 3270  3275 3280  3285 3290  3295 3300
            *          *          *          *          *          *
AATCTGACCG TTCTATTGTG TGGATGACCA CATAAGAAGG CAATTTTAGT GTATTAATCA
TTAGACTGGC AAGATAACAC ACCTACTGGT GTATTCTTCC GTTAAAATCA CATAATTAGT 3305 3310  3315 3320  3325 3330  3335 3340  3345 3350  3355 3360
            *          *          *          *          *          *
TAGATTATTA TAAACTATAA ACTTAAGGGC AAGGAGTTTA TTACAATGTA TCTTTATTAA
ATCTAATAAT ATTTGATATT TGAATTCCCG TTCCTCAAAT AATGTTACAT AGAAATAATT 3365 3370  3375 3380  3385 3390  3395 3400  3405 3410  3415 3420
            *          *          *          *          *          *
AACAAAAGGG TGTATAGTGT TCACAAACTG TGAAAATAGT GTAAGAACTG TACATTGTGA
TTGTTTTCCC ACATATCACA AGTGTTTGAC ACTTTTATCA CATTCTTGAC ATGTAACACT 3425 3430  3435 3440  3445 3450  3455 3460  3465 3470  3475 3480
            *          *          *          *          *          *
GCTCTGGTTA TTTTTCTCTT GTACCATAGA AAAATGTATA AAAATTATCA AAAAGCTAAT
CGAGACCAAT AAAAAGAGAA CATGGTATCT TTTTACATAT TTTTAATAGT TTTTCGATTA 3485 3490  3495 3500  3505 3510  3515 3520  3525 3530  3535 3540
            *          *          *          *          *          *
GTGCAGGGAT ATTGCCTTAT TTGTCTGTAA AAAATGGAGC TCAGTAACAT AACTGCTTCT
CACGTCCCTA TAACGGAATA AACAGACATT TTTTACCTCG AGTCATTGTA TTGACGAAGA 3545 3550  3555 3560  3565 3570  3575
            *          *          *
TGGAGCTTTG GAATATTTTA TCCTGTATTC TTGTTT  (SEQ ID NO:9)
ACCTCGAAAC CTTATAAAAT AGGACATAAG AACAAA
```

FIG. 8F

```
                                                                                       70
MKK7
HEP         <SASSSSSSASAFASAAPATGTFGGTYTPPTTRVSRATPTLPMLSSGPGGLNRTRPVILP.PT.PHPPV
MKK1                                                      MPKKKP--TPIQ.NPA-PDGSAVNG
MKK2                                                      MLARRKPVLPA.TINP.IAEGP.PT.
MKK3                                                          MSKPPA-----PN.TPPRN
MKK4        MAAPSPSGGGGSGGGSGSGTPGPVGSPAPGHPAVSSMQGKRKALKLNFANPPFKSTARFTLNPN.TGVQN
MKK5        <IGQVLPEATTTAFEYEDEDGDRITVRSDEEMKAMLSYYSTVMEQQVNGQLIEP.QIFPRACK.PGERN
MKK6                        MSQSKGKKRNPGLKIPKEAFEQPQ----TSSTPPRD
Consensus
          1
                                                                                      140
                                                                           I
MKK7        IEIDQKLQEIMKQT-GYLTIG------GQRYQAEI------------NDLENLGEMGSGTCGQVWKMRFR
HEP         S.T.M..KI..E..-.K.N.N-----.RQ.PTD.-------------.KH..DL.N..S.N.V..MHL
MKK1        TSSAETNL.ALQKKLEE.ELDE----Q..KRL.AFLTQKQKVGELKDD.F.KIS.L.A.NG.V.F.VSHK
MKK2        EGASEANLVDLQKKLEE.ELDE----Q..KKRL.AFLTQKAKVGELKDD.F.RIS.L.A.NG.V.T.VQH.
MKK3        ------LDSR-TFI..G-------DRNFEV.A-----------D..VTIS.L.R.AY.V.E.V.HA
MKK4        PH.ERLRTHSIESS-.K.K.SP----E.HWDFTA----------E..KD..I.R.AY.S.N..VHK
MKK5        .HGLKVNTRAGPSQHSSPAVSDSLPSNSLKKSSAELKKILANGQMNEQ.IRYRDTL.H.NG.T.Y.AYHV
MKK6        ------LDSK-ACIS.G-------N.NFEVKA----------D.L.PIM.L.R.AY.V.E...HV
Consensus                                                         D      G G G V K
        71
                                                                                      210
                                           III         IV               V
MKK7        KTGHIIAVKQMRRSGNKEENKRILMDLDVVLKSHDCPYIVQCFGTFITNTDVFIAMELM-GTCAEKLKK-
HEP         SSNT.......T.A.............K...K.L.C.VRDP..W.C.....-SM.FD..L.-
MKK1        PS.LVM.R.LIHLEIKPAIRNQ.IRE.Q.-.HECNSP...GFY.A.YSDGEIS.C..H.D.GSLDQVL.K
MKK2        PS.L.M.R.LIHLEIKPAIRNQ.IRE.Q.-.HECNSP...GFY.A.YSDGEIS.C..H.D.GSLDQVL.E
MKK3        QS.T.M....RI.A.V.SQ.Q..LL....INMRTV..F.T.TFY.ALFREG..W.C.....D-.SLD.FYRK
MKK4        PS.Q.M....RI.S.VDEK.Q.QLL....MRSS.......FY.ALFREG.CW.C....-S.SFD.FY.Y
MKK5        PS.K.L...VILLDITL.LQ.Q.MSE.EILI.-C.SS..IGFY.A.FVENRIS.CTEF.D.GSLDDIG.-
MKK6        PS.Q.M...RI.A.V.SQ.Q..LL....ISMRTV...FTVTFY.ALFREG..W.C.....D-.SLD.FY.Q
Consensus     I A K                    L                    G   I   M
       141             II
```

MKK7
Sequence Range: 1 to 1623

```
          10         20         30         40         50         60
           *          *          *          *          *          *
    GGAAAGGCAG CCTCCTGTAG GTGAAAATTC TGTTCACTAC CTGGCCACCT GGCCTGACTG
    CCTTTCCGTC GGAGGACATC CACTTTTAAG ACAAGTGATG GACCGGTGGA CCGGACTGAC 70         80         90        100        110        120
           *          *          *          *          *          *
    ACCTTCACAG CTTGATCATC TTCCTGAAGA GGCATTCAGG ATTCCCTCCA TCCCTACCCC
    TGGAAGTGTC GAACTAGTAG AAGGACTTCT CCGTAAGTCC TAAGGGAGGT AGGGATGGGG 130        140        150        160        170        180
           *          *          *          *          *          *
    TTCTGGACAA AGTCTTCCAC GTTTCCTTCC TGGGAGTTTC TTCCAGGAAC TGGAGATACC
    AAGACCTGTT TCAGAAGGTG CAAAGGAAGG ACCCTCAAAG AAGGTCCTTG ACCTCTATGG 190        200        210        220        230        240
           *          *          *          *          *          *
    CAGAGCCCTG CAACTCCCAC TGGCCAACGA TGGGGGCAGC CGCTCACCAT CCTCAGAGAG
    GTCTCGGGAC GTTGAGGGTG ACCGGTTGCT ACCCCCGTCG GCGAGTGGTA GGAGTCTCTC 250        260        270        280        290
           *          *          *          *          *
    CTCCCCACAG CACCCTACAC CCCCCACCCG GCCCCGCCAC ATG CTG GGG CTC CCA
    GAGGGGTGTC GTGGGATGTG GGGGGTGGGC CGGGGCGGTG TAC GAC CCC GAG GGT
                                                 Met Leu Gly Leu Pro>

300        310        320        330        340
           *          *          *          *          *
    TCA ACC TTG TTC ACA CCG CGC AGT ATG GAG AGC ATC GAG ATT GAC CAG
    AGT TGG AAC AAG TGT GGC GCG TCA TAC CTC TCG TAG CTC TAA CTG GTC
    Ser Thr Leu Phe Thr Pro Arg Ser Met Glu Ser Ile Glu Ile Asp Gln>

350        360        370        380        390
           *          *          *          *          *
    AAG CTG CAG GAG ATC ATG AAG CAG ACA GGG TAC CTG ACT ATC GGG GGC
    TTC GAC GTC CTC TAG TAC TTC GTC TGT CCC ATG GAC TGA TAG CCC CCG
    Lys Leu Gln Glu Ile Met Lys Gln Thr Gly Tyr Leu Thr Ile Gly Gly>

400        410        420        430
                *          *          *          *
    CAG CGT TAT CAG GCA GAA ATC AAT GAC TTG GAG AAC TTG GGT GAG ATG
    GTC GCA ATA GTC CGT CTT TAG TTA CTG AAC CTC TTG AAC CCA CTC TAC
    Gln Arg Tyr Gln Ala Glu Ile Asn Asp Leu Glu Asn Leu Gly Glu Met>

440        450        460        470        480
      *          *          *          *          *
    GGC AGT GGT ACC TGT GGT CAG GTG TGG AAG ATG CGG TTC CGG AAG ACA
    CCG TCA CCA TGG ACA CCA GTC CAC ACC TTC TAC GCC AAG GCC TTC TGT
    Gly Ser Gly Thr Cys Gly Gln Val Trp Lys Met Arg Phe Arg Lys Thr>

490        500        510        520        530
           *          *          *          *          *
    GGC CAC ATC ATT GCT GTT AAG CAA ATG CGG CGC TCT GGG AAC AAG GAA
    CCG GTG TAG TAA CGA CAA TTC GTT TAC GCC GCG AGA CCC TTG TTC CTT
    Gly His Ile Ile Ala Val Lys Gln Met Arg Arg Ser Gly Asn Lys Glu
```

FIG. 10A

MKK7

```
       540            550            560            570            580
    *    .    *    .    *    .    *    .    *    .    *    .    *    .    *    .    *
GAG AAT AAG CGC ATT TTG ATG GAC CTG GAT GTA GTA CTC AAG AGC CAT
CTC TTA TTC GCG TAA AAC TAC CTG GAC CTA CAT CAT GAG TTC TCG GTA
Glu Asn Lys Arg Ile Leu Met Asp Leu Asp Val Val Leu Lys Ser His>

590            600            610            620            630
     *    .    *    .    *    .    *    .    *    .    *    .    *    .    *    .    *
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

640            650            660            670
     *    .    *    .    *    .    *    .    *    .    *    .    *    .
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

680            690            700            710            720
  *    .    *    .    *    .    *    .    *    .    *    .    *    .    *    .    *
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

730            740            750            760            770
  *    .    *    .    *    .    *    .    *    .    *    .    *    .    *    .    *
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

780            790            800            810            820
     *    .    *    .    *    .    *    .    *    .    *    .    *    .    *    .    *
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

830            840            850            860            870
     *    .    *    .    *    .    *    .    *    .    *    .    *    .    *    .    *
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

880            890            900            910
     *    .    *    .    *    .    *    .    *    .    *    .    *    .    *
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

920            930            940            950            960
  *    .    *    .    *    .    *    .    *    .    *    .    *    .    *    .    *
GAG CGC ATC GAC CCT CCA GAT CCC ACC AAG CCT GAC TAT GAC ATC CGA
CTC GCG TAG CTG GGA GGT CTA GGG TGG TTG GGA CTG ATA CTG TAG GCT
Glu Arg Ile Asp Pro Pro Asp Pro Thr Lys Pro Asp Tyr Asp Ile Arg>
```

FIG. 10B

MKK7

```
970            980            990           1000           1010
 *      *       *       *      *      *      *      *       *      *
GCT GAT GTG TGG AGC CTG GGC ATC TCA CTG GTG GAG CTG GCA ACA GGA
CGA CTA CAC ACC TCG GAC CCG TAG AGT GAC CAC CTC GAC CGT TGT CCT
Ala Asp Val Trp Ser Leu Gly Ile Ser Leu Val Glu Leu Ala Thr Gly>

1020           1030           1040           1050           1060
        *       *      *      *      *      *      *      *      *       *
CAG TTC CCC TAT AAG AAC TGC AAG ACG GAC TTT GAG GTC CTC ACC AAA
GTC AAG GGG ATA TTC TTG ACG TTC TGC CTG AAA CTC CAG GAG TGG TTT
Gln Phe Pro Tyr Lys Asn Cys Lys Thr Asp Phe Glu Val Leu Thr Lys>

1070           1080           1090           1100           1110
        *      *       *      *       *      *      *      *      *       *
GTC CTA CAG GAA GAG CCC CCA CTC CTG CCT GGT CAC ATG GGC TTC TCA
CAG GAT GTC CTT CTC GGG GGT GAG GAC GGA CCA GTG TAC CCG AAG AGT
Val Leu Gln Glu Glu Pro Pro Leu Leu Pro Gly His Met Gly Phe Ser>

1120           1130           1140           1150
         *      *      *      *       *      *      *      *       *
GGG GAC TTC CAG TCA TTT GTC AAA GAC TGC CTT ACT AAA GAT CAC AGG
CCC CTG AAG GTC AGT AAA CAG TTT CTG ACG GAA TGA TTT CTA GTG TCC
Gly Asp Phe Gln Ser Phe Val Lys Asp Cys Leu Thr Lys Asp His Arg>

1160           1170           1180           1190           1200
 *      *       *      *       *      *      *      *      *       *
AAG AGA CCA AAG TAT AAT AAG CTA CTT GAA CAC AGC TTC ATC AAG CAC
TTC TCT GGT TTC ATA TTA TTC GAT GAA CTT GTG TCG AAG TAG TTC GTG
Lys Arg Pro Lys Tyr Asn Lys Leu Leu Glu His Ser Phe Ile Lys His>

1210           1220           1230           1240           1250
        *      *      *      *       *      *      *      *      *       *
TAT GAG ATA CTC GAG GTG GAT GTC GCG TCC TGG TTT AAG GAT GTC ATG
ATA CTC TAT GAG CTC CAC CTA CAG CGC AGG ACC AAA TTC CTA CAG TAC
Tyr Glu Ile Leu Glu Val Asp Val Ala Ser Trp Phe Lys Asp Val Met>

1260           1270           1280           1290           1300
         *      *      *      *       *      *      *      *      *       *
GCG AAG ACC GAG TCC CCA AGG ACT AGT GGA GTC CTG AGT CAG CAC CAT
CGC TTC TGG CTC AGG GGT TCC TGA TCA CCT CAG GAC TCA GTC GTG GTA
Ala Lys Thr Glu Ser Pro Arg Thr Ser Gly Val Leu Ser Gln His His>

1310           1320           1330           1340           1350           1360
         *      *       *      *      *      *      *      *       *      *      *       *
CTG CCC TTC TTC AGG TA GCCTCATGGC AGCGGCCAGC CCCGCAGGGG CCCCGGCCA
GAC GGG AAG AAG TCC AT CGGAGTACCG TCGCCGGTCG GGGCGTCCCC GGGGCCCGGT
Leu Pro Phe Phe Arg>

1370           1380           1390           1400           1410           1420
              *      *       *      *      *      *      *      *       *      *      *       *
CGGCCACCGA CCCCCCCCCC AACCTGGCCA ACCCAGCTGC CCATCAGGGG ACCTGGGACC
GCCGGTGGCT GGGGGGGGGG TTGGACCGGT TGGGTCGACG GGTAGTCCCC TGGACCCTGG
```

FIG. 10C

MKK7

```
          1430        1440        1450        1460        1470        1480
            *           *           *           *           *           *
       TGGACGACTG  CCAAGGACTG  AGGACAGAAA  GTAGGGGGTT  CCCATCCAGC  TCTGACTCCC
       ACCTGCTGAC  GGTTCCTGAC  TCCTGTCTTT  CATCCCCCAA  GGGTAGGTCG  AGACTGAGGG 1490        1500        1510        1520        1530        1540
            *           *           *           *           *           *
       TGCCTACCAG  CTGTGGACAA  AAGGGCATGC  TGGTTCCTAA  TCCCTCCCAC  TCTGGGGTCA
       ACGGATGGTC  GACACCTGTT  TTCCCGTACG  ACCAAGGATT  AGGGAGGGTG  AGACCCCAGT 1550        1560        1570        1580        1590        1600
            *           *           *           *           *           *
       GCCAGCAGTG  TGAGCCCCAT  CCCACCCCGA  CAGACACTGT  GAACGGAAGA  CAGCAGGCCA
       CGGTCGTCAC  ACTCGGGGTA  GGGTGGGGCT  GTCTGTGACA  CTTGCCTTCT  GTCGTCCGGT 1610        1620
            *           *
       AAAAAAAAAA  AAAAAAAAAA  AAA   (SEQ ID NO: 17)
       TTTTTTTTTT  TTTTTTTTTT  TTT
```

FIG. 10D

MKK7b
Sequence Range: 1 to 1465

```
              10            20            30            40            50
               *             *             *             *             *
       GC ACG AGC CCT GCT CCT GCC CCG TCC CAG CGA GCA GCC CTG CAA CTC CCA
       CG TGC TCG GGA CGA GGA CGG GGC AGG GTC GCT CGT CGG GAC GTT GAG GGT
          Thr Ser Pro Ala Pro Ala Pro Ser Gln Arg Ala Ala Leu Gln Leu Pro>

60            70            80            90
                       *             *             *             *
       CTG GCC AAC GAT GGG GGC AGC CGC TCA CCA TCC TCA GAG AGC TCC CCA
       GAC CGG TTG CTA CCC CCG TCG GCG AGT GGT AGG AGT CTC TCG AGG GGT
       Leu Ala Asn Asp Gly Gly Ser Arg Ser Pro Ser Ser Glu Ser Ser Pro>

100           110           120           130           140
       *             *             *             *             *
       CAG CAC CCT ACA CCC CCC ACC CGG CCC CGC CAC ATG CTG GGG CTC CCA
       GTC GTG GGA TGT GGG GGG TGG GCC GGG GCG GTG TAC GAC CCC GAG GGT
       Gln His Pro Thr Pro Pro Thr Arg Pro Arg His Met Leu Gly Leu Pro>

150           160           170           180           190
               *             *             *             *             *
       TCA ACC TTG TTC ACA CCG CGC AGT ATG GAG AGC ATC GAG ATT GAC CAG
       AGT TGG AAC AAG TGT GGC GCG TCA TAC CTC TCG TAG CTC TAA CTG GTC
       Ser Thr Leu Phe Thr Pro Arg Ser Met Glu Ser Ile Glu Ile Asp Gln>

200           210           220           230           240
               *             *             *             *             *
       AAG CTG CAG GAG ATC ATG AAG CAG ACA GGG TAC CTG ACT ATC GGG GGC
       TTC GAC GTC CTC TAG TAC TTC GTC TGT CCC ATG GAC TGA TAG CCC CCG
       Lys Leu Gln Glu Ile Met Lys Gln Thr Gly Tyr Leu Thr Ile Gly Gly>

250           260           270           280           290
               *             *             *             *             *
       CAG CGT TAT CAG GCA GAA ATC AAT GAC TTG GAG AAC TTG GGT GAG ATG
       GTC GCA ATA GTC CGT CTT TAG TTA CTG AAC CTC TTG AAC CCA CTC TAC
       Gln Arg Tyr Gln Ala Glu Ile Asn Asp Leu Glu Asn Leu Gly Glu Met>

300           310           320           330
                      *             *             *             *
       GGC AGT GGT ACC TGT GGT CAG GTG TGG AAG ATG CGG TTC CGG AAG ACA
       CCG TCA CCA TGG ACA CCA GTC CAC ACC TTC TAC GCC AAG GCC TTC TGT
       Gly Ser Gly Thr Cys Gly Gln Val Trp Lys Met Arg Phe Arg Lys Thr>

340           350           360           370           380
       *             *             *             *             *
       GGC CAC ATC ATT GCT GTT AAG CAA ATG CGG CGC TCT GGG AAC AAG GAA
       CCG GTG TAG TAA CGA CAA TTC GTT TAC GCC GCG AGA CCC TTG TTC CTT
       Gly His Ile Ile Ala Val Lys Gln Met Arg Arg Ser Gly Asn Lys Glu>

390           400           410           420           430
               *             *             *             *             *
       GAG AAT AAG CGC ATT TTG ATG GAC CTG GAT GTA GTA CTC AAG AGC CAT
       CTC TTA TTC GCG TAA AAC TAC CTG GAC CTA CAT CAT GAG TTC TCG GTA
       Glu Asn Lys Arg Ile Leu Met Asp Leu Asp Val Val Leu Lys Ser His>
```

FIG. 11A

MKK7b

```
         440            450            460            470            480
          .              .              .              .              .
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

490            500            510            520            530
          .              .              .              .              .
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

540            550            560            570
          .              .              .              .
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

580          590            600            610            620
  .           .              .              .              .
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

630            640            650            660            670
          .              .              .              .              .
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

680            690            700            710            720
          .              .              .              .              .
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

730            740            750            760            770
          .              .              .              .              .
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

780            790            800            810
          .              .              .              .
GAG CGC ATC GAC CCT CCA GAT CCC ACC AAG CCT GAC TAT GAC ATC CGA
CTC GCG TAG CTG GGA GGT CTA GGG TGG TTC GGA CTG ATA CTG TAG GCT
Glu Arg Ile Asp Pro Pro Asp Pro Thr Lys Pro Asp Tyr Asp Ile Arg>
```

FIG. 11B

MKK7b

```
     820           830           840           850           860
      •             •             •             •             •
GCT GAT GTG TGG AGC CTG GGC ATC TCA CTG GTG GAG CTG GCA ACA GGA
CGA CTA CAC ACC TCG GAC CCG TAG AGT GAC CAC CTC GAC CGT TGT CCT
Ala Asp Val Trp Ser Leu Gly Ile Ser Leu Val Glu Leu Ala Thr Gly>

870           880           890           900           910
      •             •             •             •             •
CAG TTC CCC TAT AAG AAC TGC AAG ACG GAC TTT GAG GTC CTC ACC AAA
GTC AAG GGG ATA TTC TTG ACG TTC TGC CTG AAA CTC CAG GAG TGG TTT
Gln Phe Pro Tyr Lys Asn Cys Lys Thr Asp Phe Glu Val Leu Thr Lys>

920           930           940           950           960
      •             •             •             •             •
GTC CTA CAG GAA GAG CCC CCA CTC CTG CCT GGT CAC ATG GGC TTC TCA
CAG GAT GTC CTT CTC GGG GGT GAG GAC GGA CCA GTG TAC CCG AAG AGT
Val Leu Gln Glu Glu Pro Pro Leu Leu Pro Gly His Met Gly Phe Ser>

970           980           990           1000          1010
      •             •             •             •             •
GGG GAC TTC CAG TCA TTT GTC AAA GAC TGC CTT ACT AAA GAT CAC AGG
CCC CTG AAG GTC AGT AAA CAG TTT CTG ACG GAA TGA TTT CTA GTG TCC
Gly Asp Phe Gln Ser Phe Val Lys Asp Cys Leu Thr Lys Asp His Arg>

1020          1030          1040          1050
      •             •             •             •
AAG AGA CCA AAG TAT AAT AAG CTA CTT GAA CAC AGC TTC ATC AAG CAC
TTC TCT GGT TTC ATA TTA TTC GAT GAA CTT GTG TCG AAG TAG TTC GTG
Lys Arg Pro Lys Tyr Asn Lys Leu Leu Glu His Ser Phe Ile Lys His>

1060         1070          1080          1090          1100
  •           •             •             •             •
TAT GAG ATA CTC GAG GTG GAT GTC GCG TCC TGG TTT AAG GAT GTC ATG
ATA CTC TAT GAG CTC CAC CTA CAG CGC AGG ACC AAA TTC CTA CAG TAC
Tyr Glu Ile Leu Glu Val Asp Val Ala Ser Trp Phe Lys Asp Val Met>

1110          1120          1130          1140          1150
      •             •             •             •             •
GCG AAG ACC GAG TCC CCA AGG ACT AGT GGA GTC CTG AGT CAG CAC CAT
CGC TTC TGG CTC AGG GGT TCC TGA TCA CCT CAG GAC TCA GTC GTG GTA
Ala Lys Thr Glu Ser Pro Arg Thr Ser Gly Val Leu Ser Gln His His>

1160          1170          1180          1190          1200          1210
      •             •             •             •             •             •
CTG CCC TTC TTC AGG T AGCCTCATGG CAGCGGCCAG CCCCGCAGGG GCCCCGGGCC
GAC GGG AAG AAG TCC A TCGGAGTACC GTCGCCGGTC GGGGCGTCCC CGGGGCCCGG
Leu Pro Phe Phe Arg> (SEQ ID NO: 20)

1220       1230       1240       1250       1260       1270
         •          •          •          •          •          •
      ACGGCCACCG ACCCCCCCCC CAACCTGGCC AACCCAGCTG CCCATCAGGG GACCTGGGAC
      TGCCGGTGGC TGGGGGGGGG GTTGGACCGG TTGGGTCGAC GGGTAGTCCC CTGGACCCTG 1280       1290       1300       1310       1320       1330
         •          •          •          •          •          •
      CTGGACGACT GCCAAGGACT GAGGACAGAA AGTAGGGGGT TCCCATCCAG CTCTGACTCC
      GACCTGCTGA CGGTTCCTGA CTCCTGTCTT TCATCCCCCA AGGGTAGGTC GAGACTGAGG
```

FIG. 11C

MKK7b

```
        1340       1350       1360       1370       1380       1390
          *          *          *          *          *          *
   CTGCCTACCA GCTGTGGACA AAAGGGCATG CTGGTTCCTA ATCCCTCCCA CTCTGGGGTC
   GACGGATGGT CGACACCTGT TTTCCCGTAC GACCAAGGAT TAGGGAGGGT GAGACCCCAG 1400       1410       1420       1430       1440       1450
          *          *          *          *          *          *
   AGCCAGCAGT GTGAGCCCCA TCCCACCCCG ACAGACACTG TGAACGGAAG ACAGCAAAAA
   TCGGTCGTCA CACTCGGGGT AGGGTGGGGC TGTCTGTGAC ACTTGCCTTC TGTCGTTTTT

1460
          *
   AAAAAAAAAA AAAAA    (SEQ ID NO: 19)
   TTTTTTTTTT TTTTT
```

FIG. 11D

Human MKK7
Sequence Range: 1 to 843

```
              10         20         30         40         50         60
               *          *          *          *          *          *
     TGTTTGTCTG CCGGACTGAC GGGCGGCCGG GCGGTGCGCG GCGGCGGTGG CGGCGGGGAA
     ACAAACAGAC GGCCTGACTG CCCGCCGGCC CGCCACGCGC CGCCGCCACC GCCGCCCCTT 70         80         90        100
               *          *          *          *
   G ATG GCG GCG TCC TCC CTG GAA CAG AAG CTG TCC CGC CTG GAA GCA AAG
   C TAC CGC CGC AGG AGG GAC CTT GTC TTC GAC AGG GCG GAC CTT CGT TTC
     Met Ala Ala Ser Ser Leu Glu Gln Lys Leu Ser Arg Leu Glu Ala Lys>

110        120        130        140        150
      *          *          *          *          *
   CTG AAG CAG GAG AAC CGG GAG GCC CGG CGG AGG ATC GAC CTC AAC CTG
   GAC TTC GTC CTC TTG GCC CTC CGG GCC GCC TCC TAG CTG GAG TTG GAC
   Leu Lys Gln Glu Asn Arg Glu Ala Arg Arg Arg Ile Asp Leu Asn Leu>

160        170        180        190        200
        *          *          *          *          *
   GAT ATC AGC CCC CAG CGG CCC AGG CCC ACC CTG CAG CTC CCG CTG GCC
   CTA TAG TCG GGG GTC GCC GGG TCC GGG TGG GAC GTC GAG GGC GAC CGG
   Asp Ile Ser Pro Gln Arg Pro Arg Pro Thr Leu Gln Leu Pro Leu Ala>

210        220        230        240        250
        *          *          *          *          *
   AAC GAT GGG GGC AGC CGC TCG CCA TCC TCA GAG AGC TCC CCG CAG CAC
   TTG CTA CCC CCG TCG GCG AGC GGT AGG AGT CTC TCG AGG GGC GTC GTG
   Asn Asp Gly Gly Ser Arg Ser Pro Ser Ser Glu Ser Ser Pro Gln His>

260        270        280        290        300
           *          *          *          *          *
   CCC ACG CCC CCC GCC CGG CCC CGC CAC ATG CTG GGG CTC CCG TCA ACC
   GGG TGC GGG GGG CGG GCC GGG GCG GTG TAC GAC CCC GAG GGC AGT TGG
   Pro Thr Pro Pro Ala Arg Pro Arg His Met Leu Gly Leu Pro Ser Thr>

310        320        330        340
           *          *          *          *
   CTG TTC ACA CCC CGC AGC ATG GAG AGC ATT GAG ATT GAC CAG AAG CTG
   GAC AAG TGT GGG GCG TCG TAC CTC TCG TAA CTC TAA CTG GTC TTC GAC
   Leu Phe Thr Pro Arg Ser Met Glu Ser Ile Glu Ile Asp Gln Lys Leu>

350        360        370        380        390
    *          *          *          *          *
   CAG GAG ATC ATG AAG CAG ACG GGC TAC CTG ACC ATC GGG GGC CAG CGC
   GTC CTC TAG TAC TTC GTC TGC CCG ATG GAC TGG TAG CCC CCG GTC GCG
   Gln Glu Ile Met Lys Gln Thr Gly Tyr Leu Thr Ile Gly Gly Gln Arg>

400        410        420        430        440
    *          *          *          *          *
   TAC CAG GCA GAA ATC AAC GAC CTG GAG AAC TTG GGC GAG ATG GGC AGC
   ATG GTC CGT CTT TAG TTG CTG GAC CTC TTG AAC CCG CTC TAC CCG TCG
   Tyr Gln Ala Glu Ile Asn Asp Leu Glu Asn Leu Gly Glu Met Gly Ser>
```

FIG. 12A

Human MKK7

```
        450         460         470         480         490
         *           *           *           *           *
GGC ACC TGC GGC CAG GTG TGG AAG ATG CGC TTC CGG AAG ACC GGC CAC
CCG TGG ACG CCG GTC CAC ACC TTC TAC GCG AAG GCC TTC TGG CCG GTG
Gly Thr Cys Gly Gln Val Trp Lys Met Arg Phe Arg Lys Thr Gly His>

500         510         520         530         540
         *           *           *           *           *
GTC ATT GCC GTT AAG CAA ATG CGG CGC TCC GGG AAC AAG GAG GAG AAC
CAG TAA CGG CAA TTC GTT TAC GCC GCG AGG CCC TTG TTC CTC CTC TTG
Val Ile Ala Val Lys Gln Met Arg Arg Ser Gly Asn Lys Glu Glu Asn>

550         560         570         580
         *           *           *           *
AAG CGC ATC CTC ATG GAC CTG GAT GTG GTG CTG AAG AGC CAC GAC TGC
TTC GCG TAG GAG TAC CTG GAC CTA CAC CAC GAC TTC TCG GTG CTG ACG
Lys Arg Ile Leu Met Asp Leu Asp Val Val Leu Lys Ser His Asp Cys>

590         600         610         620         630
   *           *           *           *           *
CCC TAC ATC GTG CAG TGC TTT GGG ACG TTC ATC ACC AAC ACG GAC GTC
GGG ATG TAG CAC GTC ACG AAA CCC TGC AAG TAG TGG TTG TGC CTG CAG
Pro Tyr Ile Val Gln Cys Phe Gly Thr Phe Ile Thr Asn Thr Asp Val>

640         650         660         670         680
  *           *           *           *           *
TTC ATC GCC ATG GAG CTC ATG GGC ACC TGC GCT GAG AAG CTC AAG AAG
AAG TAG CGG TAC CTC GAG TAC CCG TGG ACG CGA CTC TTC GAG TTC TTC
Phe Ile Ala Met Glu Leu Met Gly Thr Cys Ala Glu Lys Leu Lys Lys>

690         700         710         720         730
        *           *           *           *           *
CGG ATG CAG GGC CCC ATC CCC GAG CGC ATT CTG GGC AAG ATG ACA GTG
GCC TAC GTC CCG GGG TAG GGG CTC GCG TAA GAC CCG TTC TAC TGT CAC
Arg Met Gln Gly Pro Ile Pro Glu Arg Ile Leu Gly Lys Met Thr Val>

740         750         760         770         780
         *           *           *           *           *
GCG ATT GTG AAG GCG CTG TAC TAC CTG AAG GAG AAG CAC GGT GTC ATC
CGC TAA CAC TTC CGC GAC ATG ATG GAC TTC CTC TTC GTG CCA CAG TAG
Ala Ile Val Lys Ala Leu Tyr Tyr Leu Lys Glu Lys His Gly Val Ile>

790         800         810         820
         *           *           *           *
CAC CGC GAC GTC AAG CCC TCC AAC ATC CTG CTG GAC GAG CGG GGC CAG
GTG GCG CTG CAG TTC GGG AGG TTG TAG GAC GAC CTG CTC GCC CCG GTC
His Arg Asp Val Lys Pro Ser Asn Ile Leu Leu Asp Glu Arg Gly Gln>

830         840
 *           *
ATC AAG CTC TGC GA (SEQ ID NO: 25)
TAG TTC GAG ACG CT
Ile Lys Leu Cys> (SEQ ID NO: 26)
```

FIG. 12B

Mouse MKK7c
Sequence Range: 1 to 1643

```
                10         20         30         40         50         60
         .     *     .     *     .     *     .     *     .     *     .     *
         AGCGCAGGCG CAGTGCGGTG TTTGTCTACC CCGGACTGAC GGGTGGCCTG GCGGTGAGCG
         TCGCGTCCGC GTCACGCCAC AAACAGATGG GGCCTGACTG CCCACCGGAC CGCCACTCGC 70         80             90           100          110
         .     *     .     *         .     *       .     *     .     *
         GCGGCAGCGG CGGCGGGGAA G ATG GCG GCG TCC TCC CTG GAG CAG AAG CTG
         CGCCGTCGCC GCCGCCCCTT C TAC CGC CGC AGG AGG GAC CTC GTC TTC GAC
                                Met Ala Ala Ser Ser Leu Glu Gln Lys Leu>

120          130          140          150
         .     *      .     *      .     *      .     *      .     *
         TCC CGC CTG GAA GCC AAG CTG AAG CAG GAG AAC CGT GAG GCC CGC AGG
         AGG GCG GAC CTT CGG TTC GAC TTC GTC CTC TTG GCA CTC CGG GCG TCC
         Ser Arg Leu Glu Ala Lys Leu Lys Gln Glu Asn Arg Glu Ala Arg Arg>

160          170          180          190          200
         .     *      .     *      .     *      .     *      .     *
         AGG ATC GAC CTC AAC TTG GAT ATC AGC CCA CAG CGG CCC AGG CCC ACC
         TCC TAG CTG GAG TTG AAC CTA TAG TCG GGT GTC GCC GGG TCC GGG TGG
         Arg Ile Asp Leu Asn Leu Asp Ile Ser Pro Gln Arg Pro Arg Pro Thr>

210          220          230          240          250
         *      .     *      .     *      .     *      .     *      .
         CTG CAA CTC CCA CTG GCC AAC GAT GGG GGC AGC CGC TCA CCA TCC TCA
         GAC GTT GAG GGT GAC CGG TTG CTA CCC CCG TCG GCG AGT GGT AGG AGT
         Leu Gln Leu Pro Leu Ala Asn Asp Gly Gly Ser Arg Ser Pro Ser Ser>

260          270          280          290          300
         .     *      .     *      .     *      .     *      .     *
         GAG AGC TCC CCA CAG CAC CCT ACA CCC CCC ACC CGG CCC CGC CAC ATG
         CTC TCG AGG GGT GTC GTG GGA TGT GGG GGG TGG GCC GGG GCG GTG TAC
         Glu Ser Ser Pro Gln His Pro Thr Pro Pro Thr Arg Pro Arg His Met>

310          320          330          340          350
            .     *     .     *     .     *     .     *     .     *
            CTG GGG CTC CCA TCA ACC TTG TTC ACA CCG CGC AGT ATG GAG AGC ATC
            GAC CCC GAG GGT AGT TGG AAC AAG TGT GGC GCG TCA TAC CTC TCG TAG
            Leu Gly Leu Pro Ser Thr Leu Phe Thr Pro Arg Ser Met Glu Ser Ile>

360          370          380          390
                .     *      .     *      .     *      .     *      .
                GAG ATT GAC CAG AAG CTG CAG GAG ATC ATG AAG CAG ACA GGG TAC CTG
                CTC TAA CTG GTC TTC GAC GTC CTC TAG TAC TTC GTC TGT CCC ATG GAC
                Glu Ile Asp Gln Lys Leu Gln Glu Ile Met Lys Gln Thr Gly Tyr Leu>

400          410          420          430          440
         *      .     *      .     *      .     *      .     *      .
         ACT ATC GGG GGC CAG CGT TAT CAG GCA GAA ATC AAT GAC TTG GAG AAC
         TGA TAG CCC CCG GTC GCA ATA GTC CGT CTT TAG TTA CTG AAC CTC TTG
         Thr Ile Gly Gly Gln Arg Tyr Gln Ala Glu Ile Asn Asp Leu Glu Asn>
```

FIG. 13A

Mouse MKK7c

```
         450           460           470           480           490
          *             *             *             *             *      *
    TTG GGT GAG ATG GGC AGT GGT ACC TGT GGT CAG GTG TGG AAG ATG CGG
    AAC CCA CTC TAC CCG TCA CCA TGG ACA CCA GTC CAC ACC TTC TAC GCC
    Leu Gly Glu Met Gly Ser Gly Thr Cys Gly Gln Val Trp Lys Met Arg>

500           510           520           530           540
               *             *             *             *             *
    TTC CGG AAG ACA GGC CAC ATC ATT GCT GTT AAG CAA ATG CGG CGC TCT
    AAG GCC TTC TGT CCG GTG TAG TAA CGA CAA TTC GTT TAC GCC GCG AGA
    Phe Arg Lys Thr Gly His Ile Ile Ala Val Lys Gln Met Arg Arg Ser>

550           560           570           580           590
                     *    *        *    *        *    *        *    *        *
    GGG AAC AAG GAA GAG AAT AAG CGC ATT TTG ATG GAC CTG GAT GTA GTA
    CCC TTG TTC CTT CTC TTA TTC GCG TAA AAC TAC CTG GAC CTA CAT CAT
    Gly Asn Lys Glu Glu Asn Lys Arg Ile Leu Met Asp Leu Asp Val Val>

600           610           620           630
                 *             *    *        *    *        *    *
    CTC AAG AGC CAT GAC TGC CCT TAC ATC GTT CAG TGC TTT GGC ACC TTC
    GAG TTC TCG GTA CTG ACG GGA ATG TAG CAA GTC ACG AAA CCG TGG AAG
    Leu Lys Ser His Asp Cys Pro Tyr Ile Val Gln Cys Phe Gly Thr Phe>

640           650           660           670           680
  *    *        *    *        *    *        *    *        *    *
    ATC ACC AAC ACA GAC GTC TTT ATT GCC ATG GAG CTC ATG GGC ACA TGT
    TAG TGG TTG TGT CTG CAG AAA TAA CGG TAC CTC GAG TAC CCG TGT ACA
    Ile Thr Asn Thr Asp Val Phe Ile Ala Met Glu Leu Met Gly Thr Cys>

690           700           710           720           730
          *             *             *             *             *      *
    GCA GAG AAG CTG AAG AAA CGA ATG CAG GGC CCC ATT CCA GAG CGA ATC
    CGT CTC TTC GAC TTC TTT GCT TAC GTC CCG GGG TAA GGT CTC GCT TAG
    Ala Glu Lys Leu Lys Lys Arg Met Gln Gly Pro Ile Pro Glu Arg Ile>

740           750           760           770           780
          *             *             *    *        *    *        *
    CTG GGC AAG ATG ACT GTG GCG ATT GTG AAA GCA CTG TAC TAT CTG AAG
    GAC CCG TTC TAC TGA CAC CGC TAA CAC TTT CGT GAC ATG ATA GAC TTC
    Leu Gly Lys Met Thr Val Ala Ile Val Lys Ala Leu Tyr Tyr Leu Lys>

790           800           810           820           830
               *    *        *    *        *    *        *    *        *
    GAG AAG CAT GGC GTC ATC CAT CGC GAT GTC AAA CCC TCC AAC ATC CTG
    CTC TTC GTA CCG CAG TAG GTA GCG CTA CAG TTT GGG AGG TTG TAG GAC
    Glu Lys His Gly Val Ile His Arg Asp Val Lys Pro Ser Asn Ile Leu>

840           850           860           870
                     *    *        *    *        *    *        *
    CTA GAT GAG CGG GGC CAG ATC AAG CTC TGT GAC TTT GGC ATC AGT GGC
    GAT CTA CTC GCC CCG GTC TAG TTC GAG ACA CTG AAA CCG TAG TCA CCG
    Leu Asp Glu Arg Gly Gln Ile Lys Leu Cys Asp Phe Gly Ile Ser Gly>
```

FIG. 13B

Mouse MKK7c

```
       880           890           900           910           920
        *             *             *             *             *
  CGC CTT GTT GAC TCC AAA GCC AAA ACA CGG AGT GCT GGC TGT GCT GCC
  GCG GAA CAA CTG AGG TTT CGG TTT TGT GCC TCA CGA CCG ACA CGA CGG
  Arg Leu Val Asp Ser Lys Ala Lys Thr Arg Ser Ala Gly Cys Ala Ala>

930           940           950           960           970
        *             *             *             *             *
  TAT ATG GCT CCC GAG CGC ATC GAC CCT CCA GAT CCC ACC AAG CCT GAC
  ATA TAC CGA GGG CTC GCG TAG CTG GGA GGT CTA GGG TGG TTC GGA CTG
  Tyr Met Ala Pro Glu Arg Ile Asp Pro Pro Asp Pro Thr Lys Pro Asp>

980           990          1000          1010          1020
        *             *             *             *             *
  TAT GAC ATC CGA GCT GAT GTG TGG AGC CTG GGC ATC TCA CTG GTG GAG
  ATA CTG TAG GCT CGA CTA CAC ACC TCG GAC CCG TAG AGT GAC CAC CTC
  Tyr Asp Ile Arg Ala Asp Val Trp Ser Leu Gly Ile Ser Leu Val Glu>

1030          1040          1050          1060          1070
        *             *             *             *             *
  CTG GCA ACA GGA CAG TTC CCC TAT AAG AAC TGC AAG ACG GAC TTT GAG
  GAC CGT TGT CCT GTC AAG GGG ATA TTC TTG ACG TTC TGC CTG AAA CTC
  Leu Ala Thr Gly Gln Phe Pro Tyr Lys Asn Cys Lys Thr Asp Phe Glu>

1080          1090          1100          1110
        *             *             *             *             *
  GTC CTC ACC AAA GTC CTA CAG GAA GAG CCC CCA CTC CTG CCT GGT CAC
  CAG GAG TGG TTT CAG GAT GTC CTT CTC GGG GGT GAG GAC GGA CCA GTG
  Val Leu Thr Lys Val Leu Gln Glu Glu Pro Pro Leu Leu Pro Gly His>

1120          1130          1140          1150          1160
   *             *             *             *             *
  ATG GGC TTC TCA GGG GAC TTC CAG TCA TTT GTC AAA GAC TGC CTT ACT
  TAC CCG AAG AGT CCC CTG AAG GTC AGT AAA CAG TTT CTG ACG GAA TGA
  Met Gly Phe Ser Gly Asp Phe Gln Ser Phe Val Lys Asp Cys Leu Thr>

1170          1180          1190          1200          1210
        *             *             *             *             *
  AAA GAT CAC AGG AAG AGA CCA AAG TAT AAT AAG CTA CTT GAA CAC AGC
  TTT CTA GTG TCC TTC TCT GGT TTC ATA TTA TTC GAT GAA CTT GTG TCG
  Lys Asp His Arg Lys Arg Pro Lys Tyr Asn Lys Leu Leu Glu His Ser>

1220          1230          1240          1250          1260
        *             *             *             *             *
  TTC ATC AAG CAC TAT GAG ATA CTC GAG GTG GAT GTC GCG TCC TGG TTT
  AAG TAG TTC GTG ATA CTC TAT GAG CTC CAC CTA CAG CGC AGG ACC AAA
  Phe Ile Lys His Tyr Glu Ile Leu Glu Val Asp Val Ala Ser Trp Phe>

1270          1280          1290          1300          1310
        *             *             *             *             *
  AAG GAT GTC ATG GCG AAG ACC GAG TCC CCA AGG ACT AGT GGA GTC CTG
  TTC CTA CAG TAC CGC TTC TGG CTC AGG GGT TCC TGA TCA CCT CAG GAC
```

FIG. 13C

Mouse MKK7c

Lys Asp Val Met Ala Lys Thr Glu Ser Pro Arg Thr Ser Gly Val Leu>

```
          1320        1330        1340        1350        1360
           *  *        *  *        *  *        *  *        *  *
AGT CAG CAC CAT CTG CCC TTC TTC AGG TA GCCTCATGGC AGCGGCCAGC
TCA GTC GTG GTA GAC GGG AAG AAG TCC AT CGGAGTACCG TCGCCGGTCG
Ser Gln His His Leu Pro Phe Phe Arg>  (SEQ ID NO: 28)

1370        1380        1390        1400        1410        1420
           *  *        *  *        *  *        *  *        *  *        *  *
CCCGCAGGGG  CCCCGGGCCA  CGGCCACCGA  CCCCCCCCCC  AACCTGGCCA  ACCCAGCTGC
GGGCGTCCCC  GGGGCCCGGT  GCCGGTGGCT  GGGGGGGGGG  TTGGACCGGT  TGGGTCGACG 1430        1440        1450        1460        1470        1480
           *  *        *  *        *  *        *  *        *  *        *  *
CCATCAGGGG  ACCTGGGACC  TGGACGACTG  CCAAGGACTG  AGGACAGAAA  GTAGGGGGTT
GGTAGTCCCC  TGGACCCTGG  ACCTGCTGAC  GGTTCCTGAC  TCCTGTCTTT  CATCCCCCAA 1490        1500        1510        1520        1530        1540
           *  *        *  *        *  *        *  *        *  *        *  *
CCCATCCAGC  TCTGACTCCC  TGCCTACCAG  CTGTGGACAA  AAGGGCATGC  TGGTTCCTAA
GGGTAGGTCG  AGACTGAGGG  ACGGATGGTC  GACACCTGTT  TTCCCGTACG  ACCAAGGATT 1550        1560        1570        1580        1590        1600
           *  *        *  *        *  *        *  *        *  *        *  *
TCCCTCCCAC  TCTGGGGTCA  GCCAGCAGTG  TGAGCCCCAT  CCCACCCCGA  CAGACACTGT
AGGGAGGGTG  AGACCCCAGT  CGGTCGTCAC  ACTCGGGGTA  GGGTGGGGCT  GTCTGTGACA 1610        1620        1630        1640
           *  *        *  *        *  *        *  *
GAACGGAAGA  CAGCAGGCCA  AAAAAAAAAA  AAAAAAAAAA  AAA  (SEQ ID NO: 27)
CTTGCCTTCT  GTCGTCCGGT  TTTTTTTTTT  TTTTTTTTTT  TTT
```

FIG. 13D

MKK7d
Sequence Range: 1 to 1578

```
            10         20         30         40         50         60
             *          *          *          *          *          *
      GGAAAGGCAG CCTCCTGTAG GTGAAAATTC TGTTCACTAC CTGGCCACCT GGCCTGACTG
      CCTTTCCGTC GGAGGACATC CACTTTTAAG ACAAGTGATG GACCGGTGGA CCGGACTGAC 70         80         90        100        110        120
             *          *          *          *          *          *
      ACCTTCACAG CTTGATCATC TTCCTGAAGA GGCATTCAGG ATTCCCTCCA TCCCTACCCC
      TGGAAGTGTC GAACTAGTAG AAGGACTTCT CCGTAAGTCC TAAGGGAGGT AGGGATGGGG 130        140        150        160        170        180
             *          *          *          *          *          *
      TTCTGGACAA AGTCTTCCAC GTTTCCTTCC TGGGAGTTTC TTCCAGGAAC TGGAGATACC
      AAGACCTGTT TCAGAAGGTG CAAAGGAAGG ACCCTCAAAG AAGGTCCTTG ACCTCTATGG 190        200        210        220        230        240
             *          *          *          *          *          *
      CAGAGCCCTG CAACTCCCAC TGGCCAACGA TGGGGGCAGC CGCTCACCAT CCTCAGAGAG
      GTCTCGGGAC GTTGAGGGTG ACCGGTTGCT ACCCCCGTCG GCGAGTGGTA GGAGTCTCTC 250        260        270        280        290
             *          *          *          *          *          *
      CTCCCCACAG CACCCTACAC CCCCCACCCG GCCCCGCCAC ATG CTG GGG CTC CCA
      GAGGGGTGTC GTGGGATGTG GGGGGTGGGC CGGGGCGGTG TAC GAC CCC GAG GGT
                                                 Met Leu Gly Leu Pro>

300         310         320         330         340
             *           *           *           *           *
      TCA ACC TTG TTC ACA CCG CGC AGT ATG GAG AGC ATC GAG ATT GAC CAG
      AGT TGG AAC AAG TGT GGC GCG TCA TAC CTC TCG TAG CTC TAA CTG GTC
      Ser Thr Leu Phe Thr Pro Arg Ser Met Glu Ser Ile Glu Ile Asp Gln>

350         360         370         380         390
             *           *           *           *           *
      AAG CTG CAG GAG ATC ATG AAG CAG ACA GGG TAC CTG ACT ATC GGG GGC
      TTC GAC GTC CTC TAG TAC TTC GTC TGT CCC ATG GAC TGA TAG CCC CCG
      Lys Leu Gln Glu Ile Met Lys Gln Thr Gly Tyr Leu Thr Ile Gly Gly>

400         410         420         430
             *           *           *           *           *
      CAG CGT TAT CAG GCA GAA ATC AAT GAC TTG GAG AAC TTG GGT GAG ATG
      GTC GCA ATA GTC CGT CTT TAG TTA CTG AAC CTC TTG AAC CCA CTC TAC
      Gln Arg Tyr Gln Ala Glu Ile Asn Asp Leu Glu Asn Leu Gly Glu Met>

440        450        460        470        480
      *          *          *          *          *          *
      GGC AGT GGT ACC TGT GGT CAG GTG TGG AAG ATG CGG TTC CGG AAG ACA
      CCG TCA CCA TGG ACA CCA GTC CAC ACC TTC TAC GCC AAG GCC TTC TGT
      Gly Ser Gly Thr Cys Gly Gln Val Trp Lys Met Arg Phe Arg Lys Thr>

490        500        510        520        530
             *          *          *          *          *          *
      GGC CAC ATC ATT GCT GTT AAG CAA ATG CGG CGC TCT GGG AAC AAG GAA
      CCG GTG TAG TAA CGA CAA TTC GTT TAC GCC GCG AGA CCC TTG TTC CTT
      Gly His Ile Ile Ala Val Lys Gln Met Arg Arg Ser Gly Asn Lys Glu>
```

FIG. 14A

MKK7d

```
       540           550           560           570           580
        *    *        *    *        *    *        *    *        *    *
GAG AAT AAG CGC ATT TTG ATG GAC CTG GAT GTA GTA CTC AAG AGC CAT
CTC TTA TTC GCG TAA AAC TAC CTG GAC CTA CAT CAT GAG TTC TCG GTA
Glu Asn Lys Arg Ile Leu Met Asp Leu Asp Val Val Leu Lys Ser His>

590           600           610           620           630
         *    *        *    *        *    *        *    *        *
GAC TGC CCT TAC ATC GTT CAG TGC TTT GGC ACC TTC ATC ACC AAC ACA
CTG ACG GGA ATG TAG CAA GTC ACG AAA CCG TGG AAG TAG TGG TTG TGT
Asp Cys Pro Tyr Ile Val Gln Cys Phe Gly Thr Phe Ile Thr Asn Thr>

640           650           660           670
         *    *        *    *        *    *        *    *
GAC GTC TTT ATT GCC ATG GAG CTC ATG GGC ACA TGT GCA GAG AAG CTG
CTG CAG AAA TAA CGG TAC CTC GAG TAC CCG TGT ACA CGT CTC TTC GAC
Asp Val Phe Ile Ala Met Glu Leu Met Gly Thr Cys Ala Glu Lys Leu>

680           690           700           710           720
   *    *        *    *        *    *        *    *        *    *
AAG AAA CGA ATG CAG GGC CCC ATT CCA GAG CGA ATC CTG GGC AAG ATG
TTC TTT GCT TAC GTC CCG GGG TAA GGT CTC GCT TAG GAC CCG TTC TAC
Lys Lys Arg Met Gln Gly Pro Ile Pro Glu Arg Ile Leu Gly Lys Met>

730           740           750           760           770
   *    *        *    *        *    *        *    *        *    *
ACT GTG GCG ATT GTG AAA GCA CTG TAC TAT CTG AAG GAG AAG CAT GGC
TGA CAC CGC TAA CAC TTT CGT GAC ATG ATA GAC TTC CTC TTC GTA CCG
Thr Val Ala Ile Val Lys Ala Leu Tyr Tyr Leu Lys Glu Lys His Gly>

780           790           800           810           820
        *    *        *    *        *    *        *    *        *
GTC ATC CAT CGC GAT GTC AAA CCC TCC AAC ATC CTG CTA GAT GAG CGG
CAG TAG GTA GCG CTA CAG TTT GGG AGG TTG TAG GAC GAT CTA CTC GCC
Val Ile His Arg Asp Val Lys Pro Ser Asn Ile Leu Leu Asp Glu Arg>

830           840           850           860           870
         *    *        *    *        *    *        *    *        *
GGC CAG ATC AAG CTC TGT GAC TTT GGC ATC AGT GGC CGC CTT GTT GAC
CCG GTC TAG TTC GAG ACA CTG AAA CCG TAG TCA CCG GCG GAA CAA CTG
Gly Gln Ile Lys Leu Cys Asp Phe Gly Ile Ser Gly Arg Leu Val Asp>

880           890           900           910
         *    *        *    *        *    *        *    *
TCC AAA GCC AAA ACA CGG AGT GCT GGC TGT GCT GCC TAT ATG GCT CCC
AGG TTT CGG TTT TGT GCC TCA CGA CCG ACA CGA CGG ATA TAC CGA GGG
Ser Lys Ala Lys Thr Arg Ser Ala Gly Cys Ala Ala Tyr Met Ala Pro>

920           930           940           950           960
   *    *        *    *        *    *        *    *        *    *
GAG CGC ATC GAC CCT CCA GAT CCC ACC AAG CCT GAC TAT GAC ATC CGA
CTC GCG TAG CTG GGA GGT CTA GGG TGG TTC GGA CTG ATA CTG TAG GCT
```

FIG. 14B

MKK7d
Glu Arg Ile Asp Pro Pro Asp Pro Thr Lys Pro Asp Tyr Asp Ile Arg>

```
          970           980           990          1000          1010
            *             *             *             *             *
     *      *      *      *      *      *      *      *      *      *
    GCT GAT GTG TGG AGC CTG GGC ATC TCA CTG GTG GAG CTG GCA ACA GGA
    CGA CTA CAC ACC TCG GAC CCG TAG AGT GAC CAC CTC GAC CGT TGT CCT
    Ala Asp Val Trp Ser Leu Gly Ile Ser Leu Val Glu Leu Ala Thr Gly>

1020          1030          1040          1050          1060
            *             *             *             *             *
     *      *      *      *      *      *      *      *      *      *
    CAG TTC CCC TAT AAG AAC TGC AAG ACG GAC TTT GAG GTC CTC ACC AAA
    GTC AAG GGG ATA TTC TTG ACG TTC TGC CTG AAA CTC CAG GAG TGG TTT
    Gln Phe Pro Tyr Lys Asn Cys Lys Thr Asp Phe Glu Val Leu Thr Lys>

1070          1080          1090          1100          1110
                *             *             *             *             *
         *      *      *      *      *      *      *      *      *      *
        GTC CTA CAG GAA GAG CCC CCA CTC CTG CCT GGT CAC ATG GGC TTC TCA
        CAG GAT GTC CTT CTC GGG GGT GAG GAC GGA CCA GTG TAC CCG AAG AGT
        Val Leu Gln Glu Glu Pro Pro Leu Leu Pro Gly His Met Gly Phe Ser>

1120          1130          1140          1150
                     *             *             *             *
          *      *      *      *      *      *      *      *      *
         GGG GAC TTC CAG TCA TTT GTC AAA GAC TGC CTT ACT AAA GAT CAC AGG
         CCC CTG AAG GTC AGT AAA CAG TTT CTG ACG GAA TGA TTT CTA GTG TCC
         Gly Asp Phe Gln Ser Phe Val Lys Asp Cys Leu Thr Lys Asp His Arg>

1160          1170          1180          1190          1200
   *             *             *             *             *
   *      *      *      *      *      *      *      *      *      *
  AAG AGA CCA AAG TAT AAT AAG CTA CTT GAA CAC AGC TTC ATC ATC AAG
  TTC TCT GGT TTC ATA TTA TTC GAT GAA CTT GTG TCG AAG TAG TAG TTC
  Lys Arg Pro Lys Tyr Asn Lys Leu Leu Glu His Ser Phe Ile Ile Lys>

1210          1220          1230          1240          1250
       *             *             *             *             *
       *      *      *      *      *      *      *      *      *      *
      CAC TAT GAG ATA CTC GAG GTG GAT GTC GCG TCC TGG TTT AAG GAT GTC
      GTG ATA CTC TAT GAG CTC CAC CTA CAG CGC AGG ACC AAA TTC CTA CAG
      His Tyr Glu Ile Leu Glu Val Asp Val Ala Ser Trp Phe Lys Asp Val>

1260          1270          1280          1290          1300
            *             *             *             *             *
     *      *      *      *      *      *      *      *      *      *
    ATG GCG AAG ACC GAG TCC CCA AGG ACT AGT GGA GTC CTG AGT CAG CAC
    TAC CGC TTC TGG CTC AGG GGT TCC TGA TCA CCT CAG GAC TCA GTC GTG
    Met Ala Lys Thr Glu Ser Pro Arg Thr Ser Gly Val Leu Ser Gln His>

1310          1320          1330          1340          1350
                *             *             *             *             *
         *      *      *      *      *      *      *      *      *      *
        CAT CTG CCC TTC TTC AGT GGG AGT CTG GAG GAG TCT CCC ACT TCC CCA
        GTA GAC GGG AAG AAG TCA CCC TCA GAC CTC CTC AGA GGG TGA AGG GGT
        His Leu Pro Phe Phe Ser Gly Ser Leu Glu Glu Ser Pro Thr Ser Pro>

1360          1370          1380          1390
                     *             *             *             *
          *      *      *      *      *      *      *      *      *
         CCT TCT CCC AAG TCC TTC CCT CTG TCA CCA GCC ATC CCT CAG GCC CAG
```

FIG. 14C

MKK7d

```
GGA AGA GGG TTC AGG AAG GGA GAC AGT GGT CGG TAG GGA GTC CGG GTC
Pro Ser Pro Lys Ser Phe Pro Leu Ser Pro Ala Ile Pro Gln Ala Gln>
```

```
         1400        1410        1420        1430        1440        1450
           *           *           *           *           *           *
       GCA GAG TGG GTC TCG GGC AGG TAGGGACCTG GAGTGGCCTG GTCCCACCCT
       CGT CTC ACC CAG AGC CCG TCC ATCCCTGGAC CTCACCGGAC CAGGGTGGGA
       Ala Glu Trp Val Ser Gly Arg> (SEQ ID NO: 30)
```

```
          1460        1470        1480        1490        1500        1510
            *           *           *           *           *           *
       CTGACCTCCT CCTCAGGCCA CCAGTGTTGC CCTCTTCCCT TTTTAAAACA AAATACCCTT
       GACTGGAGGA GGAGTCCGGT GGTCACAACG GGAGAAGGGA AAAATTTTGT TTTATGGGAA
```

```
         1520        1530        1540        1550        1560        1570
           *           *           *           *           *           *
       GTTTGTAAAT CCTTAGACGC TTGAGAATAA AACCCTTCCC TTTTCTTCCG AAAAAAAAAA
       CAAACATTTA GGAATCTGCG AACTCTTATT TTGGGAAGGG AAAAGAAGGC TTTTTTTTTT
```

```
         *
       AAAAAAAA  (SEQ ID NO: 29)
       TTTTTTTT
```

FIG. 14D

MKK7e
Sequence Range: 1 to 1598

```
                10         20         30         40         50         60
                 *          *          *          *          *          *
         AGCGCAGGCG CAGTGCGGTG TTTGTCTACC CCGGACTGAC GGGTGGCCTG GCGGTGAGCG
         TCGCGTCCGC GTCACGCCAC AAACAGATGG GGCCTGACTG CCCACCGGAC CGCCACTCGC 70         80              90         100        110
                 *          *               *          *          *
         GCGGCAGCGG CGGCGGGGAA G ATG GCG GCG TCC TCC CTG GAG CAG AAG CTG
         CGCCGTCGCC GCCGCCCCTT C TAC CGC CGC AGG AGG GAC CTC GTC TTC GAC
                                 Met Ala Ala Ser Ser Leu Glu Gln Lys Leu>

120            130            140            150
                   *              *              *              *              *
         TCC CGC CTG GAA GCC AAG CTG AAG CAG GAG AAC CGT GAG GCC CGC AGG
         AGG GCG GAC CTT CGG TTC GAC TTC GTC CTC TTG GCA CTC CGG GCG TCC
         Ser Arg Leu Glu Ala Lys Leu Lys Gln Glu Asn Arg Glu Ala Arg Arg>

160        170        180        190        200
        *          *          *          *          *          *
      AGG ATC GAC CTC AAC TTG GAT ATC AGC CCA CAG CGG CCC AGG CCC ACC
      TCC TAG CTG GAG TTG AAC CTA TAG TCG GGT GTC GCC GGG TCC GGG TGG
      Arg Ile Asp Leu Asn Leu Asp Ile Ser Pro Gln Arg Pro Arg Pro Thr>

210        220        230        240        250
             *          *          *          *          *          *
         CTG CAA CTC CCA CTG GCC AAC GAT GGG GGC AGC CGC TCA CCA TCC TCA
         GAC GTT GAG GGT GAC CGG TTG CTA CCC CCG TCG GCG AGT GGT AGG AGT
         Leu Gln Leu Pro Leu Ala Asn Asp Gly Gly Ser Arg Ser Pro Ser Ser>

260        270        280        290        300
             *          *          *          *          *
         GAG AGC TCC CCA CAG CAC CCT ACA CCC CCC ACC CGG CCC CGC CAC ATG
         CTC TCG AGG GGT GTC GTG GGA TGT GGG GGG TGG GCC GGG GCG GTG TAC
         Glu Ser Ser Pro Gln His Pro Thr Pro Pro Thr Arg Pro Arg His Met>

310        320        330        340        350
                 *          *          *          *          *          *
         CTG GGG CTC CCA TCA ACC TTG TTC ACA CCG CGC AGT ATG GAG AGC ATC
         GAC CCC GAG GGT AGT TGG AAC AAG TGT GGC GCG TCA TAC CTC TCG TAG
         Leu Gly Leu Pro Ser Thr Leu Phe Thr Pro Arg Ser Met Glu Ser Ile>

360        370        380        390
                 *          *          *          *          *
         GAG ATT GAC CAG AAG CTG CAG GAG ATC ATG AAG CAG ACA GGG TAC CTG
         CTC TAA CTG GTC TTC GAC GTC CTC TAG TAC TTC GTC TGT CCC ATG GAC
         Glu Ile Asp Gln Lys Leu Gln Glu Ile Met Lys Gln Thr Gly Tyr Leu>

400        410        420        430        440
       *          *          *          *          *          *
     ACT ATC GGG GGC CAG CGT TAT CAG GCA GAA ATC AAT GAC TTG GAG AAC
     TGA TAG CCC CCG GTC GCA ATA GTC CGT CTT TAG TTA CTG AAC CTC TTG
     Thr Ile Gly Gly Gln Arg Tyr Gln Ala Glu Ile Asn Asp Leu Glu Asn>
```

FIG. 15A

Mouse MKK7e

```
     450         460         470         480         490
      *           *           *           *           *
TTG GGT GAG ATG GGC AGT GGT ACC TGT GGT CAG GTG TGG AAG ATG CGG
AAC CCA CTC TAC CCG TCA CCA TGG ACA CCA GTC CAC ACC TTC TAC GCC
Leu Gly Glu Met Gly Ser Gly Thr Cys Gly Gln Val Trp Lys Met Arg>

500         510         520         530         540
      *           *           *           *           *
TTC CGG AAG ACA GGC CAC ATC ATT GCT GTT AAG CAA ATG CGG CGC TCT
AAG GCC TTC TGT CCG GTG TAG TAA CGA CAA TTC GTT TAC GCC GCG AGA
Phe Arg Lys Thr Gly His Ile Ile Ala Val Lys Gln Met Arg Arg Ser>

550         560         570         580         590
      *           *           *           *           *
GGG AAC AAG GAA GAG AAT AAG CGC ATT TTG ATG GAC CTG GAT GTA GTA
CCC TTG TTC CTT CTC TTA TTC GCG TAA AAC TAC CTG GAC CTA CAT CAT
Gly Asn Lys Glu Glu Asn Lys Arg Ile Leu Met Asp Leu Asp Val Val>

600         610         620         630
      *           *           *           *
CTC AAG AGC CAT GAC TGC CCT TAC ATC GTT CAG TGC TTT GGC ACC TTC
GAG TTC TCG GTA CTG ACG GGA ATG TAG CAA GTC ACG AAA CCG TGG AAG
Leu Lys Ser His Asp Cys Pro Tyr Ile Val Gln Cys Phe Gly Thr Phe>

640         650         660         670         680
 *           *           *           *           *
ATC ACC AAC ACA GAC GTC TTT ATT GCC ATG GAG CTC ATG GGC ACA TGT
TAG TGG TTG TGT CTG CAG AAA TAA CGG TAC CTC GAG TAC CCG TGT ACA
Ile Thr Asn Thr Asp Val Phe Ile Ala Met Glu Leu Met Gly Thr Cys>

690         700         710         720         730
      *           *           *           *           *
GCA GAG AAG CTG AAG AAA CGA ATG CAG GGC CCC ATT CCA GAG CGA ATC
CGT CTC TTC GAC TTC TTT GCT TAC GTC CCG GGG TAA GGT CTC GCT TAG
Ala Glu Lys Leu Lys Lys Arg Met Gln Gly Pro Ile Pro Glu Arg Ile>

740         750         760         770         780
      *           *           *           *           *
CTG GGC AAG ATG ACT GTG GCG ATT GTG AAA GCA CTG TAC TAT CTG AAG
GAC CCG TTC TAC TGA CAC CGC TAA CAC TTT CGT GAC ATG ATA GAC TTC
Leu Gly Lys Met Thr Val Ala Ile Val Lys Ala Leu Tyr Tyr Leu Lys>

790         800         810         820         830
      *           *           *           *           *
GAG AAG CAT GGC GTC ATC CAT CGC GAT GTC AAA CCC TCC AAC ATC CTG
CTC TTC GTA CCG CAG TAG GTA GCG CTA CAG TTT GGG AGG TTG TAG GAC
Glu Lys His Gly Val Ile His Arg Asp Val Lys Pro Ser Asn Ile Leu>

840         850         860         870
      *           *           *           *
CTA GAT GAG CGG GGC CAG ATC AAG CTC TGT GAC TTT GGC ATC AGT GGC
GAT CTA CTC GCC CCG GTC TAG TTC GAG ACA CTG AAA CCG TAG TCA CCG
Leu Asp Glu Arg Gly Gln Ile Lys Leu Cys Asp Phe Gly Ile Ser Gly>
```

FIG. 15B

Mouse MKK7e

```
       880            890           900            910           920
        *      *       *      *      *      *       *      *      *      *
       CGC    CTT    GTT    GAC    TCC    AAA    GCC    AAA    ACA    CGG    AGT    GCT    GGC    TGT    GCT    GCC
       GCG    GAA    CAA    CTG    AGG    TTT    CGG    TTT    TGT    GCC    TCA    CGA    CCG    ACA    CGA    CGG
       Arg    Leu    Val    Asp    Ser    Lys    Ala    Lys    Thr    Arg    Ser    Ala    Gly    Cys    Ala    Ala>

930            940           950            960           970
        *      *       *      *      *      *       *      *      *      *
       TAT    ATG    GCT    CCC    GAG    CGC    ATC    GAC    CCT    CCA    GAT    CCC    ACC    AAG    CCT    GAC
       ATA    TAC    CGA    GGG    CTC    GCG    TAG    CTG    GGA    GGT    CTA    GGG    TGG    TTC    GGA    CTG
       Tyr    Met    Ala    Pro    Glu    Arg    Ile    Asp    Pro    Pro    Asp    Pro    Thr    Lys    Pro    Asp>

980            990           1000           1010          1020
             *      *       *      *       *      *      *      *      *      *
       TAT    GAC    ATC    CGA    GCT    GAT    GTG    TGG    AGC    CTG    GGC    ATC    TCA    CTG    GTG    GAG
       ATA    CTG    TAG    GCT    CGA    CTA    CAC    ACC    TCG    GAC    CCG    TAG    AGT    GAC    CAC    CTC
       Tyr    Asp    Ile    Arg    Ala    Asp    Val    Trp    Ser    Leu    Gly    Ile    Ser    Leu    Val    Glu>

1030          1040          1050          1060          1070
                  *      *      *      *      *      *      *      *      *      *
       CTG    GCA    ACA    GGA    CAG    TTC    CCC    TAT    AAG    AAC    TGC    AAG    ACG    GAC    TTT    GAG
       GAC    CGT    TGT    CCT    GTC    AAG    GGG    ATA    TTC    TTG    ACG    TTC    TGC    CTG    AAA    CTC
       Leu    Ala    Thr    Gly    Gln    Phe    Pro    Tyr    Lys    Asn    Cys    Lys    Thr    Asp    Phe    Glu>

1080          1090          1100          1110
                  *      *      *      *      *      *      *      *      *
       GTC    CTC    ACC    AAA    GTC    CTA    CAG    GAA    GAG    CCC    CCA    CTC    CTG    CCT    GGT    CAC
       CAG    GAG    TGG    TTT    CAG    GAT    GTC    CTT    CTC    GGG    GGT    GAG    GAC    GGA    CCA    GTG
       Val    Leu    Thr    Lys    Val    Leu    Gln    Glu    Glu    Pro    Pro    Leu    Leu    Pro    Gly    His>

1120           1130          1140          1150          1160
        *      *       *      *      *      *      *      *      *      *      *
       ATG    GGC    TTC    TCA    GGG    GAC    TTC    CAG    TCA    TTT    GTC    AAA    GAC    TGC    CTT    ACT
       TAC    CCG    AAG    AGT    CCC    CTG    AAG    GTC    AGT    AAA    CAG    TTT    CTG    ACG    GAA    TGA
       Met    Gly    Phe    Ser    Gly    Asp    Phe    Gln    Ser    Phe    Val    Lys    Asp    Cys    Leu    Thr>

1170           1180          1190          1200          1210
        *      *       *      *      *      *      *      *      *      *      *
       AAA    GAT    CAC    AGG    AAG    AGA    CCA    AAG    TAT    AAT    AAG    CTA    CTT    GAA    CAC    AGC
       TTT    CTA    GTG    TCC    TTC    TCT    GGT    TTC    ATA    TTA    TTC    GAT    GAA    CTT    GTG    TCG
       Lys    Asp    His    Arg    Lys    Arg    Pro    Lys    Tyr    Asn    Lys    Leu    Leu    Glu    His    Ser>

1220          1230          1240          1250          1260
             *      *      *      *      *      *      *      *      *
       TTC    ATC    ATC    AAG    CAC    TAT    GAG    ATA    CTC    GAG    GTG    GAT    GTC    GCG    TCC    TGG
       AAG    TAG    TAG    TTC    GTG    ATA    CTC    TAT    GAG    CTC    CAC    CTA    CAG    CGC    AGG    ACC
       Phe    Ile    Ile    Lys    His    Tyr    Glu    Ile    Leu    Glu    Val    Asp    Val    Ala    Ser    Trp>

1270          1280          1290          1300          1310
                  *      *      *      *      *      *      *      *      *      *
       TTT    AAG    GAT    GTC    ATG    GCG    AAG    ACC    GAG    TCC    CCA    AGG    ACT    AGT    GGA    GTC
       AAA    TTC    CTA    CAG    TAC    CGC    TTC    TGG    CTC    AGG    GGT    TCC    TGA    TCA    CCT    CAG
```

FIG. 15C

Mouse MKK7e

```
Phe Lys Asp Val Met Ala Lys Thr Glu Ser Pro Arg Thr Ser Gly Val>

1320        1330        1340        1350
         *           *           *           *
CTG AGT CAG CAC CAT CTG CCC TTC TTC AGT GGG AGT CTG GAG GAG TCT
GAC TCA GTC GTG GTA GAC GGG AAG AAG TCA CCC TCA GAC CTC CTC AGA
Leu Ser Gln His His Leu Pro Phe Phe Ser Gly Ser Leu Glu Glu Ser>

1360        1370        1380        1390        1400
   *           *           *           *           *
CCC ACT TCC CCA CCT TCT CCC AAG TCC TTC CCT CTG TCA CCA GCC ATC
GGG TGA AGG GGT GGA AGA GGG TTC AGG AAG GGA GAC AGT GGT CGG TAG
Pro Thr Ser Pro Pro Ser Pro Lys Ser Phe Pro Leu Ser Pro Ala Ile>

1410        1420        1430        1440        1450        1460
      *           *           *           *           *           *
CCT CAG GCC CAG GCA GAG TGG GTC TCG GGC AGG TAGGGACCTG GAGTGGCCTG
GGA GTC CGG GTC CGT CTC ACC CAG AGC CCG TCC ATCCCTGGAC CTCACCGGAC
Pro Gln Ala Gln Ala Glu Trp Val Ser Gly Arg> (SEQ ID NO: 32)

1470        1480        1490        1500        1510        1520
      *           *           *           *           *           *
GTCCCACCCT CTGACCTCCT CCTCAGGCCA CCAGTGTTGC CCTCTTCCCT TTTTAAAACA
CAGGGTGGGA GACTGGAGGA GGAGTCCGGT GGTCACAACG GGAGAAGGGA AAAATTTTGT 1530        1540        1550        1560        1570        1580
      *           *           *           *           *           *
AAATACCCTT GTTTGTAAAT CCTTAGACGC TTGAGAATAA AACCCTTCCC TTTTCTTCCG
TTTATGGGAA CAAACATTTA GGAATCTGCG AACTCTTATT TTGGGAAGGG AAAAGAAGGC

1590
      *    *
AAAAAAAAAA AAAAAAAA (SEQ ID NO: 31)
TTTTTTTTTT TTTTTTTT
```

FIG. 15D

ID NO:2. The invention further includes

SEQUENCE LISTING

```
(1) GENERAL INFORMATION:

(iii) NUMBER OF SEQUENCES: 34

(2) INFORMATION FOR SEQ ID NO: 1:

(i) SEQUENCE CHARACTERISTICS:
        (A) LENGTH: 2030 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 338...1291

(xi) SEQUENCE DESCRIPTION: SEQ ID NO: 1:

TGGCTGGCAA  TGGCCTTGCT  GACCTCGAGC  CGGGCCCACG  TGGGGACCTT  TGGAGCACAG      60
```

```
CCTACGATCC TGGTGCAAGG CCGGTGGATG CAGAGGCCAG TCCATATACC ACCCAGGCCT    120

GCGAGGAGCG TGGTCCCCAC CCATCCAGCC CATATGTGCA AGTGCCCTTG ACAGAGAGGC    180

TGGTCATATC CATGGTGACC ATTTATGGGC CACAACAGGT CCCCATCTGC GCAGTGAACC    240

CTGTGCTGAG CACCTTGCAG ACGTGATCTT GCTTCGTCCT GCAGCACTGT GCGGGGCAGG    300

AAAATCCAAG AGGAAGAAGG ATCTACGGAT ATCCTGC ATG TCC AAG CCA CCC GCA    355
                                         Met Ser Lys Pro Pro Ala
                                          1               5

CCC AAC CCC ACA CCC CCC CGG AAC CTG GAC TCC CGG ACC TTC ATC ACC    403
Pro Asn Pro Thr Pro Pro Arg Asn Leu Asp Ser Arg Thr Phe Ile Thr
            10              15                  20

ATT GGA GAC AGA AAC TTT GAG GTG GAG GCT GAT GAC TTG GTG ACC ATC    451
Ile Gly Asp Arg Asn Phe Glu Val Glu Ala Asp Asp Leu Val Thr Ile
        25              30                  35

TCA GAA CTG GGC CGT GGA GCC TAT GGG GTG GTA GAG AAG GTG CGG CAC    499
Ser Glu Leu Gly Arg Gly Ala Tyr Gly Val Val Glu Lys Val Arg His
    40              45                  50

GCC CAG AGC GGC ACC ATC ATG GCC GTG AAG CGG ATC CGG GCC ACC GTG    547
Ala Gln Ser Gly Thr Ile Met Ala Val Lys Arg Ile Arg Ala Thr Val
55              60                  65                  70

AAC TCA CAG GAG CAG AAG CGG CTG CTC ATG GAC CTG GAC ATC AAC ATG    595
Asn Ser Gln Glu Gln Lys Arg Leu Leu Met Asp Leu Asp Ile Asn Met
            75                  80                  85

CGC ACG GTC GAC TGT TTC TAC ACT GTC ACC TTC TAC GGG GCA CTA TTC    643
Arg Thr Val Asp Cys Phe Tyr Thr Val Thr Phe Tyr Gly Ala Leu Phe
        90                  95                  100

AGA GAG GGA GAC GTG TGG ATC TGC ATG GAG CTC ATG GAC ACA TCC TTG    691
Arg Glu Gly Asp Val Trp Ile Cys Met Glu Leu Met Asp Thr Ser Leu
    105                 110                 115

GAC AAG TTC TAC CGG AAG GTG CTG GAT AAA AAC ATG ACA ATT CCA GAG    739
Asp Lys Phe Tyr Arg Lys Val Leu Asp Lys Asn Met Thr Ile Pro Glu
120                 125                 130

GAC ATC CTT GGG GAG ATT GCT GTG TCT ATC GTG CGG GCC CTG GAG CAT    787
Asp Ile Leu Gly Glu Ile Ala Val Ser Ile Val Arg Ala Leu Glu His
135                 140                 145                 150

CTG CAC AGC AAG CTG TCG GTG ATC CAC AGA GAT GTG AAG CCC TCC AAT    835
Leu His Ser Lys Leu Ser Val Ile His Arg Asp Val Lys Pro Ser Asn
            155                 160                 165

GTC CTT ATC AAC AAG GAG GGC CAT GTG AAG ATG TGT GAC TTT GGC ATC    883
Val Leu Ile Asn Lys Glu Gly His Val Lys Met Cys Asp Phe Gly Ile
        170                 175                 180

AGT GGC TAC TTG GTG GAC TCT GTG GCC AAG ACG ATG GAT GCC GGC TGC    931
Ser Gly Tyr Leu Val Asp Ser Val Ala Lys Thr Met Asp Ala Gly Cys
    185                 190                 195

AAG CCC TAC ATG GCC CCT GAG AGG ATC AAC CCA GAG CTG AAC CAG AAG    979
Lys Pro Tyr Met Ala Pro Glu Arg Ile Asn Pro Glu Leu Asn Gln Lys
200                 205                 210

GGC TAC AAT GTC AAG TCC GAC GTC TGG AGC CTG GGC ATC ACC ATG ATT    1027
Gly Tyr Asn Val Lys Ser Asp Val Trp Ser Leu Gly Ile Thr Met Ile
215                 220                 225                 230

GAG ATG GCC ATC CTG CGG TTC CCT TAC GAG TCC TGG GGG ACC CCG TTC    1075
Glu Met Ala Ile Leu Arg Phe Pro Tyr Glu Ser Trp Gly Thr Pro Phe
            235                 240                 245

CAG CAG CTG AAG CAG GTG GTG GAG GAG CCG TCC CCC CAG CTC CCA GCC    1123
Gln Gln Leu Lys Gln Val Val Glu Glu Pro Ser Pro Gln Leu Pro Ala
        250                 255                 260

GAC CGT TTC TCC CCC GAG TTT GTG GAC TTC ACT GCT CAG TGC CTG AGG    1171
Asp Arg Phe Ser Pro Glu Phe Val Asp Phe Thr Ala Gln Cys Leu Arg
```

-continued

```
                265                 270                 275
AAG AAC CCC GCA GAG CGT ATG AGC TAC CTG GAG CTG ATG GAG CAC CCC    1219
Lys Asn Pro Ala Glu Arg Met Ser Tyr Leu Glu Leu Met Glu His Pro
        280                 285                 290

TTC TTC ACC TTG CAC AAA ACC AAG AAG ACG GAC ATT GCT GCC TTC GTG    1267
Phe Phe Thr Leu His Lys Thr Lys Lys Thr Asp Ile Ala Ala Phe Val
295                 300                 305                 310

AAG AAG ATC CTG GGA GAA GAC TCA TAGGGGCTGG GCCTCGGACC CCACTCCGGC   1321
Lys Lys Ile Leu Gly Glu Asp Ser
                315

CCTCCAGAGC CCCACAGCCC CATCTGCGGG GGCAGTGCTC ACCCACACCA TAAGCTACTG   1381

CCATCCTGGC CCAGGGCATC TGGGAGGAAC CGAGGGGGCT GCTCCCACCT GGCTCTGTGG   1441

CGAGCCATTT GTCCCAAGTG CCAAAGAAGC AGACCATTGG GGCTCCCAGC CAGGCCCTTG   1501

TCGGCCCCAC CAGTGCCTCT CCCTGCTGCT CCTAGGACCC GTCTCCAGCT GCTGAGATCC   1561

TGGACTGAGG GGGCCTGGAT GCCCCCTGTG GATGCTGCTG CCCCTGCACA GCAGGCTGCC   1621

AGTGCCTGGG TGGATGGGCC ACCGCCTTGC CCAGCCTGGA TGCCATCCAA GTTGTATATT   1681

TTTTTAATCT CTCGACTGAA TGGACTTTGC ACACTTTGGC CCAGGGTGGC ACACCTCTA    1741

TCCCGGCTTT GGTGCGGGGT ACACAAGAGG GGATGAGTTG TGTGAATACC CCAAGACTCC   1801

CATGAGGGAG ATGCCATGAG CCGCCCAAGG CCTTCCCCTG GCACTGGCAA ACAGGGCCTC   1861

TGCGGAGCAC ACTGGCTCAC CCAGTCCTGC CCGCCACCGT TATCGGTGTC ATTCACCTTT   1921

CGTGTTTTTT TTAATTTATC CTCTGTTGAT TTTTTCTTTT GCTTTATGGG TTTGGCTTGT   1981

TTTTCTTGCA TGGTTTGGAG CTGATCGCTT CTCCCCCACC CCCTAGGGG              2030
```

(2) INFORMATION FOR SEQ ID NO: 2:

(i) SEQUENCE CHARACTERISTICS:
        (A) LENGTH: 318 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 2:

```
Met Ser Lys Pro Pro Ala Pro Asn Pro Thr Pro Pro Arg Asn Leu Asp
 1               5                  10                  15

Ser Arg Thr Phe Ile Thr Ile Gly Asp Arg Asn Phe Glu Val Glu Ala
                20                  25                  30

Asp Asp Leu Val Thr Ile Ser Glu Leu Gly Arg Gly Ala Tyr Gly Val
            35                  40                  45

Val Glu Lys Val Arg His Ala Gln Ser Gly Thr Ile Met Ala Val Lys
        50                  55                  60

Arg Ile Arg Ala Thr Val Asn Ser Gln Glu Gln Lys Arg Leu Leu Met
65                  70                  75                  80

Asp Leu Asp Ile Asn Met Arg Thr Val Asp Cys Phe Tyr Thr Val Thr
                85                  90                  95

Phe Tyr Gly Ala Leu Phe Arg Glu Gly Asp Val Trp Ile Cys Met Glu
            100                 105                 110

Leu Met Asp Thr Ser Leu Asp Lys Phe Tyr Arg Lys Val Leu Asp Lys
        115                 120                 125

Asn Met Thr Ile Pro Glu Asp Ile Leu Gly Glu Ile Ala Val Ser Ile
    130                 135                 140
```

```
Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
        195                 200                 205

Pro Glu Leu Asn Gln Lys Gly Tyr Asn Val Lys Ser Asp Val Trp Ser
    210                 215                 220

Leu Gly Ile Thr Met Ile Glu Met Ala Ile Leu Arg Phe Pro Tyr Glu
225                 230                 235                 240

Ser Trp Gly Thr Pro Phe Gln Gln Leu Lys Gln Val Val Glu Glu Pro
                245                 250                 255

Ser Pro Gln Leu Pro Ala Asp Arg Phe Ser Pro Glu Phe Val Asp Phe
            260                 265                 270

Thr Ala Gln Cys Leu Arg Lys Asn Pro Ala Glu Arg Met Ser Tyr Leu
        275                 280                 285

Glu Leu Met Glu His Pro Phe Phe Thr Leu His Lys Thr Lys Lys Thr
    290                 295                 300

Asp Ile Ala Ala Phe Val Lys Lys Ile Leu Gly Glu Asp Ser
305                 310                 315
```

(2) INFORMATION FOR SEQ ID NO: 3:

(i) SEQUENCE CHARACTERISTICS:
        (A) LENGTH: 1602 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 244...1245

(xi) SEQUENCE DESCRIPTION: SEQ ID NO: 3:

```
TAGCTGCAGC ACAGCCTTCC CTAACGTTGC AACTGGGGGA AAAATCACTT TCCAGTCTGT    60

TTTGCAAGGT GTGCATTTCC ATCTTGATTC CCTGAAAGTC CATCTGCTGC ATCGGTCAAG   120

AGAAACTCCA CTTGCATGAA GATTGCACGC CTGCAGCTTG CATCTTTGTT GCAAAACTAG   180

CTACAGAAGA GAAGCAAGGC AAAGTCTTTT GTGCTCCCCT CCCCCATCAA AGGAAAGGGG   240

AAA ATG TCT CAG TCG AAA GGC AAG AAG CGA AAC CCT GGC CTT AAA ATT    288
    Met Ser Gln Ser Lys Gly Lys Lys Arg Asn Pro Gly Leu Lys Ile
    1               5                   10                  15

CCA AAA GAA GCA TTT GAA CAA CCT CAG ACC AGT TCC ACA CCA CCT AGA    336
Pro Lys Glu Ala Phe Glu Gln Pro Gln Thr Ser Ser Thr Pro Pro Arg
                20                  25                  30

GAT TTA GAC TCC AAG GCT TGC ATT TCT ATT GGA AAT CAG AAC TTT GAG    384
Asp Leu Asp Ser Lys Ala Cys Ile Ser Ile Gly Asn Gln Asn Phe Glu
            35                  40                  45

GTG AAG GCA GAT GAC CTG GAG CCT ATA ATG GAA CTG GGA CGA GGT GCG    432
Val Lys Ala Asp Asp Leu Glu Pro Ile Met Glu Leu Gly Arg Gly Ala
        50                  55                  60

TAC GGG GTG GTG GAG AAG ATG CGG CAC GTG CCC AGC GGG CAG ATC ATG    480
Tyr Gly Val Val Glu Lys Met Arg His Val Pro Ser Gly Gln Ile Met
    65                  70                  75

GCA GTG AAG CGG ATC CGA GCC ACA GTA AAT AGC CAG GAA CAG AAA CGG    528
```

-continued

```
Ala Val Lys Arg Ile Arg Ala Thr Val Asn Ser Gln Glu Gln Lys Arg
 80                  85                  90                  95

CTA CTG ATG GAT TTG GAT ATT TCC ATG AGG ACG GTG GAC TGT CCA TTC      576
Leu Leu Met Asp Leu Asp Ile Ser Met Arg Thr Val Asp Cys Pro Phe
                100                 105                 110

ACT GTC ACC TTT TAT GGC GCA CTG TTT CGG GAG GGT GAT GTG TGG ATC      624
Thr Val Thr Phe Tyr Gly Ala Leu Phe Arg Glu Gly Asp Val Trp Ile
                    115                 120                 125

TGC ATG GAG CTC ATG GAT ACA TCA CTA GAT AAA TTC TAC AAA CAA GTT      672
Cys Met Glu Leu Met Asp Thr Ser Leu Asp Lys Phe Tyr Lys Gln Val
        130                 135                 140

ATT GAT AAA GGC CAG ACA ATT CCA GAG GAC ATC TTA GGG AAA ATA GCA      720
Ile Asp Lys Gly Gln Thr Ile Pro Glu Asp Ile Leu Gly Lys Ile Ala
    145                 150                 155

GTT TCT ATT GTA AAA GCA TTA GAA CAT TTA CAT AGT AAG CTG TCT GTC      768
Val Ser Ile Val Lys Ala Leu Glu His Leu His Ser Lys Leu Ser Val
160                 165                 170                 175

ATT CAC AGA GAC GTC AAG CCT TCT AAT GTA CTC ATC AAT GCT CTC GGT      816
Ile His Arg Asp Val Lys Pro Ser Asn Val Leu Ile Asn Ala Leu Gly
                180                 185                 190

CAA GTG AAG ATG TGC GAT TTT GGA ATC AGT GGC TAC TTG GTG GAC TCT      864
Gln Val Lys Met Cys Asp Phe Gly Ile Ser Gly Tyr Leu Val Asp Ser
                    195                 200                 205

GTT GCT AAA ACA ATT GAT GCA GGT TGC AAA CCA TAC ATG GCC CCT GAA      912
Val Ala Lys Thr Ile Asp Ala Gly Cys Lys Pro Tyr Met Ala Pro Glu
        210                 215                 220

AGA ATA AAC CCA GAG CTC AAC CAG AAG GGA TAC AGT GTG AAG TCT GAC      960
Arg Ile Asn Pro Glu Leu Asn Gln Lys Gly Tyr Ser Val Lys Ser Asp
    225                 230                 235

ATT TGG AGT CTG GGC ATC ACG ATG ATT GAG TTG GCC ATC CTT CGA TTT     1008
Ile Trp Ser Leu Gly Ile Thr Met Ile Glu Leu Ala Ile Leu Arg Phe
240                 245                 250                 255

CCC TAT GAT TCA TGG GGA ACT CCA TTT CAG CAG CTC AAA CAG GTG GTA     1056
Pro Tyr Asp Ser Trp Gly Thr Pro Phe Gln Gln Leu Lys Gln Val Val
                260                 265                 270

GAG GAG CCA TCG CCA CAA CTC CCA GCA GAC AAG TTC TCT GCA GAG TTT     1104
Glu Glu Pro Ser Pro Gln Leu Pro Ala Asp Lys Phe Ser Ala Glu Phe
                    275                 280                 285

GTT GAC TTT ACC TCA CAG TGC TTA AAG AAG AAT TCC AAA GAA CGG CCT     1152
Val Asp Phe Thr Ser Gln Cys Leu Lys Lys Asn Ser Lys Glu Arg Pro
        290                 295                 300

ACA TAC CCA GAG CTA ATG CAA CAT CCA TTT TTC ACC CTA CAT GAA TCC     1200
Thr Tyr Pro Glu Leu Met Gln His Pro Phe Phe Thr Leu His Glu Ser
    305                 310                 315

AAA GGA ACA GAT GTG GCA TCT TTT GTA AAA CTG ATT CTT GGA GAC TAAAA   1250
Lys Gly Thr Asp Val Ala Ser Phe Val Lys Leu Ile Leu Gly Asp
320                 325                 330

AGCAGTGGAC TTAATCGGTT GACCCTACTG TGGATTGGTG GGTTTCGGGG TGAAGCAAGT   1310

TCACTACAGC ATCAATAGAA AGTCATCTTT GAGATAATTT AACCCTGCCT CTCAGAGGGT   1370

TTTCTCTCCC AATTTTCTTT TTACTCCCCC TCTTAAGGGG GCCTTGGAAT CTATAGTATA   1430

GAATGAACTG TCTAGATGGA TGAATTATGA TAAAGGCTTA GGACTTCAAA AGGTGATTAA   1490

ATATTTAATG ATGTGTCATA TGAGTCCTCA AAAAAAAAAA AAAAAAAAAA AAAAAAAAAA   1550

AAAAAAAAAA AAAAAAAAAA AAAAAAAAAA AAAAAAAAAA AAAAAAAAAA AA          1602
```

(2) INFORMATION FOR SEQ ID NO: 4:

(i) SEQUENCE CHARACTERISTICS:

(A) LENGTH: 334 amino acids
      (B) TYPE: amino acid
      (D) TOPOLOGY: linear (ii) MOLECULE TYPE: protein (v) FRAGMENT TYPE: internal (xi) SEQUENCE DESCRIPTION: SEQ ID NO: 4:

Met Ser Gln Ser Lys Gly Lys Lys Arg Asn Pro Gly Leu Lys Ile Pro
1               5                   10                  15

Lys Glu Ala Phe Glu Gln Pro Gln Thr Ser Thr Pro Pro Arg Asp
            20                  25                  30

Leu Asp Ser Lys Ala Cys Ile Ser Ile Gly Asn Gln Asn Phe Glu Val
            35                  40                  45

Lys Ala Asp Asp Leu Glu Pro Ile Met Glu Leu Gly Arg Gly Ala Tyr
50                      55                  60

Gly Val Val Glu Lys Met Arg His Val Pro Ser Gly Gln Ile Met Ala
65                  70                  75                  80

Val Lys Arg Ile Arg Ala Thr Val Asn Ser Gln Glu Gln Lys Arg Leu
                85                  90                  95

Leu Met Asp Leu Asp Ile Ser Met Arg Thr Val Asp Cys Pro Phe Thr
            100                 105                 110

Val Thr Phe Tyr Gly Ala Leu Phe Arg Glu Gly Asp Val Trp Ile Cys
            115                 120                 125

Met Glu Leu Met Asp Thr Ser Leu Asp Lys Phe Tyr Lys Gln Val Ile
130                 135                 140

Asp Lys Gly Gln Thr Ile Pro Glu Asp Ile Leu Gly Lys Ile Ala Val
145                 150                 155                 160

Ser Ile Val Lys Ala Leu Glu His Leu His Ser Lys Leu Ser Val Ile
                165                 170                 175

His Arg Asp Val Lys Pro Ser Asn Val Leu Ile Asn Ala Leu Gly Gln
            180                 185                 190

Val Lys Met Cys Asp Phe Gly Ile Ser Gly Tyr Leu Val Asp Ser Val
            195                 200                 205

Ala Lys Thr Ile Asp Ala Gly Cys Lys Pro Tyr Met Ala Pro Glu Arg
210                 215                 220

Ile Asn Pro Glu Leu Asn Gln Lys Gly Tyr Ser Val Lys Ser Asp Ile
225                 230                 235                 240

Trp Ser Leu Gly Ile Thr Met Ile Glu Leu Ala Ile Leu Arg Phe Pro
                245                 250                 255

Tyr Asp Ser Trp Gly Thr Pro Phe Gln Gln Leu Lys Gln Val Val Glu
            260                 265                 270

Glu Pro Ser Pro Gln Leu Pro Ala Asp Lys Phe Ser Ala Glu Phe Val
            275                 280                 285

Asp Phe Thr Ser Gln Cys Leu Lys Lys Asn Ser Lys Glu Arg Pro Thr
290                 295                 300

Tyr Pro Glu Leu Met Gln His Pro Phe Phe Thr Leu His Glu Ser Lys
305                 310                 315                 320

Gly Thr Asp Val Ala Ser Phe Val Lys Leu Ile Leu Gly Asp
                325                 330

(2) INFORMATION FOR SEQ ID NO: 5:

(i) SEQUENCE CHARACTERISTICS:
      (A) LENGTH: 3498 base pairs
      (B) TYPE: nucleic acid (C) STRANDEDNESS: double
            (D) TOPOLOGY: linear (ii) MOLECULE TYPE: cDNA (ix) FEATURE:
            (A) NAME/KEY: Coding Sequence
            (B) LOCATION: 40...1128

(xi) SEQUENCE DESCRIPTION: SEQ ID NO: 5:

```
CTAGGGTCCC CGGCGCCAGG CCACCCGGCC GTCAGCAGC ATG CAG GGT AAA CGC          54
                                           Met Gln Gly Lys Arg
                                           1                 5

AAA GCA CTG AAG TTG AAT TTT GCA AAT CCA CCT TTC AAA TCT ACA GCA        102
Lys Ala Leu Lys Leu Asn Phe Ala Asn Pro Pro Phe Lys Ser Thr Ala
                10                  15                  20

AGG TTT ACT CTG AAT CCC AAT CCT ACA GGA GTT CAA AAC CCA CAC ATA        150
Arg Phe Thr Leu Asn Pro Asn Pro Thr Gly Val Gln Asn Pro His Ile
            25                  30                  35

GAG AGA CTG AGA ACA CAC AGC ATT GAG TCA TCA GGA AAA CTG AAG ATC        198
Glu Arg Leu Arg Thr His Ser Ile Glu Ser Ser Gly Lys Leu Lys Ile
        40                  45                  50

TCC CCT GAA CAA CAC TGG GAT TTC ACT GCA GAG GAC TTG AAA GAC CTT        246
Ser Pro Glu Gln His Trp Asp Phe Thr Ala Glu Asp Leu Lys Asp Leu
    55                  60                  65

GGA GAA ATT GGA CGA GGA GCT TAT GGT TCT GTC AAC AAA ATG GTC CAC        294
Gly Glu Ile Gly Arg Gly Ala Tyr Gly Ser Val Asn Lys Met Val His
70                  75                  80                  85

AAA CCA AGT GGG CAA ATA ATG GCA GTT AAA AGA ATT CGG TCA ACA GTG        342
Lys Pro Ser Gly Gln Ile Met Ala Val Lys Arg Ile Arg Ser Thr Val
                90                  95                  100

GAT GAA AAA GAA CAA AAA CAA CTT CTT ATG GAT TTG GAT GTA GTA ATG        390
Asp Glu Lys Glu Gln Lys Gln Leu Leu Met Asp Leu Asp Val Val Met
            105                 110                 115

CGG AGT AGT GAT TGC CCA TAC ATT GTT CAG TTT TAT GGT GCA CTC TTC        438
Arg Ser Ser Asp Cys Pro Tyr Ile Val Gln Phe Tyr Gly Ala Leu Phe
        120                 125                 130

AGA GAG GGT GAC TGT TGG ATC TGT ATG GAA CTC ATG TCT ACC TCG TTT        486
Arg Glu Gly Asp Cys Trp Ile Cys Met Glu Leu Met Ser Thr Ser Phe
    135                 140                 145

GAT AAG TTT TAC AAA TAT GTA TAT AGT GTA TTA GAT GAT GTT ATT CCA        534
Asp Lys Phe Tyr Lys Tyr Val Tyr Ser Val Leu Asp Asp Val Ile Pro
150                 155                 160                 165

GAA GAA ATT TTA GGC AAA ATC ACT TTA GCA ACT GTG AAA GCA CTA AAC        582
Glu Glu Ile Leu Gly Lys Ile Thr Leu Ala Thr Val Lys Ala Leu Asn
                170                 175                 180

CAC TTA AAA GAA AAC TTG AAA ATT ATT CAC AGA GAT ATC AAA CCT TCC        630
His Leu Lys Glu Asn Leu Lys Ile Ile His Arg Asp Ile Lys Pro Ser
            185                 190                 195

AAT ATT CTT CTG GAC AGA AGT GGA AAT ATT AAG CTC TGT GAC TTC GGC        678
Asn Ile Leu Leu Asp Arg Ser Gly Asn Ile Lys Leu Cys Asp Phe Gly
        200                 205                 210

ATC AGT GGA CAG CTT GTG GAC TCT ATT GCC AAG ACA AGA GAT GCT GGC        726
Ile Ser Gly Gln Leu Val Asp Ser Ile Ala Lys Thr Arg Asp Ala Gly
    215                 220                 225

TGT AGG CCA TAC ATG GCA CCT GAA AGA ATA GAC CCA AGC GCA TCA CGA        774
Cys Arg Pro Tyr Met Ala Pro Glu Arg Ile Asp Pro Ser Ala Ser Arg
230                 235                 240                 245

CAA GGA TAT GAT GTC CGC TCT GAT GTC TGG AGT TTG GGG ATC ACA TTG        822
Gln Gly Tyr Asp Val Arg Ser Asp Val Trp Ser Leu Gly Ile Thr Leu
                250                 255                 260
```

```
TAT GAG TTG GCC ACA GGC CGA TTT CCT TAT CCA AAG TGG AAT AGT GTA      870
Tyr Glu Leu Ala Thr Gly Arg Phe Pro Tyr Pro Lys Trp Asn Ser Val
            265                 270                 275

TTT GAT CAA CTA ACA CAA GTC GTG AAA GGA GAT CCT CCG CAG CTG AGT      918
Phe Asp Gln Leu Thr Gln Val Val Lys Gly Asp Pro Pro Gln Leu Ser
        280                 285                 290

AAT TCT GAG GAA AGG GAA TTC TCC CCG AGT TTC ATC AAC TTT GTC AAC      966
Asn Ser Glu Glu Arg Glu Phe Ser Pro Ser Phe Ile Asn Phe Val Asn
    295                 300                 305

TTG TGC CTT ACG AAG GAT GAA TCC AAA AGG CCA AAG TAT AAA GAG CTT     1014
Leu Cys Leu Thr Lys Asp Glu Ser Lys Arg Pro Lys Tyr Lys Glu Leu
310                 315                 320                 325

CTG AAA CAT CCC TTT ATT TTG ATG TAT GAA GAA CGT GCC GTT GAG GTC     1062
Leu Lys His Pro Phe Ile Leu Met Tyr Glu Glu Arg Ala Val Glu Val
                330                 335                 340

GCA TGC TAT GTT TGT AAA ATC CTG GAT CAA ATG CCA GCT ACT CCC AGC     1110
Ala Cys Tyr Val Cys Lys Ile Leu Asp Gln Met Pro Ala Thr Pro Ser
            345                 350                 355

TCT CCC ATG TAT GTC GAT TGATATCGYT GCTACATCAG ACTCTAGAAA AAAGGGCT   1166
Ser Pro Met Tyr Val Asp
        360

GAGAGGAAGC AAGACGTAAA GAATTTTCAT CCCGTATCAC AGTGTTTTTA TTGCTCGCCC   1226

AGACACCATG TGCAATAAGA TTGGTGTTCG TTTCCATCAT GTCTGTATAC TCCTGTCACC   1286

TAGAACGTGC ATCCTTGTAA TACCTGATTG ATCACACAGT GTTAGTGCTG GTCAGAGAGA   1346

CCTCATCCTG CTCTTTTGTG ATGAACATAT TCATGAAATG TGGAAGTCAG TACGATCAAG   1406

TTGTTGACTG TGATTAGATC ACATCTTAAA TTCATTTCTA GACTCAAAAC CTGGAGATGC   1466

AGCTACTGGA ATGGTGTTTT GTCAGACTTC CAAATCCTGG AAGGACACAG TGATGAATGT   1526

ACTATATCTG AACATAGAAA CTCGGGCTTG AGTGAGAAGA GCTTGCACAG CCAACGAGAC   1586

ACATTGCCTT CTGGAGCTGG AGACAAAGG AGGAATTTAC TTTCTTCACC AAGTGCAATA    1646

GATTACTGAT GTGATATTCT GTTGCTTTAC AGTTACAGTT GATGTTTGGG ATCGATGTG    1706

CTCAGCCAAA TTTCCTGTTT GAAATATCAT GTTAAATTAG AATGAATTTA TCTTTACCAA   1766

AAACCATGTT GCGTTCAAAG AGGTGAACAT TAAAATATAG AGACAGGACA GAATGTGTTC   1826

TTTTCTCCTC TACCAGTCCT ATTTTTCAAT GGGAAGACTC AGGAGTCTGC CACTTGTCAA   1886

AGAAGGTGCT GATCCTAAGA ATTTTTCATT CTCAGAATTC GGTGTGCTGC AACTTGATG    1946

TTCCACCTGC ACAAACCAC CAGGACTGAA AGAAGAAAAC AGTACAGAAG GCAAAGTTTA    2006

CAGATGTTTT TAATTCTAGT ATTTTATCTG GAACAACTTG TAGCAGCTAT ATATTTCCCC   2066

TTGGTCCCAA GCCTGATACT TTAGCCATCA TAACTCACTA ACAGGGAGAA GTAGCTAGTA   2126

GCAATGTGCC TTGATTGATT AGATAAAGAT TTCTAGTAGG CAGCAAAAGA CCAAATCTCA   2186

GTTGTTTGCT TCTTGCCATC ACTGGTCCAG GTCTTCAGTT TCCGAATCTC TTTCCCTTCC   2246

CCTGTGGTCT ATTGTCGCTA TGTGACTTGC GCTTAATCCA ATATTTTGCC TTTTTTCTAT   2306

ATCAAAAAAC CTTTACAGTT AGCAGGGATG TTCCTTACCG AGGATTTTTA ACCCCAATC    2366

TCTCATAATC GCTAGTGTTT AAAAGGCTAA GAATAGTGGG GCCCAACCGA TGTGGTAGGT   2426

GATAAAGAGG CATCTTTTCT AGAGACACAT TGGACCAGAT GAGGATCCGA AACGGCAGCC   2486

TTTACGTTCA TCACCTGCTA GAACCTCTCG TAGTCCATCA CCATTTCTTG GCATTGGAAT   2546

TCTACTGGAA AAAAATACAA AAAGCAAAAC AAAACCCTCA GCACTGTTAC AAGAGGCCAT   2606

TTAAGTATCT TGTGCTTCTT CACTTACCCA TTAGCCAGGT TCTCATTAGG TTTTGCTTGG   2666

GCCTCCCTGG CACTGAACCT TAGGCTTTGT ATGACAGTGA AGCAGCACTG TGAGTGGTTC   2726
```

```
AAGCACACTG GAATATAAAA CAGTCATGGC CTGAGATGCA GGTGATGCCA TTACAGAACC   2786

AAATCGTGGC ACGTATTGCT GTGTCTCCTC TCAGAGTGAC AGTCATAAAT ACTGTCAAAC   2846

AATAAAGGGA GAATGGTGCT GTTTAAAGTC ACATCCCTGT AAATTGCAGA ATTCAAAAGT   2906

GATTATCTCT TTGATCTACT TGCCTCATTT CCCTATCTTC TCCCCCACGG TATCCTAAAC   2966

TTTAGACTTC CCACTGTTCT GAAAGGAGAC ATTGCTCTAT GTCTGCCTTC GACCACAGCA   3026

AGCCATCATC CTCCATTGCT CCCGGGGACT CAAGAGGAAT CTGTTTCTCT GCTGTCAACT   3086

TCCCATCTGG CTCAGCATAG GGTCACTTTG CCATTATGCA AATGGAGATA AAGCAATTC    3146

TGGCTGTCCA GGAGCTAATC TGACCGTTCT ATTGTGTGGA TGACCACATA AGAAGGCAAT   3206

TTTAGTGTAT TAATCATAGA TTATTATAAA CTATAAACTT AAGGGCAAGG AGTTTATTAC   3266

AATGTATCTT TATTAAAACA AAAGGGTGTA TAGTGTTCAC AAACTGTGAA ATAGTGTAA    3326

GAACTGTACA TTGTGAGCTC TGGTTATTTT TCTCTTGTAC CATAGAAAAA TGTATAAAAA   3386

TTATCAAAAA GCTAATGTGC AGGGATATTG CCTTATTTGT CTGTAAAAAA TGGAGCTCAG   3446

TAACATAACT GCTTCTTGGA GCTTTGGAAT ATTTTATCCT GTATTCTTGT TT           3498
```

(2) INFORMATION FOR SEQ ID NO: 6:

(i) SEQUENCE CHARACTERISTICS:
        (A) LENGTH: 363 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 6:

```
Met Gln Gly Lys Arg Lys Ala Leu Lys Leu Asn Phe Ala Asn Pro Pro
 1               5                  10                  15

Phe Lys Ser Thr Ala Arg Phe Thr Leu Asn Pro Asn Pro Thr Gly Val
                20                  25                  30

Gln Asn Pro His Ile Glu Arg Leu Arg Thr His Ser Ile Glu Ser Ser
            35                  40                  45

Gly Lys Leu Lys Ile Ser Pro Glu Gln His Trp Asp Phe Thr Ala Glu
        50                  55                  60

Asp Leu Lys Asp Leu Gly Glu Ile Gly Arg Gly Ala Tyr Gly Ser Val
65                  70                  75                  80

Asn Lys Met Val His Lys Pro Ser Gly Gln Ile Met Ala Val Lys Arg
                85                  90                  95

Ile Arg Ser Thr Val Asp Glu Lys Glu Gln Lys Gln Leu Leu Met Asp
               100                 105                 110

Leu Asp Val Val Met Arg Ser Ser Asp Cys Pro Tyr Ile Val Gln Phe
            115                 120                 125

Tyr Gly Ala Leu Phe Arg Glu Gly Asp Cys Trp Ile Cys Met Glu Leu
        130                 135                 140

Met Ser Thr Ser Phe Asp Lys Phe Tyr Lys Tyr Val Tyr Ser Val Leu
145                 150                 155                 160

Asp Asp Val Ile Pro Glu Glu Ile Leu Gly Lys Ile Thr Leu Ala Thr
                165                 170                 175

Val Lys Ala Leu Asn His Leu Lys Glu Asn Leu Lys Ile Ile His Arg
            180                 185                 190

Asp Ile Lys Pro Ser Asn Ile Leu Leu Asp Arg Ser Gly Asn Ile Lys
        195                 200                 205
```

-continued

```
Leu Cys Asp Phe Gly Ile Ser Gly Gln Leu Val Asp Ser Ile Ala Lys
    210                 215                 220
Thr Arg Asp Ala Gly Cys Arg Pro Tyr Met Ala Pro Glu Arg Ile Asp
225                 230                 235                 240
Pro Ser Ala Ser Arg Gln Gly Tyr Asp Val Arg Ser Asp Val Trp Ser
                245                 250                 255
Leu Gly Ile Thr Leu Tyr Glu Leu Ala Thr Gly Arg Phe Pro Tyr Pro
                260                 265                 270
Lys Trp Asn Ser Val Phe Asp Gln Leu Thr Gln Val Val Lys Gly Asp
            275                 280                 285
Pro Pro Gln Leu Ser Asn Ser Glu Glu Arg Glu Phe Ser Pro Ser Phe
    290                 295                 300
Ile Asn Phe Val Asn Leu Cys Leu Thr Lys Asp Glu Ser Lys Arg Pro
305                 310                 315                 320
Lys Tyr Lys Glu Leu Leu Lys His Pro Phe Ile Leu Met Tyr Glu Glu
                325                 330                 335
Arg Ala Val Glu Val Ala Cys Tyr Val Cys Lys Ile Leu Asp Gln Met
                340                 345                 350
Pro Ala Thr Pro Ser Ser Pro Met Tyr Val Asp
            355                 360
```

(2) INFORMATION FOR SEQ ID NO: 7:

(i) SEQUENCE CHARACTERISTICS:
  (A) LENGTH: 3554 base pairs
  (B) TYPE: nucleic acid
  (C) STRANDEDNESS: double
  (D) TOPOLOGY: linear (ii) MOLECULE TYPE: cDNA (ix) FEATURE:
  (A) NAME/KEY: Coding Sequence
  (B) LOCATION: 6...1184

(xi) SEQUENCE DESCRIPTION: SEQ ID NO: 7:

```
CAACA ATG GCG GCT CCG AGC CCG AGC GGT GGC GGC GGC AGC GGC ACC CCC     50
      Met Ala Ala Pro Ser Pro Ser Gly Gly Gly Gly Ser Gly Thr Pro
        1               5                   10                  15

GGC CCC GTA GGG TCC CCG GCG CCA GGC CAC CCG GCC GTC AGC AGC ATG        98
Gly Pro Val Gly Ser Pro Ala Pro Gly His Pro Ala Val Ser Ser Met
                20                  25                  30

CAG GGT AAA CGC AAA GCA CTG AAG TTG AAT TTT GCA AAT CCA CCT TTC       146
Gln Gly Lys Arg Lys Ala Leu Lys Leu Asn Phe Ala Asn Pro Pro Phe
            35                  40                  45

AAA TCT ACA GCA AGG TTT ACT CTG AAT CCC AAT CCT ACA GGA GTT CAA       194
Lys Ser Thr Ala Arg Phe Thr Leu Asn Pro Asn Pro Thr Gly Val Gln
        50                  55                  60

AAC CCA CAC ATA GAG AGA CTG AGA ACA CAC AGC ATT GAG TCA TCA GGA       242
Asn Pro His Ile Glu Arg Leu Arg Thr His Ser Ile Glu Ser Ser Gly
65                  70                  75

AAA CTG AAG ATC TCC CCT GAA CAA CAC TGG GAT TTC ACT GCA GAG GAC       290
Lys Leu Lys Ile Ser Pro Glu Gln His Trp Asp Phe Thr Ala Glu Asp
80                  85                  90                  95

TTG AAA GAC CTT GGA GAA ATT GGA CGA GGA GCT TAT GGT TCT GTC AAC       338
Leu Lys Asp Leu Gly Glu Ile Gly Arg Gly Ala Tyr Gly Ser Val Asn
                100                 105                 110

AAA ATG GTC CAC AAA CCA AGT GGG CAA ATA ATG GCA GTT AAA AGA ATT       386
Lys Met Val His Lys Pro Ser Gly Gln Ile Met Ala Val Lys Arg Ile
            115                 120                 125
```

```
CGG TCA ACA GTG GAT GAA AAA GAA CAA AAA CAA CTT CTT ATG GAT TTG      434
Arg Ser Thr Val Asp Glu Lys Glu Gln Lys Gln Leu Leu Met Asp Leu
        130                 135                 140

GAT GTA GTA ATG CGG AGT AGT GAT TGC CCA TAC ATT GTT CAG TTT TAT      482
Asp Val Val Met Arg Ser Ser Asp Cys Pro Tyr Ile Val Gln Phe Tyr
        145                 150                 155

GGT GCA CTC TTC AGA GAG GGT GAC TGT TGG ATC TGT ATG GAA CTC ATG      530
Gly Ala Leu Phe Arg Glu Gly Asp Cys Trp Ile Cys Met Glu Leu Met
160                 165                 170                 175

TCT ACC TCG TTT GAT AAG TTT TAC AAA TAT GTA TAT AGT GTA TTA GAT      578
Ser Thr Ser Phe Asp Lys Phe Tyr Lys Tyr Val Tyr Ser Val Leu Asp
                180                 185                 190

GAT GTT ATT CCA GAA GAA ATT TTA GGC AAA ATC ACT TTA GCA ACT GTG      626
Asp Val Ile Pro Glu Glu Ile Leu Gly Lys Ile Thr Leu Ala Thr Val
                195                 200                 205

AAA GCA CTA AAC CAC TTA AAA GAA AAC TTG AAA ATT ATT CAC AGA GAT      674
Lys Ala Leu Asn His Leu Lys Glu Asn Leu Lys Ile Ile His Arg Asp
                210                 215                 220

ATC AAA CCT TCC AAT ATT CTT CTG GAC AGA AGT GGA AAT ATT AAG CTC      722
Ile Lys Pro Ser Asn Ile Leu Leu Asp Arg Ser Gly Asn Ile Lys Leu
        225                 230                 235

TGT GAC TTC GGC ATC AGT GGA CAG CTT GTG GAC TCT ATT GCC AAG ACA      770
Cys Asp Phe Gly Ile Ser Gly Gln Leu Val Asp Ser Ile Ala Lys Thr
240                 245                 250                 255

AGA GAT GCT GGC TGT AGG CCA TAC ATG GCA CCT GAA AGA ATA GAC CCA      818
Arg Asp Ala Gly Cys Arg Pro Tyr Met Ala Pro Glu Arg Ile Asp Pro
                260                 265                 270

AGC GCA TCA CGA CAA GGA TAT GAT GTC CGC TCT GAT GTC TGG AGT TTG      866
Ser Ala Ser Arg Gln Gly Tyr Asp Val Arg Ser Asp Val Trp Ser Leu
                275                 280                 285

GGG ATC ACA TTG TAT GAG TTG GCC ACA GGC CGA TTT CCT TAT CCA AAG      914
Gly Ile Thr Leu Tyr Glu Leu Ala Thr Gly Arg Phe Pro Tyr Pro Lys
                290                 295                 300

TGG AAT AGT GTA TTT GAT CAA CTA ACA CAA GTC GTG AAA GGA GAT CCT      962
Trp Asn Ser Val Phe Asp Gln Leu Thr Gln Val Val Lys Gly Asp Pro
305                 310                 315

CCG CAG CTG AGT AAT TCT GAG GAA AGG GAA TTC TCC CCG AGT TTC ATC     1010
Pro Gln Leu Ser Asn Ser Glu Glu Arg Glu Phe Ser Pro Ser Phe Ile
320                 325                 330                 335

AAC TTT GTC AAC TTG TGC CTT ACG AAG GAT GAA TCC AAA AGG CCA AAG     1058
Asn Phe Val Asn Leu Cys Leu Thr Lys Asp Glu Ser Lys Arg Pro Lys
                340                 345                 350

TAT AAA GAG CTT CTG AAA CAT CCC TTT ATT TTG ATG TAT GAA GAA CGT     1106
Tyr Lys Glu Leu Leu Lys His Pro Phe Ile Leu Met Tyr Glu Glu Arg
                355                 360                 365

GCC GTT GAG GTC GCA TGC TAT GTT TGT AAA ATC CTG GAT CAA ATG CCA     1154
Ala Val Glu Val Ala Cys Tyr Val Cys Lys Ile Leu Asp Gln Met Pro
        370                 375                 380

GCT ACT CCC AGC TCT CCC ATG TAT GTC GAT TGATATCGYT GCTACATCAG ACT   1207
Ala Thr Pro Ser Ser Pro Met Tyr Val Asp
385                 390

CTAGAAAAAA GGGCTGAGAG GAAGCAAGAC GTAAAGAATT TCATCCCGT ATCACAGTGT    1267

TTTTATTGCT CGCCCAGACA CCATGTGCAA TAAGATTGGT GTTCGTTTCC ATCATGTCTG   1327

TATACTCCTG TCACCTAGAA CGTGCATCCT TGTAATACCT GATTGATCAC ACAGTGTTAG   1387

TGCTGGTCAG AGAGACCTCA TCCTGCTCTT TTGTGATGAA CATATTCATG AAATGTGGAA   1447

GTCAGTACGA TCAAGTTGTT GACTGTGATT AGATCACATC TTAAATTCAT TTCTAGACTC   1507
```

```
AAAACCTGGA GATGCAGCTA CTGGAATGGT GTTTTGTCAG ACTTCCAAAT CCTGGAAGGA      1567

CACAGTGATG AATGTACTAT ATCTGAACAT AGAAACTCGG GCTTGAGTGA AAGAGCTTG      1627

CACAGCCAAC GAGACACATT GCCTTCTGGA GCTGGGAGAC AAAGGAGGAA TTTACTTTCT     1687

TCACCAAGTG CAATAGATTA CTGATGTGAT ATTCTGTTGC TTTACAGTTA CAGTTGATGT     1747

TTGGGGATCG ATGTGCTCAG CCAAATTTCC TGTTTGAAAT ATCATGTTAA ATTAGAATGA     1807

ATTTATCTTT ACCAAAAACC ATGTTGCGTT CAAAGAGGTG AACATTAAAA TATAGAGACA     1867

GGACAGAATG TGTTCTTTTC TCCTCTACCA GTCCTATTTT TCAATGGGAA GACTCAGGAG     1927

TCTGCCACTT GTCAAAGAAG GTGCTGATCC TAAGAATTTT TCATTCTCAG AATTCGGTGT     1987

GCTGCCAACT TGATGTTCCA CCTGCCACAA ACCACCAGGA CTGAAAGAAG AAAACAGTAC     2047

AGAAGGCAAA GTTTACAGAT GTTTTTAATT CTAGTATTTT ATCTGGAACA ACTTGTAGCA     2107

GCTATATATT TCCCCTTGGT CCCAAGCCTG ATACTTTAGC CATCATAACT CACTAACAGG     2167

GAGAAGTAGC TAGTAGCAAT GTGCCTTGAT TGATTAGATA AAGATTTCTA GTAGGCAGCA     2227

AAAGACCAAA TCTCAGTTGT TTGCTTCTTG CCATCACTGG TCCAGGTCTT CAGTTTCCGA     2287

ATCTCTTTCC CTTCCCCTGT GGTCTATTGT CGCTATGTGA CTTGCGCTTA ATCCAATATT     2347

TTGCCTTTTT TCTATATCAA AAAACCTTTA CAGTTAGCAG GGATGTTCCT TACCGAGGAT     2407

TTTTAACCCC CAATCTCTCA TAATCGCTAG TGTTTAAAAG GCTAAGAATA GTGGGGCCCA     2467

ACCGATGTGG TAGGTGATAA AGAGGCATCT TTTCTAGAGA CACATTGGAC CAGATGAGGA     2527

TCCGAAACGG CAGCCTTTAC GTTCATCACC TGCTAGAACC TCTCGTAGTC CATCACCATT     2587

TCTTGGCATT GGAATTCTAC TGGAAAAAAA TACAAAAAGC AAAACAAAAC CCTCAGCACT     2647

GTTACAAGAG GCCATTTAAG TATCTTGTGC TTCTTCACTT ACCCATTAGC CAGGTTCTCA     2707

TTAGGTTTTG CTTGGGCCTC CCTGGCACTG AACCTTAGGC TTTGTATGAC AGTGAAGCAG     2767

CACTGTGAGT GGTTCAAGCA CACTGGAATA TAAAACAGTC ATGGCCTGAG ATGCAGGTGA     2827

TGCCATTACA GAACCAAATC GTGGCACGTA TTGCTGTGTC TCCTCTCAGA GTGACAGTCA     2887

TAAATACTGT CAAACAATAA AGGGAGAATG GTGCTGTTTA AAGTCACATC CCTGTAAATT     2947

GCAGAATTCA AAAGTGATTA TCTCTTTGAT CTACTTGCCT CATTTCCCTA TCTTCTCCCC     3007

CACGGTATCC TAAACTTTAG ACTTCCCACT GTTCTGAAAG GAGACATTGC TCTATGTCTG     3067

CCTTCGACCA CAGCAAGCCA TCATCCTCCA TTGCTCCCGG GGACTCAAGA GGAATCTGTT     3127

TCTCTGCTGT CAACTTCCCA TCTGGCTCAG CATAGGGTCA CTTTGCCATT ATGCAAATGG     3187

AGATAAAAGC AATTCTGGCT GTCCAGGAGC TAATCTGACC GTTCTATTGT GTGGATGACC     3247

ACATAAGAAG GCAATTTTAG TGTATTAATC ATAGATTATT ATAAACTATA AACTTAAGGG     3307

CAAGGAGTTT ATTACAATGT ATCTTTATTA AAACAAAAGG GTGTATAGTG TTCACAAACT     3367

GTGAAAATAG TGTAAGAACT GTACATTGTG AGCTCTGGTT ATTTTTCTCT TGTACCATAG     3427

AAAAATGTAT AAAAATTATC AAAAAGCTAA TGTGCAGGGA TATTGCCTTA TTTGTCTGTA     3487

AAAAATGGAG CTCAGTAACA TAACTGCTTC TTGGAGCTTT GGAATATTTT ATCCTGTATT     3547

CTTGTTT                                                              3554
```

(2) INFORMATION FOR SEQ ID NO: 8:

(i) SEQUENCE CHARACTERISTICS:
        (A) LENGTH: 393 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 8:

Met Ala Ala Pro Ser Pro Ser Gly Gly Gly Ser Gly Thr Pro Gly
1               5                   10                  15

Pro Val Gly Ser Pro Ala Pro Gly His Pro Ala Val Ser Ser Met Gln
            20                  25                  30

Gly Lys Arg Lys Ala Leu Lys Leu Asn Phe Ala Asn Pro Pro Phe Lys
        35                  40                  45

Ser Thr Ala Arg Phe Thr Leu Asn Pro Asn Pro Thr Gly Val Gln Asn
    50                  55                  60

Pro His Ile Glu Arg Leu Arg Thr His Ser Ile Glu Ser Ser Gly Lys
65                  70                  75                  80

Leu Lys Ile Ser Pro Glu Gln His Trp Asp Phe Thr Ala Glu Asp Leu
                85                  90                  95

Lys Asp Leu Gly Glu Ile Gly Arg Gly Ala Tyr Gly Ser Val Asn Lys
                100                 105                 110

Met Val His Lys Pro Ser Gly Gln Ile Met Ala Val Lys Arg Ile Arg
            115                 120                 125

Ser Thr Val Asp Glu Lys Glu Gln Lys Gln Leu Leu Met Asp Leu Asp
    130                 135                 140

Val Val Met Arg Ser Ser Asp Cys Pro Tyr Ile Val Gln Phe Tyr Gly
145                 150                 155                 160

Ala Leu Phe Arg Glu Gly Asp Cys Trp Ile Cys Met Glu Leu Met Ser
                165                 170                 175

Thr Ser Phe Asp Lys Phe Tyr Lys Tyr Val Tyr Ser Val Leu Asp Asp
            180                 185                 190

Val Ile Pro Glu Glu Ile Leu Gly Lys Ile Thr Leu Ala Thr Val Lys
        195                 200                 205

Ala Leu Asn His Leu Lys Glu Asn Leu Lys Ile Ile His Arg Asp Ile
    210                 215                 220

Lys Pro Ser Asn Ile Leu Leu Asp Arg Ser Gly Asn Ile Lys Leu Cys
225                 230                 235                 240

Asp Phe Gly Ile Ser Gly Gln Leu Val Asp Ser Ile Ala Lys Thr Arg
                245                 250                 255

Asp Ala Gly Cys Arg Pro Tyr Met Ala Pro Glu Arg Ile Asp Pro Ser
            260                 265                 270

Ala Ser Arg Gln Gly Tyr Asp Val Arg Ser Asp Val Trp Ser Leu Gly
        275                 280                 285

Ile Thr Leu Tyr Glu Leu Ala Thr Gly Arg Phe Pro Tyr Pro Lys Trp
    290                 295                 300

Asn Ser Val Phe Asp Gln Leu Thr Gln Val Val Lys Gly Asp Pro Pro
305                 310                 315                 320

Gln Leu Ser Asn Ser Glu Glu Arg Glu Phe Ser Pro Ser Phe Ile Asn
                325                 330                 335

Phe Val Asn Leu Cys Leu Thr Lys Asp Glu Ser Lys Arg Pro Lys Tyr
            340                 345                 350

Lys Glu Leu Leu Lys His Pro Phe Ile Leu Met Tyr Glu Glu Arg Ala
        355                 360                 365

Val Glu Val Ala Cys Tyr Val Cys Lys Ile Leu Asp Gln Met Pro Ala
    370                 375                 380

Thr Pro Ser Ser Pro Met Tyr Val Asp
385                 390

(2) INFORMATION FOR SEQ ID NO: 9:

(i) SEQUENCE CHARACTERISTICS:
        (A) LENGTH: 3576 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 10...1206

(xi) SEQUENCE DESCRIPTION: SEQ ID NO: 9:

```
CTCCCAACA ATG GCG GCT CCG AGC CCG AGC GGC GGC GGC GGC TCC GGG GGC      51
          Met Ala Ala Pro Ser Pro Ser Gly Gly Gly Gly Ser Gly Gly
            1               5                  10

GGC AGC GGC AGC GGC ACC CCC GGC CCC GTA GGG TCC CCG GCG CCA GGC         99
Gly Ser Gly Ser Gly Thr Pro Gly Pro Val Gly Ser Pro Ala Pro Gly
 15              20                  25                  30

CAC CCG GCC GTC AGC AGC ATG CAG GGT AAA CGC AAA GCA CTG AAG TTG        147
His Pro Ala Val Ser Ser Met Gln Gly Lys Arg Lys Ala Leu Lys Leu
                 35                  40                  45

AAT TTT GCA AAT CCA CCT TTC AAA TCT ACA GCA AGG TTT ACT CTG AAT        195
Asn Phe Ala Asn Pro Pro Phe Lys Ser Thr Ala Arg Phe Thr Leu Asn
                 50                  55                  60

CCC AAT CCT ACA GGA GTT CAA AAC CCA CAC ATA GAG AGA CTG AGA ACA        243
Pro Asn Pro Thr Gly Val Gln Asn Pro His Ile Glu Arg Leu Arg Thr
     65                  70                  75

CAC AGC ATT GAG TCA TCA GGA AAA CTG AAG ATC TCC CCT GAA CAA CAC        291
His Ser Ile Glu Ser Ser Gly Lys Leu Lys Ile Ser Pro Glu Gln His
     80                  85                  90

TGG GAT TTC ACT GCA GAG GAC TTG AAA GAC CTT GGA GAA ATT GGA CGA        339
Trp Asp Phe Thr Ala Glu Asp Leu Lys Asp Leu Gly Glu Ile Gly Arg
 95                 100                 105                 110

GGA GCT TAT GGT TCT GTC AAC AAA ATG GTC CAC AAA CCA AGT GGG CAA        387
Gly Ala Tyr Gly Ser Val Asn Lys Met Val His Lys Pro Ser Gly Gln
                115                 120                 125

ATA ATG GCA GTT AAA AGA ATT CGG TCA ACA GTG GAT GAA AAA GAA CAA        435
Ile Met Ala Val Lys Arg Ile Arg Ser Thr Val Asp Glu Lys Glu Gln
            130                 135                 140

AAA CAA CTT CTT ATG GAT TTG GAT GTA GTA ATG CGG AGT AGT GAT TGC        483
Lys Gln Leu Leu Met Asp Leu Asp Val Val Met Arg Ser Ser Asp Cys
            145                 150                 155

CCA TAC ATT GTT CAG TTT TAT GGT GCA CTC TTC AGA GAG GGT GAC TGT        531
Pro Tyr Ile Val Gln Phe Tyr Gly Ala Leu Phe Arg Glu Gly Asp Cys
        160                 165                 170

TGG ATC TGT ATG GAA CTC ATG TCT ACC TCG TTT GAT AAG TTT TAC AAA        579
Trp Ile Cys Met Glu Leu Met Ser Thr Ser Phe Asp Lys Phe Tyr Lys
175                 180                 185                 190

TAT GTA TAT AGT GTA TTA GAT GAT GTT ATT CCA GAA GAA ATT TTA GGC        627
Tyr Val Tyr Ser Val Leu Asp Asp Val Ile Pro Glu Glu Ile Leu Gly
                195                 200                 205

AAA ATC ACT TTA GCA ACT GTG AAA GCA CTA AAC CAC TTA AAA GAA AAC        675
Lys Ile Thr Leu Ala Thr Val Lys Ala Leu Asn His Leu Lys Glu Asn
            210                 215                 220

TTG AAA ATT ATT CAC AGA GAT ATC AAA CCT TCC AAT ATT CTT CTG GAC        723
Leu Lys Ile Ile His Arg Asp Ile Lys Pro Ser Asn Ile Leu Leu Asp
        225                 230                 235

AGA AGT GGA AAT ATT AAG CTC TGT GAC TTC GGC ATC AGT GGA CAG CTT        771
```

```
                                                                 -continued

Arg Ser Gly Asn Ile Lys Leu Cys Asp Phe Gly Ile Ser Gly Gln Leu
    240                 245                 250

GTG GAC TCT ATT GCC AAG ACA AGA GAT GCT GGC TGT AGG CCA TAC ATG        819
Val Asp Ser Ile Ala Lys Thr Arg Asp Ala Gly Cys Arg Pro Tyr Met
255                 260                 265                 270

GCA CCT GAA AGA ATA GAC CCA AGC GCA TCA CGA CAA GGA TAT GAT GTC        867
Ala Pro Glu Arg Ile Asp Pro Ser Ala Ser Arg Gln Gly Tyr Asp Val
                275                 280                 285

CGC TCT GAT GTC TGG AGT TTG GGG ATC ACA TTG TAT GAG TTG GCC ACA        915
Arg Ser Asp Val Trp Ser Leu Gly Ile Thr Leu Tyr Glu Leu Ala Thr
            290                 295                 300

GGC CGA TTT CCT TAT CCA AAG TGG AAT AGT GTA TTT GAT CAA CTA ACA        963
Gly Arg Phe Pro Tyr Pro Lys Trp Asn Ser Val Phe Asp Gln Leu Thr
        305                 310                 315

CAA GTC GTG AAA GGA GAT CCT CCG CAG CTG AGT AAT TCT GAG GAA AGG       1011
Gln Val Val Lys Gly Asp Pro Pro Gln Leu Ser Asn Ser Glu Glu Arg
    320                 325                 330

GAA TTC TCC CCG AGT TTC ATC AAC TTT GTC AAC TTG TGC CTT ACG AAG       1059
Glu Phe Ser Pro Ser Phe Ile Asn Phe Val Asn Leu Cys Leu Thr Lys
335                 340                 345                 350

GAT GAA TCC AAA AGG CCA AAG TAT AAA GAG CTT CTG AAA CAT CCC TTT       1107
Asp Glu Ser Lys Arg Pro Lys Tyr Lys Glu Leu Leu Lys His Pro Phe
                355                 360                 365

ATT TTG ATG TAT GAA GAA CGT GCC GTT GAG GTC GCA TGC TAT GTT TGT       1155
Ile Leu Met Tyr Glu Glu Arg Ala Val Glu Val Ala Cys Tyr Val Cys
            370                 375                 380

AAA ATC CTG GAT CAA ATG CCA GCT ACT CCC AGC TCT CCC ATG TAT GTC       1203
Lys Ile Leu Asp Gln Met Pro Ala Thr Pro Ser Ser Pro Met Tyr Val
        385                 390                 395

GAT TGATATCGCT GCTACATCAG ACTCTAGAAA AAAGGGCTGA GAGGAAGCAA GACGTA     1262
Asp

AAGAATTTTC ATCCCGTATC ACAGTGTTTT TATTGCTCGC CCAGACACCA TGTGCAATAA     1322

GATTGGTGTT CGTTTCCATC ATGTCTGTAT ACTCCTGTCA CCTAGAACGT GCATCCTTGT     1382

AATACCTGAT TGATCACACA GTGTTAGTGC TGGTCAGAGA GACCTCATCC TGCTCTTTTG     1442

TGATGAACAT ATTCATGAAA TGTGGAAGTC AGTACGATCA AGTTGTTGAC TGTGATTAGA     1502

TCACATCTTA AATTCATTTC TAGACTCAAA ACCTGGAGAT GCAGCTACTG GAATGGTGTT     1562

TTGTCAGACT TCCAAATCCT GGAAGGACAC AGTGATGAAT GTACTATATC TGAACATAGA     1622

AACTCGGGCT TGAGTGAGAA GAGCTTGCAC AGCCAACGAG ACACATTGCC TTCTGGAGCT     1682

GGGAGACAAA GGAGGAATTT ACTTTCTTCA CCAAGTGCAA TAGATTACTG ATGTGATATT     1742

CTGTTGCTTT ACAGTTACAG TTGATGTTTG GGGATCGATG TGCTCAGCCA AATTTCCTGT     1802

TTGAAATATC ATGTTAAATT AGAATGAATT TATCTTTACC AAAAACCATG TTGCGTTCAA     1862

AGAGGTGAAC ATTAAAATAT AGAGACAGGA CAGAATGTGT TCTTTTCTCC TCTACCAGTC     1922

CTATTTTTCA ATGGGAAGAC TCAGGAGTCT GCCACTTGTC AAAGAAGGTG CTGATCCTAA     1982

GAATTTTTCA TTCTCAGAAT TCGGTGTGCT GCCAACTTGA TGTTCCACCT GCCACAAACC     2042

ACCAGGACTG AAAGAAGAAA ACAGTACAGA AGGCAAAGTT TACAGATGTT TTTAATTCTA     2102

GTATTTTATC TGGAACAACT TGTAGCAGCT ATATATTTCC CCTTGGTCCC AAGCCTGATA     2162

CTTTAGCCAT CATAACTCAC TAACAGGGAG AAGTAGCTAG TAGCAATGTG CCTTGATTGA     2222

TTAGATAAAG ATTTCTAGTA GGCAGCAAAA GACCAAATCT CAGTTGTTTG CTTCTTGCCA     2282

TCACTGGTCC AGGTCTTCAG TTTCCGAATC TCTTTCCCTT CCCCTGTGGT CTATTGTCGC     2342

TATGTGACTT GCGCTTAATC CAATATTTTG CCTTTTTTCT ATATCAAAAA ACCTTTACAG     2402
```

-continued

```
TTAGCAGGGA TGTTCCTTAC CGAGGATTTT TAACCCCCAA TCTCTCATAA TCGCTAGTGT    2462

TTAAAAGGCT AAGAATAGTG GGGCCCAACC GATGTGGTAG GTGATAAAGA GGCATCTTTT    2522

CTAGAGACAC ATTGGACCAG ATGAGGATCC GAAACGGCAG CCTTTACGTT CATCACCTGC    2582

TAGAACCTCT CGTAGTCCAT CACCATTTCT TGGCATTGGA ATTCTACTGG AAAAAAATAC    2642

AAAAAGCAAA ACAAAACCCT CAGCACTGTT ACAAGAGGCC ATTTAAGTAT CTTGTGCTTC    2702

TTCACTTACC CATTAGCCAG GTTCTCATTA GGTTTTGCTT GGGCCTCCCT GGCACTGAAC    2762

CTTAGGCTTT GTATGACAGT GAAGCAGCAC TGTGAGTGGT TCAAGCACAC TGGAATATAA    2822

AACAGTCATG GCCTGAGATG CAGGTGATGC CATTACAGAA CCAAATCGTG GCACGTATTG    2882

CTGTGTCTCC TCTCAGAGTG ACAGTCATAA ATACTGTCAA ACAATAAAGG GAGAATGGTG    2942

CTGTTTAAAG TCACATCCCT GTAAATTGCA GAATTCAAAA GTGATTATCT CTTTGATCTA    3002

CTTGCCTCAT TTCCCTATCT TCTCCCCCAC GGTATCCTAA ACTTTAGACT TCCCACTGTT    3062

CTGAAAGGAG ACATTGCTCT ATGTCTGCCT TCGACCACAG CAAGCCATCA TCCTCCATTG    3122

CTCCCGGGGA CTCAAGAGGA ATCTGTTTCT CTGCTGTCAA CTTCCCATCT GGCTCAGCAT    3182

AGGGTCACTT TGCCATTATG CAAATGGAGA TAAAAGCAAT TCTGGCTGTC CAGGAGCTAA    3242

TCTGACCGTT CTATTGTGTG GATGACCACA TAAGAAGGCA ATTTTAGTGT ATTAATCATA    3302

GATTATTATA AACTATAAAC TTAAGGGCAA GGAGTTTATT ACAATGTATC TTTATTAAAA    3362

CAAAAGGGTG TATAGTGTTC ACAAACTGTG AAAATAGTGT AAGAACTGTA CATTGTGAGC    3422

TCTGGTTATT TTTCTCTTGT ACCATAGAAA AATGTATAAA AATTATCAAA AAGCTAATGT    3482

GCAGGGATAT TGCCTTATTT GTCTGTAAAA AATGGAGCTC AGTAACATAA CTGCTTCTTG    3542

GAGCTTTGGA ATATTTTATC CTGTATTCTT GTTT                              3576

(2) INFORMATION FOR SEQ ID NO: 10:

(i) SEQUENCE CHARACTERISTICS:
        (A) LENGTH: 399 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 10:

Met Ala Ala Pro Ser Pro Ser Gly Gly Gly Ser Gly Gly Gly Ser
  1               5                  10                  15

Gly Ser Gly Thr Pro Gly Pro Val Gly Ser Pro Ala Pro Gly His Pro
                 20                  25                  30

Ala Val Ser Ser Met Gln Gly Lys Arg Lys Ala Leu Lys Leu Asn Phe
             35                  40                  45

Ala Asn Pro Pro Phe Lys Ser Thr Ala Arg Phe Thr Leu Asn Pro Asn
         50                  55                  60

Pro Thr Gly Val Gln Asn Pro His Ile Glu Arg Leu Arg Thr His Ser
     65                  70                  75                  80

Ile Glu Ser Ser Gly Lys Leu Lys Ile Ser Pro Glu Gln His Trp Asp
                 85                  90                  95

Phe Thr Ala Glu Asp Leu Lys Asp Leu Gly Glu Ile Gly Arg Gly Ala
            100                 105                 110

Tyr Gly Ser Val Asn Lys Met Val His Lys Pro Ser Gly Gln Ile Met
            115                 120                 125
```

```
Ala Val Lys Arg Ile Arg Ser Thr Val Asp Glu Lys Glu Gln Lys Gln
    130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
                180                 185                 190

Tyr Ser Val Leu Asp Asp Val Ile Pro Glu Glu Ile Leu Gly Lys Ile
        195                 200                 205

Thr Leu Ala Thr Val Lys Ala Leu Asn His Leu Lys Glu Asn Leu Lys
    210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
                260                 265                 270

Glu Arg Ile Asp Pro Ser Ala Ser Arg Gln Gly Tyr Asp Val Arg Ser
            275                 280                 285

Asp Val Trp Ser Leu Gly Ile Thr Leu Tyr Glu Leu Ala Thr Gly Arg
    290                 295                 300

Phe Pro Tyr Pro Lys Trp Asn Ser Val Phe Asp Gln Leu Thr Gln Val
305                 310                 315                 320

Val Lys Gly Asp Pro Pro Gln Leu Ser Asn Ser Glu Glu Arg Glu Phe
                325                 330                 335

Ser Pro Ser Phe Ile Asn Phe Val Asn Leu Cys Leu Thr Lys Asp Glu
                340                 345                 350

Ser Lys Arg Pro Lys Tyr Lys Glu Leu Leu Lys His Pro Phe Ile Leu
            355                 360                 365

Met Tyr Glu Glu Arg Ala Val Glu Val Ala Cys Tyr Val Cys Lys Ile
    370                 375                 380

Leu Asp Gln Met Pro Ala Thr Pro Ser Ser Pro Met Tyr Val Asp
385                 390                 395

(2) INFORMATION FOR SEQ ID NO: 11:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO: 11:

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
                20                  25                  30

Leu Gln Lys Lys Leu Glu Glu Leu Glu Leu Asp Glu Gln Gln Arg Lys
            35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
```

```
                85                 90                 95
Lys Leu Ile His Leu Glu Ile Lys Pro Ala Ile Arg Asn Gln Ile Ile
            100                 105                 110
Arg Glu Leu Gln Val Leu His Glu Cys Asn Ser Pro Tyr Ile Val Gly
            115                 120                 125
Phe Tyr Gly Ala Phe Tyr Ser Asp Gly Glu Ile Ser Ile Cys Met Glu
            130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
            180                 185                 190
Pro Ser Asn Ile Leu Val Asn Ser Arg Gly Glu Ile Lys Leu Cys Asp
            195                 200                 205
Phe Gly Val Ser Gly Gln Leu Ile Asp Ser Met Ala Asn Ser Phe Val
            210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                245                 250                 255
Ala Val Gly Arg Tyr Pro Ile Pro Pro Asp Ala Lys Glu Leu Glu
                260                 265                 270
Leu Met Phe Gly Cys Gln Val Glu Gly Asp Ala Ala Glu Thr Pro Pro
            275                 280                 285
Arg Pro Arg Thr Pro Gly Arg Pro Leu Ser Ser Tyr Gly Met Asp Ser
290                 295                 300
Arg Pro Pro Met Ala Ile Phe Glu Leu Leu Asp Tyr Ile Val Asn Glu
305                 310                 315                 320
Pro Pro Pro Lys Leu Pro Ser Gly Val Phe Ser Leu Glu Phe Gln Asp
                325                 330                 335
Phe Val Asn Lys Cys Leu Ile Lys Asn Pro Ala Glu Arg Ala Asp Leu
            340                 345                 350
Lys Gln Leu Met Val His Ala Phe Ile Lys Arg Ser Asp Ala Glu Glu
            355                 360                 365
Val Asp Phe Ala Gly Trp Leu Cys Ser Thr Ile Gly Leu Asn Gln Pro
370                 375                 380
Ser Thr Pro Thr His Ala Ala Gly Val
385                 390

(2) INFORMATION FOR SEQ ID NO: 12:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO: 12:

Met Leu Ala Arg Arg Lys Pro Val Leu Pro Ala Leu Thr Ile Asn Pro
 1               5                  10                  15
Thr Ile Ala Glu Gly Pro Ser Pro Thr Ser Glu Gly Ala Ser Glu Ala
                20                  25                  30
Asn Leu Val Asp Leu Gln Lys Lys Leu Glu Glu Leu Glu Leu Asp Glu
            35                  40                  45
```

```
Gln Gln Lys Lys Arg Leu Glu Ala Phe Leu Thr Gln Lys Ala Lys Val
         50                  55                  60

Gly Glu Leu Lys Asp Asp Phe Glu Arg Ile Ser Glu Leu Gly Ala
 65                  70                  75                  80

Gly Asn Gly Gly Val Val Thr Lys Val Gln His Arg Pro Ser Gly Leu
                 85                  90                  95

Ile Met Ala Arg Lys Leu Ile His Leu Glu Ile Lys Pro Ala Ile Arg
             100                 105                 110

Asn Gln Ile Ile Arg Glu Leu Gln Val Leu His Glu Cys Asn Ser Pro
         115                 120                 125

Tyr Ile Val Gly Phe Tyr Gly Ala Phe Tyr Ser Asp Gly Glu Ile Ser
         130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                 165                 170                 175

Val Leu Arg Gly Leu Ala Tyr Leu Arg Glu Lys His Gln Ile Met His
             180                 185                 190

Arg Asp Val Lys Pro Ser Asn Ile Leu Val Asn Ser Arg Gly Glu Ile
         195                 200                 205

Lys Leu Cys Asp Phe Gly Val Ser Gly Gln Leu Ile Asp Ser Met Ala
         210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
             245                 250                 255

Leu Val Glu Leu Ala Val Gly Arg Tyr Pro Ile Pro Pro Pro Asp Ala
             260                 265                 270

Lys Glu Leu Glu Ala Ile Phe Gly Arg Pro Val Val Asp Gly Glu Glu
         275                 280                 285

Gly Glu Pro His Ser Ile Ser Pro Arg Pro Arg Pro Pro Gly Arg Pro
         290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
             325                 330                 335

Val Phe Thr Pro Asp Phe Gln Glu Phe Val Asn Lys Cys Leu Ile Lys
             340                 345                 350

Asn Pro Ala Glu Arg Ala Asp Leu Lys Met Leu Thr Asn His Thr Phe
         355                 360                 365

Ile Lys Arg Ser Glu Val Glu Glu Val Asp Phe Ala Gly Trp Leu Cys
         370                 375                 380

Lys Thr Leu Arg Leu Asn Gln Pro Gly Thr Pro Thr Arg Thr Ala Val
385                 390                 395                 400

(2) INFORMATION FOR SEQ ID NO: 13:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO: 13:
```

-continued

```
Gly Thr Thr Pro Arg Thr Gly Asn Ser Asn Asn Ser Asn Ser Gly Ser
  1               5                  10                  15

Ser Gly Gly Gly Gly Leu Phe Ala Asn Phe Ser Lys Tyr Val Asp Ile
             20                  25                  30

Lys Ser Gly Ser Leu Asn Phe Ala Gly Lys Leu Ser Leu Ser Ser Lys
             35                  40                  45

Gly Ile Asp Phe Ser Asn Gly Ser Ser Arg Ile Thr Leu Asp Glu
         50                  55                  60

Leu Glu Phe Leu Asp Glu Leu Gly His Gly Asn Tyr Gly Asn Val Ser
 65                  70                  75                  80

Lys Val Leu His Lys Pro Thr Asn Val Ile Met Ala Thr Lys Glu Val
                 85                  90                  95

Arg Leu Glu Leu Asp Glu Ala Lys Phe Arg Gln Ile Leu Met Glu Leu
            100                 105                 110

Glu Val Leu His Lys Cys Asn Ser Pro Tyr Ile Val Asp Phe Tyr Gly
            115                 120                 125

Ala Phe Phe Ile Glu Gly Ala Val Tyr Met Cys Met Glu Tyr Met Asp
130                 135                 140

Gly Gly Ser Leu Asp Lys Ile Tyr Asp Glu Ser Ser Glu Ile Gly Gly
145                 150                 155                 160

Ile Asp Glu Pro Gln Leu Ala Phe Ile Ala Asn Ala Val Ile His Gly
                165                 170                 175

Leu Lys Glu Leu Lys Glu Gln His Asn Ile Ile His Arg Asp Val Lys
                180                 185                 190

Pro Thr Asn Ile Leu Cys Ser Ala Asn Gln Gly Thr Val Lys Leu Cys
                195                 200                 205

Asp Phe Gly Val Ser Gly Asn Leu Val Ala Ser Leu Ala Lys Thr Met
210                 215                 220

Asn Ile Gly Cys Gln Ser Tyr Met Ala Pro Glu Arg Ile Lys Ser Leu
225                 230                 235                 240

Asn Pro Asp Arg Ala Thr Tyr Thr Val Gln Ser Asp Ile Trp Ser Leu
                245                 250                 255

Gly Leu Ser Ile Leu Glu Met Ala Leu Gly Arg Tyr Pro Tyr Pro Pro
                260                 265                 270

Glu Thr Tyr Asp Asn Ile Phe Ser Gln Leu Ser Ala Ile Val Asp Gly
            275                 280                 285

Pro Pro Pro Arg Leu Pro Ser Asp Lys Phe Ser Ser Asp Ala Gln Asp
290                 295                 300

Phe Val Ser Leu Cys Leu Gln Lys Ile Pro Glu Arg Arg Pro Thr Tyr
305                 310                 315                 320

Ala Ala Leu Thr Glu His Pro Trp Leu Val Lys Tyr Arg Asn Gln Asp
                325                 330                 335

Val His Met Ser Glu Tyr Ile Thr Glu Arg Leu Glu Arg Arg Asn Lys
                340                 345                 350

Ile Leu Arg Glu Arg Gly Glu Asn Gly Leu Ser Lys Asn Val Pro
                355                 360                 365
```

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TTYTAYGGNG CNTTYTTYAT HGA                                            23

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

ATBCTYTCNG GNGCCATKTA                                                20

(2) INFORMATION FOR SEQ ID NO: 16:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 16:

Asp Tyr Lys Asp Asp Asp Asp Lys
 1               5

(2) INFORMATION FOR SEQ ID NO: 17:

(i) SEQUENCE CHARACTERISTICS:
        (A) LENGTH: 1623 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 281...1318

(xi) SEQUENCE DESCRIPTION: SEQ ID NO: 17:

GGAAAGGCAG CCTCCTGTAG GTGAAAATTC TGTTCACTAC CTGGCCACCT GGCCTGACTG     60

ACCTTCACAG CTTGATCATC TTCCTGAAGA GGCATTCAGG ATTCCCTCCA TCCCTACCCC    120

TTCTGGACAA AGTCTTCCAC GTTTCCTTCC TGGGAGTTTC TTCCAGGAAC TGGAGATACC    180

CAGAGCCCTG CAACTCCCAC TGGCCAACGA TGGGGGCAGC CGCTCACCAT CCTCAGAGAG    240

CTCCCCACAG CACCCTACAC CCCCCACCCG GCCCCGCCAC ATG CTG GGG CTC CCA     295
                                            Met Leu Gly Leu Pro
                                              1               5

TCA ACC TTG TTC ACA CCG CGC AGT ATG GAG AGC ATC GAG ATT GAC CAG     343
Ser Thr Leu Phe Thr Pro Arg Ser Met Glu Ser Ile Glu Ile Asp Gln
             10                  15                  20

AAG CTG CAG GAG ATC ATG AAG CAG ACA GGG TAC CTG ACT ATC GGG GGC     391
Lys Leu Gln Glu Ile Met Lys Gln Thr Gly Tyr Leu Thr Ile Gly Gly
         25                  30                  35

CAG CGT TAT CAG GCA GAA ATC AAT GAC TTG GAG AAC TTG GGT GAG ATG     439
Gln Arg Tyr Gln Ala Glu Ile Asn Asp Leu Glu Asn Leu Gly Glu Met
         40                  45                  50

GGC AGT GGT ACC TGT GGT CAG GTG TGG AAG ATG CGG TTC CGG AAG ACA     487
Gly Ser Gly Thr Cys Gly Gln Val Trp Lys Met Arg Phe Arg Lys Thr
         55                  60                  65

```
GGC CAC ATC ATT GCT GTT AAG CAA ATG CGG CGC TCT GGG AAC AAG GAA    535
Gly His Ile Ile Ala Val Lys Gln Met Arg Arg Ser Gly Asn Lys Glu
 70              75                  80                  85

GAG AAT AAG CGC ATT TTG ATG GAC CTG GAT GTA GTA CTC AAG AGC CAT    583
Glu Asn Lys Arg Ile Leu Met Asp Leu Asp Val Val Leu Lys Ser His
             90                  95                 100

GAC TGC CCT TAC ATC GTT CAG TGC TTT GGC ACC TTC ATC ACC AAC ACA    631
Asp Cys Pro Tyr Ile Val Gln Cys Phe Gly Thr Phe Ile Thr Asn Thr
            105                 110                 115

GAC GTC TTT ATT GCC ATG GAG CTC ATG GGC ACA TGT GCA GAG AAG CTG    679
Asp Val Phe Ile Ala Met Glu Leu Met Gly Thr Cys Ala Glu Lys Leu
        120                 125                 130

AAG AAA CGA ATG CAG GGC CCC ATT CCA GAG CGA ATC CTG GGC AAC ATG    727
Lys Lys Arg Met Gln Gly Pro Ile Pro Glu Arg Ile Leu Gly Asn Met
    135                 140                 145

ACT GTG GCG ATT GTG AAA GCA CTG TAC TAT CTG AAG GAG AAG CAT GGC    775
Thr Val Ala Ile Val Lys Ala Leu Tyr Tyr Leu Lys Glu Lys His Gly
150                 155                 160                 165

GTC ATC CAT CGC GAT GTC AAA CCC TCC AAC ATC CTG CTA GAT GAG CGG    823
Val Ile His Arg Asp Val Lys Pro Ser Asn Ile Leu Leu Asp Glu Arg
                170                 175                 180

GGC CAG ATC AAG CTC TGT GAC TTT GGC ATC AGT GGC CGC CTT GTT GAC    871
Gly Gln Ile Lys Leu Cys Asp Phe Gly Ile Ser Gly Arg Leu Val Asp
            185                 190                 195

TCC AAA GCC AAA ACA CGG AGT GCT GGC TGT GCT GCC TAT ATG GCT CCC    919
Ser Lys Ala Lys Thr Arg Ser Ala Gly Cys Ala Ala Tyr Met Ala Pro
        200                 205                 210

GAG CGC ATC GAC CCT CCA GAT CCC ACC AAG CCT GAC TAT GAC ATC CGA    967
Glu Arg Ile Asp Pro Pro Asp Pro Thr Lys Pro Asp Tyr Asp Ile Arg
    215                 220                 225

GCT GAT GTG TGG AGC CTG GGC ATC TCA CTG GTG GAG CTG GCA ACA GGA   1015
Ala Asp Val Trp Ser Leu Gly Ile Ser Leu Val Glu Leu Ala Thr Gly
230                 235                 240                 245

CAG TTC CCC TAT AAG AAC TGC AAG ACG GAC TTT GAG GTC CTC ACC AAA   1063
Gln Phe Pro Tyr Lys Asn Cys Lys Thr Asp Phe Glu Val Leu Thr Lys
                250                 255                 260

GTC CTA CAG GAA GAG CCC CCA CTC CTG CCT GGT CAC ATG GGC TTC TCA   1111
Val Leu Gln Glu Glu Pro Pro Leu Leu Pro Gly His Met Gly Phe Ser
            265                 270                 275

GGG GAC TTC CAG TCA TTT GTC AAA GAC TGC CTT ACT AAA GAT CAC AGG   1159
Gly Asp Phe Gln Ser Phe Val Lys Asp Cys Leu Thr Lys Asp His Arg
        280                 285                 290

AAG AGA CCA AAG TAT AAT AAG CTA CTT GAA CAC AGC TTC ATC AAG CAC   1207
Lys Arg Pro Lys Tyr Asn Lys Leu Leu Glu His Ser Phe Ile Lys His
    295                 300                 305

TAT GAG ATA CTC GAG GTG GAT GTC GCG TCC TGG TTT AAG GAT GTC ATG   1255
Tyr Glu Ile Leu Glu Val Asp Val Ala Ser Trp Phe Lys Asp Val Met
310                 315                 320                 325

GCG AAG ACC GAG TCC CCA AGG ACT AGT GGA GTC CTG AGT CAG CAC CAT   1303
Ala Lys Thr Glu Ser Pro Arg Thr Ser Gly Val Leu Ser Gln His His
                330                 335                 340

CTG CCC TTC TTC AGG TAGCCTCATG GCAGCGGCCA GCCCCGCAGG GGCCCCGGGC C 1359
Leu Pro Phe Phe Arg
            345

ACGGCCACCG ACCCCCCCCC CAACCTGGCC AACCCAGCTG CCCATCAGGG GACCTGGGAC   1419

CTGGACGACT GCCAAGGACT GAGGACAGAA AGTAGGGGGT TCCCATCCAG CTCTGACTCC   1479

CTGCCTACCA GCTGTGGACA AAAGGGCATG CTGGTTCCTA ATCCCTCCCA CTCTGGGGTC   1539
```

```
AGCCAGCAGT GTGAGCCCCA TCCCACCCCG ACAGACACTG TGAACGGAAG ACAGCAGGCC    1599

AAAAAAAAAA AAAAAAAAAA AAAA                                          1623
```

(2) INFORMATION FOR SEQ ID NO: 18:

(i) SEQUENCE CHARACTERISTICS:
        (A) LENGTH: 346 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 18:

```
Met Leu Gly Leu Pro Ser Thr Leu Phe Thr Pro Arg Ser Met Glu Ser
 1               5                  10                  15

Ile Glu Ile Asp Gln Lys Leu Gln Glu Ile Met Lys Gln Thr Gly Tyr
             20                  25                  30

Leu Thr Ile Gly Gly Gln Arg Tyr Gln Ala Glu Ile Asn Asp Leu Glu
             35                  40                  45

Asn Leu Gly Glu Met Gly Ser Gly Thr Cys Gly Gln Val Trp Lys Met
 50                  55                  60

Arg Phe Arg Lys Thr Gly His Ile Ile Ala Val Lys Gln Met Arg Arg
 65                  70                  75                  80

Ser Gly Asn Lys Glu Glu Asn Lys Arg Ile Leu Met Asp Leu Asp Val
                 85                  90                  95

Val Leu Lys Ser His Asp Cys Pro Tyr Ile Val Gln Cys Phe Gly Thr
                100                 105                 110

Phe Ile Thr Asn Thr Asp Val Phe Ile Ala Met Glu Leu Met Gly Thr
            115                 120                 125

Cys Ala Glu Lys Leu Lys Lys Arg Met Gln Gly Pro Ile Pro Glu Arg
    130                 135                 140

Ile Leu Gly Asn Met Thr Val Ala Ile Val Lys Ala Leu Tyr Tyr Leu
145                 150                 155                 160

Lys Glu Lys His Gly Val Ile His Arg Asp Val Lys Pro Ser Asn Ile
                165                 170                 175

Leu Leu Asp Glu Arg Gly Gln Ile Lys Leu Cys Asp Phe Gly Ile Ser
            180                 185                 190

Gly Arg Leu Val Asp Ser Lys Ala Lys Thr Arg Ser Ala Gly Cys Ala
        195                 200                 205

Ala Tyr Met Ala Pro Glu Arg Ile Asp Pro Pro Asp Pro Thr Lys Pro
    210                 215                 220

Asp Tyr Asp Ile Arg Ala Asp Val Trp Ser Leu Gly Ile Ser Leu Val
225                 230                 235                 240

Glu Leu Ala Thr Gly Gln Phe Pro Tyr Lys Asn Cys Lys Thr Asp Phe
                245                 250                 255

Glu Val Leu Thr Lys Val Leu Gln Glu Glu Pro Pro Leu Leu Pro Gly
            260                 265                 270

His Met Gly Phe Ser Gly Asp Phe Gln Ser Phe Val Lys Asp Cys Leu
        275                 280                 285

Thr Lys Asp His Arg Lys Arg Pro Lys Tyr Asn Lys Leu Leu Glu His
    290                 295                 300

Ser Phe Ile Lys His Tyr Glu Ile Leu Glu Val Asp Val Ala Ser Trp
305                 310                 315                 320

Phe Lys Asp Val Met Ala Lys Thr Glu Ser Pro Arg Thr Ser Gly Val
```

```
                      325                 330                 335
Leu Ser Gln His His Leu Pro Phe Phe Arg
            340                 345

(2) INFORMATION FOR SEQ ID NO: 19:

(i) SEQUENCE CHARACTERISTICS:
        (A) LENGTH: 1465 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 3...1169

(xi) SEQUENCE DESCRIPTION: SEQ ID NO: 19:

GC ACG AGC CCT GCT CCT GCC CCG TCC CAG CGA GCA GCC CTG CAA CTC        47
   Thr Ser Pro Ala Pro Ala Pro Ser Gln Arg Ala Ala Leu Gln Leu
     1               5                  10                  15

CCA CTG GCC AAC GAT GGG GGC AGC CGC TCA CCA TCC TCA GAG AGC TCC       95
Pro Leu Ala Asn Asp Gly Gly Ser Arg Ser Pro Ser Ser Glu Ser Ser
             20                  25                  30

CCA CAG CAC CCT ACA CCC CCC ACC CGG CCC CGC CAC ATG CTG GGG CTC      143
Pro Gln His Pro Thr Pro Pro Thr Arg Pro Arg His Met Leu Gly Leu
         35                  40                  45

CCA TCA ACC TTG TTC ACA CCG CGC AGT ATG GAG AGC ATC GAG ATT GAC      191
Pro Ser Thr Leu Phe Thr Pro Arg Ser Met Glu Ser Ile Glu Ile Asp
     50                  55                  60

CAG AAG CTG CAG GAG ATC ATG AAG CAG ACA GGG TAC CTG ACT ATC GGG      239
Gln Lys Leu Gln Glu Ile Met Lys Gln Thr Gly Tyr Leu Thr Ile Gly
 65                  70                  75

GGC CAG CGT TAT CAG GCA GAA ATC AAT GAC TTG GAG AAC TTG GGT GAG      287
Gly Gln Arg Tyr Gln Ala Glu Ile Asn Asp Leu Glu Asn Leu Gly Glu
 80                  85                  90                  95

ATG GGC AGT GGT ACC TGT GGT CAG GTG TGG AAG ATG CGG TTC CGG AAG      335
Met Gly Ser Gly Thr Cys Gly Gln Val Trp Lys Met Arg Phe Arg Lys
                100                 105                 110

ACA GGC CAC ATC ATT GCT GTT AAG CAA ATG CGG CGC TCT GGG AAC AAG      383
Thr Gly His Ile Ile Ala Val Lys Gln Met Arg Arg Ser Gly Asn Lys
            115                 120                 125

GAA GAG AAT AAG CGC ATT TTG ATG GAC CTG GAT GTA GTA CTC AAG AGC      431
Glu Glu Asn Lys Arg Ile Leu Met Asp Leu Asp Val Val Leu Lys Ser
        130                 135                 140

CAT GAC TGC CCT TAC ATC GTT CAG TGC TTT GGC ACC TTC ATC ACC AAC      479
His Asp Cys Pro Tyr Ile Val Gln Cys Phe Gly Thr Phe Ile Thr Asn
    145                 150                 155

ACA GAC GTC TTT ATT GCC ATG GAG CTC ATG GGC ACA TGT GCA GAG AAG      527
Thr Asp Val Phe Ile Ala Met Glu Leu Met Gly Thr Cys Ala Glu Lys
160                 165                 170                 175

CTG AAG AAA CGA ATG CAG GGC CCC ATT CCA GAG CGA ATC CTG GGC AAG      575
Leu Lys Lys Arg Met Gln Gly Pro Ile Pro Glu Arg Ile Leu Gly Lys
                180                 185                 190

ATG ACT GTG GCG ATT GTG AAA GCA CTG TAC TAT CTG AAG GAG AAG CAT      623
Met Thr Val Ala Ile Val Lys Ala Leu Tyr Tyr Leu Lys Glu Lys His
            195                 200                 205

GGC GTC ATC CAT CGC GAT GTC AAA CCC TCC AAC ATC CTG CTA GAT GAG      671
Gly Val Ile His Arg Asp Val Lys Pro Ser Asn Ile Leu Leu Asp Glu
        210                 215                 220

CGG GGC CAG ATC AAG CTC TGT GAC TTT GGC ATC AGT GGC CGC CTT GTT      719
```

```
Arg Gly Gln Ile Lys Leu Cys Asp Phe Gly Ile Ser Gly Arg Leu Val
    225                 230                 235

GAC TCC AAA GCC AAA ACA CGG AGT GCT GGC TGT GCT GCC TAT ATG GCT       767
Asp Ser Lys Ala Lys Thr Arg Ser Ala Gly Cys Ala Ala Tyr Met Ala
240                 245                 250                 255

CCC GAG CGC ATC GAC CCT CCA GAT CCC ACC AAG CCT GAC TAT GAC ATC       815
Pro Glu Arg Ile Asp Pro Pro Asp Pro Thr Lys Pro Asp Tyr Asp Ile
                260                 265                 270

CGA GCT GAT GTG TGG AGC CTG GGC ATC TCA CTG GTG GAG CTG GCA ACA       863
Arg Ala Asp Val Trp Ser Leu Gly Ile Ser Leu Val Glu Leu Ala Thr
            275                 280                 285

GGA CAG TTC CCC TAT AAG AAC TGC AAG ACG GAC TTT GAG GTC CTC ACC       911
Gly Gln Phe Pro Tyr Lys Asn Cys Lys Thr Asp Phe Glu Val Leu Thr
        290                 295                 300

AAA GTC CTA CAG GAA GAG CCC CCA CTC CTG CCT GGT CAC ATG GGC TTC       959
Lys Val Leu Gln Glu Glu Pro Pro Leu Leu Pro Gly His Met Gly Phe
    305                 310                 315

TCA GGG GAC TTC CAG TCA TTT GTC AAA GAC TGC CTT ACT AAA GAT CAC      1007
Ser Gly Asp Phe Gln Ser Phe Val Lys Asp Cys Leu Thr Lys Asp His
320                 325                 330                 335

AGG AAG AGA CCA AAG TAT AAT AAG CTA CTT GAA CAC AGC TTC ATC AAG      1055
Arg Lys Arg Pro Lys Tyr Asn Lys Leu Leu Glu His Ser Phe Ile Lys
                340                 345                 350

CAC TAT GAG ATA CTC GAG GTG GAT GTC GCG TCC TGG TTT AAG GAT GTC      1103
His Tyr Glu Ile Leu Glu Val Asp Val Ala Ser Trp Phe Lys Asp Val
            355                 360                 365

ATG GCG AAG ACC GAG TCC CCA AGG ACT AGT GGA GTC CTG AGT CAG CAC      1151
Met Ala Lys Thr Glu Ser Pro Arg Thr Ser Gly Val Leu Ser Gln His
        370                 375                 380

CAT CTG CCC TTC TTC AGG TAGCCTCATG GCAGCGGCCA GCCCCGCAGG GGCCCCGG    1207
His Leu Pro Phe Phe Arg
    385

GCCACGGCCA CCGACCCCCC CCCCAACCTG GCCAACCCAG CTGCCCATCA GGGGACCTGG    1267

GACCTGGACG ACTGCCAAGG ACTGAGGACA GAAAGTAGGG GGTTCCCATC CAGCTCTGAC    1327

TCCCTGCCTA CCAGCTGTGG ACAAAAGGGC ATGCTGGTTC CTAATCCCTC CCACTCTGGG    1387

GTCAGCCAGC AGTGTGAGCC CCATCCCACC CCGACAGACA CTGTGAACGG AAGACAGCAA    1447

AAAAAAAAAA AAAAAAAA                                                  1465

(2) INFORMATION FOR SEQ ID NO: 20:

(i) SEQUENCE CHARACTERISTICS:
        (A) LENGTH: 389 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 20:

Thr Ser Pro Ala Pro Ala Pro Ser Gln Arg Ala Ala Leu Gln Leu Pro
 1               5                  10                  15

Leu Ala Asn Asp Gly Gly Ser Arg Ser Pro Ser Ser Glu Ser Ser Pro
                20                  25                  30

Gln His Pro Thr Pro Pro Thr Arg Pro Arg His Met Leu Gly Leu Pro
            35                  40                  45

Ser Thr Leu Phe Thr Pro Arg Ser Met Glu Ser Ile Glu Ile Asp Gln
        50                  55                  60
```

-continued

```
Lys Leu Gln Glu Ile Met Lys Gln Thr Gly Tyr Leu Thr Ile Gly Gly
 65                  70                  75                  80

Gln Arg Tyr Gln Ala Glu Ile Asn Asp Leu Glu Asn Leu Gly Glu Met
                 85                  90                  95

Gly Ser Gly Thr Cys Gly Gln Val Trp Lys Met Arg Phe Arg Lys Thr
            100                 105                 110

Gly His Ile Ile Ala Val Lys Gln Met Arg Arg Ser Gly Asn Lys Glu
        115                 120                 125

Glu Asn Lys Arg Ile Leu Met Asp Leu Asp Val Val Leu Lys Ser His
    130                 135                 140

Asp Cys Pro Tyr Ile Val Gln Cys Phe Gly Thr Phe Ile Thr Asn Thr
145                 150                 155                 160

Asp Val Phe Ile Ala Met Glu Leu Met Gly Thr Cys Ala Glu Lys Leu
                165                 170                 175

Lys Lys Arg Met Gln Gly Pro Ile Pro Glu Arg Ile Leu Gly Lys Met
            180                 185                 190

Thr Val Ala Ile Val Lys Ala Leu Tyr Tyr Leu Lys Glu Lys His Gly
        195                 200                 205

Val Ile His Arg Asp Val Lys Pro Ser Asn Ile Leu Leu Asp Glu Arg
    210                 215                 220

Gly Gln Ile Lys Leu Cys Asp Phe Gly Ile Ser Gly Arg Leu Val Asp
225                 230                 235                 240

Ser Lys Ala Lys Thr Arg Ser Ala Gly Cys Ala Ala Tyr Met Ala Pro
                245                 250                 255

Glu Arg Ile Asp Pro Pro Asp Pro Thr Lys Pro Asp Tyr Asp Ile Arg
            260                 265                 270

Ala Asp Val Trp Ser Leu Gly Ile Ser Leu Val Glu Leu Ala Thr Gly
        275                 280                 285

Gln Phe Pro Tyr Lys Asn Cys Lys Thr Asp Phe Glu Val Leu Thr Lys
    290                 295                 300

Val Leu Gln Glu Glu Pro Pro Leu Leu Pro Gly His Met Gly Phe Ser
305                 310                 315                 320

Gly Asp Phe Gln Ser Phe Val Lys Asp Cys Leu Thr Lys Asp His Arg
                325                 330                 335

Lys Arg Pro Lys Tyr Asn Lys Leu Leu Glu His Ser Phe Ile Lys His
            340                 345                 350

Tyr Glu Ile Leu Glu Val Asp Val Ala Ser Trp Phe Lys Asp Val Met
        355                 360                 365

Ala Lys Thr Glu Ser Pro Arg Thr Ser Gly Val Leu Ser Gln His His
    370                 375                 380

Leu Pro Phe Phe Arg
385
```

(2) INFORMATION FOR SEQ ID NO: 21:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO: 21:

```
Ser Ala Ser Ser Ser Ser Ser Ala Ser Ala Phe Ala Ser Ala Ala
  1               5                  10                  15

Pro Ala Thr Gly Thr Phe Gly Gly Thr Tyr Thr Pro Pro Thr Thr Arg
```

```
            20                  25                  30
Val Ser Arg Ala Thr Pro Thr Leu Pro Met Leu Ser Ser Gly Pro Gly
            35                  40                  45

Gly Gly Leu Asn Arg Thr Arg Pro Asn Ile Leu Pro Leu Pro Thr Pro
        50                  55                  60

Pro His Pro Pro Val Ser Glu Thr Asp Met Lys Leu Lys Ile Ile Met
 65                  70                  75                  80

Glu Gln Thr Gly Lys Leu Asn Ile Asn Gly Arg Gln Tyr Pro Thr Asp
                85                  90                  95

Ile Asn Asp Leu Lys His Leu Gly Asp Leu Gly Asn Gly Thr Ser Gly
            100                 105                 110

Asn Val Val Lys Met Met His Leu Ser Ser Asn Thr Ile Ile Ala Val
            115                 120                 125

Lys Gln Met Arg Arg Thr Gly Asn Ala Glu Glu Asn Lys Arg Ile Leu
        130                 135                 140

Met Asp Leu Asp Val Val Leu Lys Ser His Asp Cys Lys Tyr Ile Val
145                 150                 155                 160

Lys Cys Leu Gly Cys Phe Val Arg Asp Pro Asp Val Trp Ile Cys Met
                165                 170                 175

Glu Leu Met Ser Met Cys Phe Asp Lys Leu Leu Lys Leu Ser Lys Lys
            180                 185                 190

Pro Val Pro Glu Gln Ile Leu Gly Lys Val Thr Val Ala Thr Val Asn
        195                 200                 205

Ala Leu Ser Tyr Leu Lys Asp Lys His Gly Val Ile His Arg Asp Val
        210                 215                 220

Lys Pro Ser Asn Ile Leu Ile Asp Glu Arg Gly Asn Ile Lys Leu Cys
225                 230                 235                 240

Asp Phe Gly Ile Ser Gly Arg Leu Val Asp Ser Lys Ala Lys Thr Arg
                245                 250                 255

Ser Ala Gly Cys Ala Ala Tyr Met Ala Pro Glu Arg Ile Asp Pro Lys
            260                 265                 270

Lys Pro Lys Tyr Asp Ile Arg Ala Asp Val Trp Ser Leu Gly Ile Thr
        275                 280                 285

Leu Val Glu Leu Ala Thr Ala Arg Ser Pro Tyr Glu Gly Cys Asn Thr
        290                 295                 300

Asp Phe Glu Val Leu Thr Lys Val Leu Asp Ser Glu Pro Pro Cys Leu
305                 310                 315                 320

Pro Tyr Gly Glu Gly Tyr Asn Phe Ser Gln Gln Phe Arg Asp Phe Val
                325                 330                 335

Ile Lys Cys Leu Thr Lys Asn His Gln Asp Arg Pro Lys Tyr Pro Glu
            340                 345                 350

Leu Leu Ala Gln Pro Phe Ile Arg Ile Tyr Glu Ser Ala Lys Val Asp
        355                 360                 365

Val Pro Asn Gln Ser Ile Lys Asp Asn Arg Leu Arg Ala Asn Gly Asp
        370                 375                 380

Pro Thr Leu Gln Arg Leu Pro Asn Ser
385                 390
```

(2) INFORMATION FOR SEQ ID NO: 22:

(i) SEQUENCE CHARACTERISTICS:
        (A) LENGTH: 405 amino acids
        (B) TYPE: amino acid
        (D) TOPOLOGY: linear (ii) MOLECULE TYPE: protein (xi) SEQUENCE DESCRIPTION: SEQ ID NO: 22:

```
Ile Gly Gln Val Leu Pro Glu Ala Thr Thr Thr Ala Phe Glu Tyr Glu
 1               5                  10                  15

Asp Glu Asp Gly Asp Arg Ile Thr Val Arg Ser Asp Glu Met Lys
             20                  25                  30

Ala Met Leu Ser Tyr Tyr Ser Thr Val Met Glu Gln Gln Val Asn
         35                  40                  45

Gly Gln Leu Ile Glu Pro Leu Gln Ile Phe Pro Arg Ala Cys Lys Pro
 50                  55                  60

Pro Gly Glu Arg Asn Ile His Gly Leu Lys Val Asn Thr Arg Ala Gly
 65                  70                  75                  80

Pro Ser Gln His Ser Ser Pro Ala Val Ser Asp Ser Leu Pro Ser Asn
                 85                  90                  95

Ser Leu Lys Lys Ser Ser Ala Glu Leu Lys Lys Ile Leu Ala Asn Gly
             100                 105                 110

Gln Met Asn Glu Gln Asp Ile Arg Tyr Arg Asp Thr Leu Gly His Gly
         115                 120                 125

Asn Gly Gly Thr Val Glu Lys Met Arg His Val Pro Ser Gly Lys Ile
130                 135                 140

Leu Ala Val Lys Val Ile Leu Leu Asp Ile Thr Leu Glu Leu Gln Lys
145                 150                 155                 160

Gln Ile Met Ser Glu Leu Glu Ile Leu Ile Lys Cys Asp Ser Ser Tyr
                 165                 170                 175

Ile Ile Gly Phe Tyr Gly Ala Phe Phe Val Glu Asn Arg Ile Ser Ile
             180                 185                 190

Cys Thr Glu Phe Met Asp Gly Gly Ser Leu Asp Asp Ile Gly Lys Met
         195                 200                 205

Pro Glu His Val Leu Gly Arg Ile Ala Val Ala Val Lys Gly Leu
210                 215                 220

Thr Tyr Lys Gly Leu Thr Tyr Leu Trp Ser Leu Lys Ile Leu His Arg
225                 230                 235                 240

Asp Val Lys Pro Ser Asn Met Val Asn Thr Arg Gly Gln Val Lys Leu
                 245                 250                 255

Cys Asp Phe Gly Val Ser Thr Gln Leu Val Asn Ser Ile Ala Lys Thr
             260                 265                 270

Tyr Val Gly Thr Asn Ala Tyr Met Ala Pro Glu Arg Ile Ser Gly Glu
         275                 280                 285

Gln Tyr Gly Ile His Ser Asp Val Trp Ser Leu Gly Ile Thr Met Ile
290                 295                 300

Glu Leu Ala Thr Gly Arg Phe Pro Tyr Pro Lys Trp Asn Ser Val Leu
305                 310                 315                 320

Gln Leu Leu Gln Cys Ile Val Asp Glu Asp Ser Pro Val Leu Pro Val
                 325                 330                 335

Gly Glu Phe Ser Glu Pro Phe Val His Phe Ile Thr Gln Cys Met Arg
             340                 345                 350

Thr Gln Pro Lys Glu Arg Pro Ala Pro Glu Glu Leu Met Gly His Pro
         355                 360                 365

Phe Ile Val Gln Phe Asn Asp Gly Asn Ala Ala Val Val Ser Met Trp
370                 375                 380

Val Cys Arg Ala Leu Glu Glu Arg Thr Ser Arg Gly Pro Arg Glu
385                 390                 395                 400
```

```
  Ala Ala Ala Gly His
              405
```

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

```
ATNGCNGTNA ARCARATG                                                18
```

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

```
ATNCKYTCNG GNGCCATRTA                                              20
```

(2) INFORMATION FOR SEQ ID NO: 25:

(i) SEQUENCE CHARACTERISTICS:
        (A) LENGTH: 843 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 62...841

(xi) SEQUENCE DESCRIPTION: SEQ ID NO: 25:

```
TGTTTGTCTG CCGGACTGAC GGGCGGCCGG GCGGTGCGCG GCGGCGGTGG CGGCGGGGAA    60

G ATG GCG GCG TCC TCC CTG GAA CAG AAG CTG TCC CGC CTG GAA GCA AAG  109
  Met Ala Ala Ser Ser Leu Glu Gln Lys Leu Ser Arg Leu Glu Ala Lys
  1               5                  10                  15

CTG AAG CAG GAG AAC CGG GAG GCC CGG CGG AGG ATC GAC CTC AAC CTG    157
Leu Lys Gln Glu Asn Arg Glu Ala Arg Arg Arg Ile Asp Leu Asn Leu
             20                  25                  30

GAT ATC AGC CCC CAG CGG CCC AGG CCC ACC CTG CAG CTC CCG CTG GCC    205
Asp Ile Ser Pro Gln Arg Pro Arg Pro Thr Leu Gln Leu Pro Leu Ala
         35                  40                  45

AAC GAT GGG GGC AGC CGC TCG CCA TCC TCA GAG AGC TCC CCG CAG CAC    253
Asn Asp Gly Gly Ser Arg Ser Pro Ser Ser Glu Ser Ser Pro Gln His
     50                  55                  60

CCC ACG CCC CCC GCC CGG CCC CGC CAC ATG CTG GGG CTC CCG TCA ACC    301
Pro Thr Pro Pro Ala Arg Pro Arg His Met Leu Gly Leu Pro Ser Thr
 65                  70                  75                  80

CTG TTC ACA CCC CGC AGC ATG GAG AGC ATT GAG ATT GAC CAG AAG CTG    349
Leu Phe Thr Pro Arg Ser Met Glu Ser Ile Glu Ile Asp Gln Lys Leu
                 85                  90                  95

CAG GAG ATC ATG AAG CAG ACG GGC TAC CTG ACC ATC GGG GGC CAG CGC    397
Gln Glu Ile Met Lys Gln Thr Gly Tyr Leu Thr Ile Gly Gly Gln Arg
            100                 105                 110
```

```
TAC CAG GCA GAA ATC AAC GAC CTG GAG AAC TTG GGC GAG ATG GGC AGC    445
Tyr Gln Ala Glu Ile Asn Asp Leu Glu Asn Leu Gly Glu Met Gly Ser
            115                 120                 125

GGC ACC TGC GGC CAG GTG TGG AAG ATG CGC TTC CGG AAG ACC GGC CAC    493
Gly Thr Cys Gly Gln Val Trp Lys Met Arg Phe Arg Lys Thr Gly His
    130                 135                 140

GTC ATT GCC GTT AAG CAA ATG CGG CGC TCC GGG AAC AAG GAG GAG AAC    541
Val Ile Ala Val Lys Gln Met Arg Arg Ser Gly Asn Lys Glu Glu Asn
145                 150                 155                 160

AAG CGC ATC CTC ATG GAC CTG GAT GTG GTG CTG AAG AGC CAC GAC TGC    589
Lys Arg Ile Leu Met Asp Leu Asp Val Val Leu Lys Ser His Asp Cys
                165                 170                 175

CCC TAC ATC GTG CAG TGC TTT GGG ACG TTC ATC ACC AAC ACG GAC GTC    637
Pro Tyr Ile Val Gln Cys Phe Gly Thr Phe Ile Thr Asn Thr Asp Val
            180                 185                 190

TTC ATC GCC ATG GAG CTC ATG GGC ACC TGC GCT GAG AAG CTC AAG AAG    685
Phe Ile Ala Met Glu Leu Met Gly Thr Cys Ala Glu Lys Leu Lys Lys
        195                 200                 205

CGG ATG CAG GGC CCC ATC CCC GAG CGC ATT CTG GGC AAG ATG ACA GTG    733
Arg Met Gln Gly Pro Ile Pro Glu Arg Ile Leu Gly Lys Met Thr Val
    210                 215                 220

GCG ATT GTG AAG GCG CTG TAC TAC CTG AAG GAG AAG CAC GGT GTC ATC    781
Ala Ile Val Lys Ala Leu Tyr Tyr Leu Lys Glu Lys His Gly Val Ile
225                 230                 235                 240

CAC CGC GAC GTC AAG CCC TCC AAC ATC CTG CTG GAC GAG CGG GGC CAG    829
His Arg Asp Val Lys Pro Ser Asn Ile Leu Leu Asp Glu Arg Gly Gln
                245                 250                 255

ATC AAG CTG TGC GA                                                  843
Ile Lys Leu Cys
            260
```

(2) INFORMATION FOR SEQ ID NO: 26:

(i) SEQUENCE CHARACTERISTICS:
        (A) LENGTH: 260 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 26:

```
Met Ala Ala Ser Ser Leu Glu Gln Lys Leu Ser Arg Leu Glu Ala Lys
1               5                   10                  15

Leu Lys Gln Glu Asn Arg Glu Ala Arg Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Ser Pro Gln His
    50                  55                  60

Pro Thr Pro Pro Ala Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
            85                  90                  95

Gln Glu Ile Met Lys Gln Thr Gly Tyr Leu Thr Ile Gly Gly Gln Arg
        100                 105                 110

Tyr Gln Ala Glu Ile Asn Asp Leu Glu Asn Leu Gly Glu Met Gly Ser
    115                 120                 125
```

-continued

```
Gly Thr Cys Gly Gln Val Trp Lys Met Arg Phe Arg Lys Thr Gly His
    130                 135                 140
Val Ile Ala Val Lys Gln Met Arg Arg Ser Gly Asn Lys Glu Glu Asn
145                 150                 155                 160
Lys Arg Ile Leu Met Asp Leu Asp Val Val Leu Lys Ser His Asp Cys
                165                 170                 175
Pro Tyr Ile Val Gln Cys Phe Gly Thr Phe Ile Thr Asn Thr Asp Val
            180                 185                 190
Phe Ile Ala Met Glu Leu Met Gly Thr Cys Ala Glu Lys Leu Lys Lys
        195                 200                 205
Arg Met Gln Gly Pro Ile Pro Glu Arg Ile Leu Gly Lys Met Thr Val
    210                 215                 220
Ala Ile Val Lys Ala Leu Tyr Tyr Leu Lys Glu Lys His Gly Val Ile
225                 230                 235                 240
His Arg Asp Val Lys Pro Ser Asn Ile Leu Leu Asp Glu Arg Gly Gln
                245                 250                 255
Ile Lys Leu Cys
            260
```

(2) INFORMATION FOR SEQ ID NO: 27:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 82...1338

(xi) SEQUENCE DESCRIPTION: SEQ ID NO: 27:

```
AGCGCAGGCG CAGTGCGGTG TTTGTCTACC CCGGACTGAC GGGTGGCCTG GCGGTGAGCG      60

GCGGCAGCGG CGGCGGGAA G ATG GCG GCG TCC TCC CTG GAG CAG AAG CTG        111
                      Met Ala Ala Ser Ser Leu Glu Gln Lys Leu
                        1               5                  10

TCC CGC CTG GAA GCC AAG CTG AAG CAG GAG AAC CGT GAG GCC CGC AGG       159
Ser Arg Leu Glu Ala Lys Leu Lys Gln Glu Asn Arg Glu Ala Arg Arg
            15                  20                  25

AGG ATC GAC CTC AAC TTG GAT ATC AGC CCA CAG CGG CCC AGG CCC ACC       207
Arg Ile Asp Leu Asn Leu Asp Ile Ser Pro Gln Arg Pro Arg Pro Thr
        30                  35                  40

CTG CAA CTC CCA CTG GCC AAC GAT GGG GGC AGC CGC TCA CCA TCC TCA       255
Leu Gln Leu Pro Leu Ala Asn Asp Gly Gly Ser Arg Ser Pro Ser Ser
    45                  50                  55

GAG AGC TCC CCA CAG CAC CCT ACA CCC CCC ACC CGG CCC CGC CAC ATG       303
Glu Ser Ser Pro Gln His Pro Thr Pro Pro Thr Arg Pro Arg His Met
60                  65                  70

CTG GGG CTC CCA TCA ACC TTG TTC ACA CCG CGC AGT ATG GAG AGC ATC       351
Leu Gly Leu Pro Ser Thr Leu Phe Thr Pro Arg Ser Met Glu Ser Ile
75                  80                  85                  90

GAG ATT GAC CAG AAG CTG CAG GAG ATC ATG AAG CAG ACA GGG TAC CTG       399
Glu Ile Asp Gln Lys Leu Gln Glu Ile Met Lys Gln Thr Gly Tyr Leu
                95                  100                 105

ACT ATC GGG GGC CAG CGT TAT CAG GCA GAA ATC AAT GAC TTG GAG AAC       447
Thr Ile Gly Gly Gln Arg Tyr Gln Ala Glu Ile Asn Asp Leu Glu Asn
            110                 115                 120

TTG GGT GAG ATG GGC AGT GGT ACC TGT GGT CAG GTG TGG AAG ATG CGG       495
```

```
                Leu Gly Glu Met Gly Ser Gly Thr Cys Gly Gln Val Trp Lys Met Arg
                        125                 130                 135

TTC CGG AAG ACA GGC CAC ATC ATT GCT GTT AAG CAA ATG CGG CGC TCT          543
Phe Arg Lys Thr Gly His Ile Ile Ala Val Lys Gln Met Arg Arg Ser
        140                 145                 150

GGG AAC AAG GAA GAG AAT AAG CGC ATT TTG ATG GAC CTG GAT GTA GTA          591
Gly Asn Lys Glu Glu Asn Lys Arg Ile Leu Met Asp Leu Asp Val Val
155                 160                 165                 170

CTC AAG AGC CAT GAC TGC CCT TAC ATC GTT CAG TGC TTT GGC ACC TTC          639
Leu Lys Ser His Asp Cys Pro Tyr Ile Val Gln Cys Phe Gly Thr Phe
                175                 180                 185

ATC ACC AAC ACA GAC GTC TTT ATT GCC ATG GAG CTC ATG GGC ACA TGT          687
Ile Thr Asn Thr Asp Val Phe Ile Ala Met Glu Leu Met Gly Thr Cys
            190                 195                 200

GCA GAG AAG CTG AAG AAA CGA ATG CAG GGC CCC ATT CCA GAG CGA ATC          735
Ala Glu Lys Leu Lys Lys Arg Met Gln Gly Pro Ile Pro Glu Arg Ile
        205                 210                 215

CTG GGC AAG ATG ACT GTG GCG ATT GTG AAA GCA CTG TAC TAT CTG AAG          783
Leu Gly Lys Met Thr Val Ala Ile Val Lys Ala Leu Tyr Tyr Leu Lys
        220                 225                 230

GAG AAG CAT GGC GTC ATC CAT CGC GAT GTC AAA CCC TCC AAC ATC CTG          831
Glu Lys His Gly Val Ile His Arg Asp Val Lys Pro Ser Asn Ile Leu
235                 240                 245                 250

CTA GAT GAG CGG GGC CAG ATC AAG CTC TGT GAC TTT GGC ATC AGT GGC          879
Leu Asp Glu Arg Gly Gln Ile Lys Leu Cys Asp Phe Gly Ile Ser Gly
                255                 260                 265

CGC CTT GTT GAC TCC AAA GCC AAA ACA CGG AGT GCT GGC TGT GCT GCC          927
Arg Leu Val Asp Ser Lys Ala Lys Thr Arg Ser Ala Gly Cys Ala Ala
            270                 275                 280

TAT ATG GCT CCC GAG CGC ATC GAC CCT CCA GAT CCC ACC AAG CCT GAC          975
Tyr Met Ala Pro Glu Arg Ile Asp Pro Pro Asp Pro Thr Lys Pro Asp
        285                 290                 295

TAT GAC ATC CGA GCT GAT GTG TGG AGC CTG GGC ATC TCA CTG GTG GAG         1023
Tyr Asp Ile Arg Ala Asp Val Trp Ser Leu Gly Ile Ser Leu Val Glu
        300                 305                 310

CTG GCA ACA GGA CAG TTC CCC TAT AAG AAC TGC AAG ACG GAC TTT GAG         1071
Leu Ala Thr Gly Gln Phe Pro Tyr Lys Asn Cys Lys Thr Asp Phe Glu
315                 320                 325                 330

GTC CTC ACC AAA GTC CTA CAG GAA GAG CCC CCA CTC CTG CCT GGT CAC         1119
Val Leu Thr Lys Val Leu Gln Glu Glu Pro Pro Leu Leu Pro Gly His
                335                 340                 345

ATG GGC TTC TCA GGG GAC TTC CAG TCA TTT GTC AAA GAC TGC CTT ACT         1167
Met Gly Phe Ser Gly Asp Phe Gln Ser Phe Val Lys Asp Cys Leu Thr
            350                 355                 360

AAA GAT CAC AGG AAG AGA CCA AAG TAT AAT AAG CTA CTT GAA CAC AGC         1215
Lys Asp His Arg Lys Arg Pro Lys Tyr Asn Lys Leu Leu Glu His Ser
        365                 370                 375

TTC ATC AAG CAC TAT GAG ATA CTC GAG GTG GAT GTC GCG TCC TGG TTT         1263
Phe Ile Lys His Tyr Glu Ile Leu Glu Val Asp Val Ala Ser Trp Phe
        380                 385                 390

AAG GAT GTC ATG GCG AAG ACC GAG TCC CCA AGG ACT AGT GGA GTC CTG         1311
Lys Asp Val Met Ala Lys Thr Glu Ser Pro Arg Thr Ser Gly Val Leu
395                 400                 405                 410

AGT CAG CAC CAT CTG CCC TTC TTC AGG TAGCCTCATG GCAGCGGCCA GCCCCGC       1365
Ser Gln His His Leu Pro Phe Phe Arg
                415

AGGGGCCCCG GGCCACGGCC ACCGACCCCC CCCCCAACCT GGCCAACCCA GCTGCCCATC       1425

AGGGGACCTG GGACCTGGAC GACTGCCAAG GACTGAGGAC AGAAAGTAGG GGGTTCCCAT       1485
```

```
CCAGCTCTGA CTCCCTGCCT ACCAGCTGTG GACAAAAGGG CATGCTGGTT CCTAATCCCT    1545

CCCACTCTGG GGTCAGCCAG CAGTGTGAGC CCCATCCCAC CCCGACAGAC ACTGTGAACG    1605

GAAGACAGCA GGCCAAAAAA AAAAAAAAAA AAAAAAAA                            1643
```

(2) INFORMATION FOR SEQ ID NO: 28:

(i) SEQUENCE CHARACTERISTICS:
        (A) LENGTH: 419 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 28:

```
Met Ala Ala Ser Ser Leu Glu Gln Lys Leu Ser Arg Leu Glu Ala Lys
  1               5                  10                  15

Leu Lys Gln Glu Asn Arg Glu Ala Arg Arg Arg Ile Asp Leu Asn Leu
             20                  25                  30

Asp Ile Ser Pro Gln Arg Pro Arg Pro Thr Leu Gln Leu Pro Leu Ala
         35                  40                  45

Asn Asp Gly Gly Ser Arg Ser Pro Ser Ser Glu Ser Ser Pro Gln His
     50                  55                  60

Pro Thr Pro Pro Thr Arg Pro Arg His Met Leu Gly Leu Pro Ser Thr
 65                  70                  75                  80

Leu Phe Thr Pro Arg Ser Met Glu Ser Ile Glu Ile Asp Gln Lys Leu
                 85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
        115                 120                 125

Gly Thr Cys Gly Gln Val Trp Lys Met Arg Phe Arg Lys Thr Gly His
    130                 135                 140

Ile Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
        275                 280                 285

Ile Asp Pro Pro Asp Pro Thr Lys Pro Asp Tyr Asp Ile Arg Ala Asp
    290                 295                 300

Val Trp Ser Leu Gly Ile Ser Leu Val Glu Leu Ala Thr Gly Gln Phe
305                 310                 315                 320
```

```
Pro Tyr Lys Asn Cys Lys Thr Asp Phe Glu Val Leu Thr Lys Val Leu
            325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
            355                 360                 365

Pro Lys Tyr Asn Lys Leu Leu Glu His Ser Phe Ile Lys His Tyr Glu
        370                 375                 380

Ile Leu Glu Val Asp Val Ala Ser Trp Phe Lys Asp Val Met Ala Lys
385                 390                 395                 400

Thr Glu Ser Pro Arg Thr Ser Gly Val Leu Ser Gln His His Leu Pro
                405                 410                 415

Phe Phe Arg
```

(2) INFORMATION FOR SEQ ID NO: 29:

(i) SEQUENCE CHARACTERISTICS:
        (A) LENGTH: 1578 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 281...1420

(xi) SEQUENCE DESCRIPTION: SEQ ID NO: 29:

```
GGAAAGGCAG CCTCCTGTAG GTGAAAATTC TGTTCACTAC CTGGCCACCT GGCCTGACTG     60

ACCTTCACAG CTTGATCATC TTCCTGAAGA GGCATTCAGG ATTCCCTCCA TCCCTACCCC    120

TTCTGGACAA AGTCTTCCAC GTTTCCTTCC TGGGAGTTTC TTCCAGGAAC TGGAGATACC    180

CAGAGCCCTG CAACTCCCAC TGGCCAACGA TGGGGGCAGC CGCTCACCAT CCTCAGAGAG    240

CTCCCCACAG CACCCTACAC CCCCCACCCG GCCCCGCCAC ATG CTG GGG CTC CCA     295
                                            Met Leu Gly Leu Pro
                                              1               5

TCA ACC TTG TTC ACA CCG CGC AGT ATG GAG AGC ATC GAG ATT GAC CAG     343
Ser Thr Leu Phe Thr Pro Arg Ser Met Glu Ser Ile Glu Ile Asp Gln
                10                  15                  20

AAG CTG CAG GAG ATC ATG AAG CAG ACA GGG TAC CTG ACT ATC GGG GGC     391
Lys Leu Gln Glu Ile Met Lys Gln Thr Gly Tyr Leu Thr Ile Gly Gly
            25                  30                  35

CAG CGT TAT CAG GCA GAA ATC AAT GAC TTG GAG AAC TTG GGT GAG ATG     439
Gln Arg Tyr Gln Ala Glu Ile Asn Asp Leu Glu Asn Leu Gly Glu Met
        40                  45                  50

GGC AGT GGT ACC TGT GGT CAG GTG TGG AAG ATG CGG TTC CGG AAG ACA     487
Gly Ser Gly Thr Cys Gly Gln Val Trp Lys Met Arg Phe Arg Lys Thr
    55                  60                  65

GGC CAC ATC ATT GCT GTT AAG CAA ATG CGG CGC TCT GGG AAC AAG GAA     535
Gly His Ile Ile Ala Val Lys Gln Met Arg Arg Ser Gly Asn Lys Glu
70                  75                  80                  85

GAG AAT AAG CGC ATT TTG ATG GAC CTG GAT GTA GTA CTC AAG AGC CAT     583
Glu Asn Lys Arg Ile Leu Met Asp Leu Asp Val Val Leu Lys Ser His
                90                  95                 100

GAC TGC CCT TAC ATC GTT CAG TGC TTT GGC ACC TTC ATC ACC AAC ACA     631
Asp Cys Pro Tyr Ile Val Gln Cys Phe Gly Thr Phe Ile Thr Asn Thr
            105                 110                 115

GAC GTC TTT ATT GCC ATG GAG CTC ATG GGC ACA TGT GCA GAG AAG CTG     679
```

-continued

```
Asp Val Phe Ile Ala Met Glu Leu Met Gly Thr Cys Ala Glu Lys Leu
        120                 125                 130

AAG AAA CGA ATG CAG GGC CCC ATT CCA GAG CGA ATC CTG GGC AAG ATG       727
Lys Lys Arg Met Gln Gly Pro Ile Pro Glu Arg Ile Leu Gly Lys Met
    135                 140                 145

ACT GTG GCG ATT GTG AAA GCA CTG TAC TAT CTG AAG GAG AAG CAT GGC       775
Thr Val Ala Ile Val Lys Ala Leu Tyr Tyr Leu Lys Glu Lys His Gly
150                 155                 160                 165

GTC ATC CAT CGC GAT GTC AAA CCC TCC AAC ATC CTG CTA GAT GAG CGG       823
Val Ile His Arg Asp Val Lys Pro Ser Asn Ile Leu Leu Asp Glu Arg
                170                 175                 180

GGC CAG ATC AAG CTC TGT GAC TTT GGC ATC AGT GGC CGC CTT GTT GAC       871
Gly Gln Ile Lys Leu Cys Asp Phe Gly Ile Ser Gly Arg Leu Val Asp
            185                 190                 195

TCC AAA GCC AAA ACA CGG AGT GCT GGC TGT GCT GCC TAT ATG GCT CCC       919
Ser Lys Ala Lys Thr Arg Ser Ala Gly Cys Ala Ala Tyr Met Ala Pro
        200                 205                 210

GAG CGC ATC GAC CCT CCA GAT CCC ACC AAG CCT GAC TAT GAC ATC CGA       967
Glu Arg Ile Asp Pro Pro Asp Pro Thr Lys Pro Asp Tyr Asp Ile Arg
    215                 220                 225

GCT GAT GTG TGG AGC CTG GGC ATC TCA CTG GTG GAG CTG GCA ACA GGA      1015
Ala Asp Val Trp Ser Leu Gly Ile Ser Leu Val Glu Leu Ala Thr Gly
230                 235                 240                 245

CAG TTC CCC TAT AAG AAC TGC AAG ACG GAC TTT GAG GTC CTC ACC AAA      1063
Gln Phe Pro Tyr Lys Asn Cys Lys Thr Asp Phe Glu Val Leu Thr Lys
                250                 255                 260

GTC CTA CAG GAA GAG CCC CCA CTC CTG CCT GGT CAC ATG GGC TTC TCA      1111
Val Leu Gln Glu Glu Pro Pro Leu Leu Pro Gly His Met Gly Phe Ser
            265                 270                 275

GGG GAC TTC CAG TCA TTT GTC AAA GAC TGC CTT ACT AAA GAT CAC AGG      1159
Gly Asp Phe Gln Ser Phe Val Lys Asp Cys Leu Thr Lys Asp His Arg
        280                 285                 290

AAG AGA CCA AAG TAT AAT AAG CTA CTT GAA CAC AGC TTC ATC ATC AAG      1207
Lys Arg Pro Lys Tyr Asn Lys Leu Leu Glu His Ser Phe Ile Ile Lys
    295                 300                 305

CAC TAT GAG ATA CTC GAG GTG GAT GTC GCG TCC TGG TTT AAG GAT GTC      1255
His Tyr Glu Ile Leu Glu Val Asp Val Ala Ser Trp Phe Lys Asp Val
310                 315                 320                 325

ATG GCG AAG ACC GAG TCC CCA AGG ACT AGT GGA GTC CTG AGT CAG CAC      1303
Met Ala Lys Thr Glu Ser Pro Arg Thr Ser Gly Val Leu Ser Gln His
                330                 335                 340

CAT CTG CCC TTC TTC AGT GGG AGT CTG GAG GAG TCT CCC ACT TCC CCA      1351
His Leu Pro Phe Phe Ser Gly Ser Leu Glu Glu Ser Pro Thr Ser Pro
            345                 350                 355

CCT TCT CCC AAG TCC TTC CCT CTG TCA CCA GCC ATC CCT CAG GCC CAG      1399
Pro Ser Pro Lys Ser Phe Pro Leu Ser Pro Ala Ile Pro Gln Ala Gln
        360                 365                 370

GCA GAG TGG GTC TCG GGC AGG TAGGGACCTG GAGTGGCCTG GTCCCACCCT CTGA    1454
Ala Glu Trp Val Ser Gly Arg
    375                 380

CCTCCTCCTC AGGCCACCAG TGTTGCCCTC TTCCCTTTTT AAAACAAAAT ACCCTTGTTT    1514

GTAAATCCTT AGACGCTTGA GAATAAAACC CTTCCCTTTT CTTCCGAAAA AAAAAAAAA    1574

AAAA                                                                  1578
```

(2) INFORMATION FOR SEQ ID NO: 30:

(i) SEQUENCE CHARACTERISTICS:
        (A) LENGTH: 380 amino acids
        (B) TYPE: amino acid

```
        (D) TOPOLOGY: linear (ii) MOLECULE TYPE: protein (v) FRAGMENT TYPE: internal (xi) SEQUENCE DESCRIPTION: SEQ ID NO: 30:

Met Leu Gly Leu Pro Ser Thr Leu Phe Thr Pro Arg Ser Met Glu Ser
  1               5                  10                  15

Ile Glu Ile Asp Gln Lys Leu Gln Glu Ile Met Lys Gln Thr Gly Tyr
                 20                  25                  30

Leu Thr Ile Gly Gly Gln Arg Tyr Gln Ala Glu Ile Asn Asp Leu Glu
             35                  40                  45

Asn Leu Gly Glu Met Gly Ser Gly Thr Cys Gly Gln Val Trp Lys Met
         50                  55                  60

Arg Phe Arg Lys Thr Gly His Ile Ile Ala Val Lys Gln Met Arg Arg
 65                  70                  75                  80

Ser Gly Asn Lys Glu Glu Asn Lys Arg Ile Leu Met Asp Leu Asp Val
                 85                  90                  95

Val Leu Lys Ser His Asp Cys Pro Tyr Ile Val Gln Cys Phe Gly Thr
                100                 105                 110

Phe Ile Thr Asn Thr Asp Val Phe Ile Ala Met Glu Leu Met Gly Thr
            115                 120                 125

Cys Ala Glu Lys Leu Lys Lys Arg Met Gln Gly Pro Ile Pro Glu Arg
        130                 135                 140

Ile Leu Gly Lys Met Thr Val Ala Ile Val Lys Ala Leu Tyr Tyr Leu
145                 150                 155                 160

Lys Glu Lys His Gly Val Ile His Arg Asp Val Lys Pro Ser Asn Ile
                165                 170                 175

Leu Leu Asp Glu Arg Gly Gln Ile Lys Leu Cys Asp Phe Gly Ile Ser
            180                 185                 190

Gly Arg Leu Val Asp Ser Lys Ala Lys Thr Arg Ser Ala Gly Cys Ala
        195                 200                 205

Ala Tyr Met Ala Pro Glu Arg Ile Asp Pro Pro Asp Pro Thr Lys Pro
    210                 215                 220

Asp Tyr Asp Ile Arg Ala Asp Val Trp Ser Leu Gly Ile Ser Leu Val
225                 230                 235                 240

Glu Leu Ala Thr Gly Gln Phe Pro Tyr Lys Asn Cys Lys Thr Asp Phe
                245                 250                 255

Glu Val Leu Thr Lys Val Leu Gln Glu Glu Pro Pro Leu Leu Pro Gly
            260                 265                 270

His Met Gly Phe Ser Gly Asp Phe Gln Ser Phe Val Lys Asp Cys Leu
        275                 280                 285

Thr Lys Asp His Arg Lys Arg Pro Lys Tyr Asn Lys Leu Leu Glu His
    290                 295                 300

Ser Phe Ile Ile Lys His Tyr Glu Ile Leu Glu Val Asp Val Ala Ser
305                 310                 315                 320

Trp Phe Lys Asp Val Met Ala Lys Thr Glu Ser Pro Arg Thr Ser Gly
                325                 330                 335

Val Leu Ser Gln His His Leu Pro Phe Phe Ser Gly Ser Leu Glu Glu
            340                 345                 350

Ser Pro Thr Ser Pro Pro Ser Pro Lys Ser Phe Pro Leu Ser Pro Ala
        355                 360                 365

Ile Pro Gln Ala Gln Ala Glu Trp Val Ser Gly Arg
370                 375                 380
```

(2) INFORMATION FOR SEQ ID NO: 31:

(i) SEQUENCE CHARACTERISTICS:
        (A) LENGTH: 1598 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 82...1440

(xi) SEQUENCE DESCRIPTION: SEQ ID NO: 31:

```
AGCGCAGGCG CAGTGCGGTG TTTGTCTACC CCGGACTGAC GGGTGGCCTG GCGGTGAGCG      60

GCGGCAGCGG CGGCGGGAA G ATG GCG GCG TCC TCC CTG GAG CAG AAG CTG        111
                       Met Ala Ala Ser Ser Leu Glu Gln Lys Leu
                         1               5                  10

TCC CGC CTG GAA GCC AAG CTG AAG CAG GAG AAC CGT GAG GCC CGC AGG       159
Ser Arg Leu Glu Ala Lys Leu Lys Gln Glu Asn Arg Glu Ala Arg Arg
             15                  20                  25

AGG ATC GAC CTC AAC TTG GAT ATC AGC CCA CAG CGG CCC AGG CCC ACC       207
Arg Ile Asp Leu Asn Leu Asp Ile Ser Pro Gln Arg Pro Arg Pro Thr
         30                  35                  40

CTG CAA CTC CCA CTG GCC AAC GAT GGG GGC AGC CGC TCA CCA TCC TCA       255
Leu Gln Leu Pro Leu Ala Asn Asp Gly Gly Ser Arg Ser Pro Ser Ser
     45                  50                  55

GAG AGC TCC CCA CAG CAC CCT ACA CCC CCC ACC CGG CCC CGC CAC ATG       303
Glu Ser Ser Pro Gln His Pro Thr Pro Pro Thr Arg Pro Arg His Met
 60                  65                  70

CTG GGG CTC CCA TCA ACC TTG TTC ACA CCG CGC AGT ATG GAG AGC ATC       351
Leu Gly Leu Pro Ser Thr Leu Phe Thr Pro Arg Ser Met Glu Ser Ile
 75                  80                  85                  90

GAG ATT GAC CAG AAG CTG CAG GAG ATC ATG AAG CAG ACA GGG TAC CTG       399
Glu Ile Asp Gln Lys Leu Gln Glu Ile Met Lys Gln Thr Gly Tyr Leu
             95                 100                 105

ACT ATC GGG GGC CAG CGT TAT CAG GCA GAA ATC AAT GAC TTG GAG AAC       447
Thr Ile Gly Gly Gln Arg Tyr Gln Ala Glu Ile Asn Asp Leu Glu Asn
        110                 115                 120

TTG GGT GAG ATG GGC AGT GGT ACC TGT GGT CAG GTG TGG AAG ATG CGG       495
Leu Gly Glu Met Gly Ser Gly Thr Cys Gly Gln Val Trp Lys Met Arg
    125                 130                 135

TTC CGG AAG ACA GGC CAC ATC ATT GCT GTT AAG CAA ATG CGG CGC TCT       543
Phe Arg Lys Thr Gly His Ile Ile Ala Val Lys Gln Met Arg Arg Ser
    140                 145                 150

GGG AAC AAG GAA GAG AAT AAG CGC ATT TTG ATG GAC CTG GAT GTA GTA       591
Gly Asn Lys Glu Glu Asn Lys Arg Ile Leu Met Asp Leu Asp Val Val
155                 160                 165                 170

CTC AAG AGC CAT GAC TGC CCT TAC ATC GTT CAG TGC TTT GGC ACC TTC       639
Leu Lys Ser His Asp Cys Pro Tyr Ile Val Gln Cys Phe Gly Thr Phe
                175                 180                 185

ATC ACC AAC ACA GAC GTC TTT ATT GCC ATG GAG CTC ATG GGC ACA TGT       687
Ile Thr Asn Thr Asp Val Phe Ile Ala Met Glu Leu Met Gly Thr Cys
                190                 195                 200

GCA GAG AAG CTG AAG AAA CGA ATG CAG GGC CCC ATT CCA GAG CGA ATC       735
Ala Glu Lys Leu Lys Lys Arg Met Gln Gly Pro Ile Pro Glu Arg Ile
        205                 210                 215

CTG GGC AAG ATG ACT GTG GCG ATT GTG AAA GCA CTG TAC TAT CTG AAG       783
Leu Gly Lys Met Thr Val Ala Ile Val Lys Ala Leu Tyr Tyr Leu Lys
    220                 225                 230
```

```
GAG AAG CAT GGC GTC ATC CAT CGC GAT GTC AAA CCC TCC AAC ATC CTG      831
Glu Lys His Gly Val Ile His Arg Asp Val Lys Pro Ser Asn Ile Leu
235                 240                 245                 250

CTA GAT GAG CGG GGC CAG ATC AAG CTC TGT GAC TTT GGC ATC AGT GGC      879
Leu Asp Glu Arg Gly Gln Ile Lys Leu Cys Asp Phe Gly Ile Ser Gly
                255                 260                 265

CGC CTT GTT GAC TCC AAA GCC AAA ACA CGG AGT GCT GGC TGT GCT GCC      927
Arg Leu Val Asp Ser Lys Ala Lys Thr Arg Ser Ala Gly Cys Ala Ala
                270                 275                 280

TAT ATG GCT CCC GAG CGC ATC GAC CCT CCA GAT CCC ACC AAG CCT GAC      975
Tyr Met Ala Pro Glu Arg Ile Asp Pro Pro Asp Pro Thr Lys Pro Asp
                285                 290                 295

TAT GAC ATC CGA GCT GAT GTG TGG AGC CTG GGC ATC TCA CTG GTG GAG     1023
Tyr Asp Ile Arg Ala Asp Val Trp Ser Leu Gly Ile Ser Leu Val Glu
                300                 305                 310

CTG GCA ACA GGA CAG TTC CCC TAT AAG AAC TGC AAG ACG GAC TTT GAG     1071
Leu Ala Thr Gly Gln Phe Pro Tyr Lys Asn Cys Lys Thr Asp Phe Glu
315                 320                 325                 330

GTC CTC ACC AAA GTC CTA CAG GAA GAG CCC CCA CTC CTG CCT GGT CAC     1119
Val Leu Thr Lys Val Leu Gln Glu Glu Pro Pro Leu Leu Pro Gly His
                335                 340                 345

ATG GGC TTC TCA GGG GAC TTC CAG TCA TTT GTC AAA GAC TGC CTT ACT     1167
Met Gly Phe Ser Gly Asp Phe Gln Ser Phe Val Lys Asp Cys Leu Thr
                350                 355                 360

AAA GAT CAC AGG AAG AGA CCA AAG TAT AAT AAG CTA CTT GAA CAC AGC     1215
Lys Asp His Arg Lys Arg Pro Lys Tyr Asn Lys Leu Leu Glu His Ser
                365                 370                 375

TTC ATC ATC AAG CAC TAT GAG ATA CTC GAG GTG GAT GTC GCG TCC TGG     1263
Phe Ile Ile Lys His Tyr Glu Ile Leu Glu Val Asp Val Ala Ser Trp
380                 385                 390

TTT AAG GAT GTC ATG GCG AAG ACC GAG TCC CCA AGG ACT AGT GGA GTC     1311
Phe Lys Asp Val Met Ala Lys Thr Glu Ser Pro Arg Thr Ser Gly Val
395                 400                 405                 410

CTG AGT CAG CAC CAT CTG CCC TTC TTC AGT GGG AGT CTG GAG GAG TCT     1359
Leu Ser Gln His His Leu Pro Phe Phe Ser Gly Ser Leu Glu Glu Ser
                415                 420                 425

CCC ACT TCC CCA CCT TCT CCC AAG TCC TTC CCT CTG TCA CCA GCC ATC     1407
Pro Thr Ser Pro Pro Ser Pro Lys Ser Phe Pro Leu Ser Pro Ala Ile
                430                 435                 440

CCT CAG GCC CAG GCA GAG TGG GTC TCG GGC AGG TAGGGACCTG GAGTGGCCTG   1460
Pro Gln Ala Gln Ala Glu Trp Val Ser Gly Arg
                445                 450

GTCCCACCCT CTGACCTCCT CCTCAGGCCA CCAGTGTTGC CCTCTTCCCT TTTTAAAACA   1520

AAATACCCTT GTTTGTAAAT CCTTAGACGC TTGAGAATAA AACCCTTCCC TTTTCTTCCG   1580

AAAAAAAAAA AAAAAAA                                                 1598

(2) INFORMATION FOR SEQ ID NO: 32:

(i) SEQUENCE CHARACTERISTICS:
        (A) LENGTH: 453 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 32:

Met Ala Ala Ser Ser Leu Glu Gln Lys Leu Ser Arg Leu Glu Ala Lys
1               5                   10                  15
```

```
Leu Lys Gln Glu Asn Arg Glu Ala Arg Arg Ile Asp Leu Asn Leu
         20                  25                  30

Asp Ile Ser Pro Gln Arg Pro Arg Pro Thr Leu Gln Leu Pro Leu Ala
         35                  40                  45

Asn Asp Gly Gly Ser Arg Ser Pro Ser Ser Glu Ser Ser Pro Gln His
    50                  55                  60

Pro Thr Pro Pro Thr Arg Pro Arg His Met Leu Gly Leu Pro Ser Thr
65                   70                  75                  80

Leu Phe Thr Pro Arg Ser Met Glu Ser Ile Glu Ile Asp Gln Lys Leu
             85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
            115                 120                 125

Gly Thr Cys Gly Gln Val Trp Lys Met Arg Phe Arg Lys Thr Gly His
    130                 135                 140

Ile Ile Ala Val Lys Gln Met Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
            195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
    275                 280                 285

Ile Asp Pro Pro Asp Pro Thr Lys Pro Asp Tyr Asp Ile Arg Ala Asp
    290                 295                 300

Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
            325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
            355                 360                 365

Pro Lys Tyr Asn Lys Leu Leu Glu His Ser Phe Ile Ile Lys His Tyr
    370                 375                 380

Glu Ile Leu Glu Val Asp Val Ala Ser Trp Phe Lys Asp Val Met Ala
385                 390                 395                 400

Lys Thr Glu Ser Pro Arg Thr Ser Gly Val Leu Ser Gln His His Leu
            405                 410                 415

Pro Phe Phe Ser Gly Ser Leu Glu Glu Ser Pro Thr Ser Pro Pro Ser
            420                 425                 430
```

```
Pro Lys Ser Phe Pro Leu Ser Pro Ala Ile Pro Gln Ala Gln Ala Glu
        435                 440                 445

Trp Val Ser Gly Arg
    450

(2) INFORMATION FOR SEQ ID NO: 33:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO: 33:

Met Xaa Ser Pro Ala Pro Ala Pro Ser Gln Arg Ala Ala Leu Gln Leu
  1               5                  10                  15

Pro Leu Ala Asn Asp Gly Gly Ser Arg Ser Pro Ser Ser Glu Ser Ser
             20                  25                  30

Pro Gln His Pro Thr Pro Pro Thr Arg Pro Arg His
         35                  40

(2) INFORMATION FOR SEQ ID NO: 34:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO: 34:

Glu Gly Gly Gly Val Lys His Met Ala Lys Leu Tyr Val Phe Tyr Gly
  1               5                  10                  15

Ala Gly Cys Met Glu Met Ser Asp Ile Glu Leu Leu Leu His Arg Asp
             20                  25                  30

Lys Pro Asn Leu Gly Lys Cys Asp Phe Gly Ser Gly Leu Ser Ala Gly
             35                  40                  45

Tyr Met Pro Glu Arg Tyr Val Ser Asp Trp Ser Gly Glu Ala Arg Pro
         50                  55                  60

Phe Leu Val Pro Leu Phe Phe Cys Leu Lys Arg Leu His
 65                  70                  75
```

CYTOKINE-, STRESS-, AND ONCOPROTEIN-ACTIVATED HUMAN PROTEIN KINASE KINASES

CROSS-REFERENCE TO RELATED APPLICATION

This application is a divisional of application Ser. No. 08/888,429, filed Jul. 7, 1997 now U.S. Pat. No. 6,136,596, which is a continuation-in-part of U.S. patent application Ser. No. 08/530,950, now U.S. Pat. No. 5,736,381, filed Sep. 19, 1995, which is a continuation-in-part of application Ser. No. 08/446,083, now U.S. Pat. No. 5,804,427, filed May 19, 1995, which applications are incorporated herein by reference in their entirety.

STATEMENT AS TO FEDERALLY SPONSORED RESEARCH

This invention was made in part with National Cancer Institute research grant CA 58396 and CA 65861. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, MPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein Ela (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-κB (Du et al. (1993) Cell 74:887) and c-Jun (Benbrook and Jones (1990) Oncogene 5:295).

SUMMARY OF THE INVENTION

The invention is based on the identification and isolation of a new group of human mitogen-activated protein kinase kinases (MKKs). The MKK isoforms described herein, MKK3, MKK6, MKK4 (including MKK4-α, -β, and -γ), MKK7 (including murine MKK7, human MKK7, MKK7b, MKK7c, MKK7d, and MKK7e) have serine, threonine, and tyrosine kinase activity. MKK3, MKK4, and MKK6 specifically phosphorylate the human MAP kinase p38 at Thr$^{180}$ and Tyr$^{182}$. The MKK4 isoforms also phosphorylate the human MAP kinases JNK (including JNK1, JNK2, and JNK5) at Thr$^{183}$ and Tyr$^{185}$. The MKK7 isoforms phosphorylate JNK at Thr$^{183}$ and Tyr$^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2. The invention further includes MKK6 having the amino acid sequence of SEQ ID NO:4 and having serine, threonine, and tyrosine kinase activity that specifically phosphorylates human p38 MAP kinase.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:6. MKK4 isoform MKK4-β has the amino acid sequence of SEQ ID NO:8. MKK4 isoform MKK4-β has the amino acid sequence of SEQ ID NO:10.

The invention also features a substantially pure MKK polypeptide (MKK7) having serine, threonine, and tyrosine kinase activity that specifically phosphorylates mitogen-activated protein kinase JNK. MKK isoforms MKK7 (murine) and MKK7 (human) have the amino acid sequences of SEQ ID NOS:18 and 26, respectively. The MKK7 isoforms MKK7b, MKK7c, MKK7d, and MKK7e have the amino acid sequences of SEQ ID NO:20, SEQ ID NO:28, SEQ ID NO:30, and SEQ ID NO:32, respectively.

As used herein, the term "mitogen-activating protein kinase kinase" or "MKK" means a protein kinase which possesses the characteristic activity of phosphorylating and activating a human mitogen-activating protein kinase. Examples of MKKs include MKK3 and MKK6, which specifically phosphorylate and activate p38 MAP kinase at Thr$^{180}$ and Tyr$^{182}$, MKK4 isoforms which specifically phosphorylate and activate p38 MAP kinase at Thr$^{180}$ and Tyr$^{182}$, and JNK at Thr$^{183}$ and Tyr$^{185}$, and MKK7 isoforms which specifically phosphorylate JNK at Thr$^{183}$ and Tyr$^{185}$.

An "MKK7" is a mammalian isoform of mitogen-activated protein kinase kinase (MKK) polypeptide having serine, threonine, and tyrosine kinase activity, and phosphorylating mitogen-activated protein (MAP) kinase JNK but not p38.

The invention includes the specific p38 and JNK MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure MKK polypeptide (e.g., human) is at least 75%, more preferably at least 90%, and most preferably at least 99%, by weight, MKK polypeptide. A substantially pure MKK can be obtained, for example, by extraction from a natural source; by expression of a recombinant nucleic acid encoding a MKK polypeptide, or by chemically synthesizing the protein. Purity can be measured by any appropriate method, e.g., column chromatography, polyacrylamide gel electrophoresis, or HPLC analysis.

In one aspect, the invention features isolated polynucleotides which encode the MKKs of the invention. In one embodiment, the polynucleotide is the nucleotide sequence of SEQ ID NO:1. In other embodiments, the polynucleotide is the nucleotide sequence of SEQ ID NO:3, SEQ ID NO:5, SEQ ID NO:7, SEQ ID NO:9, SEQ ID NO:17, SEQ ID NO:19, SEQ ID NO:25, SEQ ID NO:27, SEQ ID NO:29, or SEQ ID NO:31, respectively.

As used herein, "polynucleotide" refers to a nucleic acid sequence of deoxyribonucleotides or ribonucleocides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

An "isolated" polynucleotide is a nucleic acid molecule that is separated in some way from sequences in the naturally occurring genome of an organism. Thus, the term "isolated polynucleotide" includes any nucleic acid molecules that are not naturally occuring. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified (Sambrook et al. (1989) in *Molecular Cloning*, 2d ed.; Cold Spring Harbor Laboratory Press, Cold Spring Harbor, N.Y.

The isolated polynucleotide sequences of the invention also include sequences complementary to the polynucleotides encoding MKK (antisense sequences). Antisense nucleic acids are DNA or RNA molecules that are complementary to at least a portion of a specific mRNA molecule (Weintraub (1990) Scientific American 262:40). The invention includes all antisense polynucleotides that inhibit production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-Sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes, tetrahymena-type (Hasselhoff (1988) Nature 334:585) and "hammerhead"-type. Tetrahymena-type ribozymes recognize sequences which are four bases in length, while "hammerhead"-type ribozymes recognize base.sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which include pooled monoclonal antibodies with different epitopic specificities, as well as distinct monoclonal antibody preparations. Monoclonal antibodies are made from antigen-containing fragments of the MKK polypeptide by methods known in the art (see, for example, Kohler et al. (1975) Nature 256:495).

The term "antibody" as used herein includes intact molecules as well as fragments thereof, such as Fa, $F(ab')_2$, and Fv, which are capable of binding an epitopic determinant. Antibodies that specifically bind MKK polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

A molecule (e.g., antibody) that "specifically binds" is one that binds to a particular polypeptide, e.g., MKK7, but that does not substantially recoginze or bind to other molecules in a sample, e.g., a biological sample which includes MKK7. References to constructs made of an antibody (or fragment thereof) coupled to a compound comprising a detectable marker include constructs made by any technique, including chemical means and recombinant techniques.

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes JNK1, JNK2, and JNK3. The term "MKK substrate" as used herein includes MKK substrates, as well as MKK substrate substrates, e.g., p38, JNK, ATF2, and c-Jun.

In one embodiment, activation of the MKK signal transduction pathway is determined by measuring activation of the appropriate MKK signal transduction pathway substrates (for example, selected from p38, JNK isoforms, ATF2, ATFa, CRE-BPa, or c-Jun). MKK activity is measured by the rate of substrate phosphorylation as determined by quantitation of the rate of labelled phosphorus (e.g., [$^{32}$]P or [$^{33}$]P) incorporation. This can also be measured using phosphorylation-specific reagents, such as antibodies. The specificity of MKK substrate phosphorylation can be tested by measuring p38 activation, JNK activation, or both, or by employing mutated p38 or JNK molecules that lack the sites for MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1–109, or a portion thereof). ATF2 is incubated with a test sample in which MKK activity is to be measured and [$\gamma$-$^{32}$P]ATP, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

In another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Total cellular or polyadenylated [poly(A)$^+$] mRNA is isolated from a test sample. The RNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful for screening reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$]P-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$]P-ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects.

The invention is particularly useful for screening reagents that inhibit MKK activity. Such reagents are useful for the treatment or prevention of MKK-mediated disorders, for example, inflammation and oxidative damage.

The invention further features a method of treating a MKK-mediated disorder by administering to a subject in need thereof, an effective dose of a therapeutic reagent that inhibits the activity of MKK.

An "MKK-mediated disorder" is a pathological condition resulting, at least in part, from excessive activation of an MKK signal transduction pathway. The MKK signal transduction pathways are activated by several factors, including inflammation and stress. MKK-mediated disorders include, for example, ischemic heart disease, burns due to heat or radiation (UV, X-ray, $\gamma$, $\beta$, etc.), kidney failure, liver damage due to oxidative stress or alcohol, respiratory distress syndrome, septic shock, rheumatoid arthritis, autoimmune disorders, and other types of inflammatory diseases.

A "therapeutic reagent" any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of MKK inhibit cell growth.or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by under expression of the MKK polypeptide, or expression of a mutant MKK polypeptide. In addition, portions of DNA encoding an MKK polypeptide can be introduced into cells that under express an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the methods of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, and from the claims.

DETAILED DESCRIPTION

The drawings will first be described.
Drawings

FIG. 1 is a comparison of the amino acid sequences of MKK3 (SEQ ID NO:2), MKK4-α (SEQ ID NO:6), the human MAP kinase kinases MEK1 (SEQ ID NO:11) and MEK2 (SEQ ID NO:12), and the yeast HOG1 MAP kinase kinase PBS2 (SEQ ID NO:13). Sequences were compared using the PILE-UP program (version 7.2; Wisconsin Genetics Computer Group). The protein sequences are presented in single letter code (A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr). The PBS2 sequence is truncated at both the $NH_2$— (<) and COOH— (>) termini. Gaps introduced into the sequences to optimize the alignment are illustrated by a dash. Identical residues are indicated by a period. The sites of activating phosphorylation in MEK are indicated by asterisks.

FIG. 2A is a dendrogram showing the relationship between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the Saccharomyces cerevisiae (sc) MAP kinase kinases PBS2, MKK1, and STE7; and the Saccharomyces pombe (sp) MAP kinase kinases WIS1 and BYR1 are presented.

FIG. 2B is a dendrogram showing the relationship between MKKs. The dendrogram was created as described for FIG. 2A.

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and JNK subgroups of MAP kinase.

FIGS. 4A–4D are a representation of the nucleic acid (SEQ ID NO:1) and amino acid sequences (SEQ ID NO:2) for MKK3.

FIGS. 5A–5C are a representation of the nucleic acid (SEQ ID NO:3) and amino acid sequences (SEQ ID NO:4) for MKK6.

FIGS. 6A–6F are a representation of the nucleic acid (SEQ ID NO:5) and amino acid sequences (SEQ ID NO:6) for MKK4α.

FIGS. 7A–7F are a representation of the nucleic acid (SEQ ID NO:7) and amino acid sequences (SEQ ID NO:8) for MKK4β.

FIGS. 8A–8F are a representation of the nucleic acid (SEQ ID NO:9) and amino acid sequences (SEQ ID NO:10) for MKK4γ.

Figure 9B:
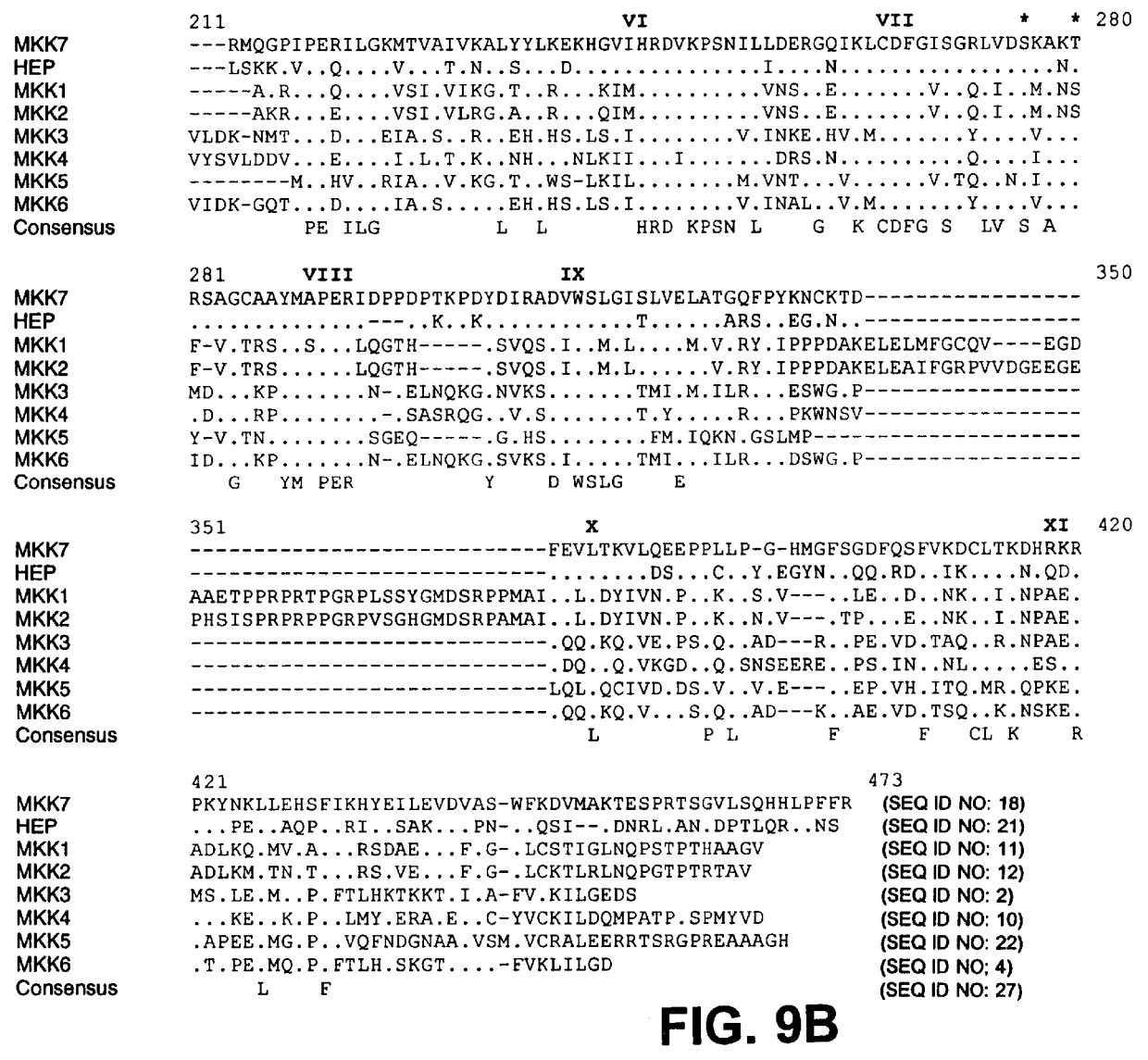

FIGS. 9A–9B are [FIG. 9 is] a representation of the deduced primary structure of MKK7 (SEQ ID NO:18) compared with hep (SEQ ID NO:21), the MAP kinase kinases MEK1 (MKK1; SEQ ID NO:11), MEK2 (MKK2; SEQ ID NO:12), MKK3 (SEQ ID NO:2), MKK4γ (SEQ ID NO:10), MKK5 (SEQ ID NO:22), and MKK6 (SEQ ID NO:4) using the PILE-UP program (version 7,2; Wisconsin Genetics Computer Group). Gaps introduced into the sequences to optimize the alignment are illustrated with a dash (-) Identity is indicated with a dot (.). The sites of activating phosphorylation of MAP kinase kinases (2, 27, 37, and 38) are indicated with asterisks (*).

FIGS. 10A–10D are a representation of the nucleic acid (SEQ ID NO:17) and amino acid (SEQ ID NO:18) sequences for MKK7.

FIGS. 11A–11D are a representation of the nucleic acid (SEQ ID NO:19) and amino acid (SEQ ID NO:20) sequences of MKK7b.

FIGS. 12A–12B are a representation of the nucleic acid (SEQ ID NO:25) and amino acid (SEQ ID NO:26) sequences of human MKK7.

FIGS. 13A–13D are a representation of the nucleic acid (SEQ ID NO:27) and amino acid (SEQ ID NO:28) sequences of murine MKK7c.

FIGS. 14A–14D are a representation of the nucleic acid (SEQ ID NO:29) and amino acid (SEQ ID NO:30) sequences of murine MKK7d.

FIGS. 15A–15D are a representation of the nucleic acid (SEQ ID NO:31) and amino acid (SEQ ID NO:32) sequences of murine MKK7e.

Figure 16A:
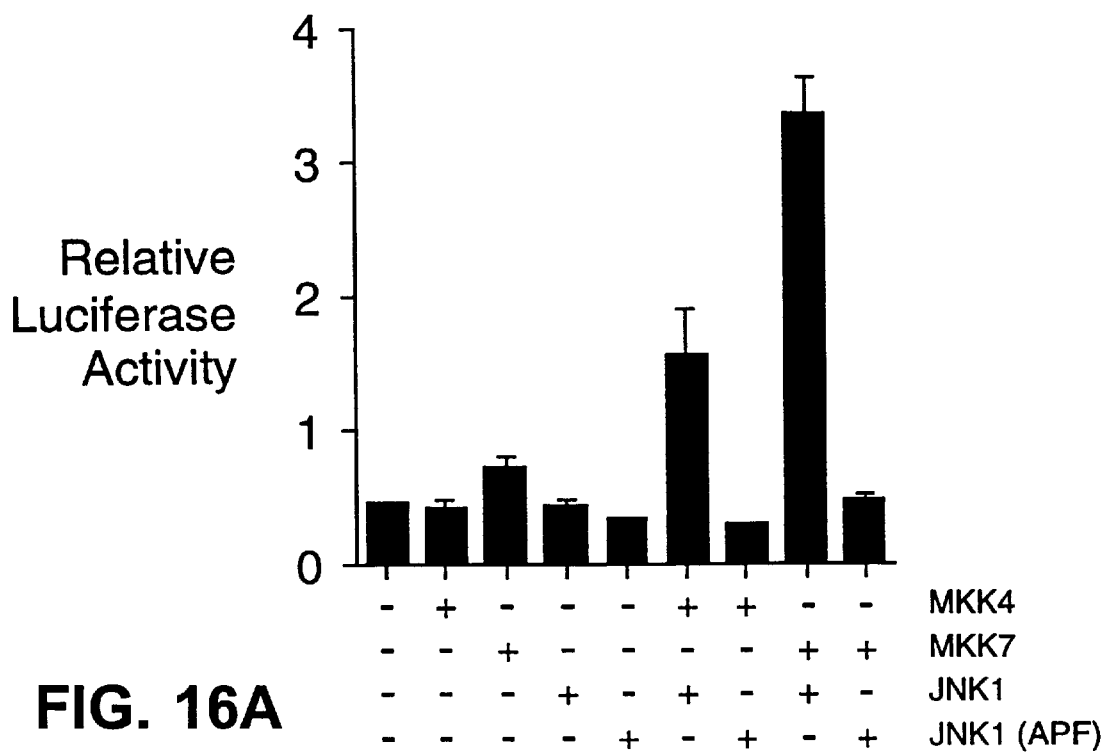

FIG. 16A is a graph of data from a transfection assay in which cells were co-transfected with AP-1 reporter plasmid pTRE-Luciferase with expression vectors for MKK4, MKK7, JNK1, JNK1(APF), or control vector.

Figure 16B:
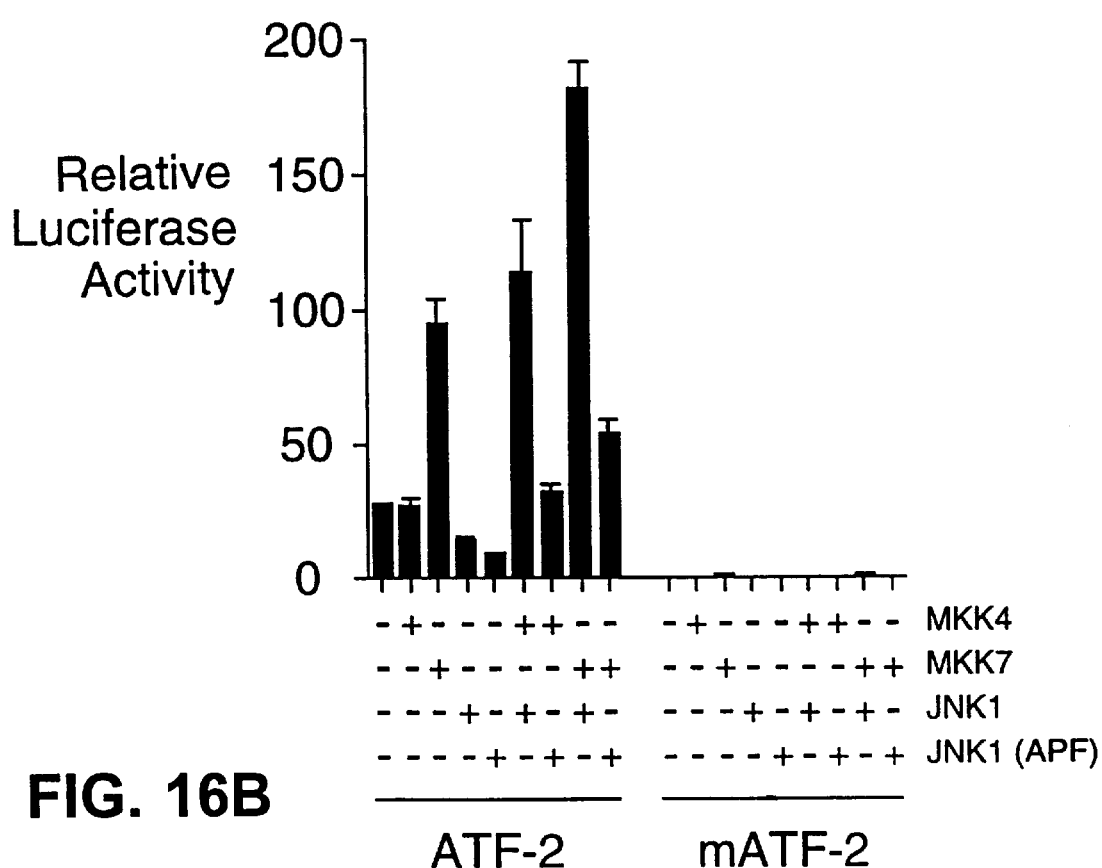

FIG. 16B is a graph of a transfection assay in which cells were co-transfected with a GAL4-ATF2 fusion vector and an expression vector for MKK4, MKK7, JNK1, JNK1(APF), or control vector.

Human Mitogen-Activated Protein Kinase Kinases

The human MAP kinase kinases MKK3 and MKK4 (MKK3/4), and MKK7, described herein mediate the transduction of specific signals from the cell surface to the nucleus along specific pathways. These signal transduction pathways are initiated by factors such as cytokines, UV radiation, osmotic shock, and oxidative stress. Activation of MKK3/4, MKK6, and MKK7 results in activation of the MAP kinases. p38 is activated by MKK3 and MKK4. JNK is activated by MKK4 and MKK7. p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and Green (1993) Science 262:395), transforming growth factor-b2 (Kim et al. (1992) supra), interferon-β (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The JNK group of MAP kinases is activated by exposure of cells to environmental stress or by treatment of cells with pro-inflammatory cytokines (Gupta et al. (1994) EMBO J. 15:2760–2770; Dérijard et al. (1991) Cell 76:1025–1037;

Kyriakis et al. (1994) Nature 369:156–160; Sluss et al. (1994) Mol. Cell. Biol. 14:8376–8384; Kallunki et al. (1994) Genes & Dev. 8:2996–3007). Targets of the JNK signal transduction pathway include the transcription factors ATF2 and c-jun (Whitmarsh & Davis (1996) J. Mol. Med. 74:589–607). These transcription factors are members of the bZIP group that bind as homo- and hetero-dimeric complexes to AP-1 and AP-1-like sites in the promoters of many genes (Curran & Franza (1988) Cell 55:395–397). JNK binds to an $NH_2$-terminal region of ATF2 and c-Jun and phosphorylates two sites within the activation domain of each transcription factor (Dérijard et al. (1994) Cell 76:1025–1037; van Dam et al. (1995) EMBO J. 14:1798–1811; Livingstone et al. (1995) EMBO J. 14:1785–1797). This phosphorylation leads to increased transcriptional activity (Whitmarsh, supra). Together, these biochemical studies indicate that the JNK signal transduction pathway contributes to the regulation of AP-1 transcriptional activity in response to cytokines and environmental stress (Whitmarsh, supra). Strong support for this hypothesis is provided by genetic evidence indicating that the JNK signaling pathway is required for the normal regulation of AP-1 transcriptional activity (Yang et al. (1997) Proc. Natl. Acad. Sci. USA, 94:3004–3009).

JNK is activated by dual phosphorylation on Thr-183 and Tyr-185 (Dérijard, supra). MKK4 (also known as SEK1) was the first MAP kinase kinase identified as a component of the JNK signal transduction pathway (Dérijard et al. (1995) Science 267:682–685; Lin et al. (1995) Science 268:286–290; Sanchez et al. (1994) Nature 372:794–798). Biochemical studies demonstrate that MKK4 phosphorylates and activates JNK (Dérijard et al. (1995) Science 267:682–685; Lin et al. (1995) Science 268:286–290; Sanchez et al. (1994) Nature 372:794–798). However, the function of MKK4 may not be restricted to the JNK signal transduction pathway because MKK4 also phosphorylates and activates p38 MAP kinase (Dérijard et al. (1995) Science 267:682–685; Lin et al. (1995) Science 268:286–290). This specificity of MKK4 to activate both JNK and p38 MAP kinase provides a mechanism that may account for the co-ordinate activation of these MAP kinases in cells treated with cytokines or environmental stress (Davis (1994) Trends Biochem. Sci. 19:470–473). However, this-co-ordinate activation is not always observed. For example, JNK activation in the liver correlates with decreased p38 MAP kinase activity (Mendelson et al. (1996) Proc. Natl. Acad. Sci. USA 93:12908–12913). These data suggest that the properties of MKK4 are insufficient to account for the regulation of JNK in vivo.

Figure 1:
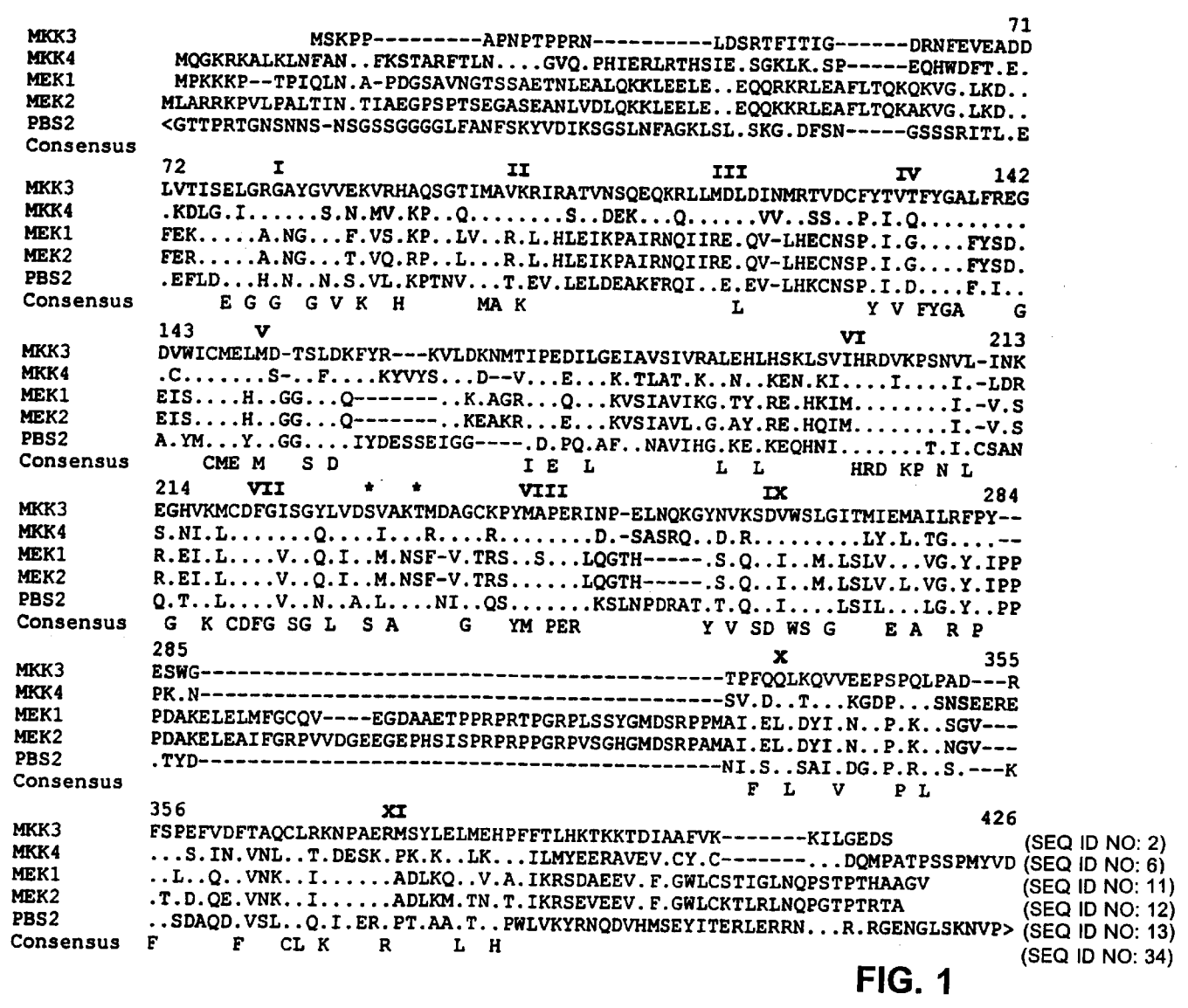

The isolation of human MKKs is described in Example 1, Example 22, Dérijard et al. ((1995) Science 267:682–685, hereby specifically incorporated by reference), and Raingeaud et al. ((1995) Mol. Cell. Biol. 16:1247–1255). Distinctive regions of the yeast PBS2 sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the $NH_2$-terminal, identified as α, β, and γ. The amino acid sequences of MKK3 (SEQ ID NO:2), MKK4-α (SEQ ID NO:6), MKK4β (SEQ ID NO:8), and MKK4-γ (SEQ ID NO:10) are shown in FIG. 1. The nucleic acid and amino acid sequences of MKK3 (FIG. 4), MKK6 (FIG. 5), MKK4-α (FIG. 6), MKK4β (FIG. 7), and MKK4-γ (FIG. 8) are also provided. MKK6 was isolated from a human skeletal muscle library by cross-hybridization with MKK3. Except for differences at the N-terminus, MKK6 is highly homologous to MKK3. Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites $Thr^{180}$ and $Tyr^{182}$ with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with [$γ$-$^{32}$P]ATP, and JNK1, p38, or ERK2 was found to phosphorylate both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with [$γ$-$^{32}$P]ATP and ATF2. The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive $NH_2$-terminal domain deletion GST-ATF2 fusion proteins were generated, and phosphorylation by JNK1 isolated from UV-irradiated cells was examined. The results showed that JNK1 requires the presence of ATF2 residues 1–60 for phosphorylation of the $NH_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with $[\gamma^{32}P]$ ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 9). Phosphoamino acid analysis of the full-length ATF2 molecule (residues 1–505) demonstrated that JNK phosphorylated both Thr and Ser residues. The major sites of Thr and Ser phosphorylation were located in the $NH_2$ and COOH terminal domains, respectively. The $NH_2$-terminal sites of phosphorylation were identified as $Thr^{69}$ and $Thr^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type ($Thr^{69, 71}$) and phosphorylation-defective ($Ala^{69, 71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of $Thr^{69}$ and $Thr^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at $Thr^{69}$ and/or $Thr^{71}$ of ATF2 significantly decreased the transcriptional activity of ATF2 relative to the wild-type molecule, indicating the physiological relevance of phosphorylation at these sites for activity.

The binding of JNK1 to the $NH_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating $Thr^{183}$ and $Tyr^{185}$ phosphorylation with Ala and Phe, respectively ($Ala^{183}$,$Phe^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the $NH_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on $Thr^{69}$ and $Thr^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MBP (Erickson et al. (1990) J. Biol. Chem. 265:19728), EGF-R (Northwood et al. (1991) J. Biol. Chem. 266:15266), cytoplasmic phospholipase $A_2$ ($cPLA_2$) (Lin et al. (1993) Cell 72:269), c-Myc (Alvarez et al. (1991) J. Biol. Chem. 266:15277), IκB, c-Jun, and wild-type ($Thr^{69, 71}$) or mutated ($Ala^{69,71}$) ATF2. p38 phosphorylated MBP and EGF-R, and to a lesser extent IKB, but not the other ERK substrates, demonstrating that the substrate specificity of p38 differs from both the ERK and JNK groups of MAP kinases. Wild-type ATF2, but not mutated ATF2 ($Ala^{69,71}$), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing $Thr^{69}$ and $Thr^{71}$ with Ala ($Ala^{69,71}$). It was found that p38 did not phosphorylate mutated ATF2, which demonstrates that p38 phosphorylates ATF2 within the $NH_2$-terminal activation domain on $Thr^{69}$ and $Thr^{71}$.

A comparison of the binding of JNK and p38 to ATF2 was conducted by incubating extracts of cells expressing JNK1 or p38 with epitope alone (GST) or GST-ATF2 (residues 1–109 containing the activation domain) (Example 16).

Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-1, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type ($Thr^{180}$, $Tyr^{182}$) or mutant p38 ($Ala^{180}$, $Phe^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoamino acid analysis of p38 isolated from [$\gamma$-$^{32}$P]phosphate-labeled cells. This analysis also demonstrated that UV radiation caused increased Thr phosphorylation of p38. Significantly, the increased phosphorylation on $Thr^{180}$ and $Tyr^{182}$ was blocked by the $Ala^{180}/Phe^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to inhibit p38 activity. The inhibitory effect of MKP1 was greater than PAC1. In contrast, cells transfected with a catalytically inactive mutant phosphatase (mutant PAC1 $Cys^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated for 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type ($Thr^{183}$, $Tyr^{185}$) or mutated ($Ala^{183}$, $Phe^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

Figure 3:
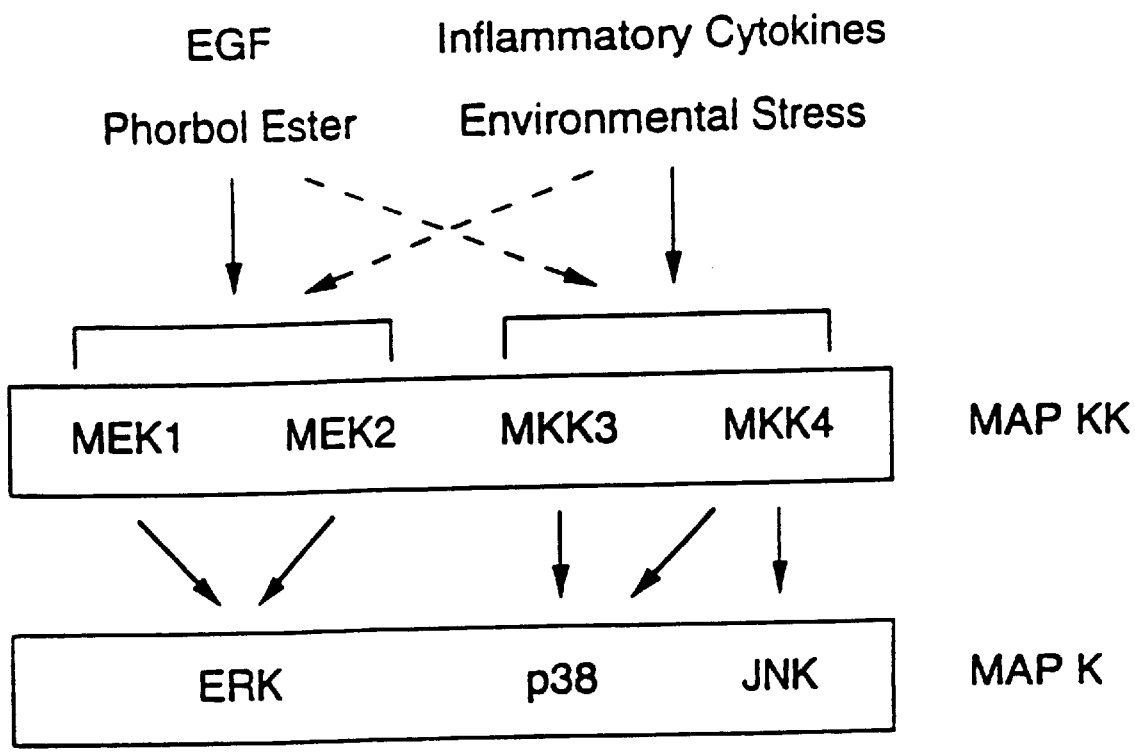

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3, MKK4, and MKK6) are distinct.

The isolation of murine and human MKK7 is described in Example 22. Distinctive regions of the Drosophila MAP kinase kinase hep sequence were used to design polymerase chain reaction (PCR) primers. Amplification of murine testis mRNA with these primers resulted in the formation of specific products which were cloned into a plasmid vector and sequenced. One sequence related to hep was identified and used to screen a murine testis library. Five DNAs (cDNAs) that encoded protein kinases were identified: one encoding a MAP protein kinase kinase (MKK7). The others encoded various splice variants: MKK7b (a partial sequence appears in FIG. 11), MKK7c (FIG. 13), MKK7d (FIG. 14), MKK7e (FIG. 15). The deduced amino acid sequences of MKK7 (SEQ ID NO:18) and hep (SEQ ID NO:21) are shown in FIG. 9, and compared to the MAP kinase kinases MEK1 (SEQ ID NO:11), MEK2 (SEQ ID NO:12), MKK3 (SEQ ID NO:2), MKK4 (SEQ ID NO:10), MKK5 (SEQ ID NO:22), and MKK6 (SEQ ID NO:4). A human MKK7 was identified by screening a human cDNA library with a full-length (mouse) MKK7 cDNA probe. The identified partial sequence (lacking the 3' end) is homologous to mouse MKK7c.

The expression of MKK7 and MKK4 isoforms was examined by Northern (RNA) blot analysis of poly A+ mRNA isolated from eight murine tissues (Example 23). Both protein kinases were found to be widely expressed.

The substrate specificity of MKK7 was investigated in an in vitro phosphorylation assay with recombinant, epitope-tagged MAP kinases (JNK1, p38, and ERK2) as substrates (Example 24). MKK7 phosphorylated JNK, but did not phosphorylate p38 or ERK2. MKK7 was phosphorylated by p38 and JNK1.

MKK7 was found to specifically activate JNK protein kinase in vivo (Example 25). CHO cells were co-transfected with an epitope-tagged MAP kinase (JNK1, p38, or ERK2) together with an empty expression vector or an expression vector encoding MKK1, MKK4, MKK6, or MKK7 and the product of the phosphorylation reaction analyzed. MKK7 activated only JNK1, and did so to a greater extent than did MKK4.

To test whether MKK7 could cause increased AP-1 transcriptional activity, a co-transfection assay was employed (Example 26). Co-expression of MKK7 with JNK caused an increase in AP-1 reporter gene expression that was greater than the increase seen with MKK4 and JNK. A similar result was seen when ATF2 was used as the reporter gene. In addition, MKK7 alone was able to increase expression of ATF2 (FIG. 16).

MKK isoforms are useful for screening reagents which modulate MKK activity. Described in the Use section following the Examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

EXAMPLES

The following examples are meant to illustrate, not limit, the invention.

Example 1

MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:14) and ATBCTYTCNGGNGCCATKTA (SEQ ID NO:15) were designed based on the sequence of PBS2 (Brewster et al. (1993) Science 259:1760; Maeda et al. (1994) Nature 369:242). The primers were used in a PCR reaction with human brain mRNA as template. Two, sequences that encoded fragments of PBS2-related protein kinases were identified. Full-length human cDNA clones were isolated by screening of a human fetal brain library (Dérijard et al. (1995) Science 267:682–685). The cDNA clones were examined by sequencing with an Applied Biosystems model 373A machine. The largest clones obtained for MKK3 (2030 base pairs (bp)) and MKK4 (3576 bp) contained the entire coding region of these protein kinases.

The primary structures of MKK3 (SEQ ID NO:2) and MKK4-α (SEQ ID NO:6) are shown in FIG. 1. An in-frame termination codon is located in the 5' untranslated region of the MKK3 cDNA, but not in the 5' region of the MKK4 cDNA. The MKK4 protein sequence presented starts at the second in-frame initiation codon.

These sequences were compared to those of the human MAP kinase kinases MEK1 (SEQ ID NO:11) and MEK2 (SEQ ID NO:12) (Zheng and Guan (1993) J. Biol. Chem 268:11435) and of the yeast MAP kinase kinase PBS2 (SEQ ID NO:13) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4α, 52%/73%; and PBS2, 40%/59%). The identity and similarity of the kinases with human MKK4α were calculated to be as follows (percent of identity to percent of similarity): MEK1, 44%/63%; MEK2, 45%/61%; MKK3, 52%/73%; and PBS2, 44%/58%.

The cDNA sequences of MKK3 and MKK4γ have been deposited in GenBank with accession numbers L36719 and L36870, respectively. The MKK4γ cDNA sequence contains both the cDNA sequences of MKK4α and MKK4β, which are generated in vivo from alternate splicing sites. One of ordinary skill in the art can readily determine the amino acid sequences of MKK3 and MKK4 isoforms from the deposited cDNA sequences.

Example 2

Expression of MKK3 and MKK4 mRNA in Adult Human Tissue

Northern blot analysis was performed with polyadenylated [poly(A)$^+$] mRNA (2 μg) isolated from human heart, brain, placenta, lung, liver, muscle, kidney, and pancreas tissues. The mRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

Figure 2A:
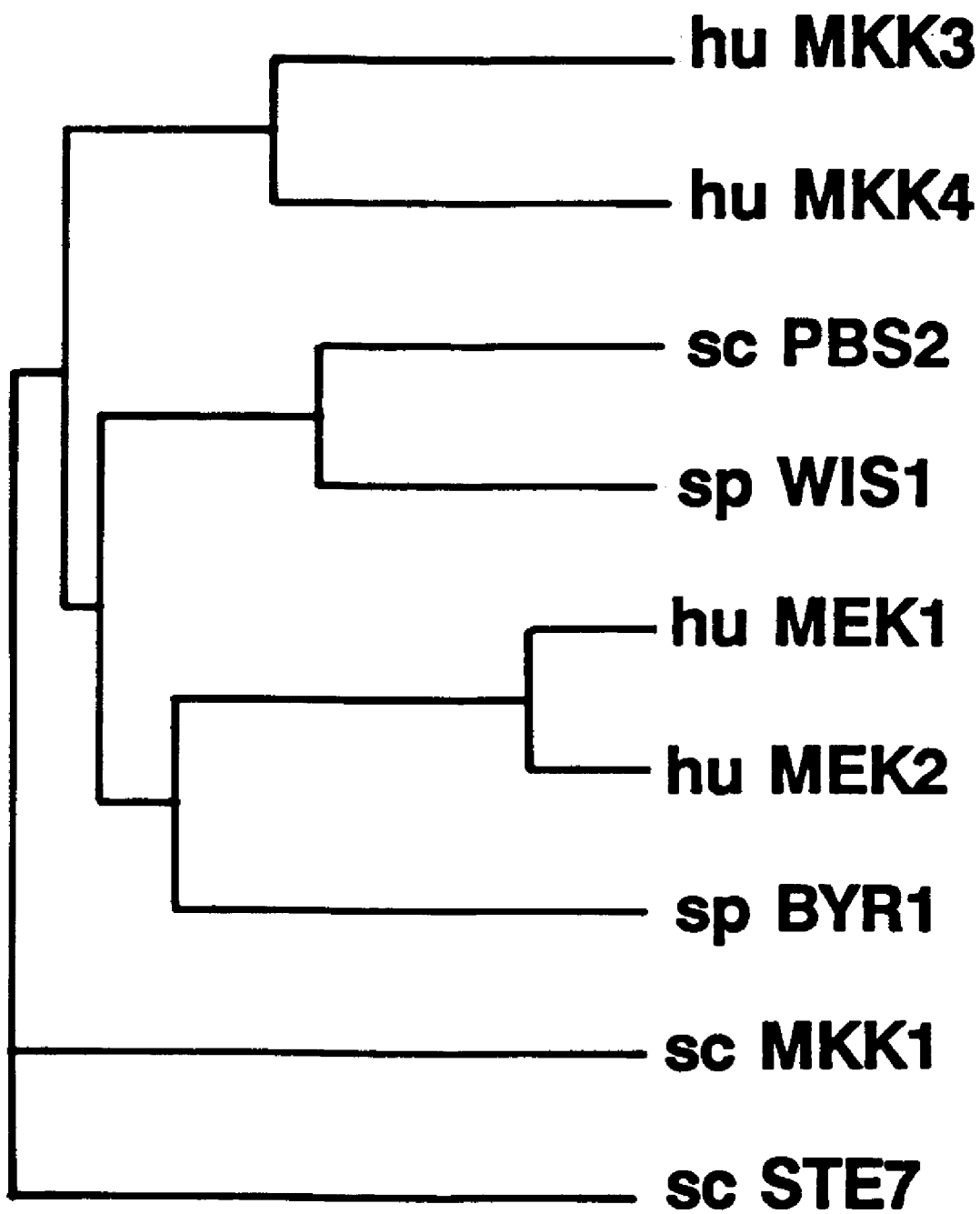
Figure 2B:
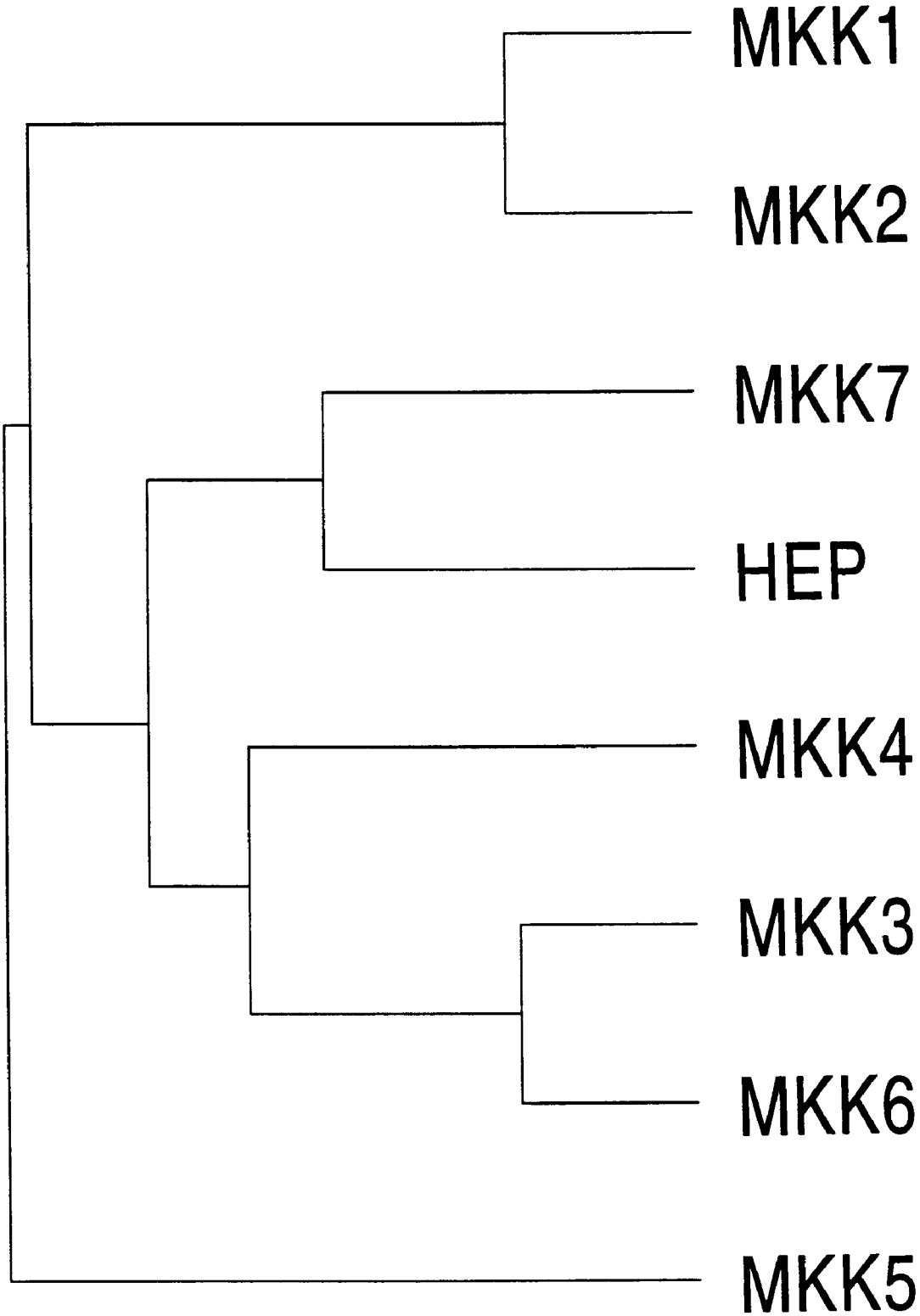

The relation between members of the human and yeast MAP kinase kinase group is presented as a dendrogram (FIG. 2). MKK3/4 form a unique subgroup of human MAP kinase kinases.

Example 3

In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) supra). The plasmid pCMV-Flag-p38 MAP kinase was prepared with the expression vector PCMVS (Andersson et al. (1989) J. Biol. Chem. 264:8222) and the p38 MAP kinase cDNA. The expression vectors for MKK3 and MKK4 were prepared by subcloning of the cDNAs into the polylinker of pCDNA3 (Invitrogen). The Flag epitope (Asp-Tyr-Lys-Asp-Asp-Asp-Asp-Lys (SEQ ID NO:16); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM β-glycerophosphate, 25 mM MgCl$_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 μg of substrate proteins and 50 μm [γ-$^{32}$P]ATP (10 Ci/mmol) in a final volume of 25 μl. The reactions were terminated after 30 minutes at 25° C. by addition of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace Thr$^{180}$ and Tyr$^{182}$ of p38, with Ala and Phe, respectively. The sequence of all plasmids was confirmed by automated sequencing on an Applied Biosystems model 373A machine. GST-MKK3 was incubated with [γ-$^{32}$P]ATP and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

Example 4

In Vitro Phosphorylation and Activation of JNK and p38 MAP Kinase by MKK4

Protein kinase assays were conducted as described in Example 3. Recombinant GST-MKK4 was incubated with [γ-$^{32}$P]ATP and buffer, GST-JNK1, GST-p38 MAP kinase, or GST-ERK2. JNK1 and p38 were phosphorylated, as was MKK4 incubated with JNK1 and p38.

GST-MKK4 was incubated with [γ-$^{32}$P]ATP and buffer, wild-type JNK1 (Thr$^{183}$, Tyr$^{185}$), or mutated GST-JNK1 (Ala$^{183}$, Phe$^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

Example 5

Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%)(Gibco-BRL). The cells were transfected with the lipofectamine reagent according to the manufacturer's recommendations (Gibco-BRL) and treated with UV radiation or EGF as described (Dérijard et al. (1994) supra)

The cells were exposed in the absence and presence of UV-C (40 J/m$^2$). The cells were solubilized with lysis buffer (20 mM tris, pH 7.4, 1% TRITON® X-100, 10% glycerol, 137 mM NaCl, 2 mM EDTA, 25 mM β-glycerophosphate, 1 mM Na orthovanadate, 1 mM phenylmethylsulfonyl fluoride, and leupeptin (10 μg/ml)) and centrifuged at 100, 000×g for 15 minutes at 40° C. MKK3 was isolated by immunoprecipitation. The epitope-tagged protein kinases were incubated for 1 hour at 4° C. with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

Example 6

Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4α. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunocomplex with [γ-$^{32}$P]ATP and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and UV-irradiated groups. MKK3 and MKK4 phosphorylation of ATF2 was similar to that seen with p38 MAP kinase isolated from UV-irradiated cells.

Example 7

Phosphorylation of ATF2 by JNK1 and JNK2

COS-1 cells were maintained in Dulbecco's modified Eagle's medium supplemented with bovine serum albumin (5%) (Gibco-BRL). Metabolic labeling with $^{32}$P was performed by incubation of cells for 3 hours in phosphate-free modified Eagle's medium (Flow Laboratories Inc.) supplemented with [$^{32}$P]orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-BRL). After 48 hours of incubation, some cultures were exposed to 40 J/m$^2$ UV radiation and incubated for 1 hour at 37° C.

Cells were lysed in 20 mM Tris, pH 7.5, 25 mM β-glycerophosphate, 10% glycerol, 1% Triton® X-100, 0.5% (w/v) deoxycholate, 0.1% (w/v) SDS, 0.137 M NaCl, 2 mM pyrophosphate, 1 mM orthovanadate, 2 mM EDTA, 10 μg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues 1–505) in the gel, and incubation with [γ-$^{32}$P]ATP (Dérijard et al. (1994) supra). The incorporation of [$^{32}$P]phosphate was visualized by autoradiography and quantitated with a Phosphorimager and ImageQuant software (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

Example 8

Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine. The GST-ATF2 proteins were purified as described (Smith and Johnson (1988) Gene 67:31), resolved by SDS-PAGE and stained with Coomassie blue. GST-ATF2 fusion proteins contained residues 1–505, 1–349, 350–505, 1–109, 20–109, 40–109, and 60–109.

The phosphorylation of GST-ATF2 fusion proteins by JNK1 isolated from UV-irradiated cells was examined in an immunocomplex kinase assay. Immunecomplex kinase assays were performed with Flag epitope-tagged JNK1 and the monoclonal antibody M2 (IBI-Kodak) as described by Dérijard et al. (1994) supra). Immunecomplex protein kinase assays were also performed with a rabbit antiserum prepared with recombinant JNK1 as an antigen. The cells were solubilized with 20 mM Tris, pH 7.5, 10% glycerol, 1% Triton® X-100, 0.137 M NaCl, 25 mM β-glycerophosphate, 2 mM EDTA, 1 mM orthovanadate, 2 mM pyrophosphate, 10 µg/ml leupeptin, and 1 mM PMSF. JNK1 was immunoprecipitated with protein β-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM MgCl$_2$, 25 mM β-glycerophosphate, 100 µM Na orthovanadate, 2 mM dithiothreitol). The kinase assays were performed at 25° C. for 10 minutes with 1 µg of substrate, 20 µM adenosine triphosphate and 10 µCi of [γ-$^{32}$P]ATP in 30 µl of kinase buffer. The reactions were terminated with Laemmli sample buffer and the products were resolved by SDS-PAGE (10% gel). JNK1 phosphorylates GST-ATF2 fusion proteins containing residues 1–505, 1–349, 1–109, 20–109, and 40–109, but not 60–109. These results indicate that the presence of ATF2 residues 1–60 are required for phosphorylation by JNK.

The binding of immobilized GST-ATF2 fusion proteins was examined in a solid-phase kinase assay as described by Hibi et al. ((1993) Genes Dev. 7:2135, herein specifically incorporated by reference). JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of [γ-$^{32}$P]ATP. JNK1 bound GST-ATF2 fusion proteins containing residues 1–505, 1–349, 1–109, 20–109, and 40–109, indicating that the presence of residues 20–60 were required for binding of JNK1 to ATF2.

Example 9

Phosphorylation of the NH$_2$-terminal Activation Domain of ATF2 on Thr$^{69}$ and Thr$^{71}$ by JNK1

The effect of UV radiation on the properties of wild-type (Thr$^{69,71}$) and phosphorylation-defective (Ala$^{69, 71}$) ATF2 molecules was examined. Mock-transfected and JNK1-transfected COS cells were treated without and with 40 J/m$^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an NH$_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem. 266:15277). The horizontal dimension of the peptide maps was electrophoresis and the vertical dimension was chromatography. The NH$_2$-terminal sites of phosphorylation were identified as Thr$^{69}$ and Thr$^{71}$ by phosphopeptide mapping and mutational analysis. Site-directed mutagenesis was performed as described above, replacing Thr$^{69}$ and Thr$^{71}$ with Ala. Phosphorylation of mutated ATF2 was not observed.

Example 10

Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 J/m$^2$), IL-1α (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

Example 11

Increased ATF2 Phosphorylation After Activation of JNK

COS-1 cells were transfected without (control) and with an ATF2 expression vector (ATF2), as described above (Hai et al. (1989) supra). The effect of exposure of the cells to 40 J/m$^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type (Thr$^{69,71}$) ATF2 and mutated (Ala$^{69, 71}$) ATF2 was examined in cells labeled with [$^{32}$]P, treated without and with 40 J/m$^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phosphoamino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1 cells. A map was also prepared with a sample composed of equal amounts of in vivo and in vitro phosphorylated ATF2 (Mix). Mutation of ATF2 at $Thr^{69}$ and $Thr^{71}$ resulted in the loss of two tryptic phosphopeptides in maps of ATF2 isolated from UV-irradiated cells. These phosphopeptides correspond to mono- and bis-phosphorylated peptides containing $Thr^{69}$ and $Thr^{71}$. Both of these phosphopeptides were found in maps of ATF2 phosphorylated by JNK1 in vitro.

Example 12

Inhibition of ATF2-Stimulated Gene Expression by Mutation of the Phosphorylation Sites $Thr^{69}$ and $Thr^{7}$ A fusion protein consisting of ATF2 and the GAL4 DNA binding domain was expressed in CHO cells as described above. The activity of the GAL4-ATF2 fusion protein was measured in co-transfection assays with the reporter plasmid pG5E1bLuc (Seth et al. (1992) J. Biol. Chem. 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results shown in Table 1, demonstrate the importance of phosphorylation at $Thr^{69}$ and $Thr^{71}$ for transcriptional activity.

TABLE 1

INHIBITION OF ATF-2 STIMULATED GENE EXPRESSION BY MUTATION OF THE PHOSPHORYLATION SITES $THR^{69,71}$

| PROTEIN | LUCIFERASE ACTIVITY (Light Units/OD) |
| --- | --- |
| GAL4 | 45 |
| GAL4-ATF2 (wild type) | 320,000 |
| GAL4-ATF2 ($Ala^{69}$) | 24,000 |
| GAL4-ATF2 ($Ala^{71}$) | 22,000 |
| GAL4-ATF2 ($Ala^{69,71}$) | 29,000 |
| GAL4-ATF2 ($Glu^{69}$) | 27,000 |

Example 13

Effect of Dominant-Negative JNK1 Mutant on ATF2 Function

The luciferase reporter plasmid system was used to determine the effect of point mutations at the ATF2 phosphorylation sites $Thr^{69}$ and $Thr^{71}$ in serum-treated CHO cells transfected with wild-type ($Thr^{183}$, $Tyr^{185}$) or mutant ($Ala^{183}$, $Phe^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

Example 14

Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1–505), as described above. Cells were transfected with wild-type ($Thr^{69,71}$) or mutated ($Ala^{69,71}$) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on $Thr^{69}$ and $Thr^{71}$) plus either Rb or E1A for maximal transcriptional activity.

Example 15

Substrate Specificity of p38 MAP Kinase

Substrate phosphorylation by p38 MAP kinase was examined by incubation of bacterially-expressed p38 MAP kinase with IKB, cMyc, EGF-R, cytoplasmic phospholipase $A_2$ ($cPLA_2$), c-Jun, and mutated ATF2 ($Thr^{69,71}$) and ATP [$\gamma$-$^{32}P$] (Raingeaud et al. (1995) J. Biol. Chem 270:7420, herein specifically incorporated by reference). GST-IKB was provided by Dr D. Baltimore (Massachusetts Institute of Technology). GST-cMyc (Alvarez et al. (1991) J. Biol. Chem. 266:15277), GST-EGF-R (residues 647–688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by PhosphorImager (Molecular Dynamics Inc.) analysis. The relative phosphorylation of ATF2, MBP, EGF-R, and IKB was 1.0, 0.23, 0.04, and 0.001, respectively.

Example 16

Binding of p38 MAP Kinase to ATF2

Cell extracts expressing epitope-tagged JNK1 and p38 MAP kinase were incubated with a GST fusion protein containing the activation domain of ATF2 (residues 1–109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). Immuno-complexes were detected using enhanced chemiluminescence (Amersham International PLC). Control experiments were performed using immobilized GST.

Example 17 p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38

MAP kinase and JNK1 activity were measured in immunecomplex protein kinase assays using ATP [γ-$^{32}$P] and ATF2 as substrates. TNFα and IL-1α were from Genzyme Corp. Lipolysaccharide (LPS) was isolated from lyophilized *Salmonella minesota* Re595 bacteria as described (Mathison et a. (1988) J. Clin. Invest. 81:1925). Phorbol myristate acetate was from Sigma. EGF was purified from mouse salivary glands (Davis (1988) J. Biol. Chem. 263:9462). Kinase assays were performed using immunoprecipitates of p38 and JNK. The immunocomplexes were washed twice with kinase buffer (described above), and the assays initiated by the addition of 1 μg of ATF2 and 50 μM [γ-$^{32}$P]ATP (10 Ci/mmol) in a final volume of 25 μl. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/m$^2$ UV-C, 300 mM sorbitol, 10 ng/ml interleukin-1, and 10 ng/ml TNFα strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

|  | Relative Protein Kinase Activity | |
| --- | --- | --- |
|  | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/m$^2$) | 7.4 | 17.1 |

Example 18 p8 MAP Kinase Activation by Dual Phosphorylation on Tyr and Thr

COS-1 cells expressing wild-type (Thr$^{180}$, Tyr$^{182}$) or mutated (Ala$^{180}$, Phe$^{182}$) p38 MAP kinase were treated without and with UV-C (40 J/m$^2$). The cells were harvested 30 minutes following exposure with or without UV radiation. Control experiments were performed using mock-transfected cells. The level of expression of epitope-tagged p38 MAP kinase and the state of Tyr phosphorylation of p38 MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P]phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [γ-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

Example 19

MAP Kinase Phosphatase Inhibits p38 MAP Kinase Activation

The cells were treated without and with 40 J/m$^2$ UV-C. Control experiments were performed using mock-transfected cells (control) and cells transfected with the catalytically inactive mutated phosphatase mPAC1 (Cys$^{257}$/Ser) and human MKP1. The activity of p38 MAP kinase was measured with an immunecomplex protein kinase assay employing [γ-$^{32}$P] ATP and GST-ATF2 as substrates. The expression of PAC1 or MKP1 was found to inhibit p38 phosphorylation, demonstrating that p38 can be regulated by the dual specificity phosphatases PAC1 and MKP1.

Example 20

Subcellular Distribution of p38 MAP Kinase

Epitope-tagged p38 MAP kinase was expressed in COS cells. The cells were treated without or with 40 J/m$^2$ UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry

Coverslips (22 mm×22 mm No. 1; Gold Seal Cover Glass; Becton-Dickinson) were pre-treated by boiling in 0.1 N HCl for 10 minutes, rinsed in distilled water, autoclaved and coated with 0.01% poly-L-lysine (Sigma; St. Louis Mo.). The coverslips were placed at the bottom of 35 mm multi-well tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). Twenty-four hours post-transfection, the cells were rinsed once and incubated at 37° C. for 30 minutes in 25 mM Hepes, pH 7.4, 137 mM NaCl, 6 mM KCl, 1 mM MgCl$_2$, 1 mM CaCl$_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 22° C. The cells were permeabilized with 0.25% Triton® X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% Triton® X-100) for 5 minutes. The primary antibody (M2 anti-FLAG monoclonal antibody, Eastman-Kodak Co., New Haven, Conn.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, Md.) was applied at a 1:250 dilution for 1 hour at 22° C. in a humidified environment. The cells were then washed three times in DWB and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60x Planapo objective (numerical aperture=1.4) on a Zeiss IM-35 microscope equipped for epifluorescence as previously described (Carrington et al. (1990) in: *Non-invasive Techniques in Cell Biology*, Fosbett & Grinstein, eds., Wiley-Liss, N.Y.; pp. 53–72; Fay et al. (1989) J. Microsci. 153:133–149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125 μm intervals of a 0.3 μm diameter fluorescently labeled latex bead (Molecular Probes Inc.). The image restoration algorithm used is based upon the theory of ill-posed problems and obtains quantitative dye density values within the cell that are substantially more accurate than those in an unprocessed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

Example 21

Activation of the MKK Signal Transduction Pathway by Osmotic Shock

CHO cells were co-transfected with the plasmid pCMV-Flag-Jnk1 and pRSV-Neo (Dérijard et al. (1994) supra) . A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% TRITON® X-100, 2 mM EDTA, 137 mM NaCl, 25 mM β-glycerophosphate, 1 mM orthovanadate, 2 mM pyrophosphate, 10% glycerol, 1 mM phenylmethylsulfonyl fluoride, 10 μg/ml leupeptin) and a soluble extract was obtained by centrifugation at 100,000 g for 30 minutes at 40° C. The epitope-tagged JNK1 was isolated by immunoprecipitation with the monoclonal antibody M2 (Immunex Corp.). The immunoprecipitates were washed extensively with lysis buffer. Immunecomplex kinase assays were done in 25 μl of 25 mM Hepes, pH 7.4, 25 mM MgCl$_2$, 25 mM β-glycerophosphate, 2 mM dithiothreitol, 100 AM orthovanadate, and 50 AM ATP [γ-$^{32}$P] (10 Ci/mmole) with 2.5 μg of bacterially expressed c-Jun (residues 1–79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed at all concentrations of sorbitol exposure.

The time course of JNK1 protein kinase activation was measured in cells incubated in medium supplemented with 300 mM sorbitol as described above. Increased JNK1 activity was observed within 5 minutes of exposure to sorbitol, with maximum activity occurring after 15–30 minutes.

Mutation of JNK1 at the phosphorylation sites Thr$^{183}$ and Tyr$^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Example 22

Molecular Cloning of MKK7

RT-PCR was employed to identify a fragment of a novel mammalian MAP kinase kinase. The primers designed for the protocol, ATNGCNGTNAARCARATG (SEQ ID NO;23) and ATNCKYTCNGGNGCCATRTA (SEQ ID NO:24), were based on the sequence of the Drosophila MAP kinase kinase hep (Glise et al. (1995) Cell 83:451–461). Murine testis mRNA was used as the template. A single product (461 bp) was detected following RT-PCR amplification of murine testis mRNA. Sequence analysis identified this PCR product as a fragment of a novel mammalian MAP kinase kinase. Full-length murine cDNA clones were isolated by screening a murine testis library (Stratagene Inc.). The cDNA clones were examined by sequencing with an Applied Biosystems model 373A machine. A group of seven clones was identified by sequence analysis to contain a single long open reading frame that: encoded a putative protein kinase (FIG. 9 and FIG. 10; SEQ ID NO:17 and SEQ ID NO:18). In-frame termination codons were detected in the 5' and 3' regions of these clones. This sequence includes protein kinase sub-domains I–XI and is related to the MAP kinase kinase group. The novel protein kinase was designated MKK7. The sites of activating phosphorylation of MAP kinase kinases located in sub-domain VIII are conserved in MKK7. Comparison of MKK7 with other members of the mammalian MAP kinase kinase group demonstrates that MKK7 is related to the JNK activator MKK4.

One additional cDNA clone isolated from the X phage library differed from the other seven clones. This clone contained the same 3' untranslated region and coding region of MKK7, but had a different 5' region that lacked an in-frame termination codon. This clone represents an alternatively spliced form of MKK7 (MKK7b; FIG. 11; SEQ ID NO:19). The MKK7b cDNA clone does not have an initiation codon in the alternative 5' region; this cDNA therefore encodes the same MKK7 protein kinase as the other clones that were isolated. However, if the MKK7b cDNA clone is not full-length it is possible that additional 5' sequence may include an in-frame initiation codon. If true, MKK7b is predicted to fuse the sequence M-[?]-SPAPAPSQRAALQLPLANDGGSRSPSSESSPQHPT PTRPRH-(SEQ ID NO:33) to the initiating methionine of MKK7 (FIG. 9).

Although the Drosophila MAP kinase kinase hep shares substantial sequence similarity with MKK7, the sequence of the NH2-terminal extension of MKK7b is not conserved in the hep protein kinase. Three additional clones encoded MKK7 splice variants that differ in the 5' and 3' regions. These clones (MKK7c (FIG. 13), MKK7d (FIG. 14), and MKK7e (FIG. 15)) are full-length because of the presence of in-frame termination codons in the 5' and 3' regions.

A human cDNA library was screened with a full-length mouse MKK7 cDNA probe. A single clone was identified and squenced. A partial MKK7 sequence was identified (FIG. 12; SEQ ID NO:25 and SEQ ID NO:26) that is missing the 3' end. The sequence is most homologous to mouse MKK7c.

The sequences of MKK7, MKK7b, hep, and human MKK7 cDNAs have been deposited in Genbank with accession numbers U93030, U93031, U93032, and AF00319 respectively.

Example 23

Expression of MKK7

MKK7 expression was examined by Northern blot analysis of mRNA isolated from different tissues. The analysis was done with poly A+ mRNA (2 µg) isolated from different tissues and fractionated by denaturing agarose gel electrophoresis and transferred to a nylon membrane (Clontech). The blot was probed with MKK4 and MKK7 cDNAs labeled by random priming with $[\alpha^{-32}P]dATP$ (Amersham International PLC).

MKK7 was found to be widely expressed in murine tissues. A single MKK7 transcript (approximately 4.0-kb) was detected in all of the tissues examined, except for testis where two MKK7 transcripts (4.0 kb and 1.6 kb) were detected. The highest levels of MKK7 expression were in testis. Significant expression of MKK7 was also observed in heart, brain, lung, liver, and kidney. This contrasts with MKK4 expression which was highest in brain although significant amounts of expression were observed in brain, liver, muscle, heart, and kidney. Although MKK4 and MKK7 are co-expressed, the relative abundance of each MAP kinase kinase is different in each of the tissues examined.

Example 24

Specific Activation of JNK by MKK7 in vitro

To examine the specificity of MKK7, in vitro protein kinase assays were performed. A bacterial MKK7 expression vector was prepared by sub-cloning an MKK7 cDNA (Eco RI and Pvu II fragment) into the Eco RI and Sma I sites of pGEX-5X1 (Pharmacia-LKB). The glutathione-S-transferase (GST) fusion protein was purified by affinity chromatography (Smith and Johnson (1988) Gene 67:31–40). The recombinant proteins GST-ATF2 (Gupta et al. (1995) Science 267:389–393), GST-cJun (Dérijard (1994) supra), GST-cMyc (Alvarez et al. (1991) J. Biol. Chem. 266:15277–15285), GST-ERK2 (Seth et al. (1992) J. Biol. Chem. 267:24796–24804), GST-p38, (Raingeaud et al. (1995) J. Biol. Chem. 270:7420–7426), and GST-JNK1 (Dérijard (1994) supra) have been described.

Protein kinase assays were performed in kinase buffer (25 mM 4-(2-hydroxyethyl)-l-piperazineethansulfonic acid (pH 7.4), 25 mM β-glycerophosphate, 25 mM $MgCl_2$, 2 mM dithiothreitol, 0.1 mM orthovanadate). The assays were initiated by the addition of 1 µg of substrate proteins and 50 µM $[\gamma\text{-}32P]ATP$ (10 Ci/mmol) in a final volume of 25 µl. The reactions were terminated after 30 minutes at 25° C. by addition of Laemmli sample buffer. The phosphorylation of the substrate proteins was examined after SDS-polyacrylamide gel electrophoresis (PAGE) by autoradiography.

Recombinant MAP kinases were incubated with GST (control) or GST-MKK7 using the substrate ATP $[\gamma\text{-}^{32}P]$. Recombinant MKK7 purified from bacteria was not observed to autophosphorylate. Incubation of the recombinant MKK7 with MAP kinases demonstrated that MKK7 phosphorylated JNK1, but not p38 or ERK2. MKK7 was phosphorylated by p38 and JNK1. The significance of the retrophosphorylation of the MAP kinase kinase by the MAP kinase is unclear, but similar retrophosphorylation has been detected in kinase assays using MKK4 (Dérijard (1995) supra) and the Drosophila JNK activator hep (Sluss (1996) supra).

To test whether the phosphorylation of JNK1 by MKK7 caused increased protein kinase activity, experiments using ATF2 as the JNK substrate were performed. GST-MKK7 was incubated in a protein kinase assay with recombinant JNK1. JNK activity was measured by including the JNK substrate ATF2 in each assay. ATF2 was not phosphorylated by MKK7, but was weakly phosphorylated by JNK1. Incubation of MKK7 with JNK1 caused phosphorylation of JNK1 and a large increase in ATF2 phosphorylation. These data indicate that MKK7 phosphorylates and activates JNK1. To confirm this conclusion, the effect of replacement of the JNK dual phosphorylation motif Thr-Pro-Tyr with Ala-Pro-Phe was examined. MKK7 did not phosphorylate the mutated JNK1 (APF) protein. Furthermore, MKK7 did not increase ATF2 phosphorylation by the mutated JNK1 protein kinase. Thus, MKK7 is a JNK activator in vitro.

Example 25

Specific Activation of JNK by MKK7 in vivo

To examine the specificity of MKK7 in vivo, cotransfection assays were performed. CHO cells were maintained in Dulbecco's modified Eagle's medium supplemented with fetal calf serum (5%; Gibco-BRL). The cells were transfected with the lipofectamine reagent according to the manufacturer's recommendations (Gibco-BRL)(Dérijard (1994) supra). Cells were co-transfected with vectors encoding epitope-tagged JNK1 together with an empty expression vector (control) or an expression vector encoding MKK4 or MKK7. The epitope tag was derived from the hemagglutinin protein (HA) of the influenza virus. JNK1 was isolated by immunoprecipitation of cell lysates. The cells were solubilized with lysis buffer (20 mM Tris (pH 7.4), 1% TRITON X-100®, 10% glycerol, 137 mM NaCl, 2 mM EDTA, 25 mM β-glycerophosphate, 1 mM Na orthovanadate, 2 mM pyrophosphate, 1 mM PMSF, 10 µg/ml leupeptin) and centrifuged at 100,000×g for 15 minutes at 4° C. The epitope-tagged protein kinases were immunoprecipitated by incubation for 3 hours at 4° C. with an anti-HA monoclonal antibody bound to protein-G Sepharose (Pharmacia-LKB Biotechnology Inc.). The immunoprecipitates were washed three times with lysis buffer (Gupta et al. (1995) Science 267:389–393). Protein kinase activity was measured in the immunecomplex with $[\gamma\text{-}^{32}P]ATP$ and c-Jun as substrates. The product of the phosphorylation reaction was visualized after SDS-PAGE by autoradiography. The ERK2 and p38 MAP kinases were not activated by co-expressed MKK7. Control experiments demonstrated that the ERK2 and p38 MAP kinases were activated by their respective cognate MAP kinase kinases, MKK1 and MKK6. In contrast, MKK7 did activate JNK1. Interestingly, the activation of JNK1 by co-expressed MKK7 was greater than that caused by the previously described JNK activator MKK4. Together, these data establish that MKK7 can function as a specific activator of JNK in cultured cells.

Example 26

Activation of the JNK Signal Transduction Pathway by MKK7

The JNK signaling pathway is known to regulate AP-1 transcriptional activity (Whitmarsh (1996) supra). To test the hypothesis that the expression of MKK7 would cause increased AP-1 transcriptional activity, a co-transfection assay was employed using a luciferase reporter gene that contains three AP-1 sites cloned upstream of a minimal promoter element (Rincon and Flavell (1994) EMBO J. 13:4370–4381). Luciferase reporter gene expression was measured in co-transfection assays using the 0.5 μg of the reporter plasmid pTRE-luciferase (Rincon (1994) supra) and 0.25 μg of the β-galactosidase expression vector pCH110 (Pharmacia-LKB). Experiments using GAL4 fusion proteins were performed using 0.25 μg of pGAL4-ATF2 (residues 1–109), 0.5 μg of the reporter plasmid pG5E1bLuc, and 0.25 μg of pCH110 (Gupta et al. (1995) supra). The effect of protein kinases was examined by co-transfection with 0.3 μg of an empty expression vector or a protein kinase expression vector. The ERK2, p38, JNK1, MKK1, MKK3, MKK4, and MKK6 expression vectors have been described. The cells were harvested 36 hours post-transfection. The β-galactosidase and luciferase activity in the cell lysates was measured as described (Gupta (1995) supra). Expression of MKK4, MKK7, or JNK1 did not cause marked changes in AP-1 reporter gene expression (FIG. 16A). In contrast, co-expression of MKK7 with JNK1 caused increased AP-1-dependent reporter gene expression. Consistent with the observation that MKK4 causes weaker activation of JNK than MKK7, co-expression of MKK4 with JNK caused a smaller increase in AP-1 reporter gene expression (FIG. 16A). Together, these data demonstrate that MKK7 can function as an activator of the JNK signal transduction pathway.

To further examine the effect of MKK7 on transcriptional activity, the effect of MKK7 on the transcription factor ATF2 was investigated. Previous studies have demonstrated that ATF2 is a target of the JNK signal transduction pathway (van Dam et al. (1995) supra; Gupta et al. (1995) supra; Livingstone et al (1995) supra). JNK phosphorylates two sites (Thr-69 and Thr-71) in the NH$_2$-terminal activation domain of ATF2 and increases transcriptional activity. A GAL4 fusion protein strategy was employed to monitor the transcriptional activity of the activation domain of ATF2 (Gupta (1995) supra). Measurement of reporter gene expression demonstrated that the co-expression of MKK4 with JNK1 caused increased transcriptional activity (FIG. 16B). A similar level of reporter gene expression was caused by expression of MKK7 and a larger increase was detected when MKK7 was co-expressed with JNK1. The more potent effect of MKK7, compared with MKK4, on transcriptional activity is consistent with the relative effects of MKK7 and MKK4 on JNK activation. To confirm that the increased reporter gene expression was mediated by ATF2 phosphorylation, the effect of replacement of the sites of ATF2 phosphorylation (Thr-69 and Thr-71) with Ala was examined. The mutated ATF2 protein was not regulated by MKK4, MKK7, or JNK1 (FIG. 16B). Together, these data demonstrate that MKK7 can regulate a physiological target of the JNK signaling pathway.

Use

The MKK polypeptides and polynucleotides of the invention are useful for identifying reagents that modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, a kinase assay (see, for example, Example 3) is used. A range of reagent concentrations (e.g., 1.0 nM to 100 mM) are added to a test system that includes an MKK substrate and a radioactive marker such as [γ-$^{32}$P]ATP. Appropriate substrate molecules include p38, JNK1, JNK2, or ATF2. The incorporation of labelled phosphorus (e.g., [$^{32}$]P or [$^{33}$]P) into the substrate is determined, and the results obtained with the test reagent compared to control values. Of particular interest are reagents that result in inhibition of $^{32}$P incorporation of about 80% or more. Phosphorylation may also be examined using a reagent that is phosphorylation-dependent, for example, an antibody. Phosphorylation-dependent antibodies may be made using MKK7 phosphorylated on the activating sites, Ser$^{198}$ and Thr$^{202}$. This may be accomplished by immunizing animals with a synthetic peptide (for example, approximately 15 amino acids in length) corresponding to the MKK7 sequence with phosphorylated Ser$^{198}$ and Thr$^{202}$. Methods of producing such antibodies are known in the art. Such antibodies are useful for the detection of activated MKK7 in tissues and cell extracts (e.g. on Western blots) and may be used in a kit.

Assays that test the effect of a reagent on MKK synthesis can also be used to identify compounds that inhibit MKK signal transduction pathways. The effect of the test reagent on MKK expression is measured by, for example, Western blot analysis with an antibody specific for an MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, Remington's Pharmaceutical Sciences. 18th ed., Gennaro, ed., Mack Publishing Company, Easton, Pa., 1990). Dosages may range from about 0.1–10 mg/kilo/day.

The invention provides methods for both acute and prophylactic treatment of stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent that inhibits MKK function or activity is administered to control inflammatory responses by inhibiting the secretion of inflammatory cytokines, including TNF and IL-1.

Stress-related proliferative disorders can also be treated by the method of the invention by administering a therapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to decrease protein kinase activity. Dominant-negative forms can be created by mutations within the catalytic domain of the protein kinases, using methods known in the art, and as described above (Example 13). The catalytic residues are conserved in all the MKK isoforms. For example, mutation of $Lys^{76}$ inhibits MKK7 activity. Similarly, mutation of the conserved sites of activating phosphorylation ($Ser^{198}_1$, $Thr^{202}$) inhibits MKK7 activity. These kinase-inactive forms of MKK7 act as dominant-negative inhibitors.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When an MKK-mediated disorder is associated with under-expression of MKK, or expression of a mutant MKK polypeptide, a sense polynucleotide sequence (the DNA coding strand) or MKK polypeptide can be introduced into the cell to enhance normal MKK activity. If necessary, these treatments are targeted to specific cells by their mode of administration (e.g., by use of cell-type specific viral vectors), or by placing MKK7 nucleic acids in recombinant constructs with cell-type specific or inducible promoters by methods known in the art. For example, MKK7 nucleic acid-containing vectors can be constructed by recombinant DNA technology methods standard in the art. Vectors can be plasmid, viral, or others known in the art, used for replication and expression in mammalian cells. Expression of the sequence encoding the MKK7 nucleic acid can be by any promoter known in the art to act in mammalian, preferably human cells. Such promoters can be inducible or constitutive. Such promoters include, but are not limited to: the SV40 early promoter region (Bernoist et al., Nature 290:304, 1981); the promoter contained in the 3' long terminal repeat of Rous sarcoma virus (Yamamoto et al., Cell 22:787–797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Transgenic Animals

MKK polypeptides can also be expressed in transgenic animals. These animals represent a model system for the study of disorders that are caused by or exacerbated by overexpression or underexpression of MKK, and for the development of therapeutic agents that modulate the expression or activity of MKK. For example, dominant-negative and constitutively activated alleles could be expressed in mice to establish physiological function.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce a MKK transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl Acac. Sci. USA* 94:3004–3009, 1997)

The present invention provides for transgenic animals that carry the MKK transgene in all their cells, as well as animals that carry the transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the MKK transgene be integrated into the chromosomal site of the endogenous MKK gene, gene targeting is preferred. Briefly, when such a technique is to be used, vectors containing some nucleotide sequences homologous to an endogenous MKK gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous MKK gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional MKK gene.

Once transgenic animals have been generated, the expression of the recombinant MKK gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of MKK gene-expressing tissue can also be evaluated immunocytochemically using antibodies specific for the MKK transgene product.

For a review of techniques that can be used to generate and assess transgenic animals, skilled artisans can consult Gordon (*Intl. Rev. Cytol.* 115:171–229, 1989), and may obtain additional guidance from, for example: Hogan et al. *Manipulating the Mouse Embryo*, Cold Spring Harbor Press, Cold Spring Harbor, N.Y., 1986);, Krimpenfort et al. (*Bio/Technology* 9:86, 1991), Palmiter et al. (*Cell* 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science*, 244:1281, 1986), Wagner et al. (U.S. Pat. No. 5,175,385), and Krimpenfort et al. (U.S. Pat. No. 5,175,384) (the latter two publications are hereby incorporated by reference).

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A substantially pure mammalian mitogen-activated protein kinase kinase (MKK) polypeptide having serine, threonine, and tyrosine kinase activity, and phosphorylating mitogen-activated protein (MAP) kinase JNK, but not p38 and comprising the amino acid sequence of SEQ ID NO:18, SEQ ID NO:20, SEQ ID NO:28, SEQ ID NO:30, or SEQ ID NO:32.

2. A polypeptide of claim 1 consisting of the amino acid sequence of SEQ ID NO:18, SEQ ID NO:20, SEQ ID NO:28, SEQ ID NO:30, or SEQ ID NO:32.

3. A polypeptide consisting of SEQ ID NO:26.

4. A substantially pure mammalian mitogen-activated protein kinase kinase (MKK) polypeptide having serine, threonine, and tyrosine kinase activity, and phosphorylating mitogen-activated protein (MAP) kinase JNK, but not p38, encoded by a nucleic acid sequence that hybridizes to any of SEQ ID NOS:17, 19, 27, 29, or 31, the hybridization conditions comprising hybridization in 50% formamide at 42° C. and washing in 0.2×SSC and 0.1% SDS at 68° C.

* * * * *